US009096835B2

(12) United States Patent
Holliger et al.

(10) Patent No.: US 9,096,835 B2
(45) Date of Patent: Aug. 4, 2015

(54) DNA POLYMERASE

(75) Inventors: Philipp Holliger, Cambridge (GB); Farid Ghadessy, Singapore (SG); Marc d'Abbadie, Cambridge (GB)

(73) Assignee: Medical Research Council, London (GB)

( * ) Notice: Subject to any disclaimer, the term of this patent is extended or adjusted under 35 U.S.C. 154(b) by 67 days.

(21) Appl. No.: 13/527,342

(22) Filed: Jun. 19, 2012

(65) Prior Publication Data

US 2014/0127694 A1     May 8, 2014

Related U.S. Application Data

(60) Continuation of application No. 12/538,392, filed on Aug. 10, 2009, now abandoned, which is a division of application No. 11/417,403, filed on May 3, 2006, now abandoned, which is a continuation of application No. PCT/GB2004/004643, filed on Nov. 3, 2004.

(30) Foreign Application Priority Data

Nov. 3, 2003    (GB) .................................... 0325650.0
May 14, 2004   (GB) .................................... 0410871.8

(51) Int. Cl.
*C12N 9/12* (2006.01)

(52) U.S. Cl.
CPC .................................... *C12N 9/1252* (2013.01)

(58) Field of Classification Search
None
See application file for complete search history.

(56) References Cited

U.S. PATENT DOCUMENTS 6,635,463 B2    10/2003  Ma et al.
2003/0134349 A1  7/2003  Ma et al.

FOREIGN PATENT DOCUMENTS

| WO | WO-0190337 A2 | 11/2001 |
|----|---------------|---------|
| WO | WO-02/22869   | 3/2002  |
| WO | WO-03/44187   | 5/2003  |
| WO | WO-03066804   | 8/2003  |
| WO | WO-03089606   | 10/2003 |
| WO | WO-2005/045015| 5/2005  |

OTHER PUBLICATIONS

Dictionary of Biochemistry and Molecular Biology 97 (John Wiley & Sons, 2nd ed., 1989).
Darnell J. et al., Molecular Cell Biology 51, 2nd ed 1990.
Astatke et al., "A single side chain prevents *Escherichia coli* DNA polymerase I (Klenow fragment) from incorporating ribonucleotides," Proc. Natl. Acad. Sci. USA (1998) 95: 3402-3407.
Barnes, "PCR amplification of up to35-kb DNA with high fidelity and high yield from λ bacteriophage templates," Proc. Natl. Acad. Sci. USA (1994) 91: 2216-2220.
Doublie et al, "Crystal structure of a bacteriophage T7 DNA replication complex at 2.2 Å resolution," Nature (1998) 391: 251-158.
Embleton et al., "In-cell PCR from mRNA: amplifying and linking the rearranged immunoglobulin heavy and light chain V-genes within single cells," Nucleic Acids (1992) 20: 3831-3937.
Ghadessy et al., "Directed evolution of polymerase function by compartmentalized self-replication," PNAS (2001), vol. 98, pp. 4552-4557.
Ghadessy et al., "Generic expansion of the substrate spectrum of a DNA polymerase by directed evolution," Nature Biotechnology (2004), vol. 22, pp. 755-759.
Haase et al., "Amplification and detection of lentiviral DNA inside cells," Proc. Natl. Acad. Sci. USA (1990) 87: 4971-4975.
Huang, et al., "Extension of base mispairs by Taq DNA polymerase: implications for single nucleotide discrimination in PCR," Nucleic Acids Research (1992), vol. 20, pp. 4567-4573.
Jestin et al., "A Method for the Selection of Catalytic Activity Using Phage Display and Proximity Coupling," Angew. Chem. Int. Ed. (1999) 38: 1124-1127.
Johnson et al., "Eukaryotic polymerases ι and ζ act sequentially to bypass DNA lesions," Nature (2000) 406: 1015-1019.
Johnson et al., "Processive DNA synthesis observed in a polymerase crystal suggests a mechanism for the prevention of frameshift mutations," Proc. Natl. Acad. Sci. USA (2003) 100: 3895-3900.
Kwok et al., "Effects of primer-template mismatches on the polymerase chain reaction: Human immunodeficiency virus type 1 model studies," Nucleic Acids Res. (1990) 18: 999-1005.
Lawyer et al. "Isolation, Characterization, and Expression in *Escherichia coli* of the DNA Polymerase Gene from *Thermus aquaticus*," J Biol. Chem. (1989) 264: 6427-6437.
Li et al, "Crystal structures of open and closed forms of binary and ternary complexes of the large fragment of *Thermus aquaticus* DNA polymerase I: structural basis for nucleotide incorporation," EMBO J. (1998) 17: 7514-7525.
Li et al, "Structure-based design of Taq DNA polymerases with improved properties of dideoxynucleotide incorporation," Proc. Natl. Acad. Sci. USA (1999) 96: 9491-9496.
Loakes, "Survey and Summary—The applications of universal DNA base analogues," Nucleic Acids Research (2001) 29: 2437-2447.
Oberholzer, et al., "Polymerase chain reaction in liposomes," Chemistry & Biology (1995) 2: 677-682.
Patel et al., "Prokaryotic DNA Polymerase I: Evolution, Structure, and "Base Flipping" Mechanism for Nucleotide Selection," J. Mol. Biol. (2001) 308: 823-837.
Patel & Loeb, "Getting a grip on how DNA polymerases function," Nature Struc. Biol (2001) 8: 656-659.
Schaaper, "Base Selection, Proofreading, and Mismatch Repair during DNA Replication in *Escherichia coli*," J. Biol. Chem. (1993) 268: 23762-23765.

(Continued)

*Primary Examiner* — Richard Hutson
(74) *Attorney, Agent, or Firm* — Sunstein Kann Murphy & Timbers LLP

(57) ABSTRACT

The present invention relates to DNA polymerases. In particular the invention relates to a method for the generation of DNA polymerases exhibiting a relaxed substrate specificity. Uses of mutant polymerases produced using the methods of the invention are also described.

5 Claims, 29 Drawing Sheets

(56) References Cited

OTHER PUBLICATIONS

Tawfik et al., "Man-made cell-like compartments for molecular evolution," Nature Biotechnology (1998) 16:652-656.
Vaisman et al., "Human DNA Polymerase ι Promiscuous Mismatch Extension," J. Biol. Chem. (2001) 276: 30615-30622.
Washington et al, "Human DINB1-encoded DNA polymerase κ is a promiscuous extender of mispaired primer termini," Proc. Natl. Acad. Sci. USA (2002) 99: 1910-1914.
Xia et al., "Directed evolution of novel polymerase activities: Mutation of a DNA polymerase into an efficient RNA polymerase," Proc. Natl. Acad. Sci. USA (2002) 99: 6597-6602.
Zhao et al., "Molecular evolution by staggered extension process (StEP) in vitro recombination," Nature Biotechnol. (1998) 16: 258-261.

M1 nucleic acid sequence

```
ATGCTCCCTCTTTTTGAGCCCAAAGGCCGCGTCCTCCTGGTGGACGGCCACCACCTGGCCT
ACCGCACCTTCCACGCCCTGAAGGGCCTCACCACCAGCCGGGGGGAGCCGGTGCAGGCGG
TCTACGGCTTCGCCAAGAGCCTCCTCAAGGCCCTCAAGGAGGACGGGGACGCGGTGATCG
TGGTCTTTGACGCCAAGGCCCCCTCCTTCCGCCACGAGGCCTACGGGGGGTACAAGGCGG
CCCGGGCCCCCACGCCGGAGGACTTTCCCCGGCAACTCGCCCTCATCAAGGAGCTGGTGG
ATCTCCTGGGGCTGGCGCGCCTCGAGGTCCCGGGCTACGAGGCGGACGACGTCCTGGCCA
GCCTGGCCAAGAAGGCGGAAAAGGAGGGCTACGAGGTCCGCATCCTCACCGCCGACAAA
GGCCTTTACCAGCTCCTTTCCGACCGCATCCACGTCCTCCACCCCGAGGGGTACCTCATCA
CCCCGGCCTGGCTTTGGGAAAAGTACGGCCTGAGGCCCGACCAGTGGGCCGACTACCGGG
CCCTGACCGGGGACGAGTCCGACAACCTTCCCGGGGTCAAGGGCATCGGGGAGAAGACG
GCGAGGAAGCTTCTGGAGGAGTGGGGGAGCCTGGAAGCCCTCCTCAAGAACCTGGACCG
GCTGAAGCCCGCCATCCGGGAGAAGATCCTGGCCCACATGGACGATCTGAAGCTCTCCTG
GGATCTGGCCAAGGTGCGCACCGACCTGCCCCTGGAGGTGGACTTCGCCAAAAGGCGGGA
GCCCGACCGGGAGAGGCTTAGGGCCTTTCTGGAGAGGCTTGAGTTTGGCAGCCTCCTCCA
CGAGTTCGGCCTTCTGGAAAGCCCCAAGGCCCTGGAGGAGGCCCCCTGGCCCCGCCGGA
AGGGGCCTTCGTGGGCTTTGTCCTTTCCCGCAGGGAGCCCATGTGGGCCGATCTTCTGGCC
CTGGCCGCCGCCAGGGGGGGCCGGGTCCACCGGGCCCCCGAGCCTTATAAAGCCCTCAGG
GACCTGAAGGAGGCGCGGGGGCTTCTCGCCAAAGACCTGAGCGTTCTGGCCCTGAGGGAA
GGCCTTGGCCTCCCCGCCGGCGACGACCCCATGCTCCTCGCCTACCTCCTGGACCCTTCCA
ACACCACCCCCGAGGGGGTGGCCCGGCGCTACGGCGGGGAGTGGACGGAGGAGGCGGGG
GAGCGGGCCGCCCTTTCCGAGAGGCTCTTCGCCAACCTGTGGGGGAGGCTTGAGGGGGAG
GAGAGGCTCCTTTGGCTTTACCGGGAGGTGGAGAGGCCCCTTTCCGCTGTCCTGGCCCACA
TGGAGGCCACGGGGGTGCGCCTGGACGTGGCCTATCTCAGGGCCTTGTCCCTGGAGGTGG
CCGAGGAGATCGCCCGCCTCGAGGCCGAGGTCTTCCGCCTGGCCGGCCACCCCTTCAACC
TCAACTCCCGGGACCAGCTGGAAAGGGTCCTCTTTGACGAGCTAGGGCTTCCCGCCATCG
GCAAGACGGAGAAGACCGGCAAGCGCTCCACCAGCGCCGCCGTCCTGGGGGCCCTCCGC
GAGGCCCACCCCATCGTGGAGAAGATCCTGCAGTACCGGGAGCTCACCAAGCTGAAGAGC
ACCTACATTGACCCCTTACCGGACCTCATCCACCCCAGGACGGGCCGCCTCCACACCCGCT
TCAACCAGACGGCCACGGCCACGGGCCAGGCTAAGTAGCTCCGATCCCAACCTCCAGAACA
TCCCCGTCCGCACCCCGCTTGGGCAGAGGATCCGCCGGGCCTTCATCGCCGAGGAGGGT
GGCTATTGGTGGTCCTGGACTATAGCCAGATAGAGCTCAGGGTGCTGGCCCACCTCTCCG
GCGACGAGAACCTGATCCGGGTCTTCCAGGAGGGGCGGGACATCCACACGGAGACCGCC
AGCTGGATGTTCGGCGTCCCCCGGGAGGCCGTGGACCCCCTGATGCGCCGGGCGGCCAAG
ACCATCAACTTCGGGGTCCTCTACGGCATGTCGGCCCACCGCCTCTCCCAGGAGCTAGCCA
TCCCTTACGAGGAGGCCCAGGCCTTCATTGAGCGCTACTTTCAGAGCTTCCCCAAGGTGCG
GGCCTGGATTGAGAAGACCCTGGAGGAGGGCAGGAGGCGGGGGTACGTGGAGACCCTCT
TCGGCCGCCGCCGCTACGTGCCAGACCTAGAGGCCCGGGTGAAGAGCGTGCGGGGGCG
GCCGAGCGCATGGCCTTCAACATGCCCGTCCAGGGCACCGCCGCCGACCTCATGAAGCTG
GCTATGGTGAAGCTCTTCCCCAGGCTGGAGGAAATGGGGGCCAGGATGCTCCTTCAGGTC
CACGACGAGCTGGTCCTCGAGGCCCCAAAAGAGAGGGCGGAGGCCGTGGCCCGGCTGGC
CAAGGAGGTCATGGAGGGGGTGTATCCCCTGGCCGTGCCCCTGGAGGTGGAGGTGGGGAT
AGGGGAGGACTGGCTCTCCGCCAAGGAGTGA
```

FIG. 1a

SEQ 1

M1 amino acid sequence:

MRGMLPLFEPKGRVLLVDGHHLAYRTFHALKGLTTSRGEPVQAVYGFAKSLLKALKEDGDAVIVVFDAKAPSFRH
EAYGGYKAARAPTPEDFPRQLALIKELVDLLGLARLEVPGYEADDVLASLAKKAEKEGYEVRILTADKGLYQLLS
DRIHVLHPEGYLITPAWLWEKYGLRPDQWADYRALTGDESDNLPGVKGIGEKTARKLLEEWGSLEALLKNLDRLK
PAIREKILAHMDDLKLSWDLAKVRTDLPLEVDFAKRREPDRERLRAFLERLEFGSLLHEFGLLESPKALEEAPWP
PPEGAFVGFVLSRREPMWADLLALAAARGGRVHRAPEPYKALRDLKEARGLLAKDLSVLALREGLGLPPGDDPML
LAYLLDPSNTTPEGVARRYGGEWTEEAGERAALSERLFANLWGRLEGEERLLWLYREVERPLSAVLAHMEATGVR
LDVAYLRALSLEVAEEIARLEAEVFRLAGHPFNLNSRDQLERVLFDELGLPAIGKTEKTGKRSTSAAVLGALREA
HPIVEKILQYRELTKLKSTYIDPLPDLIHPRTGRLHTRFNQTATATGRLSSSDPNLQNIPVRTPLGQRIRRAFIA
EEGWLLVVLDYSQIELRVLAHLSGDENLIRVFQEGRDIHTETASWMFGVPREAVDPLMRRAAKTINFGVLYGMSA
HRLSQELAIPYEEAQAFIERYFQSFPKVRAWIEKTLEEGRRRGYVETLFGRRRYVPDLEARVKSVRGAAERMAFN
MPVQGTAADLMKLAMVKLFPRLEEMGARMLLQVHDELVLEAPKERAEAVARLAKEVMEGVYPLAVPLEVEVGIGE
DWLSAKE

FIG. 1b

M4 nucleic acid sequence

```
ATGCTCCCTCTTTATGAGCCCAAGGGCCGCGTCCTCCTGGTGGACGGCCACCACCTGGCCT
ACCGCACCTTCCACGCCCTGAAGGGCCTCACCACCAGCCGGGGGGAGCCGGTGCAGGCGG
TCTACGGCTTCGCCAAGAGCCTCCTCAAGGCCCTCAAGGAGGGCGGGGACGCGGTGATCG
TGGTCTTTGACGCCAAGGCCCCCTCCTTCCCCCATGAGGCCTACGGGGGGTACAAGGCGG
GCCGGGCCCCCACGCCGGAGGACTTTCCCCGACAACTCGCCCTCATCAAGGAGCTGGTGG
ACCTCCTGGGGCTGACGCGCCTCGAGGTCCCGGGCTACGAGGCGGACGACGTCCTGGCCA
GCCTGGCCAAGAAGGCGGAAAAGGAGGGCTACGAGGTCCGCATCCTCACCGCCGACAAA
GACCTTTACCAGCTCCTTTCCGACCGCATCCACGTCCTCCACCCCGAGGGGTACCTCATCA
CCCCGGCCTGGCTTTGGGAAAAGTACGGCCTGAGGCCCGACCAGTGGGCCGACTACCGGG
CCCTGACCGGGGACGAGTCCGACAACCTTCCCGGGGTCAAGGGCATCGGGGAGAAGACG
GCGAGGAAGCTTCTGGAGGAGTGGGGGAGCCTGGAAGCCCTCCTCAAGAACCTGGACCG
GCTGAAGCCCGCCATCCGGGAGAAGATCCTGGCCCACATGGACGATCTGAAGCTCTCCTG
GGACCGGGCCAAGGTGCGCACCGACCTGCCCCTGGAGGTGGACTTCGCCAAAAGGCGGG
AGCCCGACCGGGAGAGGCTTAGGGCCTTTCTGGAGAGGCTTGAGTTTGGCAGCCTCCTCC
ACGAGTTCGGCCTTCTGGAAAGCCCCAAGGCCCTGGAGGAGGCCCCTGGCCCCGCCGG
AAGGGGCCTTCGTGGGCTTTGTGCTTTCCCGCAAGGAGCCCATGTGGGCCGATCTTCTAGC
CCTGGCCGCCGCCAGGGGGGGCCGGGTCCACCGGGCCCCCGAGCCTTATAAAGCCCTCGG
GGACCTGAAGGAGGCGCGGGGGCTTCTCGCCAAAGACCTGAGCGTTCTGGCCCTGAGGGA
AGGCCTTGGCCTCCCGCCCGACGACGACGACCATGCTCCTCGCCTACCTCCTGGACCCTTCC
AACACCACCCCCGAGGGGGTGGCCCGGCGCTACGGCGGGGAGTGGACGGAGGAGGCAGG
GGAGCGGGCCGCCCTTTCCGAGAGGCTCTTCGCCAACCTGTGGGGAGGCTTGAGGGGGA
GGAAAGGCTCCTTTGGCTTTACCGGGAGGTGGAGAGGCCCCTTTCCGCTGTCCTGGCCCAC
ATGGAGGCCACGGGGGTGCGCCTGGACGTGGCCTATCTCAGGGCCTTGTCCCTGGAGGTG
GCCGAGGAGATCGCCCGCCTCGAGGCCGAGGTCTTCCGCCTGGCCGGCCACCCCTTCAAC
CTCAACTCCCGGGACCAGCTGGAAAGGGTCCTCTTTGACGAGCTAGGGCTTCCCGCCATC
GGCAAGACGGAGAAGACCGGCAAGCGCTCCACCAGCGCCGCCGTCCTGGGGGCCCTCCG
CGAGGCCCACCCCATCGTGGAGAAGATCCTGCAGTACCGGGAGCTCACCAAGCTGAAGAG
CACCTACATTGACCCCTTGCCGGACCTCATCCACCCCAGGACGGGCCGCCTCCACACCCGC
TTCAACCAGACGGCCACGGCCACGGGCAGGCTAAGTAGCTCCGATCCCAACCTCCAGAGC
ATCCCCGTCCGCACCCCGCTTGGGCAGAGGATCCGCCGGGCCTTCATCGCCGAGGAGGGG
TGGCTATTGGTGGCCCTGGACTATAGCCAGATAGAGCTCAGGGTGCTGGCCCACCTCTCCG
GCGACGAGAACCTGATCCGGGTCTTCCAGGAGGGGCGGGACATCCACACGGAGACCGCC
AGCTGGATGTTCGGCGTCCCCCGGGAGGCCGTGGACCCCCTGATGCGCCGGGCGGCCAAG
ACCATCAACTTCGGGGTCCTCTACGGCATGTCGGCCCACCGCCTCTCCCAGGAGCTAGCCA
TCCCTTACGAGGAGGCCCAGGCCTTCATTAAGCGCTACTTTCAGAGCTTCCCCAAGGTGCG
GGCCTGGATTGAGAAGACCCTGGAGGAGGGCAGGAGGCGGGGGTACGTGGAGACCCTCT
TCGGCCGCCGCCGCTACGTGCCAGACCTAGAGGCCCGGGTGAAGAGCGTGCGGGAGCCG
GCCGAGCGCATGGCCTTCAACATGCCCGTCCAGGGTACCGCCGCCGACCTCATGAAGCTG
GCTATGGTGAAGCTCTTCCCCAGGCTGGAGGAAATGGGGGCCAGGATGCTCCTTCAGGTC
CACGACGAGCTGGTCCTCGAGGCCCCAAAAGAGAGGGCGGAGGCCGTGGCCCGGCTGGC
CAAGGAGGTCATGGAGGGGTGTATCCCCTGGCCGTGCCCCTGGAGGTGGAGGTGGGGAT
AGGGGAGGACTGGCTCTCCGCCAAGGAGTGA
```

FIG. 2a

SEQ 2

M4 amino acid sequence:

MRGMLPLYEPKGRVLLVDGHHLAYRTFHALKGLTTSRGEPVQAVYGFAKSLLKALKEGGDAVIVVFDAKAPSFPH
EAYGGYKAGRAPTPEDFPRQLALIKELVDLLGLTRLEVPGYEADDVLASLAKKAEKEGYEVRILTADKDLYQLLS
DRIHVLHPEGYLITPAWLWEKYGLRPDQWADYRALTGDESDNLPGVKGIGEKTARKLLEEWGSLEALLKNLDRLK
PAIREKILAHMDDLKLSWDRAKVRTDLPLEVDFAKRREPDRERLRAFLERLEFGSLLHEFGLLESPKALEEAPWP
PPEGAFVGFVLSRKEPMWADLLALAAARGGRVHRAPEPYKALGDLKEARGLLAKDLSVLALREGLGLPPDDDPML
LAYLLDPSNTTPEGVARRYGGEWTEEAGERAALSERLFANLWGRLEGEERLLWLYREVERPLSAVLAHMEATGVR
LDVAYLRALSLEVAEEIARLEAEVFRLAGHPFNLNSRDQLERVLFDELGLPAIGKTEKTGKRSTSAAVLGALREA
HPIVEKILQYRELTKLKSTYIDPLPDLIHPRTGRLHTRFNQTATATGRLSSSDPNLQSIPVRTPLGQRIRRAFIA
EEGWLLVALDYSQIELRVLAHLSGDENLIRVFQEGRDIHTETASWMFGVPREAVDPLMRRAAKTINFGVLYGMSA
HRLSQELAIPYEEAQAFIKRYFQSFPKVRAWIEKTLEEGRRRGYVETLFGRRRYVPDLEARVKSVREPAERMAFN
MPVQGTAADLMKLAMVKLFPRLEEMGARMLLQVHDELVLEAPKERAEAVARLAKEVMEGVYPLAVPLEVEVGIGE
DWLSAKE

FIG. 2b

Mismatch extension properties of selected polymerases.

Mismatch extension properties of selected polymerases.

Polymerase activity on unnatural substrates (αS dNTP)

FITC-12-dATP          Biotin-16-dUTP

Polymerase activity on unnatural substrates.

Polymerase activity on unnatural substrates (5NI)

Long range PCR.

Experiment I.
ELISA with Fluorescein 12-dATP on clones selected for 4-mismatch extension using the primer FITC4
(5'-
TAGCTACCATTTTCGCCGGCTTCCGTCGCGACCACGTTP1TTCGTGGTCGCGA
CGGAAGCCG-3', P1=Biotin)

High Limit = 1.600
Low Limit = 0.000

| | 1 | 2 | 3 | 4 | 5 | 6 | 7 | 8 | 9 | 10 | 11 | 12 |
|---|---|---|---|---|---|---|---|---|---|---|---|---|
| A | 0.315 | 0.489 | 0.846 | 1.558 | 0.652 | 1.378 | 0.360 | 0.216 | 0.566 | 0.290 | 0.259 | 0.042 |
| B | 0.513 | 0.038 | 0.061 | 0.461 | 0.449 | 0.640 | 0.523 | 0.444 | 0.412 | 0.222 | 0.404 | 0.476 |
| C | 0.467 | 1.125 | 0.588 | 0.818 | 0.311 | 0.718 | 0.292 | 1.169 | 0.736 | 0.551 | 0.222 | 0.260 |
| D | 0.627 | 0.574 | 0.340 | 0.422 | 0.593 | 0.581 | 0.399 | 0.556 | 0.347 | 0.280 | 0.472 | 0.157 |
| E | 1.056 | 0.357 | 0.316 | 0.927 | 1.021 | 0.843 | 0.636 | 1.018 | 1.057 | 0.632 | 0.933 | 0.638 |
| F | 0.046 | 0.499 | 0.906 | 0.489 | 0.774 | 0.408 | 0.444 | 0.867 | 0.576 | 0.366 | 1.344 | 1.070 |
| G | 0.404 | 0.286 | 0.455 | 0.335 | 1.140 | 0.972 | 0.467 | 1.448 | 0.366 | 0.408 | 0.988 | 0.410 |
| H | 1.512 | 1.291 | 0.063 | 1.034 | 0.663 | 0.419 | 0.346 | 1.117 | 1.204 | 0.936 | 1.239 | 0.750 |

Experiment II.

ELISA with Bio-11-dATP on clones selected for 4-mismatch extension and displayed activity with Fluorescein 12-dATP in the ELISA assaying the primer FITC102

(5'-TAGCTACCATTTTTTTTTTCGCCGGCTTCCGTCGCGACCACGTTP1TTCGTGGTCGCGACGGAAGCCG--3', P1=Biotin)

High Limit = 1.200
Low Limit = 0.000

0.044  0.048  0.200  0.660  0.464  0.459  0.053  0.042  0.325  0.067  0.035  0.027
0.275  0.097  0.014  0.107  0.161  0.059  0.092  0.138  0.070  0.044  0.050  0.160
0.204  0.373  0.177  0.219  0.142  0.080  0.033  0.821  0.147  0.310  0.050  0.032
0.288  0.094  0.038  0.050  0.381  0.076  0.057  0.264  0.052  0.044  0.056  0.031
0.540  0.061  0.054  0.928  1.106  0.151  0.152  0.441  0.342  0.381  0.345  0.802
0.038  0.069  0.639  0.089  0.184  0.045  0.055  0.401  0.154  0.072  0.715  0.647
0.062  0.043  0.135  0.057  0.904  0.546  0.182  0.844  0.054  0.064  0.250  0.188
1.332  0.758  0.036  0.535  0.212  0.057  0.049  0.214  1.070  0.494  0.570  0.839

Experiment III.

ELISA with CyDye 5-dCTP on clones selected for 4-mismatch extension using the primer ELISAC4P (5'-TAGCTACCAGGGGCTCCGGCTTCCGTCGCGACCACGTTP1TTCGTGGTCGCGACGGAAGCCG-3', P1=Biotin)

High Limit = 0.200
Low Limit = 0.000

0.053 0.062 0.054 0.058 0.048 0.083 0.063 0.043 0.081 0.066 0.065 0.058
0.079 0.057 0.055 0.084 0.058 0.078 0.060 0.061 0.061 0.058 0.054 0.075
0.113 0.136 0.134 0.129 0.120 0.122 0.111 0.176 0.109 0.119 0.112 0.115
0.081 0.075 0.068 0.068 0.083 0.076 0.065 0.072 0.060 0.061 0.065 0.065
0.119 0.079 0.074 0.092 0.142 0.106 0.091 0.103 0.084 0.092 0.077 0.101
0.086 0.079 0.112 0.092 0.113 0.079 0.075 0.089 0.081 0.086 0.133 0.131
0.076 0.085 0.077 0.084 0.105 0.115 0.088 0.126 0.068 0.074 0.090 0.101
0.422 0.209 0.143 0.175 0.197 0.142 0.144 0.155 0.182 0.168 0.156 0.156

Experiment IV.

ELISA with CyDye 3-dUTP on clones selected for 4-mismatch extension using the ELISA primer ELISAT3P (5'-
TAGCTCGGTAAACGCCGGCTTCCGTCGCGACCACGTTP5TTCGTGGTCGCGACGGAAGCCG
–3', P1=Biotin)

High Limit = 1.650
Low Limit = 0.000

```
0.104  0.141  0.226  0.316  0.244  0.878  0.352  0.107  0.310  0.147  0.090  0.022
0.578  0.014  0.029  0.255  0.297  0.629  0.541  0.347  0.346  0.191  0.206  0.522
0.261  0.516  0.399  0.643  0.188  0.339  0.285  1.051  0.546  0.501  0.174  0.183
0.651  0.277  0.372  0.540  0.444  0.485  0.311  0.569  0.236  0.173  0.222  0.077
0.716  0.143  0.215  0.574  0.782  0.492  0.509  0.910  0.617  0.615  0.515  0.719
0.019  0.380  0.331  0.336  0.582  0.187  0.253  0.768  0.391  0.285  0.829  0.789
0.291  0.174  0.388  0.363  0.735  0.827  0.435  1.072  0.230  0.332  0.545  0.394
1.673  0.724  0.031  0.795  0.454  0.400  0.297  0.649  1.139  0.755  0.407  0.509
```

Experiment V.

ELISA on clones selected for 4-mismatch extension using a hairpin ELISA primer containing an abasic site (Primer: Pscreen1Abas; 1= abasic site, 5= U biotin; sequence:
AGCTACCATGCCTGCACGCAG1CGGCATCCGTCGCGACCACGTT5TTCGTGGTCGCGAC
GGATGCCG)

High Limit = 1.200
Low Limit = 0.000

| 0.075 | 0.092 | 0.137 | 0.882 | 0.453 | 0.441 | 0.185 | 0.058 | 0.931 | 0.108 | 0.040 | 0.023 |
|---|---|---|---|---|---|---|---|---|---|---|---|
| 0.445 | 0.011 | 0.035 | 0.096 | 0.095 | 0.086 | 0.059 | 0.093 | 0.089 | 0.071 | 0.037 | 0.113 |
| 0.314 | 0.512 | 0.091 | 0.113 | 0.086 | 0.092 | 0.083 | 0.746 | 0.122 | 0.304 | 0.065 | 0.093 |
| 0.144 | 0.098 | 0.063 | 0.071 | 0.129 | 0.093 | 0.107 | 0.095 | 0.019 | 0.089 | 0.110 | 0.079 |
| 1.170 | 0.220 | 0.073 | 0.563 | 0.343 | 0.099 | 0.280 | 0.099 | 0.596 | 0.442 | 0.135 | 0.883 |
| 0.025 | 0.077 | 0.913 | 0.094 | 0.150 | 0.062 | 0.229 | 0.092 | 0.087 | 0.071 | 0.814 | 0.912 |
| 0.099 | 0.075 | 0.102 | 0.021 | 0.742 | 0.666 | 0.990 | 0.659 | 0.063 | 0.095 | 0.070 | 0.105 |
| 0.913 | 0.957 | 0.038 | 1.382 | 0.575 | 0.101 | 0.105 | 0.125 | 0.761 | 1.099 | 0.285 | 0.808 |

Four Mismatch Extension in PCR.

Abasic site bypass in PCR.

PCR amplification of a mix of extracts of cave hyenas (*Crocuta spelea*) that had not previously produced an amplification product.

| Experiment | Sample | Dilution | SuperTaq | | Mutant blend | | Improvement |
|---|---|---|---|---|---|---|---|
| | | | Positive PCR | Negative PCR | Positive PCR | Negative PCR | |
| 1 | GS3-7 | 500 | 24 | 12 | 28 | 8 | 16% |
| 2 | GS3-7 | 2000 | 2 | 22 | 5 | 19 | 150% |
| 3 | GS3-7 | 1000 | 21 | 27 | 24 | 24 | 14% |
| 4 | 366 | 5 | 2 | 2 | 4 | 0 | 100% |
| 5 | 366 | 10 | 12 | 12 | 16 | 8 | 33% |
| 6 | GS3-7 | 1000 | 12 | 36 | 14 | 34 | 16% |
| 7 | GS3-7 | 1000 | 10 | 14 | 7 | 17 | -30% |
| 8 | GS3-7 | 1000 | 12 | 36 | 13 | 35 | 8% |
| 9 | GS3-7 | 1000 | 12 | 36 | 13 | 35 | 8% |
| | | | | | | | |
| Total | | | 107 | 197 | 124 | 180 | 15% |

PCRS in the presence of limiting amounts of cave bear aDNA

FIG. 14

Microarray analysis of FITC-labeled probes.

Fig. 21:
Microarray signals from FITC-labelled probes.
A
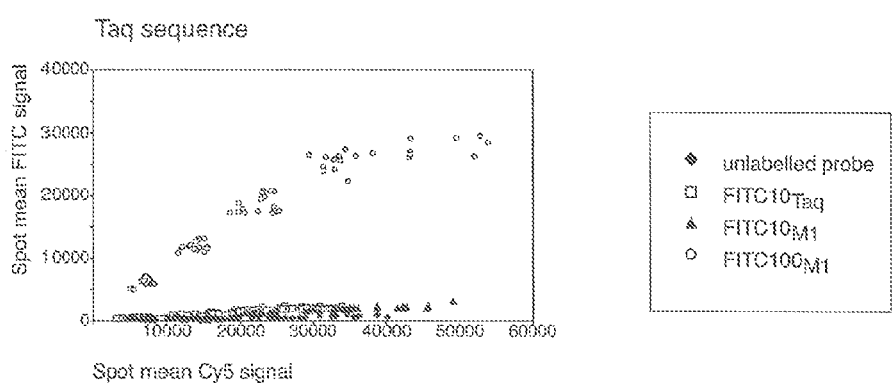
B
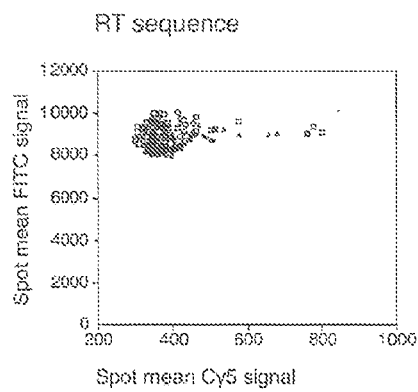
C
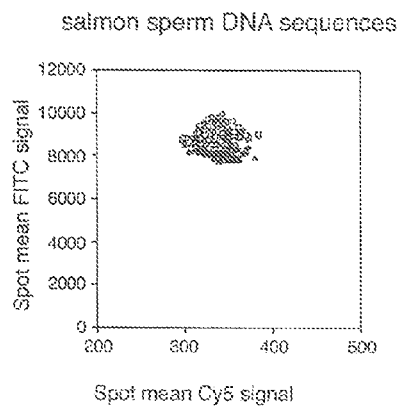
D Comparison of background for FITC probes
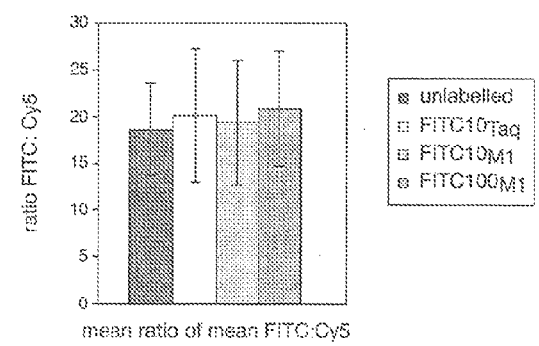

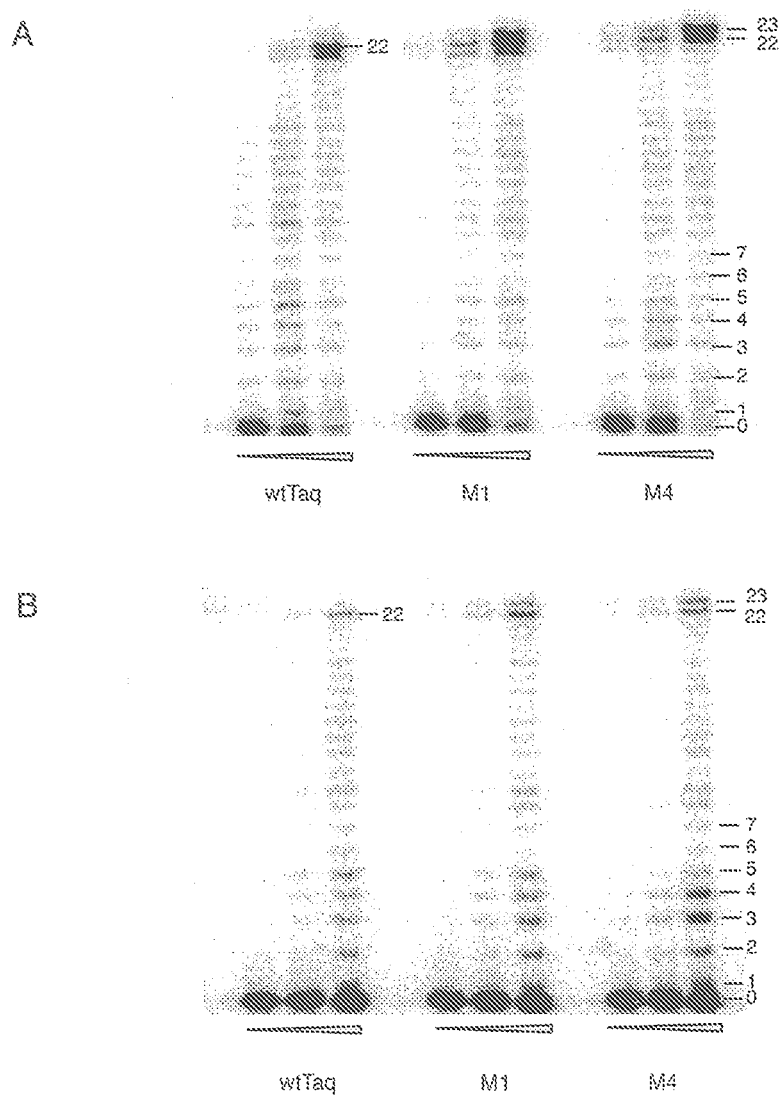
Fig. 23: Processivity

SEQUENCE LISTING

<160> NUMBER OF SEQ ID NOS: 118

<210> SEQ ID NO 1
<211> LENGTH: 832
<212> TYPE: PRT
<213> ORGANISM: Artificial sequence
<220> FEATURE:
<223> OTHER INFORMATION: Mutant Thermus aquaticus DNA polymerase

<400> SEQUENCE: 1

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Ala Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Gly
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Arg Glu Pro Met Trp Ala Asp
305                 310                 315                 320

Leu Leu Ala Leu Ala Ala Ala Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro

```
              355                 360                 365
Pro Gly Asp Asp Pro Met Leu Leu Ala Tyr Leu Leu Asp Pro Ser Asn
            370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Arg Leu Leu Trp Leu Tyr Arg Glu
                420                 425                 430
Val Glu Arg Pro Leu Ser Ala Val Leu Ala His Met Glu Ala Thr Gly
                435                 440                 445
Val Arg Leu Asp Val Ala Tyr Leu Arg Ala Leu Ser Leu Glu Val Ala
            450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
                500                 505                 510
Ser Thr Ser Ala Ala Val Leu Gly Ala Leu Arg Glu Ala His Pro Ile
            515                 520                 525
Val Glu Lys Ile Leu Gln Tyr Arg Glu Leu Thr Lys Leu Lys Ser Thr
            530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
                580                 585                 590
Arg Ile Arg Arg Ala Phe Ile Ala Glu Glu Gly Trp Leu Leu Val Val
            595                 600                 605
Leu Asp Tyr Ser Gln Ile Glu Leu Arg Val Leu Ala His Leu Ser Gly
            610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
                660                 665                 670
Met Ser Ala His Arg Leu Ser Gln Glu Leu Ala Ile Pro Tyr Glu Glu
            675                 680                 685
Ala Gln Ala Phe Ile Glu Arg Tyr Phe Gln Ser Phe Pro Lys Val Arg
            690                 695                 700
Ala Trp Ile Glu Lys Thr Leu Glu Glu Gly Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Gly Ala Ala Glu Arg Met Ala Phe Asn Met Pro
                740                 745                 750
Val Gln Gly Thr Ala Ala Asp Leu Met Lys Leu Ala Met Val Lys Leu
            755                 760                 765
Phe Pro Arg Leu Glu Glu Met Gly Ala Arg Met Leu Leu Gln Val His
            770                 775                 780
```

```
Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
        820                 825                 830

<210> SEQ ID NO 2
<211> LENGTH: 832
<212> TYPE: PRT
<213> ORGANISM: Artificial sequence
<220> FEATURE:
<223> OTHER INFORMATION: Mutant Thermus aquaticus DNA polymerase

<400> SEQUENCE: 2

Met Arg Gly Met Leu Pro Leu Tyr Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Gly Gly Asp Ala Val Ile Val
    50                  55                  60

Val Phe Asp Ala Lys Ala Pro Ser Phe Pro His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Thr Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Arg Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320
```

```
Leu Leu Ala Leu Ala Ala Ala Arg Gly Gly Arg Val His Arg Ala Pro
            325                 330                 335

Glu Pro Tyr Lys Ala Leu Gly Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Asp Asp Asp Pro Met Leu Leu Ala Tyr Leu Leu Asp Pro Ser Asn
            370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Lys Thr Gly Lys Arg
            500                 505                 510

Ser Thr Ser Ala Ala Val Leu Gly Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Ser Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Lys Arg Tyr Phe Gln Ser Phe Pro Lys Val Arg
            690                 695                 700

Ala Trp Ile Glu Lys Thr Leu Glu Glu Gly Arg Arg Gly Tyr Val
705                 710                 715                 720

Glu Thr Leu Phe Gly Arg Arg Tyr Val Pro Asp Leu Glu Ala Arg
            725                 730                 735
```

```
Val Lys Ser Val Arg Glu Pro Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 3
<211> LENGTH: 38
<212> TYPE: DNA
<213> ORGANISM: Artificial sequence
<220> FEATURE:
<223> OTHER INFORMATION: PCR primer for generating mutant Taq polymerase

<400> SEQUENCE: 3
caggaaacag ctatgacaaa atctagata acgaggga                              38

<210> SEQ ID NO 4
<211> LENGTH: 45
<212> TYPE: DNA
<213> ORGANISM: Artificial sequence
<220> FEATURE:
<223> OTHER INFORMATION: PCR primer for generating mutant Taq polymerase

<400> SEQUENCE: 4
gtaaaacgac ggccagtacc accgaactgc gggtgacgcc aagcc                     45

<210> SEQ ID NO 5
<211> LENGTH: 2490
<212> TYPE: DNA
<213> ORGANISM: Artificial sequence
<220> FEATURE:
<223> OTHER INFORMATION: DNA encodiong mutant Thermus aquaticus DNA
      polymerase

<400> SEQUENCE: 5
atgctccctc tttttgagcc caaaggccgc gtcctcctgg tggacggcca ccacctggcc      60
taccgcacct tccacgccct gaagggcctc accaccagcc ggggggagcc ggtgcaggcg     120
gtctacggct tcgccaagag cctcctcaag gccctcaagg aggacgggga cgcggtgatc     180
gtggtctttg acgccaaggc ccctccttc gccacgagg cctacggggg gtacaaggcg       240
gcccgggccc ccacgccgga ggactttccc cggcaactcg ccctcatcaa ggagctggtg     300
gatctcctgg gctggcgcg cctcgaggtc ccgggctacg aggcggacga cgtcctggcc      360
agcctggcca agaaggcgga aaaggagggc tacgaggtcc gcatcctcac cgccgacaaa     420
ggcctttacc agctcctttc cgaccgcatc cacgtcctcc accccgaggg gtacctcatc     480
accccggcct ggctttggga aaagtacggc ctgaggcccg accagtgggc cgactaccgg     540
gccctgaccg ggacgagtc cgacaacctt cccggggtca aggcatcgg ggagaagacg      600 gcgaggaagc ttctggaggagtggggagc ctggaagccc tcctcaagaa cctggaccgg    660
ctgaagcccg ccatccggga aagatcctg gcccacatgg acgatctgaa gctctcctgg    720
gatctggcca aggtgcgcac cgacctgccc ctggaggtgg acttcgccaa aaggcgggag    780
```

```
cccgaccggg agaggcttag ggcctttctg gagaggcttg agtttggcag cctcctccac        840
gagttcggcc ttctggaaag ccccaaggcc ctggaggagg cccctggcc cccgccggaa         900 ggggccttcg tgggctttgt cctttccgc agggagccca tgtgggccga tcttctggcc         960
ctggccgccg ccaggggggg ccgggtccac cgggcccccg agccttataa agccctcagg       1020
gacctgaagg aggcgcgggg gcttctcgcc aaagacctga gcgttctggc cctgagggaa      1080
ggccttggcc tcccgccgg cgacgacccc atgctcctcg cctacctcct ggacccttcc        1140
aacaccaccc ccgagggggt ggcccggcgc tacggcgggg agtggacgga ggaggcgggg      1200
gagcgggccg ccctttccga gaggctcttc gccaacctgt gggggaggct tgaggggag      1260 gagaggctcc tttggcttta ccgggaggtg gagaggcccc tttccgctgt cctggcccac     1320
atggaggcca cggggtgcg cctggacgtg gcctatctca gggccttgtc cctggaggtg        1380
gccgaggaga tcgcccgcct cgaggccgag gtcttccgcc tggccggcca ccccttcaac      1440
ctcaactccc gggaccagct ggaaaggtc tctttgacg agctagggct tcccgccatc        1500
ggcaagacgg agaagaccgg caagcgctcc accagcgccg ccgtcctggg ggccctccgc      1560
gaggcccacc ccatcgtgga aagatcctg cagtaccggg agctcaccaa gctgaagagc        1620
acctacattg acccttacc ggacctcatc cacccagga cgggccgcct ccacacccgc         1680
ttcaaccaga cggccacggc cacgggcagg ctaagtagct ccgatcccaa cctccagaac      1740
atccccgtcc gcaccccgct gggcagagg atccgccggg ccttcatcgc cgaggagggg      1800
tggctattgg tggtcctgga ctatagccag atagagctca gggtgctggc ccacctctcc     1860
ggcgacgaga acctgatccg ggtcttccag gaggggcggg acatccacac ggagaccgcc     1920
agctggatgt tcggcgtccc ccgggaggcc gtggaccccc tgatgcgccg ggcggccaag      1980
accatcaact tcggggtcct ctacggcatg tcggcccacc gcctctccca ggagctagcc     2040
atcccttacg aggaggccca ggccttcatt gagcgctact ttcagagctt ccccaaggtg      2100
cgggcctgga ttgagaagac cctggaggag gcaggaggc gggggtacgt ggagaccctc      2160
ttcggccgcc gccgctacgt gccagaccta gaggcccggg tgaagagcgt gcgggggcg     2220 gccgagcgca tggccttcaa catgcccgtc cagggcaccg ccgccgacct catgaagctg      2280
gctatggtga agctcttccc caggctggag gaaatggggg ccaggatgct ccttcaggtc       2340
cacgacgagc tggtcctcga ggccccaaaa gagagggcgg aggccgtggc ccggctggcc      2400
aaggaggtca tggagggggt gtatccctg ccgtgcccc tggaggtgga ggtggggata       2460
ggggaggact ggctctccgc caaggagtga                                        2490
```

<210> SEQ ID NO 6
<211> LENGTH: 2490
<212> TYPE: DNA
<213> ORGANISM: Artificial sequence
<220> FEATURE:
<223> OTHER INFORMATION: DNA encoding mutant Thermus aquaticus DNA
      polymerase

<400> SEQUENCE: 6

```
atgctccctc tttatgagcc caagggccgc gtcctcctgg tggacggcca ccacctggcc        60
taccgcacct tccacgccct gaaggcctc accaccagcc ggggggagcc ggtgcaggcg       120
gtctacggct tcgccaagag cctcctcaag gccctcaagg agggcgggga cgcggtgatc      180
gtggtctttg acgccaaggc ccctcctttc ccccatgagg cctacggggg gtacaaggcg      240
ggccgggccc ccacgccgga ggactttccc cgacaactcg ccctcatcaa ggagctggtg      300
```

```
gacctcctgg ggctgacgcg cctcgaggtc ccgggctacg aggcggacga cgtcctggcc    360
agcctggcca agaaggcgga aaaggagggc tacgaggtcc gcatcctcac cgccgacaaa    420
gacctttacc agctcctttc cgaccgcatc cacgtcctcc accccgaggg gtacctcatc    480
accccggcct ggctttggga aaagtacggc ctgaggcccg accagtgggc cgactaccgg    540
gccctgaccg gggacgagtc cgacaacctt cccggggtca agggcatcgg ggagaagacg    600
gcgaggaagc ttctggagga gtgggggagc ctggaagccc tcctcaagaa cctgaccgg    660
ctgaagcccg ccatccggga agatcctg gcccacatgg acgatctgaa gctctcctgg    720
gaccgggcca aggtgcgcac cgacctgccc ctggaggtgg acttcgccaa aaggcgggag    780
cccgaccggg agaggcttag ggcctttctg gagaggcttg agtttggcag cctcctccac    840
gagttcggcc ttctggaaag ccccaaggcc ctggaggagg cccccctgcc cccgccggaa    900
ggggccttcg tgggctttgt gctttcccgc aaggagccca tgtgggccga tcttctagcc    960
ctggccgccg ccaggggggg ccgggtccac cgggcccccg agccttataa agccctcggg   1020
gacctgaagg aggcgcgggg gcttctcgcc aaagacctga gcgttctggc cctgagggaa   1080
ggccttggcc tcccgcccga cgacgacccc atgctcctcg cctacctcct ggacccttcc   1140
aacaccaccc ccgaggggt ggccggcgc tacggcgggg agtggacgga ggaggcaggg   1200
gagcgggccg ccctttccga gaggctcttc gccaacctgt ggggggaggct tgaggggag   1260
gaaaggctct tttggcttta cggggaggtg gagaggcccc tttccgctgt cctggcccac   1320
atggaggcca cggggggtgcg cctggacgtg gcctatctca gggccttgtc cctggaggtg   1380
gccgaggaga tcgcccgcct cgaggccgag gtcttccgcc tggccggcca ccccttcaac   1440
ctcaactccc gggaccagct ggaaagggtc ctctttgacg agctagggct tcccgccatc   1500
ggcaagacg agaagaccgg caagcgctcc accagcgccg ccgtcctggg ggccctccgc   1560
gaggccacc ccatcgtgga aagatcctg cagtaccggg agctcaccaa gctgaagagc   1620
acctacattg acccccttgcc ggacctcatc caccccagga cgggccgcct ccacacccgc   1680
ttcaaccaga cggccacggc cacgggcagg ctaagtagct ccgatcccaa cctccagagc   1740
atccccgtcc gcaccccgct gggcagagg atccgccggg ccttcatcgc cgaggagggg   1800
tggctattgg tggccctgga ctatagccag atagagctca gggtgctggc ccacctctcc   1860
ggcgacgaga acctgatccg ggtcttccag gaggggcggg acatccacac ggagaccgcc   1920
agctggatgt tcggcgtccc ccgggaggcc gtggacccc tgatgcgccg ggcggccaag   1980
accatcaact cggggtcct ctacggcatg tcggcccacc gcctctccca ggagctagcc   2040
atcccttacg aggaggccca ggccttcatt aagcgctact ttcagagctt ccccaaggtg   2100
cgggcctgga ttgagaagac cctggaggag ggcaggaggc gggggtacgt ggagaccctc   2160
ttcggccgcc gccgctacgt gccagaccta gaggcccggg tgaagagcgt gcgggagccg   2220
gccgagcgca tggccttcaa catgcccgtc cagggtaccg ccgccgacct catgaagctg   2280
gctatggtga agctcttccc caggctggag gaaatggggg ccaggatgct ccttcaggtc   2340
cacgacgagc tggtcctcga ggccccaaaa gagagggcgg aggccgtggc ccggctggcc   2400
aaggaggtca tggaggggt gtatcccctg gccgtgcccc tggaggtgga ggtgggata   2460
ggggaggact ggctctccgc caaggagtga                                    2490

<210> SEQ ID NO 7
<211> LENGTH: 60
<212> TYPE: DNA
<213> ORGANISM: Artificial sequence
```

```
<220> FEATURE:
<223> OTHER INFORMATION: Primer used in mismatch extension assays.
<220> FEATURE:
<221> NAME/KEY: misc_feature
<222> LOCATION: (38)..(38)
<223> OTHER INFORMATION: Biotinylated T residue

<400> SEQUENCE: 7
tagctaccat tttcgccggc ttccgtcgcg accacgtttt cgtggtcgcg acggaagccg     60

<210> SEQ ID NO 8
<211> LENGTH: 66
<212> TYPE: DNA
<213> ORGANISM: Artificial sequence
<220> FEATURE:
<223> OTHER INFORMATION: Primer used in mismatch extension assay

<400> SEQUENCE: 8
tagctaccat ttttttttc gccggcttcc gtcgcgacca cgttttcgtg gtcgcgacgg     60
aagccg                                                               66

<210> SEQ ID NO 9
<211> LENGTH: 60
<212> TYPE: DNA
<213> ORGANISM: Artificial sequence
<220> FEATURE:
<223> OTHER INFORMATION: Primer used in mismatch extension assay

<400> SEQUENCE: 9
tagctaccag gggctccggc ttccgtcgcg accacgtttt cgtggtcgcg acggaagccg     60

<210> SEQ ID NO 10
<211> LENGTH: 59
<212> TYPE: DNA
<213> ORGANISM: Artificial sequence
<220> FEATURE:
<223> OTHER INFORMATION: Primer used in mismatch extension assay

<400> SEQUENCE: 10
tagctcggta aacgccggct tccgtcgcga ccacgttttc gtggtcgcga cggaagccg      59

<210> SEQ ID NO 11
<211> LENGTH: 65
<212> TYPE: DNA
<213> ORGANISM: Artificial sequence
<220> FEATURE:
<223> OTHER INFORMATION: Primer used in mismatch extension assay

<400> SEQUENCE: 11
agctaccatg cctgcacgca gcggcatccg tcgcgaccac gttttcgtgg tcgcgacgga     60
tgccg                                                                65

<210> SEQ ID NO 12
<211> LENGTH: 155
<212> TYPE: DNA
<213> ORGANISM: Artificial sequence
<220> FEATURE:
<223> OTHER INFORMATION: Sequence amplified from Cave bear mitochondrial
      D loop

<400> SEQUENCE: 12
accccatgca tataggcatg tacatattat gcttgatctt acatgaggac ttacatctca     60
aaagtttatt tcaagtgtat agtctgtaag catgtatttc acttagtcca ggagcttaat    120
caccaggcct cgagaaacca gcaacccttg cgagt                                155
```

<210> SEQ ID NO 13
<211> LENGTH: 23
<212> TYPE: DNA
<213> ORGANISM: Artificial sequence
<220> FEATURE:
<223> OTHER INFORMATION: Primer used in generation of mutant polymerase

<400> SEQUENCE: 13
aaaaatctag ataacgaggg caa                                              23

<210> SEQ ID NO 14
<211> LENGTH: 28
<212> TYPE: DNA
<213> ORGANISM: Artificial sequence
<220> FEATURE:
<223> OTHER INFORMATION: Primer used in generation of mutant polymerase

<400> SEQUENCE: 14
accaccgaac tgcgggtgac gccaagcg                                         28

<210> SEQ ID NO 15
<211> LENGTH: 24
<212> TYPE: DNA
<213> ORGANISM: Artificial sequence
<220> FEATURE:
<223> OTHER INFORMATION: Primer used in mismatch extension assays

<400> SEQUENCE: 15
gaactgcggg tgacgccaag cgca                                             24

<210> SEQ ID NO 16
<211> LENGTH: 25
<212> TYPE: DNA
<213> ORGANISM: Artificial sequence
<220> FEATURE:
<223> OTHER INFORMATION: Primer used in mismatch extension assays

<400> SEQUENCE: 16
ccgaactgcg ggtgacgcca agcgg                                            25

<210> SEQ ID NO 17
<211> LENGTH: 24
<212> TYPE: DNA
<213> ORGANISM: Artificial sequence
<220> FEATURE:
<223> OTHER INFORMATION: Primer used in mismatch extension assays

<400> SEQUENCE: 17
gaactgcggg tgacgccaag cgcg                                             24

<210> SEQ ID NO 18
<211> LENGTH: 23
<212> TYPE: DNA
<213> ORGANISM: Artificial sequence
<220> FEATURE:
<223> OTHER INFORMATION: Primer used in generating and/or analyzing
      mutant polymerases

<400> SEQUENCE: 18
aaaaatctag ataacgaggg caa                                              23

<210> SEQ ID NO 19
<211> LENGTH: 27
<212> TYPE: DNA
<213> ORGANISM: Artificial sequence

```
<220> FEATURE:
<223> OTHER INFORMATION: Primer used in generating or analyzing mutant
      polymerases

<400> SEQUENCE: 19
ccgactggcc aagattagag agtatgg                                          27

<210> SEQ ID NO 20
<211> LENGTH: 27
<212> TYPE: DNA
<213> ORGANISM: Artificial sequence
<220> FEATURE:
<223> OTHER INFORMATION: Primer used in generating or analyzing mutant
      polymerases

<400> SEQUENCE: 20
gatttccacg gataagactc cgcatcc                                          27

<210> SEQ ID NO 21
<211> LENGTH: 28
<212> TYPE: DNA
<213> ORGANISM: Artificial sequence
<220> FEATURE:
<223> OTHER INFORMATION: Primer used in generating and/or analyzing
      mutant polymerases

<400> SEQUENCE: 21
ggcagacgat gatgcagata accagagc                                         28

<210> SEQ ID NO 22
<211> LENGTH: 27
<212> TYPE: DNA
<213> ORGANISM: Artificial sequence
<220> FEATURE:
<223> OTHER INFORMATION: Primer used in generating and/or analyzing
      mutant polymerases

<400> SEQUENCE: 22
gccgatagat agccacggac ttcgtag                                          27

<210> SEQ ID NO 23
<211> LENGTH: 26
<212> TYPE: DNA
<213> ORGANISM: Artificial sequence
<220> FEATURE:
<223> OTHER INFORMATION: Primer used in generating and/or analyzing
      mutant polymerases

<400> SEQUENCE: 23
ggagtagatg cttgcttttc tgagcc                                           26

<210> SEQ ID NO 24
<211> LENGTH: 26
<212> TYPE: DNA
<213> ORGANISM: Artificial sequence
<220> FEATURE:
<223> OTHER INFORMATION: Primer used in generating and/or analyzing
      mutant polymerases

<400> SEQUENCE: 24
gagttcgtgc ttaccgcaga atgcag                                           26

<210> SEQ ID NO 25
<211> LENGTH: 25
<212> TYPE: DNA
<213> ORGANISM: Artificial sequence
<220> FEATURE:
```

<223> OTHER INFORMATION: Primer used in generating and/or analyzing
      mutant polymerases

<400> SEQUENCE: 25
accgaactgc gggtgacgcc aagcg                                              25

<210> SEQ ID NO 26
<211> LENGTH: 25
<212> TYPE: DNA
<213> ORGANISM: Artificial sequence
<220> FEATURE:
<223> OTHER INFORMATION: Primer used in generating and/or analyzing
      mutant polymerases

<400> SEQUENCE: 26
accgaactgc gggtgacgcc aagcc                                              25

<210> SEQ ID NO 27
<211> LENGTH: 24
<212> TYPE: DNA
<213> ORGANISM: Artificial sequence
<220> FEATURE:
<223> OTHER INFORMATION: Primer used in generating and/or analyzing
      mutant polymerases

<400> SEQUENCE: 27
accgaactgc gggtgacgcc aagc                                               24

<210> SEQ ID NO 28
<211> LENGTH: 31
<212> TYPE: DNA
<213> ORGANISM: Artificial sequence
<220> FEATURE:
<223> OTHER INFORMATION: Primer used in generating and/or analyzing
      mutant polymerases

<400> SEQUENCE: 28
aaacagcgct tggcgtcacc cgcagttcgg t                                       31

<210> SEQ ID NO 29
<211> LENGTH: 28
<212> TYPE: DNA
<213> ORGANISM: Artificial sequence
<220> FEATURE:
<223> OTHER INFORMATION: Primer used in generating and/or analyzing
      mutant polymerases

<400> SEQUENCE: 29
cagggcttgg cgtcacccgc agttcggt                                           28

<210> SEQ ID NO 30
<211> LENGTH: 31
<212> TYPE: DNA
<213> ORGANISM: Artificial sequence
<220> FEATURE:
<223> OTHER INFORMATION: Primer used in generating and/or analyzing
      mutant polymerases

<400> SEQUENCE: 30
aaacagagct tggcgtcacc cgcagttcgg t                                       31

<210> SEQ ID NO 31
<211> LENGTH: 31
<212> TYPE: DNA
<213> ORGANISM: Artificial sequence
<220> FEATURE:
<223> OTHER INFORMATION: Primer used in generating and/or analyzing -continued mutant polymerases

<400> SEQUENCE: 31
aaacaccgct tggcgtcacc cgcagttcgg t				31

<210> SEQ ID NO 32
<211> LENGTH: 51
<212> TYPE: DNA
<213> ORGANISM: Artificial sequence
<220> FEATURE:
<223> OTHER INFORMATION: Primer used in generating and/or analyzing
      mutant polymerases

<400> SEQUENCE: 32
agctaccatg cctgcacgaa ttcggcatcc gtcgcgacca cggtcgcagc g				51

<210> SEQ ID NO 33
<211> LENGTH: 51
<212> TYPE: DNA
<213> ORGANISM: Artificial sequence
<220> FEATURE:
<223> OTHER INFORMATION: Primer used in generating and/or analyzing
      mutant polymerases
<220> FEATURE:
<221> NAME/KEY: misc_feature
<222> LOCATION: (22)..(22)
<223> OTHER INFORMATION: Abasic site

<400> SEQUENCE: 33
agctaccatg cctgcacgac ancggcatcc gtcgcgacca cggtcgcagc g				51

<210> SEQ ID NO 34
<211> LENGTH: 51
<212> TYPE: DNA
<213> ORGANISM: Artificial sequence
<220> FEATURE:
<223> OTHER INFORMATION: Primer used in generating and/or analyzing
      mutant polymerases
<220> FEATURE:
<221> NAME/KEY: misc_feature
<222> LOCATION: (21)..(22)
<223> OTHER INFORMATION: nn is a CPD dimer

<400> SEQUENCE: 34
agctaccatg cctgcacgaa nncggcatcc gtcgcgacca cggtcgcagc g				51

<210> SEQ ID NO 35
<211> LENGTH: 20
<212> TYPE: DNA
<213> ORGANISM: Artificial sequence
<220> FEATURE:
<223> OTHER INFORMATION: Primer used in generating and/or analyzing
      mutant polymerases

<400> SEQUENCE: 35
cgtggtcgcg acggatgccg				20

<210> SEQ ID NO 36
<211> LENGTH: 23
<212> TYPE: DNA
<213> ORGANISM: Artificial sequence
<220> FEATURE:
<223> OTHER INFORMATION: Primer used in generating and/or analyzing
      mutant polymerases

<400> SEQUENCE: 36
taatacgact cactataggg aga				23

```
<210> SEQ ID NO 37
<211> LENGTH: 28
<212> TYPE: DNA
<213> ORGANISM: Artificial sequence
<220> FEATURE:
<223> OTHER INFORMATION: Primer used in generating and/or analyzing
      mutant polymerases
<220> FEATURE:
<221> NAME/KEY: misc_feature
<222> LOCATION: (5)..(5)
<223> OTHER INFORMATION: n is 5NI

<400> SEQUENCE: 37
actgntctcc ctatagtgag tcgtatta                                          28

<210> SEQ ID NO 38
<211> LENGTH: 40
<212> TYPE: DNA
<213> ORGANISM: Artificial sequence
<220> FEATURE:
<223> OTHER INFORMATION: Primer used in staggered extension gene
      shuffling protocol

<400> SEQUENCE: 38
caggaaacag ctatgacaaa aatctagata acgagggcaa                             40

<210> SEQ ID NO 39
<211> LENGTH: 45
<212> TYPE: DNA
<213> ORGANISM: Artificial sequence
<220> FEATURE:
<223> OTHER INFORMATION: Primer used in staggered extension gene
      shuffling protocol

<400> SEQUENCE: 39
gtaaaacgac ggccagtacc accgaactgc gggtgacgcc aagcg                       45

<210> SEQ ID NO 40
<211> LENGTH: 36
<212> TYPE: DNA
<213> ORGANISM: Artificial sequence
<220> FEATURE:
<223> OTHER INFORMATION: Mismatch extension primer

<400> SEQUENCE: 40
gtaaaacgac ggccagttta ttaaccaccg aactgc                                 36

<210> SEQ ID NO 41
<211> LENGTH: 41
<212> TYPE: DNA
<213> ORGANISM: Artificial sequence
<220> FEATURE:
<223> OTHER INFORMATION: Mismatch extension primer

<400> SEQUENCE: 41
caggaaacag ctatgactcg acaaaaatct agataacgac c                           41

<210> SEQ ID NO 42
<211> LENGTH: 17
<212> TYPE: DNA
<213> ORGANISM: Artificial sequence
<220> FEATURE:
<223> OTHER INFORMATION: Outnested amplification primer

<400> SEQUENCE: 42
gtaaaacgac ggccagt                                                      17
```

<210> SEQ ID NO 43
<211> LENGTH: 17
<212> TYPE: DNA
<213> ORGANISM: Artificial sequence
<220> FEATURE:
<223> OTHER INFORMATION: Outnested amplification primer

<400> SEQUENCE: 43
caggaaacag ctatgac                                                    17

<210> SEQ ID NO 44
<211> LENGTH: 44
<212> TYPE: DNA
<213> ORGANISM: Artificial sequence
<220> FEATURE:
<223> OTHER INFORMATION: Mismatch extension primer

<400> SEQUENCE: 44
caggaaacag ctatgacaaa agtgaaatga atagttcgac tttt                      44

<210> SEQ ID NO 45
<211> LENGTH: 43
<212> TYPE: DNA
<213> ORGANISM: Artificial sequence
<220> FEATURE:
<223> OTHER INFORMATION: Mismatch extension primer

<400> SEQUENCE: 45
gtaaaacgac ggccagtctt cacaggtcaa gcttattaag gtg                       43

<210> SEQ ID NO 46
<211> LENGTH: 44
<212> TYPE: DNA
<213> ORGANISM: Artificial sequence
<220> FEATURE:
<223> OTHER INFORMATION: Mismatch extension primer

<400> SEQUENCE: 46
caggaaacag ctatgaccat tgatagagtt attttaccac aggg                      44

<210> SEQ ID NO 47
<211> LENGTH: 43
<212> TYPE: DNA
<213> ORGANISM: Artificial sequence
<220> FEATURE:
<223> OTHER INFORMATION: Mismatch extension primer

<400> SEQUENCE: 47
gtaaaacgac ggccagtctt cacaggtcaa gcttattaag gtg                       43

<210> SEQ ID NO 48
<211> LENGTH: 38
<212> TYPE: DNA
<213> ORGANISM: Artificial sequence
<220> FEATURE:
<223> OTHER INFORMATION: Mismatch extension primer

<400> SEQUENCE: 48
caggaaacag ctatgacaaa aatctagata acgaggga                             38

<210> SEQ ID NO 49
<211> LENGTH: 45
<212> TYPE: DNA
<213> ORGANISM: Artificial sequence
<220> FEATURE:
<223> OTHER INFORMATION: Mismatch extension primer

<400> SEQUENCE: 49
gtaaaacgac ggccagtacc accgaactgc gggtgacgcc aagcc        45

<210> SEQ ID NO 50
<211> LENGTH: 41
<212> TYPE: DNA
<213> ORGANISM: Artificial sequence
<220> FEATURE:
<223> OTHER INFORMATION: Mismatch extension primer

<400> SEQUENCE: 50
caggaaacag ctatgactcg acaaaaatct agataacgac c        41

<210> SEQ ID NO 51
<211> LENGTH: 36
<212> TYPE: DNA
<213> ORGANISM: Artificial sequence
<220> FEATURE:
<223> OTHER INFORMATION: Mismatch extension primer

<400> SEQUENCE: 51
gtaaaacgac ggccagttta ttaaccaccg aactgc        36

<210> SEQ ID NO 52
<211> LENGTH: 67
<212> TYPE: DNA
<213> ORGANISM: Artificial sequence
<220> FEATURE:
<223> OTHER INFORMATION: Hairpin primer and template for polymerase
      assay
<220> FEATURE:
<221> NAME/KEY: misc_feature
<222> LOCATION: (45)..(45)
<223> OTHER INFORMATION: n is dU-biotin

<400> SEQUENCE: 52
agctaccatg cctgcacgca gtcggcatcc gtcgcgacca cgttnttcgt ggtcgcgacg        60
gatgccg        67

<210> SEQ ID NO 53
<211> LENGTH: 67
<212> TYPE: DNA
<213> ORGANISM: Artificial sequence
<220> FEATURE:
<223> OTHER INFORMATION: Mismatch extension primer
<220> FEATURE:
<221> NAME/KEY: misc_feature
<222> LOCATION: (22)..(22)
<223> OTHER INFORMATION: n is an abasic site
<220> FEATURE:
<221> NAME/KEY: misc_feature
<222> LOCATION: (45)..(45)
<223> OTHER INFORMATION: n is dU-biotin

<400> SEQUENCE: 53
agctaccatg cctgcacgca gncggcatcc gtcgcgacca cgttnttcgt ggtcgcgacg        60
gatgccg        67

<210> SEQ ID NO 54
<211> LENGTH: 67
<212> TYPE: DNA
<213> ORGANISM: Artificial sequence
<220> FEATURE:
<223> OTHER INFORMATION: Hairpin primer/template for polymerase assay
<220> FEATURE:
<221> NAME/KEY: misc_feature

```
<222> LOCATION: (22)..(22)
<223> OTHER INFORMATION: n is hydantoin
<220> FEATURE:
<221> NAME/KEY: misc_feature
<222> LOCATION: (45)..(45)
<223> OTHER INFORMATION: n is dU-biotin

<400> SEQUENCE: 54
agctaccatg cctgcacgca gncggcatcc gtcgcgacca cgttnttcgt ggtcgcgacg    60
gatgccg                                                              67

<210> SEQ ID NO 55
<211> LENGTH: 2502
<212> TYPE: DNA
<213> ORGANISM: Artificial sequence
<220> FEATURE:
<223> OTHER INFORMATION: Mutant Taq polymerase

<400> SEQUENCE: 55
atggcgatgc ttcccctctt tgagcccaag ggccgcgtcc tcctggtgga cggccaccac    60
ctggcctacc gcaccttctt cgccctgaag ggccccacca cgagccgggg cgaaccggtg   120
caggtggtct acggcttcgc caagagcctc ctcaaggccc tgaaggagga cgggtacaag   180
gccgtcttcg tggtctttga cgccaaggcc ccctcattcc gccacaaggc ctacgaggcc   240
tacagggcgg ggagggcccc gaccccgag gacttccccc ggcagctcgc cctcatcaag    300
gagctggtgg acctcctggg gtttacccgc ctcgaggtcc ccggctacga ggcggacgac   360
gttctcgcca ccgtggccaa gaaggcgaa aaggaggggt acgaggtggg catcctcacc    420
gccgaccgcg gcctctacca actcgtctct gaccgcgtcg ccgtcctcca ccccgagggc   480
cacctcatca ccccggagtg gctttgggag aagtacggcc tcaggccgga gcagtgggtg   540
gacttccgcg ccctcgtggg ggaccctcc gacaacctcc ccggggtcaa gggcatcggg   600
gagaagaccg ccctcaagct cctcaaggag tggggaagcc tggaaaacct cctcaagaac   660
ctggaccggg taaagccaga aaacgtccgg gagaagatca aggcccacct ggaagacctc   720
aggctctcct ggagctctc ccgggtgcgc accgacctcc ccctggaggt ggacctcgcc    780
caggggcggg agcccgaccg ggaggggctt agggcctttc tggagaggct tgagtttggc   840
agcctcctcc acgagttcgg ccttctggaa agccccaagg ccctggagga ggcccctgg    900 cccccgccgg aaggggcctt cgtgggcttt gtgctttccc gcaaggagcc catgtgggcc   960
gatcttctgg ccctggccgc cgccaggggg gccgggtcc accgggcccc cgagccttat   1020
aaagccctca gagacctgaa ggaggcgcgg gggcttctcg ccaaagacct gagcgttctg   1080
gccctgaggg aaggccttgg cctcccgccc ggcgacgacc ccatgctcct cgcctacctc   1140 ctggacccctt ccaacaccac ccccgagggg gtggcccggc gctacggcgg ggagtggacg   1200
gaggaggcgg gggagcgggc cgcccttttcc gagaggctct cgccaacct gtggggagg    1260 cttgaggggg aggagaggct cctttggctt taccggagg tggagaggcc cctttccgtt   1320
gtcctggccc acatggaggc cacaggggtg cgcctggacg tggcctatct cagggccttg   1380
tccctggagg tggccgagga gatcgcccgc ctcgaggccg aggtcttccg cctggccggc   1440
caccccttca acctcaactc ccgggaccag ctggaaaggg tcctctttga cgagctaggg   1500
cttcccgcca tcggcaagac ggagaagacc ggcaagcgct ccaccggcgc cgccgtcctg   1560
gaggccctcc acgaggccca ccccatcgtg gagaagatcc tgcagtaccg ggagctcacc   1620
aagctgaaga gcacctacat tgacccctig ccggactca tccacccag gacgggccgc    1680
```

```
ctccacaccc gcttcaacca gacggccacg gccacgggca ggctaagtag ctccgatccc    1740
aacctccaga acatccccgt ccgcacccag cttgggcaga ggatccgccg ggccttcatc    1800
gccgaggagg ggtggctatt ggtggtcctg gactatagcc agatagagct caggtgctg    1860 gcccacctct ccggcgacga gaacctgatc cgggtcttcc aggaggggcg ggacatccac    1920
acggaaaccg ccagctggat gttcggcgtc ccccaggagg ccgtggaccc cctgatgcgc    1980
cgggcggcca agaccatcaa cttcgggttt ctctacggca tgtcggccta ccgcctctcc    2040
caggagctag ccatcccta cgaggaggcc caggccttca ttgagcgcta ctttcagagc    2100
ttccccaagg tgcgggcctg gattgggaag accctggagg agggcaggag gcgggggtac    2160
gtggagaccc tcttcggccg ccgccgctac gtgccagacc tagaggcccg ggtgaagagc    2220
gtgcgggagg cggccgagcg catggccttc aacacgcccg tccagggcac cgccgccgac    2280
ctcatgaagc tagctatggt gaagctcttc cccaggctgg aggaaatggg ggccaggatg    2340
ctccttcagg tccacgacga gctggtcctc gaggccccaa aagagagggc ggaggccgtg    2400
gcccggctgg ccaaggaggt catggagggg gtgtatcccc tggccgtgcc cctggaggtg    2460
gaggtgggga taggggagga ctggctctcc gccaaggagt ga                       2502
```

<210> SEQ ID NO 56
<211> LENGTH: 833
<212> TYPE: PRT
<213> ORGANISM: Artificial sequence
<220> FEATURE:
<223> OTHER INFORMATION: Mutant Taq polymerase

<400> SEQUENCE: 56

```
Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Pro
            20                  25                  30

Thr Thr Ser Arg Gly Glu Pro Val Gln Val Val Tyr Gly Phe Ala Lys
        35                  40                  45

Ser Leu Leu Lys Ala Leu Lys Glu Asp Gly Tyr Lys Ala Val Phe Val
    50                  55                  60

Val Phe Asp Ala Lys Ala Pro Ser Phe Arg His Lys Ala Tyr Glu Ala
65                  70                  75                  80

Tyr Arg Ala Gly Arg Ala Pro Thr Pro Glu Asp Phe Pro Arg Gln Leu
                85                  90                  95

Ala Leu Ile Lys Glu Leu Val Asp Leu Leu Gly Phe Thr Arg Leu Glu
            100                 105                 110

Val Pro Gly Tyr Glu Ala Asp Asp Val Leu Ala Thr Val Ala Lys Lys
        115                 120                 125

Ala Glu Lys Glu Gly Tyr Glu Val Gly Ile Leu Thr Ala Asp Arg Gly
    130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asp Asn
            180                 185                 190

Leu Pro Gly Val Lys Gly Ile Gly Glu Lys Thr Ala Leu Lys Leu Leu
        195                 200                 205

Lys Glu Trp Gly Ser Leu Glu Asn Leu Leu Lys Asn Leu Asp Arg Val
    210                 215                 220
```

```
Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
            245                 250                 255

Val Asp Leu Ala Gln Gly Arg Glu Pro Asp Arg Glu Gly Leu Arg Ala
        260                 265                 270

Phe Leu Glu Arg Leu Glu Phe Gly Ser Leu His Glu Phe Gly Leu
    275                 280                 285

Leu Glu Ser Pro Lys Ala Leu Glu Glu Ala Pro Trp Pro Pro Glu
290                 295                 300

Gly Ala Phe Val Gly Phe Val Leu Ser Arg Lys Glu Pro Met Trp Ala
305                 310                 315                 320

Asp Leu Leu Ala Leu Ala Ala Arg Gly Gly Arg Val His Arg Ala
            325                 330                 335

Pro Glu Pro Tyr Lys Ala Leu Arg Asp Leu Lys Glu Ala Arg Gly Leu
            340                 345                 350

Leu Ala Lys Asp Leu Ser Val Leu Ala Leu Arg Glu Gly Leu Gly Leu
            355                 360                 365

Pro Pro Gly Asp Asp Pro Met Leu Leu Ala Tyr Leu Leu Asp Pro Ser
370                 375                 380

Asn Thr Thr Pro Glu Gly Val Ala Arg Arg Tyr Gly Gly Glu Trp Thr
385                 390                 395                 400

Glu Glu Ala Gly Glu Arg Ala Ala Leu Ser Glu Arg Leu Phe Ala Asn
                405                 410                 415

Leu Trp Gly Arg Leu Glu Gly Glu Arg Leu Leu Trp Leu Tyr Arg
            420                 425                 430

Glu Val Glu Arg Pro Leu Ser Val Val Leu Ala His Met Glu Ala Thr
            435                 440                 445

Gly Val Arg Leu Asp Val Ala Tyr Leu Arg Ala Leu Ser Leu Glu Val
450                 455                 460

Ala Glu Glu Ile Ala Arg Leu Glu Ala Glu Val Phe Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
            500                 505                 510

Arg Ser Thr Gly Ala Ala Val Leu Glu Ala Leu His Glu Ala His Pro
            515                 520                 525

Ile Val Glu Lys Ile Leu Gln Tyr Arg Glu Leu Thr Lys Leu Lys Ser
530                 535                 540

Thr Tyr Ile Asp Pro Leu Pro Asp Leu Ile His Pro Arg Thr Gly Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Gln Leu Gly
            580                 585                 590

Gln Arg Ile Arg Arg Ala Phe Ile Ala Glu Glu Gly Trp Leu Leu Val
            595                 600                 605

Val Leu Asp Tyr Ser Gln Ile Glu Leu Arg Val Leu Ala His Leu Ser
            610                 615                 620

Gly Asp Glu Asn Leu Ile Arg Val Phe Gln Glu Gly Arg Asp Ile His
625                 630                 635                 640
```

```
Thr Glu Thr Ala Ser Trp Met Phe Gly Val Pro Gln Glu Ala Val Asp
                645                 650                 655
Pro Leu Met Arg Arg Ala Ala Lys Thr Ile Asn Phe Gly Val Leu Tyr
            660                 665                 670
Gly Met Ser Ala Tyr Arg Leu Ser Gln Glu Leu Ala Ile Pro Tyr Glu
        675                 680                 685
Glu Ala Gln Ala Phe Ile Glu Arg Tyr Phe Gln Ser Phe Pro Lys Val
    690                 695                 700
Arg Ala Trp Ile Gly Lys Thr Leu Glu Glu Gly Arg Arg Arg Gly Tyr
705                 710                 715                 720
Val Glu Thr Leu Phe Gly Arg Arg Arg Tyr Val Pro Asp Leu Glu Ala
                725                 730                 735
Arg Val Lys Ser Val Arg Glu Ala Ala Glu Arg Met Ala Phe Asn Thr
            740                 745                 750
Pro Val Gln Gly Thr Ala Ala Asp Leu Met Lys Leu Ala Met Val Lys
        755                 760                 765
Leu Phe Pro Arg Leu Glu Glu Met Gly Ala Arg Met Leu Leu Gln Val
    770                 775                 780
His Asp Glu Leu Val Leu Glu Ala Pro Lys Glu Arg Ala Glu Ala Val
785                 790                 795                 800
Ala Arg Leu Ala Lys Glu Val Met Glu Gly Val Tyr Pro Leu Ala Val
                805                 810                 815
Pro Leu Glu Val Glu Val Gly Ile Gly Glu Asp Trp Leu Ser Ala Lys
            820                 825                 830
Glu

<210> SEQ ID NO 57
<211> LENGTH: 2502
<212> TYPE: DNA
<213> ORGANISM: Artificial sequence
<220> FEATURE:
<223> OTHER INFORMATION: Mutant Taq polymerase

<400> SEQUENCE: 57
atgcgtggta tgcctcctct ttttgagccc aagggccgcg tcctcctggt ggacggccac      60
ctggcctacc gcaccttctt cgccctgaag ggccccacca cgagccgggg cgaaccggtg     120
caggcggtct acggcttcgc caagagcctc ctcaaggccc tgaaggagga cgggtacaag     180
gccgtcttcg tggtctttga cgccaaggcc ccctccctcc gccacgaggc ctacgaggcc     240
tacaaggcgg ggagggcccc gaccccgag gacttccccc ggcagctcgc cctcatcaag     300
gagctggtgg acctcctggg gtttacccgc tcgaggtcc ccggctacga ggcggacgac     360
gttctcgcca ccctggccaa gaaggcggaa aaggaggggt acgaggtgcg catcctcacc     420
gccgaccgcg acctctacca actcgtctcc gaccgcgtcg ccgtcctcca ccccgagggc     480
cacctcatca cccccgagtg gctttgggag aagtacggcc tcaggccgga gcagtgggtg     540
gacttccgcg ccctcgtggg ggaccccctcc gacaacctcc ccgggtcaa gggcatcggg     600 gagaggaccg ccctcaagct cctcaaggag tggggaagcc tggaaaacct cctcaagaac     660
ctggaccggg taaagccaga aaacgtccgg gagaagatca ggcccacct ggaagacctc     720 aggctctcct ggagctctc ccgggtgcgc accgacctcc ccctggaggt ggacctcgcc     780
caggggcggg agcccgaccg ggagaggctt agggcctttc tggagaggct tgagtttggc     840
agcctcctcc acgagttcgg ccttctggaa agccccaagg ccctggagga ggccccctgg     900 ccccgccgg aaggggcctt cgtgggcttt gtgctttccc gcaaggagcc catgtgggcc     960
```

-continued

```
gatcttctgg ccctggccgc cgccagggyt ggtcgggtcc accgggcccc cgagccttat    1020
aaagccctca gggacttgaa ggaggcgcgg gggcttctcg ccaaagacct gagcgttctg    1080
gccctaaggg aaggccttgg cctcccgccc ggcgacgacc ccatgctcct cgcctacctc    1140 ctggacccctt ccaacaccac ccccgagggg gtggcccggc gctacggcgg ggagtggacg    1200
gaggaggcgg gggagcgggc cgccctttcc gagaggctct tcgccaacct gtgggggaag    1260
cttgaggggg aggagaggct cctttggctt taccggaggg tggataggcc cctttccgct    1320
gtcctggccc acatggaggc cacaggggtg cgcctggacg tggcctatct cagggcctcg    1380
tccctggagg tggccgagga gatcgcccgc ctcgaggccg aggtcttccg cctggccggc    1440
caccccttca acctcaactc ccgggaccag ctggaaaggg tcctctttga cgagctaggg    1500
cttcccgcca tcggcaagac ggagaagacc ggcaagcgct ccaccagcgc cgccgtcctg    1560
gaggccctcc gcgaggccca ccccatcgtg gagaagatcc tgcagtaccg ggagctcacc    1620
aagctgaaga gcacctacat tgaccccttg ccggacctca tccacccag acgggccgc    1680 ctccacaccc gcttcaacca gacggccacg gccacaggca ggctaagtag ctccgatccc    1740
aacctccaga acatccccgt ccgcaccccg cttgggcaga ggatccgccg ggccttcatc    1800
gccgaggagg ggtggctatt ggtggccctg gactatagcc agatagagct caggggtgctg    1860 gcccacctct ccggcgacga gaacctgatc cgggtcttcc aggaggggcg ggacatccac    1920
acggagaccg ccagttggat gttcggcgtc ccccgggagg ccgtggaccc cctgatgcgc    1980
cgggcggcca agaccatcaa cttcggggtc ctctacggca tgtcggcccg ccgcctctcc    2040
caggagctag ccatccctta cgaggaggcc caggccttca ttgagcgcta ctttcagagc    2100
ttccccaagg tgcgggcctg gattgagaag accctggagg agggcaggag gcgggggtac    2160
gtggagaccc tcttcggccg ccgccgctac gtgccagacc tagaggcccg ggtgaagagc    2220
gtgcgggagc cggccgagcg catggccttc aacatgccg tccagggcac cgccgccgac    2280
ctcatgaagc tggctatggt gaagctcttc ccccaggctgg aggaaatggg ggccaggatg    2340
ctccttcagg tccacgacga gctggtcctc gaggccccaa agagagggc ggaggccgtg    2400 gcccggctgg ccaaggaggt catggagggg gtgtatcccc tggccgtgcc cctggaggtg    2460
gaggtgggga tagggaggga ctggctctcc gccaaggagt ga                       2502
```

<210> SEQ ID NO 58
<211> LENGTH: 833
<212> TYPE: PRT
<213> ORGANISM: Artificial sequence
<220> FEATURE:
<223> OTHER INFORMATION: Mutant Taq polymerase

<400> SEQUENCE: 58

```
Met Arg Gly Met Pro Pro Leu Phe Glu Pro Lys Gly Arg Val Leu Leu
1               5                   10                  15

Val Asp Gly His Leu Ala Tyr Arg Thr Phe Phe Ala Leu Lys Gly Pro
            20                  25                  30

Thr Thr Ser Arg Gly Glu Pro Val Gln Ala Val Tyr Gly Phe Ala Lys
        35                  40                  45

Ser Leu Leu Lys Ala Leu Lys Glu Asp Gly Tyr Lys Ala Val Phe Val
    50                  55                  60

Val Phe Asp Ala Lys Ala Pro Ser Leu Arg His Glu Ala Tyr Glu Ala
65                  70                  75                  80

Tyr Lys Ala Gly Arg Ala Pro Thr Pro Glu Asp Phe Pro Arg Gln Leu
```

```
            85                  90                  95
Ala Leu Ile Lys Glu Leu Val Asp Leu Leu Gly Phe Thr Arg Leu Glu
            100                 105                 110

Val Pro Gly Tyr Glu Ala Asp Val Leu Ala Thr Leu Ala Lys Lys
            115                 120                 125

Ala Glu Lys Glu Gly Tyr Glu Val Arg Ile Leu Thr Ala Asp Arg Asp
            130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
            165                 170                 175

Glu Gln Trp Val Asp Phe Arg Ala Leu Val Gly Asp Pro Ser Asp Asn
            180                 185                 190

Leu Pro Gly Val Lys Gly Ile Gly Glu Arg Thr Ala Leu Lys Leu Leu
            195                 200                 205

Lys Glu Trp Gly Ser Leu Glu Asn Leu Leu Lys Asn Leu Asp Arg Val
            210                 215                 220

Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
                    245                 250                 255

Val Asp Leu Ala Gln Gly Arg Glu Pro Asp Arg Glu Arg Leu Arg Ala
            260                 265                 270

Phe Leu Glu Arg Leu Glu Phe Gly Ser Leu Leu His Glu Phe Gly Leu
            275                 280                 285

Leu Glu Ser Pro Lys Ala Leu Glu Glu Ala Pro Trp Pro Pro Glu
            290                 295                 300

Gly Ala Phe Val Gly Phe Val Leu Ser Arg Lys Glu Pro Met Trp Ala
305                 310                 315                 320

Asp Leu Leu Ala Leu Ala Ala Ala Arg Gly Gly Arg Val His Arg Ala
                    325                 330                 335

Pro Glu Pro Tyr Lys Ala Leu Arg Asp Leu Lys Glu Ala Arg Gly Leu
            340                 345                 350

Leu Ala Lys Asp Leu Ser Val Leu Ala Leu Arg Glu Gly Leu Gly Leu
            355                 360                 365

Pro Pro Gly Asp Asp Pro Met Leu Leu Ala Tyr Leu Leu Asp Pro Ser
            370                 375                 380

Asn Thr Thr Pro Glu Gly Val Ala Arg Arg Tyr Gly Gly Glu Trp Thr
385                 390                 395                 400

Glu Glu Ala Gly Glu Arg Ala Ala Leu Ser Glu Arg Leu Phe Ala Asn
                    405                 410                 415

Leu Trp Gly Lys Leu Glu Gly Glu Glu Arg Leu Leu Trp Leu Tyr Arg
            420                 425                 430

Glu Val Asp Arg Pro Leu Ser Ala Val Leu Ala His Met Glu Ala Thr
            435                 440                 445

Gly Val Arg Leu Asp Val Ala Tyr Leu Arg Ala Ser Ser Leu Glu Val
            450                 455                 460

Ala Glu Glu Ile Ala Arg Leu Glu Ala Glu Val Phe Arg Leu Ala Gly
465                 470                 475                 480

His Pro Phe Asn Leu Asn Ser Arg Asp Gln Leu Glu Arg Val Leu Phe
                    485                 490                 495

Asp Glu Leu Gly Leu Pro Ala Ile Gly Lys Thr Glu Lys Thr Gly Lys
            500                 505                 510
```

```
Arg Ser Thr Ser Ala Ala Val Leu Glu Ala Leu Arg Glu Ala His Pro
            515                 520                 525

Ile Val Glu Lys Ile Leu Gln Tyr Arg Glu Leu Thr Lys Leu Lys Ser
        530                 535                 540

Thr Tyr Ile Asp Pro Leu Pro Asp Leu Ile His Pro Arg Thr Gly Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590

Gln Arg Ile Arg Arg Ala Phe Ile Ala Glu Glu Gly Trp Leu Leu Val
        595                 600                 605

Ala Leu Asp Tyr Ser Gln Ile Glu Leu Arg Val Leu Ala His Leu Ser
    610                 615                 620

Gly Asp Glu Asn Leu Ile Arg Val Phe Gln Glu Gly Arg Asp Ile His
625                 630                 635                 640

Thr Glu Thr Ala Ser Trp Met Phe Gly Val Pro Arg Glu Ala Val Asp
                645                 650                 655

Pro Leu Met Arg Arg Ala Ala Lys Thr Ile Asn Phe Gly Val Leu Tyr
            660                 665                 670

Gly Met Ser Ala Arg Arg Leu Ser Gln Glu Leu Ala Ile Pro Tyr Glu
        675                 680                 685

Glu Ala Gln Ala Phe Ile Glu Arg Tyr Phe Gln Ser Phe Pro Lys Val
    690                 695                 700

Arg Ala Trp Ile Glu Lys Thr Leu Glu Glu Gly Arg Arg Arg Gly Tyr
705                 710                 715                 720

Val Glu Thr Leu Phe Gly Arg Arg Arg Tyr Val Pro Asp Leu Glu Ala
                725                 730                 735

Arg Val Lys Ser Val Arg Glu Ala Ala Glu Arg Met Ala Phe Asn Met
            740                 745                 750

Pro Val Gln Gly Thr Ala Ala Asp Leu Met Lys Leu Ala Met Val Lys
        755                 760                 765

Leu Phe Pro Arg Leu Glu Glu Met Gly Ala Arg Met Leu Leu Gln Val
    770                 775                 780

His Asp Glu Leu Val Leu Glu Ala Pro Lys Glu Arg Ala Glu Ala Val
785                 790                 795                 800

Ala Arg Leu Ala Lys Glu Val Met Glu Gly Val Tyr Pro Leu Ala Val
                805                 810                 815

Pro Leu Glu Val Glu Val Gly Ile Gly Glu Asp Trp Leu Ser Ala Lys
            820                 825                 830

Glu

<210> SEQ ID NO 59
<211> LENGTH: 2502
<212> TYPE: DNA
<213> ORGANISM: Artificial sequence
<220> FEATURE:
<223> OTHER INFORMATION: Mutant Taq polymerase coding sequence

<400> SEQUENCE: 59
atgcgtggta tgcatcctct ttttgagccc aagggccgcg tcctcctggt ggacggccac      60
cacctggcct accgcacctt ccacgccctg aagggctca ccaccagccg ggggagccg       120 gtgcgggcgg tccacggctt cgccaagagc ctcctcaagg ccctgaagga ggacgggtac     180
```

```
aaggccgtct tcgtggtctt tgacgccaag gcccctcct tccgccacga ggcctacgag    240
gcctacaagg cggggagggc cccgacccc gaggacttcc cccggcagct cgccctcatc    300
aaggagctgg tggacctcct ggggtttacc cgcctcgagg tccccggcta cgaggcggac    360
gacgttctcg ccaccctggc caagaaggcg aaaaggagg ggtacgaggt gcgcatcctc    420
accgccgacc gcgacctcta ccaactcgtc tccgaccgcg tcgccgtcct ccaccccgag    480
ggccacctca tcaccccgga gtggctttgg gagaagtacg gcctcaggcc ggagcagtgg    540
gtggacttcc gcgccctcgt ggggacccc tccgacaacc tccccggggt caagggcatc    600
ggggagaaga ccgccctcaa gctcctcaag gagtggggaa gctggaaaa cctcctcaag    660 aacctggacc ggctgaagcc cgccatccgg gagaagatcc tggcccacat ggacgatctg    720
aagctctcct gggacctggc caaggtgcgc accgacctgc cctagaggt ggacttcgcc    780 aaaaggcggg agcccgaccg ggagaggctt agggcctttc tggagaggct tgagcttggc    840
agcctcctcc acgagttcgg ccttctggaa agccccaaga ccctggagga ggcctcctgg    900
cccccgccgg aaggggcctt cgtgggcttt gtgctttccc gcaaggagcc catgtgggcc    960
gatcttctgg ccctggccgc cgccaggggg ggccgggtcc accgggcccc cgagccttat   1020
aaagccctca gagacctgaa ggaggcgcgg gggcttctcg ccaaagacct gagcgttctg   1080
gccctgaggg aaggccttgg cctcccgccc ggcgacgacc ccatgctcct cgcctacctc   1140 ctggacccctt ccaacaccac ccccgagggg gtggcccggc gctacggcgg ggagtggacg   1200
gaggaggcgg gggagcgggc cgcccttcc gagaggctct tcgccaacct gtggggagg   1260 cttgaggggg aggagaggct cctttggctt taccgggagg tggagaggcc cctttccgtt   1320
gtcctggccc acatggaggc cacaggggtg cgcctggacg tggcctatct cagggccttg   1380
tccctggagg tggccgagga gatcgcccgc ctcgaggccg aggtcttccg cctggccggc   1440
caccccttca acctcaactc ccgggaccag ctggaaaggg tcctctttga cgagctaggg   1500
cttcccgcca tcggcaagac ggagaagacc ggcaagcgct ccaccggcgc cgccgtcctg   1560
gaggccctcc gcgaggccca ccccatcgtg gagaagatcc tgcagtaccg ggagctcacc   1620
aagctgaaga gcacctacat tgacccccttg ccggacctca tccacccag gacgggccgc   1680 ctccacaccc gcttcaacca gacggccacg gccacgggca ggctaagtag ctccgatccc   1740
aacctccaga acatcccgt ccgcacccag cttgggcaga ggatccgccg ggccttcatc   1800
gccgaggagg ggtggctatt ggtggtcctg gactatagcc agatagagct cagggtgctg   1860
gcccacctct ccggcgacga gaacctgatc cgggtcttcc aggaggggcg ggacatccac   1920
acggaaaccg ccagctggat gttcggcgtc ccccaggagg ccgtggaccc cctgatgcgc   1980
cgggcggcca agaccatcaa cttcggggtt ctctacggca tgtcggccta ccgcctctcc   2040
caggagctag ccatccctta cgaggaggcc caggccttca ttgagcgcta ctttcagagc   2100
ttccccaagg tgcgggcctg gattgggaag accctggagg agggcaggag gcggggtac   2160 gtggagaccc tcttcggccg ccgccgctac gtgccagacc tagaggcccg ggtgaagagc   2220
gtgcgggagg cggccgagcg catggccttc aacacgcccg tccagggcac cgccgccgac   2280
ctcatgaagc tggctatggt gaagctcttc cccaggctgg aggaaatggg ggccaggatg   2340
ctccttcagg tccacgacga gctagtcctc gaggccccaa aagagagggc ggaggccgtg   2400
gcccggctgg ccaaggaggt catggagggg gtgtatcccc tggccgtgcc cctggaggtg   2460
gaggtgggga taggggagga ctggctctcc gccaaggagt ga                     2502
```

<210> SEQ ID NO 60
<211> LENGTH: 833
<212> TYPE: PRT
<213> ORGANISM: Artificial sequence
<220> FEATURE:
<223> OTHER INFORMATION: Mutant Taq polymerase

<400> SEQUENCE: 60

```
Met Arg Gly Met His Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Arg Ala Val His Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Leu Lys Pro Ala Ile Arg Glu Lys Ile Leu Ala His Met Asp Asp Leu
225                 230                 235                 240

Lys Leu Ser Trp Asp Leu Ala Lys Val Arg Thr Asp Leu Pro Leu Glu
                245                 250                 255

Val Asp Phe Ala Lys Arg Arg Glu Pro Asp Arg Glu Arg Leu Arg Ala
            260                 265                 270

Phe Leu Glu Arg Leu Glu Leu Gly Ser Leu Leu His Glu Phe Gly Leu
        275                 280                 285

Leu Glu Ser Pro Lys Thr Leu Glu Glu Ala Ser Trp Pro Pro Pro Glu
    290                 295                 300

Gly Ala Phe Val Gly Phe Val Leu Ser Arg Lys Glu Pro Met Trp Ala
305                 310                 315                 320

Asp Leu Leu Ala Leu Ala Ala Ala Arg Gly Gly Arg Val His Arg Ala
                325                 330                 335

Pro Glu Pro Tyr Lys Ala Leu Arg Asp Leu Lys Glu Ala Arg Gly Leu
            340                 345                 350

Leu Ala Lys Asp Leu Ser Val Leu Ala Leu Arg Glu Gly Leu Gly Leu
        355                 360                 365

Pro Pro Gly Asp Asp Pro Met Leu Leu Ala Tyr Leu Leu Asp Pro Ser
```

```
              370                 375                 380
Asn Thr Thr Pro Glu Gly Val Ala Arg Arg Tyr Gly Gly Glu Trp Thr
385                 390                 395                 400
Glu Glu Ala Gly Glu Arg Ala Ala Leu Ser Glu Arg Leu Phe Ala Asn
                405                 410                 415
Leu Trp Gly Arg Leu Glu Gly Glu Arg Leu Leu Trp Leu Tyr Arg
        420                 425                 430
Glu Val Glu Arg Pro Leu Ser Val Leu Ala His Met Glu Ala Thr
            435                 440                 445
Gly Val Arg Leu Asp Val Ala Tyr Leu Arg Ala Leu Ser Leu Glu Val
        450                 455                 460
Ala Glu Glu Ile Ala Arg Leu Glu Ala Glu Val Phe Arg Leu Ala Gly
465                 470                 475                 480
His Pro Phe Asn Leu Asn Ser Arg Asp Gln Leu Glu Arg Val Leu Phe
                485                 490                 495
Asp Glu Leu Gly Leu Pro Ala Ile Gly Lys Thr Glu Lys Thr Gly Lys
            500                 505                 510
Arg Ser Thr Gly Ala Ala Val Leu Glu Ala Leu Arg Glu Ala His Pro
        515                 520                 525
Ile Val Glu Lys Ile Leu Gln Tyr Arg Glu Leu Thr Lys Leu Lys Ser
        530                 535                 540
Thr Tyr Ile Asp Pro Leu Pro Asp Leu Ile His Pro Arg Thr Gly Arg
545                 550                 555                 560
Leu His Thr Arg Phe Asn Gln Thr Ala Thr Ala Thr Gly Arg Leu Ser
                565                 570                 575
Ser Ser Asp Pro Asn Leu Gln Asn Ile Pro Val Arg Thr Gln Leu Gly
            580                 585                 590
Gln Arg Ile Arg Arg Ala Phe Ile Ala Glu Glu Gly Trp Leu Leu Val
        595                 600                 605
Val Leu Asp Tyr Ser Gln Ile Glu Leu Arg Val Leu Ala His Leu Ser
        610                 615                 620
Gly Asp Glu Asn Leu Ile Arg Val Phe Gln Glu Gly Arg Asp Ile His
625                 630                 635                 640
Thr Glu Thr Ala Ser Trp Met Phe Gly Val Pro Gln Glu Ala Val Asp
                645                 650                 655
Pro Leu Met Arg Arg Ala Ala Lys Thr Ile Asn Phe Gly Val Leu Tyr
            660                 665                 670
Gly Met Ser Ala Tyr Arg Leu Ser Gln Glu Leu Ala Ile Pro Tyr Glu
        675                 680                 685
Glu Ala Gln Ala Phe Ile Glu Arg Tyr Phe Gln Ser Phe Pro Lys Val
        690                 695                 700
Arg Ala Trp Ile Gly Lys Thr Leu Glu Glu Gly Arg Arg Arg Gly Tyr
705                 710                 715                 720
Val Glu Thr Leu Phe Gly Arg Arg Arg Tyr Val Pro Asp Leu Glu Ala
                725                 730                 735
Arg Val Lys Ser Val Arg Glu Ala Ala Glu Arg Met Ala Phe Asn Thr
            740                 745                 750
Pro Val Gln Gly Thr Ala Ala Asp Leu Met Lys Leu Ala Met Val Lys
        755                 760                 765
Leu Phe Pro Arg Leu Glu Glu Met Gly Ala Arg Met Leu Leu Gln Val
        770                 775                 780
His Asp Glu Leu Val Leu Glu Ala Pro Lys Glu Arg Ala Glu Ala Val
785                 790                 795                 800
```

```
Ala Arg Leu Ala Lys Glu Val Met Glu Gly Val Tyr Pro Leu Ala Val
                805                 810                 815

Pro Leu Glu Val Glu Val Gly Ile Gly Glu Asp Trp Leu Ser Ala Lys
            820                 825                 830

Glu

<210> SEQ ID NO 61
<211> LENGTH: 2502
<212> TYPE: DNA
<213> ORGANISM: Artificial sequence
<220> FEATURE:
<223> OTHER INFORMATION: Mutant Taq polymerase coding sequence

<400> SEQUENCE: 61
```

| | | | | | |
|---|---|---|---|---|---|
| atgcgtggta | tgcttcctct | ttttgagccc | aagggccgcg | tcctcctggt | ggacggccac | 60 |
| cacctggcct | accgcacctt | cttcgccctg | aagggcctca | ccacgagccg | ggcgaaccg | 120 |
| gtgcaggcgg | tctacggctt | cgccaagagc | ctcctcaagg | ccctgaagga | ggacgggtac | 180 |
| aaggccgtct | tcgtggtctt | tgacgccaag | gccccctccc | tccgccacga | ggcctacgag | 240 |
| gcctacaagg | cggggagggc | cccgacccc | gaggacttcc | ccggcagct | cgccctcatc | 300 |
| aaggagctgg | tggacctcct | ggggtttacc | cgcctcgagg | tccccggcta | cgaggcggac | 360 |
| gacgttctcg | ccaccctggc | caagaaggcg | aaaaggagg | gtacgaggt | gcgcatcctc | 420 |
| accgccgacc | gcgacctcta | ccaactcgtc | tccgaccgcg | tcgccgtcct | ccaccccgag | 480 |
| ggccacctca | tcaccccgga | gtggctttgg | gagaagtacg | gcctcaggcc | ggagcagtgg | 540 |
| gtggacttcc | gcgccctcgt | gggggacccc | tccgacaacc | tccccgggt | caagggcatc | 600 |
| ggggagaaga | ccgccctcaa | gctcctcaag | gagtggggaa | gctggaaaa | cctcctcaag | 660 |
| aacctggacc | ggctgaagcc | cgccatccgg | gagaagatcc | tggcccacat | ggacgatctg | 720 |
| aagctctcct | gggacctggc | caaggtgcgc | accgacctgc | cctggaggt | ggacttcgcc | 780 |
| aaaaggcggg | agcccgaccg | ggagaggctt | agggcctttc | tggagaggct | tgagcttggc | 840 |
| agcctcctcc | acgagttcgg | ccttctggaa | agccccaagg | ccctggagga | ggcctcctgg | 900 |
| ccccgccgg | aagggccctt | cgtgggcttt | gtgcttaccc | gcaaggagcc | catgtgggcc | 960 |
| gatcttctgg | ccctggccgc | cgccaggggg | ggccgggtcc | accgggcccc | cgagccttat | 1020 |
| aaagccctca | gggacctgaa | ggaggcgcgg | gggcttctcg | ccaaagacct | gagcgttctg | 1080 |
| gccctgaggg | aaggccttgg | cctcccgccc | ggcgacgacc | ccatgctcct | cgcctacctc | 1140 |
| ctggaccctt | ccaacaccac | ccccgagggg | gtggcccggc | gctacggcgg | ggagtggacg | 1200 |
| gaggaggcgg | gggagcgggc | cgccctttcc | gagaggctct | tcgccaacct | gtggggagg | 1260 |
| cttgaggggg | aggagaggct | cctttggctt | accggagg | tggagagacc | ctttccgct | 1320 |
| gtcctggccc | acatggaggc | cacggggtg | cgcctggacg | tggcctatct | cagggccttg | 1380 |
| tccctggagg | tggccgagga | gatcgcccgc | ctcgaggccg | aggtcttccg | cctgccggc | 1440 |
| caccccttca | acctcaactc | ccgagaccag | ctggaaaggg | tcctctttga | cgagctaggg | 1500 |
| cttcccgcca | tcggcaagac | ggagaagacc | ggcaagcgct | ccaccagcgc | cgccgtcctg | 1560 |
| gaggccctcc | gcgaggccca | ccccatcgtg | gagaagatcc | tgcagtaccg | ggagctcacc | 1620 |
| aagctgaaga | gcacctacat | tgacccttg | ccggacctca | tccaccccag | gacgggccgc | 1680 |
| ctccacaccc | gcttcaacca | gacggccacg | gccacgggca | ggctaagtag | ctccgatccc | 1740 |
| aacctccaga | acatccccgt | ccgcacccg | cttgggcaga | ggatccgccg | ggccttcatc | 1800 |

-continued

```
gccgaggagg ggtggctatt ggtggccctg gactatagcc agatagagct cagggtgctg    1860
gcccacctct ccggcgacga gaacctgatc cgggtcttcc aggaggggcg ggacatccac    1920
acggagaccg ccagctggat gttcggcgtc ccccgggagg ccgtggaccc cctgatgcgc    1980
cgggcggcca agaccatcaa cttcggggtc ctctacggca tgtcggccca ccgcctctcc    2040
caggagctag ccatcccta cgaggaggcc caggccttca ttgagcgcta ctttcagagc    2100
ttccccaagg tgcgggcctg gattgagaag accctggagg agggcaggag gcggggggtac    2160 gtggagaccc tcttcggccg ccgccgctac gtgccagacc tagaggcccg ggtgaagagc    2220
gtgcgggagg cggccgagcg catggccttc aacatgcccg tccagggcac cgccgccgac    2280
cttatgaagc tcgccatggt gaagctcttc ccccgcctcc gggagatggg ggcccgcatg    2340
ctcctccagg tccacgacga gctcctcctg gaggcccccc aagcgcgggc cgaggaggtg    2400
gcggctttgg ccaaggaggc catggagaag gcctatcccc tcgccgtacc cctggaggtg    2460
aaggtgggga tcggggagga ctggctctcc gccaaggagt ga                       2502
```

<210> SEQ ID NO 62
<211> LENGTH: 833
<212> TYPE: PRT
<213> ORGANISM: Artificial sequence
<220> FEATURE:
<223> OTHER INFORMATION: Mutant Taq polymerase

<400> SEQUENCE: 62

```
Met Arg Gly Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Leu Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Leu Lys Pro Ala Ile Arg Glu Lys Ile Leu Ala His Met Asp Asp Leu
225                 230                 235                 240
```

```
Lys Leu Ser Trp Asp Leu Ala Lys Val Arg Thr Asp Leu Pro Leu Glu
                245                 250                 255

Val Asp Phe Ala Lys Arg Arg Glu Pro Asp Arg Glu Arg Leu Arg Ala
            260                 265                 270

Phe Leu Glu Arg Leu Glu Leu Gly Ser Leu Leu His Glu Phe Gly Leu
        275                 280                 285

Leu Glu Ser Pro Lys Ala Leu Glu Glu Ala Ser Trp Pro Pro Pro Glu
    290                 295                 300

Gly Ala Phe Val Gly Phe Val Leu Thr Arg Lys Glu Pro Met Trp Ala
305                 310                 315                 320

Asp Leu Leu Ala Leu Ala Ala Arg Gly Gly Arg Val His Arg Ala
                325                 330                 335

Pro Glu Pro Tyr Lys Ala Leu Arg Asp Leu Lys Glu Ala Arg Gly Leu
                340                 345                 350

Leu Ala Lys Asp Leu Ser Val Leu Ala Leu Arg Glu Gly Leu Gly Leu
            355                 360                 365

Pro Pro Gly Asp Asp Pro Met Leu Leu Ala Tyr Leu Leu Asp Pro Ser
        370                 375                 380

Asn Thr Thr Pro Glu Gly Val Ala Arg Arg Tyr Gly Gly Glu Trp Thr
385                 390                 395                 400

Glu Glu Ala Gly Glu Arg Ala Ala Leu Ser Glu Arg Leu Phe Ala Asn
                405                 410                 415

Leu Trp Gly Arg Leu Glu Gly Glu Arg Leu Leu Trp Leu Tyr Arg
                420                 425                 430

Glu Val Glu Arg Pro Leu Ser Ala Val Leu Ala His Met Glu Ala Thr
            435                 440                 445

Gly Val Arg Leu Asp Val Ala Tyr Leu Arg Ala Leu Ser Leu Glu Val
        450                 455                 460

Ala Glu Glu Ile Ala Arg Leu Glu Ala Glu Val Phe Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
            500                 505                 510

Arg Ser Thr Ser Ala Ala Val Leu Glu Ala Leu Arg Glu Ala His Pro
        515                 520                 525

Ile Val Glu Lys Ile Leu Gln Tyr Arg Glu Leu Thr Lys Leu Lys Ser
    530                 535                 540

Thr Tyr Ile Asp Pro Leu Pro Asp Leu Ile His Pro Arg Thr Gly Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590

Gln Arg Ile Arg Arg Ala Phe Ile Ala Glu Gly Trp Leu Leu Val
        595                 600                 605

Ala Leu Asp Tyr Ser Gln Ile Glu Leu Arg Val Leu Ala His Leu Ser
    610                 615                 620

Gly Asp Glu Asn Leu Ile Arg Val Phe Gln Glu Gly Arg Asp Ile His
625                 630                 635                 640

Thr Glu Thr Ala Ser Trp Met Phe Gly Val Pro Arg Glu Ala Val Asp
                645                 650                 655

Pro Leu Met Arg Arg Ala Ala Lys Thr Ile Asn Phe Gly Val Leu Tyr
```

```
                660               665              670
Gly Met Ser Ala His Arg Leu Ser Gln Glu Leu Ala Ile Pro Tyr Glu
                675               680              685

Glu Ala Gln Ala Phe Ile Glu Arg Tyr Phe Gln Ser Phe Pro Lys Val
            690               695              700

Arg Ala Trp Ile Glu Lys Thr Leu Glu Glu Gly Arg Arg Arg Gly Tyr
705              710              715                  720

Val Glu Thr Leu Phe Gly Arg Arg Tyr Val Pro Asp Leu Glu Ala
                    725              730              735

Arg Val Lys Ser Val Arg Glu Ala Ala Glu Arg Met Ala Phe Asn Met
                740              745              750

Pro Val Gln Gly Thr Ala Ala Asp Leu Met Lys Leu Ala Met Val Lys
                755              760              765

Leu Phe Pro Arg Leu Arg Glu Met Gly Ala Arg Met Leu Leu Gln Val
                770              775              780

His Asp Glu Leu Leu Leu Glu Ala Pro Gln Ala Arg Ala Glu Glu Val
785              790              795              800

Ala Ala Leu Ala Lys Glu Ala Met Glu Lys Ala Tyr Pro Leu Ala Val
                805              810              815

Pro Leu Glu Val Lys Val Gly Ile Gly Glu Asp Trp Leu Ser Ala Lys
                820              825              830

Glu

<210> SEQ ID NO 63
<211> LENGTH: 2502
<212> TYPE: DNA
<213> ORGANISM: Artificial sequence
<220> FEATURE:
<223> OTHER INFORMATION: Mutant Taq polymerase coding sequence

<400> SEQUENCE: 63
atggcgatgc ttcccctctt tgagcccaag ggccgcgtcc tcctggtgga cggccaccac      60
ctggcctacc gcaccttctt cgccctgaag ggccccacca cgagccgggg cgaaccggtg     120
caggtggtct acggcttcgc caagagcctc ctcaaggccc tgaaggagga cgggtacaag     180
gccgtcttcg tggtctttga cgccaaggcc cctcattcc gccacaaggc ctacgaggcc      240
tacagggcgg ggagggcccc gaccccgag gacttccccc ggcagctcgc cctcatcaag     300
gagctggtgg acctcctggg gtttaccgc ctcgaggtcc ccggctacga ggcggacgac     360
gttctcgcca ccctggccaa gaaggcggaa aaggaggggt acgaggtgcg catcctcacc     420
gccgaccgcg gcctatacca actcgtctat gaccgcgtcg ccgtcctcca ccccgagggc     480
cacctcatca cccccggagtg gctttgggag aagtacggcc tcaggccgga gcagtgggtg     540
gacttccgcg ccctcgtggg ggaccctcc gacaacctcc ccggggtcaa gggcatcggg     600
gagaagaccg ccctcaagct cctcaaggag tggggaagcc tggaaaacct cctcaagaac     660
ctggaccggg taaagccaga aaacgtccgg gagaagatca ggcccacct ggaagacctc     720 aggctctcct ggagctctc ccgggtgcgc accgacctcc cctggaggt ggacctcgcc     780 caggggcggg agcccgaccg ggaggggctt agggcctttc tggagaggct tgagtttggc     840
agcctcctcc acgagttcgg ccttctggaa agccccaagg cctggagga ggccccctgg     900 ccccccgccgg aagggggcctt cgtgggcttt gtgcttttcc gcaaggagcc catgtgggcc     960
gatcttctgg ccctggccgc cgccaggggt ggtcgagtcc accgggcccc cgagccttat    1020
aaagccctca gggacctgaa ggaggcgcgg gggcttctcg ccaaagacct gagcgttctg    1080
```

-continued

```
gccctaaggg aaggccttgg cctcccgccc ggcgacgacc ccatgctcct cgcctacctc    1140
ctggacccTT ccaacaccac ccccgagggg gtggcccggc gctacggcgg ggagtggacg    1200
gaggaggcgg gggagcgggc cgccctttcc gagaggctct tcgccaacct gtgggggagg    1260
cttgaggggg aggagaggct cctttggctt taccggGagg tggagaggcc cctttccgct    1320
gtcctggccc acatggaggc cacggggGtg cgcctggacg tggcctatct cagggccttg    1380
tccctggagg tggccgagga gatcgcccgc ctcgaggccg aggtcttccg cctgccggc    1440
caccccttca acctcaactc ccgggaccag ctggaaatgg tgctctttga cgagcttagg    1500
cttcccgcct tggggaagac gcaaaagacg ggcaagcgct ccaccagcgc cgccgtcctg    1560
gaggccctcc gcgaggccca cccatcgtg gagaagatcc tgcagtaccg ggagctcacc    1620
aagctgaaga gcacctacat tgaccccttg tcggacctca tccacccag gacgggccgc    1680
ctccacaccc gcttcaacca gacggccacg gccacgggca ggctaagtag ctccgatccc    1740
aacctccaga acatccccgt ccgcaccccg cttgggcaga ggatccgccg ggcctttcatc    1800
gccgaggagg ggtggctact ggtggtcctg gactatagcc agatagagct caggGtgctg    1860
gcccacctct ccggcgacga aaacctgatc agggtcttcc aggaggggcg ggacatccac    1920
acggagaccg ccagctggat gttcggcgtc ccccgggagg ccgtggaccc cctgatgcgc    1980
cgggcggcca agaccatcaa cttcggggtc ctctacggca tgtcggccca ccgcctctcc    2040
caggagctag ccatcccTta cgaggaggcc caggccttca ttgagcgcta ctttcagagc    2100
ttccccaagg tgcgggcctg gattgagaag accctggagg agggcaggag gcgggggtac    2160
gtggagaccc tcttcggccg ccgccgctac gtgccagacc tagaggcccg ggtgaagagc    2220
gtgcgggagc cggccgagcg catggccttc aacatgcccg tccagggcac cgccgccgac    2280
ctcatgaagc tggctatggt gaagctcttc ccccagctgg aggaaaTggg ggccaggatg    2340
ctccTtcagg tccacgacga gctggtcctc gaggccccaa aagagagggc ggaggccgtg    2400
gcccggctgg ccaaggaggt catggagggg gtgtatcccc tggccgtgcc cctggaggtg    2460
gaggtgggga taggggagga ctggctctcc gccaaggagt ga                      2502
```

<210> SEQ ID NO 64
<211> LENGTH: 833
<212> TYPE: PRT
<213> ORGANISM: Artificial sequence
<220> FEATURE:
<223> OTHER INFORMATION: Mutant Taq polymerase

<400> SEQUENCE: 64

```
Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Pro
            20                  25                  30

Thr Thr Ser Arg Gly Glu Pro Val Gln Val Val Tyr Gly Phe Ala Lys
        35                  40                  45

Ser Leu Leu Lys Ala Leu Lys Glu Asp Gly Tyr Lys Ala Val Phe Val
    50                  55                  60

Val Phe Asp Ala Lys Ala Pro Ser Phe Arg His Lys Ala Tyr Glu Ala
65                  70                  75                  80

Tyr Arg Ala Gly Arg Ala Pro Thr Pro Glu Asp Phe Pro Arg Gln Leu
                85                  90                  95

Ala Leu Ile Lys Glu Leu Val Asp Leu Leu Gly Phe Thr Arg Leu Glu
            100                 105                 110
```

```
Val Pro Gly Tyr Glu Ala Asp Val Leu Ala Thr Leu Ala Lys Lys
            115                 120                 125

Ala Glu Lys Glu Gly Tyr Glu Val Arg Ile Leu Thr Ala Asp Arg Gly
        130                 135                 140

Leu Tyr Gln Leu Val Tyr Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asp Asn
            180                 185                 190

Leu Pro Gly Val Lys Gly Ile Gly Glu Lys Thr Ala Leu Lys Leu Leu
        195                 200                 205

Lys Glu Trp Gly Ser Leu Glu Asn Leu Leu Lys Asn Leu Asp Arg Val
210                 215                 220

Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
                245                 250                 255

Val Asp Leu Ala Gln Gly Arg Glu Pro Asp Arg Glu Gly Leu Arg Ala
            260                 265                 270

Phe Leu Glu Arg Leu Glu Phe Gly Ser Leu Leu His Glu Phe Gly Leu
        275                 280                 285

Leu Glu Ser Pro Lys Ala Leu Glu Glu Ala Pro Trp Pro Pro Pro Glu
290                 295                 300

Gly Ala Phe Val Gly Phe Val Leu Ser Arg Lys Glu Pro Met Trp Ala
305                 310                 315                 320

Asp Leu Leu Ala Leu Ala Ala Arg Gly Gly Arg Val His Arg Ala
                325                 330                 335

Pro Glu Pro Tyr Lys Ala Leu Arg Asp Leu Lys Glu Ala Arg Gly Leu
            340                 345                 350

Leu Ala Lys Asp Leu Ser Val Leu Ala Leu Arg Glu Gly Leu Gly Leu
        355                 360                 365

Pro Pro Gly Asp Asp Pro Met Leu Leu Ala Tyr Leu Leu Asp Pro Ser
370                 375                 380

Asn Thr Thr Pro Glu Gly Val Ala Arg Arg Tyr Gly Gly Glu Trp Thr
385                 390                 395                 400

Glu Glu Ala Gly Glu Arg Ala Ala Leu Ser Glu Arg Leu Phe Ala Asn
                405                 410                 415

Leu Trp Gly Arg Leu Glu Gly Glu Glu Arg Leu Leu Trp Leu Tyr Arg
            420                 425                 430

Glu Val Glu Arg Pro Leu Ser Ala Val Leu Ala His Met Glu Ala Thr
        435                 440                 445

Gly Val Arg Leu Asp Val Ala Tyr Leu Arg Ala Leu Ser Leu Glu Val
450                 455                 460

Ala Glu Glu Ile Ala Arg Leu Glu Ala Glu Val Phe Arg Leu Ala Gly
465                 470                 475                 480

His Pro Phe Asn Leu Asn Ser Arg Asp Gln Leu Glu Met Val Leu Phe
                485                 490                 495

Asp Glu Leu Arg Leu Pro Ala Leu Gly Lys Thr Gln Lys Thr Gly Lys
            500                 505                 510

Arg Ser Thr Ser Ala Ala Val Leu Glu Ala Leu Arg Glu Ala His Pro
        515                 520                 525
```

```
Ile Val Glu Lys Ile Leu Gln Tyr Arg Glu Leu Thr Lys Leu Lys Ser
    530                 535                 540
Thr Tyr Ile Asp Pro Leu Ser Asp Leu Ile His Pro Arg Thr Gly Arg
545                 550                 555                 560
Leu His Thr Arg Phe Asn Gln Thr Ala Thr Ala Thr Gly Arg Leu Ser
                565                 570                 575
Ser Ser Asp Pro Asn Leu Gln Asn Ile Pro Val Arg Thr Pro Leu Gly
            580                 585                 590
Gln Arg Ile Arg Arg Ala Phe Ile Ala Glu Gly Trp Leu Leu Val
        595                 600                 605
Val Leu Asp Tyr Ser Gln Ile Glu Leu Arg Val Leu Ala His Leu Ser
    610                 615                 620
Gly Asp Glu Asn Leu Ile Arg Val Phe Gln Glu Gly Arg Asp Ile His
625                 630                 635                 640
Thr Glu Thr Ala Ser Trp Met Phe Gly Val Pro Arg Glu Ala Val Asp
                645                 650                 655
Pro Leu Met Arg Arg Ala Ala Lys Thr Ile Asn Phe Gly Val Leu Tyr
            660                 665                 670
Gly Met Ser Ala His Arg Leu Ser Gln Glu Leu Ala Ile Pro Tyr Glu
        675                 680                 685
Glu Ala Gln Ala Phe Ile Glu Arg Tyr Phe Gln Ser Phe Pro Lys Val
    690                 695                 700
Arg Ala Trp Ile Glu Lys Thr Leu Glu Glu Gly Arg Arg Arg Gly Tyr
705                 710                 715                 720
Val Glu Thr Leu Phe Gly Arg Arg Tyr Val Pro Asp Leu Glu Ala
                725                 730                 735
Arg Val Lys Ser Val Arg Glu Ala Ala Glu Arg Met Ala Phe Asn Met
            740                 745                 750
Pro Val Gln Gly Thr Ala Ala Asp Leu Met Lys Leu Ala Met Val Lys
        755                 760                 765
Leu Phe Pro Arg Leu Glu Glu Met Gly Ala Arg Met Leu Leu Gln Val
    770                 775                 780
His Asp Glu Leu Val Leu Glu Ala Pro Lys Glu Arg Ala Glu Ala Val
785                 790                 795                 800
Ala Arg Leu Ala Lys Glu Val Met Glu Gly Val Tyr Pro Leu Ala Val
                805                 810                 815
Pro Leu Glu Val Glu Val Gly Ile Gly Glu Asp Trp Leu Ser Ala Lys
            820                 825                 830
Glu
```

<210> SEQ ID NO 65
<211> LENGTH: 2502
<212> TYPE: DNA
<213> ORGANISM: Artificial sequence
<220> FEATURE:
<223> OTHER INFORMATION: Mutant Taq polymerase coding sequence

<400> SEQUENCE: 65

| | | | | | |
|---|---|---|---|---|---|
| atggcgatgc | ttcccctctt | tgagcccaag | ggccgcgtcc | tcctggtgga | cggccaccac | 60 |
| ctggcctacc | gcaccttctt | cgccctgaag | ggccccacca | cgagccgggg | cgaaccggtg | 120 |
| caggtggtct | acggcttcgc | caagagcctc | ctcaaggccc | tgaaggagga | cgggtacaag | 180 |
| gccgtcttcg | tggtctttga | cgccaaggcc | ccctcattcc | gccacaaggc | ctacgaggcc | 240 |
| tacagggcgg | ggagggcccc | gaccccgag | gacttccccc | ggcagctcgc | cctcatcaag | 300 |

```
gagctggtgg acctcctggg gtttacccgc ctcgaggtcc ccggctacga ggcggacgac    360
gttctcgcca ccttcgccaa gaaggcggaa aaggaggggt acgaggtgcg catcctcacc    420
gccgaccgcg gcctctacca actcgtctct gaccgcgtcg ccgtcctcca ccccgagggc    480
cacctcatca ccccggagtg gctttgggag aagtacggcc tcaggccgga gcagtgggtg    540
gacttccgcg ccctcgtggg gaaccccctcc gacaacctcc ccggggtcaa gggcatcggg    600
gagaagaccg ccctcaagct cctcaaggag tggggaagcc tggaaaacct cctcaagaac    660
ctggaccggg taaagccaga aaacgtccgg gagaagatca aggcccacct ggaagacctc    720
aggctctcct tggagctctc ccgggtgcgc accgacctcc ccctggaggt ggacctcgcc    780
caggggcggg agcccgaccg ggaggggctt agggcctttc tggagaggct tgagtttggc    840
agcctcctcc acgagttcgg ccttctggaa agccccaagg ccctggagga ggcccccctgg    900
ccccccgccgg aaggggcctt cgtgggcttt gtgctttccc gcaaggagcc catgtgggcc    960
gatcttctgg ccctggccgc cgccaggggt ggtcgagtcc accgggcccc cgagccttat   1020
aaagccctca gggacctgaa ggaggcgcgg gggcttctcg ccaaagacct gagcgttctg   1080
gccctaaggg aaggccttgg cctcccgccc ggcgacgacc ccatgctcct cgcctacctc   1140
ctggacccctt ccaacaccac ccccgagggg gtggcccggc gctacggcgg ggagtggacg   1200
gaggaggcgg gggagcgggc cgcccttttcc gagaggctct cgccaacct gtggggggagg   1260
cttgaggggg aggagaggct ccctttggctt taccgggagg tggagaggcc cctttccgct   1320
gtcctggccc acatggaggc cacggggggtg cgcctggacg tggcctatct cagggccttg   1380
tccctggagg tggccgagga gatcgcccgc ctcgaggccg aggtcttccg cctggccggc   1440
caccccttca acctcaactc ccgggaccag ctggaaaggg tcctctttga cgagctaggg   1500
cttcccgcca tcggcaagac ggagaagacc ggcaagcgct ccaccagcgc cgccgtcctg   1560
gaggccctcc gcgaggccca ccccatcgtg gagaagatcc tgcagtaccg ggagctcacc   1620
aagctgaaga gcacctacat tgacccctttg ccggacctca tccaccccag gacgggccgc   1680
ctccacaccc gcttcaacca gacggccacg gccacgggca ggctaagtag ctccgatccc   1740
aacctccaga acatccccgt ccgcacccccg ctcgggcaga ggatccgccg ggccttcatc   1800
gccgaggagg ggtggctatt ggtggtcctg gactatagcc agatagagct cagggtgctg   1860
gcccacctct ccggcgacga gaacctgatc cgggtcttcc aggagggggg ggacatccac   1920
acggaaaccg ccagctggat gttcggcgtc ccccgggagg ccgtggaccc cctaatgcgc   1980
cgggcggcca gaccatcaa cttcgggggtc ctctacggca tgtcggcccg ccgcctctcc   2040
caggagctag ccatccctta cgaggaggcc caggccttca ttgagcgcta ctttcagagc   2100
ttccccaagg tgcgggcctg gattgagaag accctggagg agggcaggag gcgggggtac   2160
gtggagaccc tcttcggccg ccgccgctac gtgccagacc tagaggcccg ggtgaagagc   2220
gtgcgggagg cggccgagcg catggccttc aacatgcccg tccagggcac cgccgccgac   2280
ctcatgaagc tggctatggt gaagctcttc ccaggctgg aggaaatggg ggccaggatg   2340
ctccttcagg tccacgacga gctggtcctc gaggccccaa aagagagggc ggaggccgtg   2400
gcccggctgg ccaaggaggt catggagggg gtgtatcccc tggccgtgcc cctggaggtg   2460
gaggtgggga taggggagga ctggcttttcc gccaagggtt ag                    2502
```

<210> SEQ ID NO 66
<211> LENGTH: 833
<212> TYPE: PRT
<213> ORGANISM: Artificial sequence
<220> FEATURE:
<223> OTHER INFORMATION: Mutant Taq polymerase

<400> SEQUENCE: 66

```
Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Pro
            20                  25                  30

Thr Thr Ser Arg Gly Glu Pro Val Gln Val Val Tyr Gly Phe Ala Lys
        35                  40                  45

Ser Leu Leu Lys Ala Leu Lys Glu Asp Gly Tyr Lys Ala Val Phe Val
    50                  55                  60

Val Phe Asp Ala Lys Ala Pro Ser Phe Arg His Lys Ala Tyr Glu Ala
65                  70                  75                  80

Tyr Arg Ala Gly Arg Ala Pro Thr Pro Glu Asp Phe Pro Arg Gln Leu
                85                  90                  95

Ala Leu Ile Lys Glu Leu Val Asp Leu Leu Gly Phe Thr Arg Leu Glu
            100                 105                 110

Val Pro Gly Tyr Glu Ala Asp Asp Val Leu Ala Thr Phe Ala Lys Lys
        115                 120                 125

Ala Glu Lys Glu Gly Tyr Glu Val Arg Ile Leu Thr Ala Asp Arg Gly
    130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asn Pro Ser Asp Asn
            180                 185                 190

Leu Pro Gly Val Lys Gly Ile Gly Glu Lys Thr Ala Leu Lys Leu Leu
        195                 200                 205

Lys Glu Trp Gly Ser Leu Glu Asn Leu Leu Lys Asn Leu Asp Arg Val
    210                 215                 220

Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
                245                 250                 255

Val Asp Leu Ala Gln Gly Arg Glu Pro Asp Arg Glu Gly Leu Arg Ala
            260                 265                 270

Phe Leu Glu Arg Leu Glu Phe Gly Ser Leu Leu His Glu Phe Gly Leu
        275                 280                 285

Leu Glu Ser Pro Lys Ala Leu Glu Glu Ala Pro Trp Pro Pro Pro Glu
    290                 295                 300

Gly Ala Phe Val Gly Phe Val Leu Ser Arg Lys Glu Pro Met Trp Ala
305                 310                 315                 320

Asp Leu Leu Ala Leu Ala Ala Ala Arg Gly Gly Arg Val His Arg Ala
                325                 330                 335

Pro Glu Pro Tyr Lys Ala Leu Arg Asp Leu Lys Glu Ala Arg Gly Leu
            340                 345                 350

Leu Ala Lys Asp Leu Ser Val Leu Ala Leu Arg Glu Gly Leu Gly Leu
        355                 360                 365

Pro Pro Gly Asp Asp Pro Met Leu Leu Ala Tyr Leu Leu Asp Pro Ser
    370                 375                 380

Asn Thr Thr Pro Glu Gly Val Ala Arg Arg Tyr Gly Gly Glu Trp Thr
385                 390                 395                 400
```

-continued

```
Glu Glu Ala Gly Glu Arg Ala Ala Leu Ser Glu Arg Leu Phe Ala Asn
            405                 410                 415
Leu Trp Gly Arg Leu Glu Gly Glu Glu Arg Leu Leu Trp Leu Tyr Arg
            420                 425                 430
Glu Val Glu Arg Pro Leu Ser Ala Val Leu Ala His Met Glu Ala Thr
            435                 440                 445
Gly Val Arg Leu Asp Val Ala Tyr Leu Arg Ala Leu Ser Leu Glu Val
            450                 455                 460
Ala Glu Glu Ile Ala Arg Leu Glu Ala Glu Val Phe Arg Leu Ala Gly
465                 470                 475                 480
His Pro Phe Asn Leu Asn Ser Arg Asp Gln Leu Glu Arg Val Leu Phe
            485                 490                 495
Asp Glu Leu Gly Leu Pro Ala Ile Gly Lys Thr Glu Lys Thr Gly Lys
            500                 505                 510
Arg Ser Thr Ser Ala Ala Val Leu Glu Ala Leu Arg Glu Ala His Pro
            515                 520                 525
Ile Val Glu Lys Ile Leu Gln Tyr Arg Glu Leu Thr Lys Leu Lys Ser
            530                 535                 540
Thr Tyr Ile Asp Pro Leu Pro Asp Leu Ile His Pro Arg Thr Gly Arg
545                 550                 555                 560
Leu His Thr Arg Phe Asn Gln Thr Ala Thr Ala Thr Gly Arg Leu Ser
            565                 570                 575
Ser Ser Asp Pro Asn Leu Gln Asn Ile Pro Val Arg Thr Pro Leu Gly
            580                 585                 590
Gln Arg Ile Arg Arg Ala Phe Ile Ala Glu Glu Gly Trp Leu Leu Val
            595                 600                 605
Val Leu Asp Tyr Ser Gln Ile Glu Leu Arg Val Leu Ala His Leu Ser
            610                 615                 620
Gly Asp Glu Asn Leu Ile Arg Val Phe Gln Glu Gly Arg Asp Ile His
625                 630                 635                 640
Thr Glu Thr Ala Ser Trp Met Phe Gly Val Pro Arg Glu Ala Val Asp
            645                 650                 655
Pro Leu Met Arg Arg Ala Ala Lys Thr Ile Asn Phe Gly Val Leu Tyr
            660                 665                 670
Gly Met Ser Ala Arg Arg Leu Ser Gln Glu Leu Ala Ile Pro Tyr Glu
            675                 680                 685
Glu Ala Gln Ala Phe Ile Glu Arg Tyr Phe Gln Ser Phe Pro Lys Val
            690                 695                 700
Arg Ala Trp Ile Glu Lys Thr Leu Glu Glu Gly Arg Arg Arg Gly Tyr
705                 710                 715                 720
Val Glu Thr Leu Phe Gly Arg Arg Arg Tyr Val Pro Asp Leu Glu Ala
            725                 730                 735
Arg Val Lys Ser Val Arg Glu Ala Ala Glu Arg Met Ala Phe Asn Met
            740                 745                 750
Pro Val Gln Gly Thr Ala Ala Asp Leu Met Lys Leu Ala Met Val Lys
            755                 760                 765
Leu Phe Pro Arg Leu Glu Glu Met Gly Ala Arg Met Leu Leu Gln Val
            770                 775                 780
His Asp Glu Leu Val Leu Glu Ala Pro Lys Glu Arg Ala Glu Ala Val
785                 790                 795                 800
Ala Arg Leu Ala Lys Glu Val Met Glu Gly Val Tyr Pro Leu Ala Val
            805                 810                 815
```

Pro Leu Glu Val Glu Val Gly Ile Gly Glu Asp Trp Leu Ser Ala Lys
        820                 825                 830

Gly

<210> SEQ ID NO 67
<211> LENGTH: 2502
<212> TYPE: DNA
<213> ORGANISM: Artificial sequence
<220> FEATURE:
<223> OTHER INFORMATION: Mutant Taq polymerase coding sequence

<400> SEQUENCE: 67

| | | | | |
|---|---|---|---|---|
| atggtgatgc | ttcccctctt | tgagcccaag | ggccgcgtcc | tcctggtgga cggccaccac | 60 |
| ctggcctacc | gcaccttctt | cgccctgaag | ggcctcacca | cgagccgggg cgaaccggtg | 120 |
| caggcggtct | acggcttcgc | caagagcctc | tcaaggccc | tgaaggagga cgggtacaag | 180 |
| gccgtcttcg | tggtctttga | cgccaaggcc | tcctccttcc | gccacgaggc ctacgaggcc | 240 |
| tacaaggcgg | ggagggcccc | gacccccgag | gacttccccc | ggcagctcgc cctcatcaag | 300 |
| gagctggtgg | acctcctggg | gtttaccgc | ctcgaggtcc | ccggctacga ggtggacgac | 360 |
| gtcctggcca | gctggccaa | gaaggtggaa | aaggaggggt | acgaggtgcg catcctcacc | 420 |
| gccgaccgcg | acctctacca | actcgtctcc | gaccgcgtcg | ccgtcctcca ccccgagggc | 480 |
| cacctcatca | ccccggagtg | gctttgggag | aagtacggcc | tcaggccgga gcagtgggtg | 540 |
| gacttccgcg | ccctcgtggg | ggaccctcc | gacaacctcc | ccggggtcaa gggcatcggg | 600 |
| gagaagaccg | ccctcaagct | cctcaaggag | tggggaggcc | tggaaaacct cctcaagaac | 660 |
| ctggaccggg | taaagccaga | aaacgtccgg | gagaagatca | aggcccacct ggaagacctc | 720 |
| aggctctcct | ggagctctc | ccgggtgcgc | accgacctcc | cctggaggt ggacctcgcc | 780 |
| caggggcggg | aacccgaccg | ggagaggctt | agggcctttc | tggagaggct tgagtttggc | 840 |
| agcctcctcc | acgagttcgg | ccttctggaa | agccccaagg | ccctggagga ggcccccgg | 900 |
| cccccgccgg | aagggggcctt | cgtgggcttt | gtgctttccc | gcaaggagcc catgtgggcc | 960 |
| gatcttctgg | ccctggccgc | cgccaggggt | ggtcggtcc | accggacccc cgagccttat | 1020 |
| aaagccctca | gggacttgaa | ggaggcgcgg | gggcttctcg | ccaaagacct gagcgttctg | 1080 |
| gccctaaggg | aaggcttgg | cctcccgccc | ggcgacgacc | ccatgctcct cgcctacctc | 1140 |
| ctggaccctt | ccaacaccac | ccccgagggg | gtggcccggc | gctacggcgg ggagtggacg | 1200 |
| gaggaggcgg | gggagcgggc | cgccctttcc | gagaggctct | cgccaacct gtggggagg | 1260 |
| cttgaggggg | aggagaggct | cctttggctt | taccggagg | tggataggcc cctttccgct | 1320 |
| gtcctggccc | acatggaggc | cacaggggtg | cgcctggacg | tggcctacct cagggccttg | 1380 |
| tccctggagg | tggccgagga | gatcgcccgc | ctcgaggccg | aggtcttccg cctggccggc | 1440 |
| caccccttca | acctcaactc | ccgggaccag | ctggaaaggg | tcctctttga cgagctaggg | 1500 |
| cttcccgcca | tcggcaagac | ggagaagacc | ggcaagcgct | ccaccagcgc cgccgtcctg | 1560 |
| gaggccctcc | gcgaggccca | ccccatcgtg | gagaagatcc | tgcagtaccg ggagctcacc | 1620 |
| aagctgaaga | gcacctacat | tgacccccttg | ccggacctca | tccacccag acgggccgc | 1680 |
| ctccacaccc | gcttcaacca | gacggccacg | gccacgggca | ggctaagtag ctccgatccc | 1740 |
| aacctccaga | acatccccgt | ccgcaccccg | ctcgggcaga | ggatccgccg ggccttcatc | 1800 |
| gccgaggagg | ggtggctatt | ggtggtcctg | gactatagcc | agatagagct cagggtgctg | 1860 |
| gcccacctct | ccggcgacga | gaacctgatc | cgggtcttca | aggagggggcg ggacatccac | 1920 |

```
acggaaaccg ccagctggat gttcggcgtc cccgggagg ccgtggaccc cctaatgcgc  1980
cgggcggcca agaccatcaa cttcggggtt ctctacggca tgtcggccca ccgcctctcc  2040
caggagctag ccatccctta cgaggaggcc caggccttca ttgagcgcta ctttcagagc  2100
ttccccaagg tgcgggcctg gattgagaag accctggagg agggcaggag gcggggtac   2160
gtggagaccc tcttcggccg ccgtcgctac gtgccagacc tagaggcccg ggtgaagagc  2220
gtgcgggagg cggccgagcg catggccttc aacatgcccg tccagggcac cgccgccgac  2280
ctcatgaagc tggctatggt gaagctcttc cccaggctgg aagaaacggg ggccaggatg  2340
ctccttcagg tccacgacga gctggtcctc gaggccccaa agagagggc ggaggccgtg  2400
gcccggctgg ccaaggaggc catggagggg gtgtatcccc tggccgtgcc cctggaggtg  2460
gaggtgggga tagggaggga ctggctctcc gccaaggagt ga                    2502
```

<210> SEQ ID NO 68
<211> LENGTH: 833
<212> TYPE: PRT
<213> ORGANISM: Artificial sequence
<220> FEATURE:
<223> OTHER INFORMATION: Mutant Taq polymerase

<400> SEQUENCE: 68

```
Met Val Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Leu
            20                  25                  30

Thr Thr Ser Arg Gly Glu Pro Val Gln Ala Val Tyr Gly Phe Ala Lys
        35                  40                  45

Ser Leu Leu Lys Ala Leu Lys Glu Asp Gly Tyr Lys Ala Val Phe Val
    50                  55                  60

Val Phe Asp Ala Lys Ala Ser Ser Phe Arg His Glu Ala Tyr Glu Ala
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Phe Thr Arg Leu Glu
            100                 105                 110

Val Pro Gly Tyr Glu Val Asp Asp Val Leu Ala Ser Leu Ala Lys Lys
        115                 120                 125

Val Glu Lys Glu Gly Tyr Glu Val Arg Ile Leu Thr Ala Asp Arg Asp
    130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asp Asn
            180                 185                 190

Leu Pro Gly Val Lys Gly Ile Gly Glu Lys Thr Ala Leu Lys Leu Leu
        195                 200                 205

Lys Glu Trp Gly Gly Leu Glu Asn Leu Leu Lys Asn Leu Asp Arg Val
    210                 215                 220

Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
                245                 250                 255

Val Asp Leu Ala Gln Gly Arg Glu Pro Asp Arg Glu Arg Leu Arg Ala
```

-continued

```
                260                 265                 270
Phe Leu Glu Arg Leu Glu Phe Gly Ser Leu Leu His Glu Phe Gly Leu
            275                 280                 285
Leu Glu Ser Pro Lys Ala Leu Glu Glu Ala Pro Trp Pro Pro Pro Glu
        290                 295                 300
Gly Ala Phe Val Gly Phe Val Leu Ser Arg Lys Glu Pro Met Trp Ala
305                 310                 315                 320
Asp Leu Leu Ala Leu Ala Ala Arg Gly Gly Arg Val His Arg Thr
                325                 330                 335
Pro Glu Pro Tyr Lys Ala Leu Arg Asp Leu Lys Glu Ala Arg Gly Leu
            340                 345                 350
Leu Ala Lys Asp Leu Ser Val Leu Ala Leu Arg Glu Gly Leu Gly Leu
        355                 360                 365
Pro Pro Gly Asp Asp Pro Met Leu Leu Ala Tyr Leu Leu Asp Pro Ser
    370                 375                 380
Asn Thr Thr Pro Glu Gly Val Ala Arg Arg Tyr Gly Gly Glu Trp Thr
385                 390                 395                 400
Glu Glu Ala Gly Glu Arg Ala Ala Leu Ser Glu Arg Leu Phe Ala Asn
                405                 410                 415
Leu Trp Gly Arg Leu Glu Gly Glu Glu Arg Leu Leu Trp Leu Tyr Arg
            420                 425                 430
Glu Val Asp Arg Pro Leu Ser Ala Val Leu Ala His Met Glu Ala Thr
        435                 440                 445
Gly Val Arg Leu Asp Val Ala Tyr Leu Arg Ala Leu Ser Leu Glu Val
    450                 455                 460
Ala Glu Glu Ile Ala Arg Leu Glu Ala Glu Val Phe Arg Leu Ala Gly
465                 470                 475                 480
His Pro Phe Asn Leu Asn Ser Arg Asp Gln Leu Glu Arg Val Leu Phe
                485                 490                 495
Asp Glu Leu Gly Leu Pro Ala Ile Gly Lys Thr Glu Lys Thr Gly Lys
            500                 505                 510
Arg Ser Thr Ser Ala Ala Val Leu Glu Ala Leu Arg Glu Ala His Pro
        515                 520                 525
Ile Val Glu Lys Ile Leu Gln Tyr Arg Glu Leu Thr Lys Leu Lys Ser
    530                 535                 540
Thr Tyr Ile Asp Pro Leu Pro Asp Leu Ile His Pro Arg Thr Gly Arg
545                 550                 555                 560
Leu His Thr Arg Phe Asn Gln Thr Ala Thr Ala Thr Gly Arg Leu Ser
                565                 570                 575
Ser Ser Asp Pro Asn Leu Gln Asn Ile Pro Val Arg Thr Pro Leu Gly
            580                 585                 590
Gln Arg Ile Arg Arg Ala Phe Ile Ala Glu Glu Gly Trp Leu Leu Val
        595                 600                 605
Val Leu Asp Tyr Ser Gln Ile Glu Leu Arg Val Leu Ala His Leu Ser
    610                 615                 620
Gly Asp Glu Asn Leu Ile Arg Val Phe Gln Glu Gly Arg Asp Ile His
625                 630                 635                 640
Thr Glu Thr Ala Ser Trp Met Phe Gly Val Pro Arg Glu Ala Val Asp
                645                 650                 655
Pro Leu Met Arg Arg Ala Ala Lys Thr Ile Asn Phe Gly Val Leu Tyr
            660                 665                 670
Gly Met Ser Ala His Arg Leu Ser Gln Glu Leu Ala Ile Pro Tyr Glu
        675                 680                 685
```

```
Glu Ala Gln Ala Phe Ile Glu Arg Tyr Phe Gln Ser Phe Pro Lys Val
        690                 695                 700
Arg Ala Trp Ile Glu Lys Thr Leu Glu Glu Gly Arg Arg Arg Gly Tyr
705                 710                 715                 720
Val Glu Thr Leu Phe Gly Arg Arg Arg Tyr Val Pro Asp Leu Glu Ala
                725                 730                 735
Arg Val Lys Ser Val Arg Glu Ala Ala Glu Arg Met Ala Phe Asn Met
            740                 745                 750
Pro Val Gln Gly Thr Ala Ala Asp Leu Met Lys Leu Ala Met Val Lys
        755                 760                 765
Leu Phe Pro Arg Leu Glu Glu Thr Gly Ala Arg Met Leu Leu Gln Val
    770                 775                 780
His Asp Glu Leu Val Leu Glu Ala Pro Lys Glu Arg Ala Glu Ala Val
785                 790                 795                 800
Ala Arg Leu Ala Lys Glu Ala Met Glu Gly Val Tyr Pro Leu Ala Val
                805                 810                 815
Pro Leu Glu Val Glu Val Gly Ile Gly Glu Asp Trp Leu Ser Ala Lys
            820                 825                 830
Glu

<210> SEQ ID NO 69
<211> LENGTH: 2550
<212> TYPE: DNA
<213> ORGANISM: Artificial sequence
<220> FEATURE:
<223> OTHER INFORMATION: Mutant Taq polymerase coding sequence

<400> SEQUENCE: 69
atggtgatgc ttcccctctt tgagcccaag ggccgcgtcc tcctggtgga cggccaccac      60
ctggcctacc gcaccttctt cgccctgaag ggcctcacca cgagccgggg cgaaccggtg     120
caggcggtct acggcttcgc caagagcctc ctcaaggccc tgaaggagga cgggtacaag     180
gccgtcttcg tggtctttga cgccaaggcc tcctccttcc gccacgaggc ctacgaggcc     240
tacaaggcgg ggagggcccc gaccccgag gacttccccc ggcagctcgc cctcatcaag     300
gagctggtgg acctcctggg gtttacccgc ctcgaggtcc ccggctacga ggtggacgac     360
gtcctggcca gctgggccaa gaaggtggaa aaggaggggt acgaggtgcg catcctcacc     420
gccgaccgcg ccctctacca actcgtctct gaccgcgtcg ccgtcctcca ccccgagggc     480
cacctcatca ccccggagtg gctttgggag aagtacggcc tcaggccgga gcagtgggtg     540
gacttccgcg ccctcgtggg ggacccctcc gacaacctcc ccggggtcaa gggcatcggg     600
gagaagaccg ccctcaagct cctcaaggag tgggaagcc tggaaaacct cctcaagaac     660
ctggaccggg taaagccaga aaacgtccgg gagaagatca ggcccacct ggaagacctc     720
aggctctcct ggagctctc ccgggtgcgc accgacctcc cctggaggt ggacctcgcc     780
caggggcggg agcccgaccg ggagaggctt agggcctttc tggagaggct tgagtttggc     840
agcctcctcc acgagttcgg ccttctggaa agccccaagg ccctggagga ggcccctgg     900
cccccgccgg aagggccctt cgtgggcttt gtgctttccc gcaaggagcc catgtgggcc     960
gatcttctgg ccctggccgc cgccaggggt ggtcgggtcc accgggcccc cgagccttat    1020
aaagccctca gggacttgaa ggaggcgcgg gggcttctcg ccaaagacct gagcgttctg    1080
gccctaaggg aaggccttgg cctccgcgcc ggcgacgacc ccatgctcct cgcctacctc    1140
ctggaccctt ccaacaccac cccgagggg gtggcccggc gctacggcgg ggagtggacg    1200
```

```
gaggaggcgg gggagcgggc cgcccttttcc gagaggctct tcgccaacct gtggggagg    1260 cttgaggggg aggagaggct cctttggctt taccgggagg tggataggcc cctttccgct    1320
gtcctggccc acatggaggc cacaggggtg cgcctggacg tggcctatct cagggccttg    1380
tccctggagg tggccgagga gatcgcccgc ctcgaggccg aggtcttccg cctggccggc    1440
caccccttca acctcaactc ccgggaccag ctggaaaggg tcctctttga cgagctaggg    1500
cttcccgcca tcgcaagac ggagaagacc ggcaagcgct ccaccagcgc cgccatcctg    1560
gaggccctcc gcgaggccca ccccatcgtg gagaagatcc tgcagtaccg ggagctcacc    1620
aagctgaaga gcacctacat tgaccccttg ccggacctca tccacccag acgggccgc    1680 ctccacaccc gcttcaacca gacggccacg gccacgggca ggctaagtag ctccgatccc    1740
aacctccaga acatccccgt ccgcacccc ctcgggcaga ggatccgccg ggccttcatc    1800
gccgaggagg ggtggctatt ggtggtcctg gactatagcc agatagagct cagggtgctg    1860
gcccacctct ccggcgacga gaacctgacc cgggtcttcc aggaggggcg ggacatccac    1920
acggaaaccg ccagctggat gttcggcgtc ccccggggag ccgtggaccc cctgatgcgc    1980
cgggcggcca agaccatcaa cttcggggtt ctctacggca tgtcggccca ccgcctctcc    2040
caggagctgg ccatcccta cgaggaggcc caggccttca tagagcgcta cttccaaagc    2100
ttccccaagg tgcgggcctg gatagaaaag accctggagg aggggaggaa gcggggctac    2160
gtggaaaccc tcttcggaag aaggcgctac gtgcccgacc tcaacgcccg ggtgaagagt    2220
gtcagggagg ccgcggagcg catggccttc aacatgcccg tccagggcac cgccgccgac    2280
cttatgaagc tcgccatggt gaagctcttc cccgcctcc gggagatggg ggcccgcatg    2340
ctcctccagg tccacgacga gctcctcctg gagcccccc aagcgcgggc cgaggaggtg    2400
gcggctttgg ccaaggaggc catggagaag gcctatcccc tcgccgtacc cctggaggtg    2460
aaggtgggga tcgggagga ctggctctcc gcccaaggag tgagtcgacc tgcaggcagc    2520
gcttggcgtc acccgcagtt cggtggttaa                                    2550
```

<210> SEQ ID NO 70
<211> LENGTH: 849
<212> TYPE: PRT
<213> ORGANISM: Artificial sequence
<220> FEATURE:
<223> OTHER INFORMATION: Mutant Taq polymerase

<400> SEQUENCE: 70

```
Met Val Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Leu
                20                  25                  30

Thr Thr Ser Arg Gly Glu Pro Val Gln Ala Val Tyr Gly Phe Ala Lys
            35                  40                  45

Ser Leu Leu Lys Ala Leu Lys Glu Asp Gly Tyr Lys Ala Val Phe Val
        50                  55                  60

Val Phe Asp Ala Lys Ala Ser Ser Phe Arg His Glu Ala Tyr Glu Ala
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Phe Thr Arg Leu Glu
                100                 105                 110

Val Pro Gly Tyr Glu Val Asp Asp Val Leu Ala Ser Leu Ala Lys Lys
```

-continued

```
            115                 120                 125
Val Glu Lys Glu Gly Tyr Glu Val Arg Ile Leu Thr Ala Asp Arg Gly
            130                 135                 140
Leu Tyr Gln Leu Val Ser Asp Arg Val Ala Val Leu His Pro Glu Gly
145                 150                 155                 160
His Leu Ile Thr Pro Glu Trp Leu Trp Glu Lys Tyr Gly Leu Arg Pro
                165                 170                 175
Glu Gln Trp Val Asp Phe Arg Ala Leu Val Gly Asp Pro Ser Asp Asn
                180                 185                 190
Leu Pro Gly Val Lys Gly Ile Gly Glu Lys Thr Ala Leu Lys Leu Leu
                195                 200                 205
Lys Glu Trp Gly Ser Leu Glu Asn Leu Leu Lys Asn Leu Asp Arg Val
                210                 215                 220
Lys Pro Glu Asn Val Arg Glu Lys Ile Lys Ala His Leu Glu Asp Leu
225                 230                 235                 240
Arg Leu Ser Leu Glu Leu Ser Arg Val Arg Thr Asp Leu Pro Leu Glu
                245                 250                 255
Val Asp Leu Ala Gln Gly Arg Glu Pro Asp Arg Glu Arg Leu Arg Ala
                260                 265                 270
Phe Leu Glu Arg Leu Glu Phe Gly Ser Leu Leu His Glu Phe Gly Leu
                275                 280                 285
Leu Glu Ser Pro Lys Ala Leu Glu Glu Ala Pro Trp Pro Pro Glu
290                 295                 300
Gly Ala Phe Val Gly Phe Val Leu Ser Arg Lys Glu Pro Met Trp Ala
305                 310                 315                 320
Asp Leu Leu Ala Leu Ala Ala Arg Gly Gly Arg Val His Arg Ala
                325                 330                 335
Pro Glu Pro Tyr Lys Ala Leu Arg Asp Leu Lys Glu Ala Arg Gly Leu
                340                 345                 350
Leu Ala Lys Asp Leu Ser Val Leu Ala Leu Arg Glu Gly Leu Gly Leu
                355                 360                 365
Pro Pro Gly Asp Asp Pro Met Leu Leu Ala Tyr Leu Leu Asp Pro Ser
370                 375                 380
Asn Thr Thr Pro Glu Gly Val Ala Arg Arg Tyr Gly Gly Glu Trp Thr
385                 390                 395                 400
Glu Glu Ala Gly Glu Arg Ala Ala Leu Ser Glu Arg Leu Phe Ala Asn
                405                 410                 415
Leu Trp Gly Arg Leu Glu Gly Glu Glu Arg Leu Leu Trp Leu Tyr Arg
                420                 425                 430
Glu Val Asp Arg Pro Leu Ser Ala Val Leu Ala His Met Glu Ala Thr
                435                 440                 445
Gly Val Arg Leu Asp Val Ala Tyr Leu Arg Ala Leu Ser Leu Glu Val
                450                 455                 460
Ala Glu Glu Ile Ala Arg Leu Glu Ala Glu Val Phe Arg Leu Ala Gly
465                 470                 475                 480
His Pro Phe Asn Leu Asn Ser Arg Asp Gln Leu Glu Arg Val Leu Phe
                485                 490                 495
Asp Glu Leu Gly Leu Pro Ala Ile Gly Lys Thr Glu Lys Thr Gly Lys
                500                 505                 510
Arg Ser Thr Ser Ala Ala Ile Leu Glu Ala Leu Arg Glu Ala His Pro
                515                 520                 525
Ile Val Glu Lys Ile Leu Gln Tyr Arg Glu Leu Thr Lys Leu Lys Ser
                530                 535                 540
```

Thr Tyr Ile Asp Pro Leu Pro Asp Leu Ile His Pro Arg Thr Gly Arg
545                 550                 555                 560

Leu His Thr Arg Phe Asn Gln Thr Ala Thr Ala Thr Gly Arg Leu Ser
            565                 570                 575

Ser Ser Asp Pro Asn Leu Gln Asn Ile Pro Val Arg Thr Pro Leu Gly
        580                 585                 590

Gln Arg Ile Arg Arg Ala Phe Ile Ala Glu Glu Gly Trp Leu Leu Val
    595                 600                 605

Val Leu Asp Tyr Ser Gln Ile Glu Leu Arg Val Leu Ala His Leu Ser
610                 615                 620

Gly Asp Glu Asn Leu Thr Arg Val Phe Gln Glu Gly Arg Asp Ile His
625                 630                 635                 640

Thr Glu Thr Ala Ser Trp Met Phe Gly Val Pro Arg Glu Ala Val Asp
            645                 650                 655

Pro Leu Met Arg Arg Ala Ala Lys Thr Ile Asn Phe Gly Val Leu Tyr
        660                 665                 670

Gly Met Ser Ala His Arg Leu Ser Gln Glu Leu Ala Ile Pro Tyr Glu
    675                 680                 685

Glu Ala Gln Ala Phe Ile Glu Arg Tyr Phe Gln Ser Phe Pro Lys Val
690                 695                 700

Arg Ala Trp Ile Glu Lys Thr Leu Glu Glu Gly Arg Lys Arg Gly Tyr
705                 710                 715                 720

Val Glu Thr Leu Phe Gly Arg Arg Arg Tyr Val Pro Asp Leu Asn Ala
            725                 730                 735

Arg Val Lys Ser Val Arg Glu Ala Ala Glu Arg Met Ala Phe Asn Met
        740                 745                 750

Pro Val Gln Gly Thr Ala Ala Asp Leu Met Lys Leu Ala Met Val Lys
    755                 760                 765

Leu Phe Pro Arg Leu Arg Glu Met Gly Ala Arg Met Leu Leu Gln Val
770                 775                 780

His Asp Glu Leu Leu Leu Glu Ala Pro Gln Ala Arg Ala Glu Glu Val
785                 790                 795                 800

Ala Ala Leu Ala Lys Glu Ala Met Glu Lys Ala Tyr Pro Leu Ala Val
            805                 810                 815

Pro Leu Glu Val Lys Val Gly Ile Gly Glu Asp Trp Leu Ser Ala Gln
        820                 825                 830

Gly Val Ser Arg Pro Ala Gly Ser Ala Trp Arg His Pro Gln Phe Gly
    835                 840                 845

Gly

<210> SEQ ID NO 71
<211> LENGTH: 2505
<212> TYPE: DNA
<213> ORGANISM: Artificial sequence
<220> FEATURE:
<223> OTHER INFORMATION: Mutant Taq polymerase coding sequence

<400> SEQUENCE: 71

```
atgcgtggta tgcttcctct ttttgagccc aagggccgcg tcctcctggt ggacggccac      60
cacctggcct accgcacctt cttcgccctg aagggcccca ccacgagccg ggcgaaccg      120 gtgcaggcgg tctacggctt cgccaagagc ctcctcaagg ccctgaagga ggacgggtac     180
aaggccgcct tcgtggtctt tgacgccaag gccccctcct ccgccacga ggcctacgag      240 gcctacaagg cggggagggc cccgaccccc gaggacttcc ccggcagct cgccctcatc      300
```

```
aaggagctgg tggacctcct ggggtttacc cgcctcgagg tccctggcta cgaggcggac    360
gacgtcctcg ccaccctggc caagaaggcg gaaaaggagg ggtacgaggt gcgcatcctc    420
accgccgacc gcgacctcta ccaactcgtc tccgaccgcg tcgccgtcct ccaccccgag    480
ggccacctca tcaccccgga gtggctttgg agaagtacg gcctcaggcc ggagcagtgg     540
gtggacttcc gcgccctcgt gggggacccc tccgacaacc tccccggggt caagggcatc    600
ggggagaaga ccgccctcaa gctcctcaag gagtggggaa gcctggaaaa cctcctcaag    660
aacctggacc gggtaaagcc agaaaacgtc cgggagaaga tcaaggccca cctggaagac    720
ctcaggctct ccttggagct ctcccgggtg cgcaccgacc tccccctgga ggtggacctc    780
gcccaggggc gggagctcga ccgggagagg cttagggcct ttctggagag gcttgagttt    840
ggcggcctcc tccacgagtt cggccttctg gaaagcccca aggccctgga ggaggccccc    900 tggccccgc cggaaggggc cttcgtgggc tttgtgcttt cccgcaagga gcccatgtgg     960
gccgatcttc tggccctggc cgccgccagg ggtggtcggg tccaccgggc ccccgagcct   1020
tataaagccc tcagggactt gaaggaggcg cgggggcttc tcgccaaaga cctgagcgtt   1080
ctggccctaa gggaaggcct tggcctcccg cccggcgacg accccatgct cctcgcctac   1140
ctcctggacc cttccaacac cgcccccgag ggggtggccc ggcgctacgg cggggagtgg   1200
acggaggagg cggggggagcg ggccgccctt tccgagaggc tcttcgccaa cctgtggggg   1260
aggcttgagg gggaggagag gctcctttgg ctttaccggg aggtggatag ccccctttcc   1320
gctgtcctgg cccacatgga ggccacaggg gtacggctgg acgtggcctg cctgcaggcc   1380 cttttccctgg agcttgcgga ggagatccgc cgcctcgagg aggaggtctt ccgcttggcg   1440 ggccaccccct tcaacctcaa ctcccgggac cagctggaaa gggtcctctt tgacgagcta   1500
gggcttcccg ccatcggcaa gacggagaag accggcaagc gctccaccag cgccgccatc   1560
ctggaggccc tccgcgaggc ccaccccatc gtggagaaga tcctgcagta ccggagctc    1620 accaagctga agagcaccta cattgacccc ttgccggacc tcatccaccc caggacgggc   1680
cgcctccaca cccgcttcaa ccagacggcc acggccacgg gcaggctaag tagctccgat   1740
cccaacctcc agaacatccc cgtccgcacc ccgctcgggc agaggatccg ccgggccttc   1800
gtcgccgagg aggggtggct attggtggtc ctggactata gccagataga gctcagggtg   1860
ctggcccacc tctccggcga cgagaacctg acccgggtct tcctggaggg gcgggacatc   1920
cacacggaaa ccgccagctg gatgttcggc gtcccccggg aggccgtgga ccccctgatg   1980 cgccgggcg ccaagaccat caacttcggg gttctctacg gcatgtcggc ccaccgcctc    2040
tcccaggagc tggccatccc ttacgaggag gcccaggcct tcatagagcg ctacttccaa   2100 agcttccccca aggtgcgggc ctggatagaa aagaccctgg aggaggggag gaagcggggc   2160
tacgtggaaa ccctcttcgg aagaaggcgc tacgtgcccg acctcaacgc ccgggtgaag   2220
agtgtcaggg aggccgcgga gcgcatggcc ttcaacatgc ccgtccaggg caccgccgcc   2280
gaccttatga agctcgccat ggtgaagctc ttcccccgcc tccgggagat gggggcccgc   2340
atgctcctcc aggtccacga cgagctcctc ctggaggccc ccaagcgcgg ggccgaggag   2400
gtggcggctt tggccaagga ggccatggag aaggcctatc ccctgccgt acccctggag   2460 gtgaaggtgg ggatcgggga ggactggctc tccgccaagg agtga               2505
```

<210> SEQ ID NO 72
<211> LENGTH: 834
<212> TYPE: PRT

<213> ORGANISM: Artificial sequence
<220> FEATURE:
<223> OTHER INFORMATION: Mutant Taq polymerase

<400> SEQUENCE: 72

```
Met Arg Gly Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Pro Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Ala Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Leu Asp Arg Glu Arg Leu Arg
            260                 265                 270

Ala Phe Leu Glu Arg Leu Glu Phe Gly Gly Leu Leu His Glu Phe Gly
        275                 280                 285

Leu Leu Glu Ser Pro Lys Ala Leu Glu Ala Pro Trp Pro Pro Pro
    290                 295                 300

Glu Gly Ala Phe Val Gly Phe Val Leu Ser Arg Lys Glu Pro Met Trp
305                 310                 315                 320

Ala Asp Leu Leu Ala Leu Ala Ala Ala Arg Gly Gly Arg Val His Arg
                325                 330                 335

Ala Pro Glu Pro Tyr Lys Ala Leu Arg Asp Leu Lys Glu Ala Arg Gly
            340                 345                 350

Leu Leu Ala Lys Asp Leu Ser Val Leu Ala Leu Arg Glu Gly Leu Gly
        355                 360                 365

Leu Pro Pro Gly Asp Asp Pro Met Leu Leu Ala Tyr Leu Leu Asp Pro
    370                 375                 380

Ser Asn Thr Ala Pro Glu Gly Val Ala Arg Arg Tyr Gly Gly Glu Trp
```

```
            385                 390                 395                 400

Thr Glu Ala Gly Glu Arg Ala Ala Leu Ser Glu Arg Leu Phe Ala
                        405                 410                 415

Asn Leu Trp Gly Arg Leu Glu Gly Glu Glu Arg Leu Leu Trp Leu Tyr
                    420                 425                 430

Arg Glu Val Asp Arg Pro Leu Ser Ala Val Leu Ala His Met Glu Ala
                        435                 440                 445

Thr Gly Val Arg Leu Asp Val Ala Cys Leu Gln Ala Leu Ser Leu Glu
                    450                 455                 460

Leu Ala Glu Glu Ile Arg Arg Leu Glu Glu Val Phe Arg Leu Ala
        465                 470                 475                 480

Gly His Pro Phe Asn Leu Asn Ser Arg Asp Gln Leu Glu Arg Val Leu
                        485                 490                 495

Phe Asp Glu Leu Gly Leu Pro Ala Ile Gly Lys Thr Glu Lys Thr Gly
                    500                 505                 510

Lys Arg Ser Thr Ser Ala Ala Ile Leu Glu Ala Leu Arg Glu Ala His
                    515                 520                 525

Pro Ile Val Glu Lys Ile Leu Gln Tyr Arg Glu Leu Thr Lys Leu Lys
                    530                 535                 540

Ser Thr Tyr Ile Asp Pro Leu Pro Asp Leu Ile His Pro Arg Thr Gly
        545                 550                 555                 560

Arg Leu His Thr Arg Phe Asn Gln Thr Ala Thr Ala Thr Gly Arg Leu
                        565                 570                 575

Ser Ser Ser Asp Pro Asn Leu Gln Asn Ile Pro Val Arg Thr Pro Leu
                    580                 585                 590

Gly Gln Arg Ile Arg Arg Ala Phe Val Ala Glu Gly Trp Leu Leu
                    595                 600                 605

Val Val Leu Asp Tyr Ser Gln Ile Glu Leu Arg Val Leu Ala His Leu
                    610                 615                 620

Ser Gly Asp Glu Asn Leu Thr Arg Val Phe Leu Glu Gly Arg Asp Ile
        625                 630                 635                 640

His Thr Glu Thr Ala Ser Trp Met Phe Gly Val Pro Arg Glu Ala Val
                        645                 650                 655

Asp Pro Leu Met Arg Arg Ala Ala Lys Thr Ile Asn Phe Gly Val Leu
                    660                 665                 670

Tyr Gly Met Ser Ala His Arg Leu Ser Gln Glu Leu Ala Ile Pro Tyr
                    675                 680                 685

Glu Glu Ala Gln Ala Phe Ile Glu Arg Tyr Phe Gln Ser Phe Pro Lys
                    690                 695                 700

Val Arg Ala Trp Ile Glu Lys Thr Leu Glu Glu Gly Arg Lys Arg Gly
        705                 710                 715                 720

Tyr Val Glu Thr Leu Phe Gly Arg Arg Tyr Val Pro Asp Leu Asn
                        725                 730                 735

Ala Arg Val Lys Ser Val Arg Glu Ala Ala Glu Arg Met Ala Phe Asn
                    740                 745                 750

Met Pro Val Gln Gly Thr Ala Ala Asp Leu Met Lys Leu Ala Met Val
                    755                 760                 765

Lys Leu Phe Pro Arg Leu Arg Glu Met Gly Ala Arg Met Leu Leu Gln
                    770                 775                 780

Val His Asp Glu Leu Leu Leu Glu Ala Pro Gln Ala Arg Ala Glu Glu
        785                 790                 795                 800

Val Ala Ala Leu Ala Lys Glu Ala Met Glu Lys Ala Tyr Pro Leu Ala
                        805                 810                 815
```

Val Pro Leu Glu Val Lys Val Gly Ile Gly Glu Asp Trp Leu Ser Ala
        820                 825                 830

Lys Glu

<210> SEQ ID NO 73
<211> LENGTH: 2502
<212> TYPE: DNA
<213> ORGANISM: Artificial sequence
<220> FEATURE:
<223> OTHER INFORMATION: Mutant Taq polymerase coding sequence

<400> SEQUENCE: 73

```
atggcgatgc ttcccctctt tgagcccaag ggccgcgtcc tcctggtgga cggccaccac      60
ctggcctacc gcaccttctt cgccctgaag ggccccacca cgagccgggg cgaaccggtg     120
caggtggtct acggcttcgc caagagcctc ctcaaggccc tgaaggagga cgggtacaag     180
gccgtcttcg tggtctttga cgccaaggcc cctcattccg ccacaaggc ctacgaggcc      240
tacagggcgg ggagggcccc gacccccgag gacttccccc ggcagctcgc cctcatcaag     300
gagctggtgg acctcctggg gtttacccgc tcgaggtcc ccggctacga ggcggacgac     360
gttctcgcca ccctggccaa gaaggcgaa aaggaggggt acgaggtgcg catcctcacc     420
gccgaccgcg gcctctacca actcgtctct gaccgcgtcg ccgtcctcca ccccgagggc     480
cacctcatca ccccggagtg gctttgggag aagtacggcc tcaggccgga gcagtgggtg     540
gacttccgcg ccctcgtggg ggaccctcc gacaacctcc cggggtcaa gggcatcggg     600
gagaagaccg ccctcaagct cctcaaggag tggggaagcc tggaaaacct cctcaagaac     660
ctggaccggg taaagccaga aaacgtccgg gagaagatca ggcccacct ggaagacctc     720
aggctctcct ggagctctc ccgggtgcgc accgacctcc cctggaggt ggacctcgcc      780
caggggcggg agcccgaccg ggagggggctt agggccttc tggagaggct tgagtttggc     840
agcctcctcc acgagttcgg ccttctggaa agccccaagg ccctggagga ggccccctgg     900
cccccgccgg aaggggcctt cgtgggcttt gtgctttccc gcaaggagcc catgtgggcc     960
gatcttctgg ccctggccgc cgccaggggt ggtcgagtcc accggccccc cgagccttat    1020
aaagccctca gggacctgaa ggaggcgcgg gggcttctcg ccaaagacct gagcgttctg    1080
gccctaaggg aaggccttgg cctccccgcc ggcgacgacc ccatgctcct cgcctacctc    1140
ctggaccctt ccaacaccac ccccgagggg gtggcccggc gctacggcgg ggagtggacg    1200
gaggaggcgg gggagcgggc cgccccttcc gagaggctct cgccaacct gtggggggag    1260
cttgaggggg aggagaggct cctttggctt taccgggagg tggagaggcc cctttccgct    1320
gtcctggccc acatggaggc cacggggtg cgcctggacg tggcctatct cagggccttg    1380
tccctggagg tggccgagga tcgcccgc ctcgaggccg aggtcttccg cctggccggc    1440
cacccttca acctcaactc ccgggaccag ctggaaatgg tgctctttga cgagcttagg    1500
cttccccgcct tggggaagac gcaaaagacg ggcaagcgct ccaccagcgc cgccgtcctg    1560
gaggccctcc gcgaggccca ccccatcgtg gagaagatcc tgcagtaccg ggagctcacc    1620
aagctgaaga gcacctacat tgaccccttg tcggacctca tccacccag acgggccgc    1680
ctccacaccc gcttcaacca gacggccacg gccacgggca ggctaagtag ctccgatccc    1740
aacctccaga acatccccgt ccgcacccg cttgggcaga ggatccgccg ggccttcatc    1800
gccgaggagg ggtggctact ggtggtcctg actatagcc agatagagct cagggtgctg    1860
gcccacctct ccggcgacga aaacctgatc aggtcttcc aggagggggcg ggacatccac    1920
```

```
acggagaccg ccagctggat gttcggcgtc ccccgggagg ccgtggaccc cctgatgcgc   1980
cgggcggcca agaccatcaa cttcggggtc ctctacggca tgtcggccca ccgcctctcc   2040
caggagctag ccatccctta cgaggaggcc caggccttca ttgagcgcta ctttcagagc   2100
ttccccaagg tgcgggcctg gattgagaag accctggagg agggcaggag gcgggggtac   2160
gtggagaccc tcttcggccg ccgccgctac gtgccagacc tagaggcccg ggtgaagagc   2220
gtgcgggagg cggccgagcg catggccttc aacatgcccg tccagggcac cgccgccgac   2280
ctcatgaagc tggctatggt gaagctcttc cccaggctgg aggaaacggg ggccaggatg   2340
ctccttcagg tccacgacga gctggtcctt gaggccccaa agagagggc ggaggccgtg   2400 gcccggctgg ccaaggaggt catggagggg gtgtatcccc tggccgtgtc cctggaggtg   2460
gaggtgggga tagggagga ctggctctcc gccaaggagt ga                      2502
```

<210> SEQ ID NO 74
<211> LENGTH: 833
<212> TYPE: PRT
<213> ORGANISM: Artificial sequence
<220> FEATURE:
<223> OTHER INFORMATION: Mutant Taq polymerase

<400> SEQUENCE: 74

```
Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Pro
            20                  25                  30

Thr Thr Ser Arg Gly Glu Pro Val Gln Val Val Tyr Gly Phe Ala Lys
        35                  40                  45

Ser Leu Leu Lys Ala Leu Lys Glu Asp Gly Tyr Lys Ala Val Phe Val
    50                  55                  60

Val Phe Asp Ala Lys Ala Pro Ser Phe Arg His Lys Ala Tyr Glu Ala
65                  70                  75                  80

Tyr Arg Ala Gly Arg Ala Pro Thr Pro Glu Asp Phe Pro Arg Gln Leu
                85                  90                  95

Ala Leu Ile Lys Glu Leu Val Asp Leu Leu Gly Phe Thr Arg Leu Glu
            100                 105                 110

Val Pro Gly Tyr Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Gly
    130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asp Asn
            180                 185                 190

Leu Pro Gly Val Lys Gly Ile Gly Glu Lys Thr Ala Leu Lys Leu Leu
        195                 200                 205

Lys Glu Trp Gly Ser Leu Glu Asn Leu Leu Lys Asn Leu Asp Arg Val
    210                 215                 220

Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
                245                 250                 255
```

```
Val Asp Leu Ala Gln Gly Arg Glu Pro Asp Arg Glu Gly Leu Arg Ala
            260                 265                 270

Phe Leu Glu Arg Leu Glu Phe Gly Ser Leu Leu His Glu Phe Gly Leu
            275                 280                 285

Leu Glu Ser Pro Lys Ala Leu Glu Glu Ala Pro Trp Pro Pro Pro Glu
            290                 295                 300

Gly Ala Phe Val Gly Phe Val Leu Ser Arg Lys Glu Pro Met Trp Ala
305                 310                 315                 320

Asp Leu Leu Ala Leu Ala Ala Arg Gly Gly Arg Val His Arg Ala
                325                 330                 335

Pro Glu Pro Tyr Lys Ala Leu Arg Asp Leu Lys Glu Ala Arg Gly Leu
            340                 345                 350

Leu Ala Lys Asp Leu Ser Val Leu Ala Leu Arg Glu Gly Leu Gly Leu
            355                 360                 365

Pro Pro Gly Asp Asp Pro Met Leu Leu Ala Tyr Leu Leu Asp Pro Ser
            370                 375                 380

Asn Thr Thr Pro Glu Gly Val Ala Arg Arg Tyr Gly Gly Glu Trp Thr
385                 390                 395                 400

Glu Glu Ala Gly Glu Arg Ala Ala Leu Ser Glu Arg Leu Phe Ala Asn
                405                 410                 415

Leu Trp Gly Arg Leu Glu Gly Glu Glu Arg Leu Leu Trp Leu Tyr Arg
            420                 425                 430

Glu Val Glu Arg Pro Leu Ser Ala Val Leu Ala His Met Glu Ala Thr
            435                 440                 445

Gly Val Arg Leu Asp Val Ala Tyr Leu Arg Ala Leu Ser Leu Glu Val
450                 455                 460

Ala Glu Glu Ile Ala Arg Leu Glu Ala Glu Val Phe Arg Leu Ala Gly
465                 470                 475                 480

His Pro Phe Asn Leu Asn Ser Arg Asp Gln Leu Glu Met Val Leu Phe
                485                 490                 495

Asp Glu Leu Arg Leu Pro Ala Leu Gly Lys Thr Gln Lys Thr Gly Lys
            500                 505                 510

Arg Ser Thr Ser Ala Ala Val Leu Glu Ala Leu Arg Glu Ala His Pro
            515                 520                 525

Ile Val Glu Lys Ile Leu Gln Tyr Arg Glu Leu Thr Lys Leu Lys Ser
530                 535                 540

Thr Tyr Ile Asp Pro Leu Ser Asp Leu Ile His Pro Arg Thr Gly Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590

Gln Arg Ile Arg Arg Ala Phe Ile Ala Glu Glu Gly Trp Leu Leu Val
            595                 600                 605

Val Leu Asp Tyr Ser Gln Ile Glu Leu Arg Val Leu Ala His Leu Ser
            610                 615                 620

Gly Asp Glu Asn Leu Ile Arg Val Phe Gln Glu Gly Arg Asp Ile His
625                 630                 635                 640

Thr Glu Thr Ala Ser Trp Met Phe Gly Val Pro Arg Glu Ala Val Asp
                645                 650                 655

Pro Leu Met Arg Arg Ala Ala Lys Thr Ile Asn Phe Gly Val Leu Tyr
            660                 665                 670

Gly Met Ser Ala His Arg Leu Ser Gln Glu Leu Ala Ile Pro Tyr Glu
```

```
             675                 680                 685
Glu Ala Gln Ala Phe Ile Glu Arg Tyr Phe Gln Ser Phe Pro Lys Val
    690                 695                 700

Arg Ala Trp Ile Glu Lys Thr Leu Glu Glu Gly Arg Arg Gly Tyr
705                 710                 715                 720

Val Glu Thr Leu Phe Gly Arg Arg Arg Tyr Val Pro Asp Leu Glu Ala
                    725                 730                 735

Arg Val Lys Ser Val Arg Glu Ala Ala Glu Arg Met Ala Phe Asn Met
                740                 745                 750

Pro Val Gln Gly Thr Ala Ala Asp Leu Met Lys Leu Ala Met Val Lys
                755                 760                 765

Leu Phe Pro Arg Leu Glu Glu Thr Gly Ala Arg Met Leu Leu Gln Val
    770                 775                 780

His Asp Glu Leu Val Leu Glu Ala Pro Lys Glu Arg Ala Glu Ala Val
785                 790                 795                 800

Ala Arg Leu Ala Lys Glu Val Met Glu Gly Val Tyr Pro Leu Ala Val
                    805                 810                 815

Ser Leu Glu Val Glu Val Gly Ile Gly Glu Asp Trp Leu Ser Ala Lys
                820                 825                 830

Glu
```

<210> SEQ ID NO 75
<211> LENGTH: 2502
<212> TYPE: DNA
<213> ORGANISM: Artificial sequence
<220> FEATURE:
<223> OTHER INFORMATION: Mutant Taq polymerase coding sequence

<400> SEQUENCE: 75

```
atggcgatgc ttcccctctt tgagcccaag ggccgcgtcc tcctggtgga cggccaccac      60
ctggcctacc gcaccttctt cgccctgaag ggccccaccg cgagccgggg cgaaccggtg     120
caggtggtct acggcttcgc caagagcctc ctcaaggccc tgaaggagga cgggtacaag     180
gccgtcttcg tggtctttga cgccaaggcc cctcattcc gccacaaggc ctacgaggcc     240
tacagggcgg ggagggcccc gaccccccgag gacttccccc ggcagctcgc cctcatcaag     300
gagctggtgg acctcctggg gtttacccgc ctcgaggtcc ccggctacga ggcggacgac     360
gttctcgccc cctggccaa gaaggcgaaa aggaggggt tcgaggtgcg catcctcccc     420
gccgtccgcg cctctgccc tctcgtctct gaccgcgtcg ccgtcctcct ccccgagggc     480
cacctcatca cccccggagtg gctttgggag aagtacggcc tcaggccgga gcagtgggtg     540
gacttccgcg ccctcgtggg ggaccctcc gacaacctcc ccggggtcaa gggcatcggg     600
aagaagaccg cccctcaagct cctcaaggag tggggaagcc tggaaaacct cctcaagaac     660
ctggaccggg taaagccaga aaacgtccgg gagaagatca aggcccacct ggaagacctc     720
aggctctcct tggagctctc ccgggtgcgc accgacctcc cctggaggt ggacctcgcc     780
caggggcggg agcccgaccg ggaggggctt agggcctttc tggagaggct tgagtttggc     840
agcctcctcc acgagttcgg ccttctggaa agccccaagg ccctggagga ggccccctgg     900
ccccccgccg aaggggcctt cgtggcttt gtgctttccc gcaaggagcc catgtgggcc     960
gatcttctgg ccctggccgc cgccaggggt ggtcgggtcc accgggcccc cgagccttat    1020
aaagccctca gggacttgaa ggaggcgcgg gggcttctcg ccaaagacct gagcgttctg    1080
gccctaaggg aaggccttgg cctccgcgcc ggcgacgacc ccatgctcct cgcctacctc    1140
```

```
ctggacccctt ccaacaccac ccccgagggg gtggcccggc gctacggcgg ggagtggacg    1200
gaggaggcgg gggagcgggc cgcccttttcc gagaggctct tcgccaacct gtggggggagg   1260 cttgaggggg aggagaggct cctgtggctt taccgggagg tggataggcc cctttccgct    1320
gtcctggccc acatggaggc cacagggggta cggctgacg tggcctgcct gcaggcccttt   1380 tccctggagc ttgcggagga gatccgccgc ctcgaggagg aggtcttccg cttggcgggc    1440
caccccttca acctcaactc ccgggaccag ctggaaaggg tcctctttga cgagctaggg    1500
cttcccgcca tcggcaagac ggagaagacc ggcaagcgct ccaccagcgc cgccatcctg    1560
gaggccctcc gcgaggccca ccccatcgtg gagaagatcc tgcagtaccg ggagctcacc    1620
aagctgaaga gcacctacat tgaccccttg ccggacctca tccacccag gacgggccgc     1680 ctccacaccc gcttcaacca gacggccacg gccacgggca ggctaagtag ctccgatccc   1740
aacctccaga acatccccgt ccgcaccccg ctcgggcaga ggatccgccg ggccttcatc    1800
gccgaggagg ggtggctatt ggtggtcctg gactatagcc agatagagct cagggtgctg   1860
gcccacctct ccggcgacga gaacctgacc cgggtcttcc aggaggggcg ggacatccac   1920
acggaaaccg ccagctggat gttcggcgtc ccccggggagg ccgtggaccc cctgatgcgc   1980
cgggcggcca agaccatcaa cttcggggtt ctctacggca tgtcggccca ccgcctctcc    2040
caggagctgg ccatccctta cgaggaggcc caggccttca tagagcgcta cttccaaagc    2100
ttccccaagg tgcgggcctg gatagaaaag accctggagg aggggaggaa gcggggctac    2160
gtggaaaccc tcttcggaag aaggcgctac gtgcccgacc tcaacgcccg ggtgaagagt    2220
gtcagggagg ccgcggagcg catggccttc aacatgcccg tccagggcac cgccgccgac   2280
cttatgaagc tcgccatggt gaagctcttc ccccgcctcc gggagatggg ggcccgcatg    2340
ctcctccagg tccacgacga gctcctcctg gaggcccccc aagcgcgggc cgaggaggtg    2400
gcggctttgg ccaaggaggc catggagaag gcctatcccc tcgccgtacc cctggaggtg    2460
aaggtgggga tcgggagga ctggctctcc gccaaggagt ga                        2502
```

<210> SEQ ID NO 76
<211> LENGTH: 833
<212> TYPE: PRT
<213> ORGANISM: Artificial sequence
<220> FEATURE:
<223> OTHER INFORMATION: Mutant Taq polymerase

<400> SEQUENCE: 76

Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Pro
            20                  25                  30

Thr Ala Ser Arg Gly Glu Pro Val Gln Val Val Tyr Gly Phe Ala Lys
        35                  40                  45

Ser Leu Leu Lys Ala Leu Lys Glu Asp Gly Tyr Lys Ala Val Phe Val
    50                  55                  60

Val Phe Asp Ala Lys Ala Pro Ser Phe Arg His Lys Ala Tyr Glu Ala
65                  70                  75                  80

Tyr Arg Ala Gly Arg Ala Pro Thr Pro Glu Asp Phe Pro Arg Gln Leu
                85                  90                  95

Ala Leu Ile Lys Glu Leu Val Asp Leu Leu Gly Phe Thr Arg Leu Glu
            100                 105                 110

Val Pro Gly Tyr Glu Ala Asp Asp Val Leu Ala Pro Leu Ala Lys Lys
        115                 120                 125

```
Ala Glu Lys Glu Gly Phe Glu Val Arg Ile Leu Pro Ala Val Arg Gly
            130                 135                 140

Leu Cys Pro Leu Val Ser Asp Arg Val Ala Val Leu Leu Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asp Asn
            180                 185                 190

Leu Pro Gly Val Lys Gly Ile Gly Lys Lys Thr Ala Leu Lys Leu Leu
        195                 200                 205

Lys Glu Trp Gly Ser Leu Glu Asn Leu Leu Lys Asn Leu Asp Arg Val
210                 215                 220

Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
                245                 250                 255

Val Asp Leu Ala Gln Gly Arg Glu Pro Asp Arg Glu Gly Leu Arg Ala
            260                 265                 270

Phe Leu Glu Arg Leu Glu Phe Gly Ser Leu Leu His Glu Phe Gly Leu
        275                 280                 285

Leu Glu Ser Pro Lys Ala Leu Glu Glu Ala Pro Trp Pro Pro Pro Glu
290                 295                 300

Gly Ala Phe Val Gly Phe Val Leu Ser Arg Lys Glu Pro Met Trp Ala
305                 310                 315                 320

Asp Leu Leu Ala Leu Ala Ala Arg Gly Gly Arg Val His Arg Ala
                325                 330                 335

Pro Glu Pro Tyr Lys Ala Leu Arg Asp Leu Lys Glu Ala Arg Gly Leu
            340                 345                 350

Leu Ala Lys Asp Leu Ser Val Leu Ala Leu Arg Glu Gly Leu Gly Leu
        355                 360                 365

Pro Pro Gly Asp Asp Pro Met Leu Leu Ala Tyr Leu Leu Asp Pro Ser
370                 375                 380

Asn Thr Thr Pro Glu Gly Val Ala Arg Arg Tyr Gly Gly Glu Trp Thr
385                 390                 395                 400

Glu Glu Ala Gly Glu Arg Ala Ala Leu Ser Glu Arg Leu Phe Ala Asn
                405                 410                 415

Leu Trp Gly Arg Leu Glu Gly Glu Glu Arg Leu Leu Trp Leu Tyr Arg
            420                 425                 430

Glu Val Asp Arg Pro Leu Ser Ala Val Leu Ala His Met Glu Ala Thr
        435                 440                 445

Gly Val Arg Leu Asp Val Ala Cys Leu Gln Ala Leu Ser Leu Glu Leu
450                 455                 460

Ala Glu Glu Ile Arg Arg Leu Glu Glu Glu Val Phe Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
            500                 505                 510

Arg Ser Thr Ser Ala Ala Ile Leu Glu Ala Leu Arg Glu Ala His Pro
        515                 520                 525

Ile Val Glu Lys Ile Leu Gln Tyr Arg Glu Leu Thr Lys Leu Lys Ser
530                 535                 540
```

Thr Tyr Ile Asp Pro Leu Pro Asp Leu Ile His Pro Arg Thr Gly Arg
545                 550                 555                 560

Leu His Thr Arg Phe Asn Gln Thr Ala Thr Ala Thr Gly Arg Leu Ser
        565                 570                 575

Ser Ser Asp Pro Asn Leu Gln Asn Ile Pro Val Arg Thr Pro Leu Gly
            580                 585                 590

Gln Arg Ile Arg Arg Ala Phe Ile Ala Glu Glu Gly Trp Leu Leu Val
        595                 600                 605

Val Leu Asp Tyr Ser Gln Ile Glu Leu Arg Val Leu Ala His Leu Ser
        610                 615                 620

Gly Asp Glu Asn Leu Thr Arg Val Phe Gln Glu Gly Arg Asp Ile His
625                 630                 635                 640

Thr Glu Thr Ala Ser Trp Met Phe Gly Val Pro Arg Glu Ala Val Asp
                645                 650                 655

Pro Leu Met Arg Arg Ala Ala Lys Thr Ile Asn Phe Gly Val Leu Tyr
            660                 665                 670

Gly Met Ser Ala His Arg Leu Ser Gln Glu Leu Ala Ile Pro Tyr Glu
        675                 680                 685

Glu Ala Gln Ala Phe Ile Glu Arg Tyr Phe Gln Ser Phe Pro Lys Val
        690                 695                 700

Arg Ala Trp Ile Glu Lys Thr Leu Glu Glu Gly Arg Lys Arg Gly Tyr
705                 710                 715                 720

Val Glu Thr Leu Phe Gly Arg Arg Arg Tyr Val Pro Asp Leu Asn Ala
                725                 730                 735

Arg Val Lys Ser Val Arg Glu Ala Ala Glu Arg Met Ala Phe Asn Met
            740                 745                 750

Pro Val Gln Gly Thr Ala Ala Asp Leu Met Lys Leu Ala Met Val Lys
        755                 760                 765

Leu Phe Pro Arg Leu Arg Glu Met Gly Ala Arg Met Leu Leu Gln Val
        770                 775                 780

His Asp Glu Leu Leu Leu Glu Ala Pro Gln Ala Arg Ala Glu Glu Val
785                 790                 795                 800

Ala Ala Leu Ala Lys Glu Ala Met Glu Lys Ala Tyr Pro Leu Ala Val
                805                 810                 815

Pro Leu Glu Val Lys Val Gly Ile Gly Glu Asp Trp Leu Ser Ala Lys
            820                 825                 830

Glu

<210> SEQ ID NO 77
<211> LENGTH: 2502
<212> TYPE: DNA
<213> ORGANISM: Artificial sequence
<220> FEATURE:
<223> OTHER INFORMATION: Mutant Taq polymerase coding sequence

<400> SEQUENCE: 77
atggcgatgc ttccctctct tgagcccaaa ggccgggtcc tcctggtgga cggccaccac    60
ctggcctacc gcaccttctt cgccctgaag ggcctcatca cgagccgggg cgaaccggtg   120
caggcggtct acggtttcgc caagagcctc ctcaaggccc tgaaggagga cgggtacaag   180
gccgtcttcg tggtctttga cgccaaggcc cctccttcc gccacgaggc ctacgaggcc   240
tacaaggcgg ggagggcccc gacccccgag gacttccccc ggcagctcgc cctcatcaag   300
gagctggtgg acctcctggg gtttacccgc ctcgaggtcc aaggctacga ggcggacgac   360
gtcctcgcca ccctggccaa gaaggcggaa aagaagggt acgaggtgcg catcctcacc   420

```
gccgaccggg acctctacca gctcgtctcc gaccgcgtcg ccgtcctcca ccccgagggc    480
cacctcatca ccccggagtg gctttgggag aagtacggcc tcaggccgga gcagtgggtg    540
gacttccgcg ccctcgtggg ggaccccctcc gacaacctcc ccggggtcaa gggcatcggg    600
gagaagaccg ccctcaagct cctcaaggag tggggaagcc tggaaaatct cctcaagaac    660
ctggatcggg taaagccgga aaacgtccgg gagaagatca aggcccacct ggaagacctc    720
aggctctcct tggagctctc ccgggtgcgt accgacctcc cctggaggt ggacctcgcc    780 caggggcggg agcccgaccg ggaagggctt agggccttcc tggagaggct ggagttcggc    840
agcctcctcc atgagttcgg ccttctggaa agccccaagg ccctggagga ggcccctgg    900 ccccgccgg aagggcctt cgtgggcttt gtgctttccc gcaaggagcc catgtgggcc    960
gatcttctgg ccctggccgc cgccaggggt ggtcgggtcc accgggcccc cgagccttat   1020
aaagccctca gggacttgaa ggaggcgcgg gggcttctcg ccaaagacct gagcgttctg   1080
gccctaaggg aaggccttgg cctcccgccc ggcgacgacc ccatgctcct cgcctacctc   1140 ctggacccctt ccaacaccac ccccgagggg gtggcccggc gctacggcgg ggagtggacg   1200
gaggaggcgg gggagcgggc cgcccttccc gagaggctct cgccaacct gtggggggagg   1260 cttgagggg aggagaggct cctttggctt taccgggagg tggataggcc cctttccgct   1320
gtcctggccc acatggaggc cacaggggtg cgcctggacg tggcctatct cagggccttg   1380
tccctggagg tggccgagga gatcgcccgc ctcgaggccg aggtcttccg cctggccggc   1440 cacccttca acctcaactc ccgggaccag ctggaaaggg tcctctttga cgagttaggg   1500
cttccccgca tcggcaagac ggagaggacc ggcaagcgct ccaccagcgc cgccgtcctg   1560
gaggccctcc gcgaggccca cccatcgtg gagaagatcc tgcagtaccg ggagctcacc   1620
aagctgaaga gcacctacat tgaccccttg ccggacctca tcccccag acgggccgc   1680 ctccacaccc gcttcaacca gacgcccacg gccacgggca ggctaagtag ctccgatccc   1740
aacctccaga acatccccgt ccgcaccccg cttgggcaga ggatccgccg ggccttcatc   1800
gccgaggagg ggtggctatt ggtgcccctg gactatagcc agatagagct cagggtgctg   1860
gcccacctct ccggcgacga aacctgatc cgggtcttcc aggaggggcg ggacatccac   1920
acggagaccg ccagctggat gttcggtgtc cccccggagg ccgtggaccc cctgatgcgc   1980
cgggcggcca agacggtgaa cttcggcgtc tctacggca tgtccgccca taggctctcc   2040
caggagcttt ccatcccta cgaggaggcg gtggccttta tagagcgcta cttccaaagc   2100
ttccccaagg tgcgggcctg gatagaaaag acctgggagg aggggaggaa gcgggcgctac   2160 gtggaaaccc tcttcggaag aaggcgctac gtgcccgacc tcaacgcccg ggtgaagagc   2220
gtcagggagg ccgcggagcg catggccttc aacatgcccg tccagggcac cgccgccgac   2280
ctcatgaagc tcgccatggt gaagctcttc ccccgcctcc gggagatggg ggcccgcatg   2340
ctcctccagg tccacgacga gctcctcctg gaggccccc aagcgcgggc cgaggaggtg   2400
gcggctttgg ccaaggaggc catggagaag gcctatcccc tcgccgtacc cctggaggtg   2460
gaggtgggga tcggggagga ctggctctcc gccaaggagt ga                       2502
```

<210> SEQ ID NO 78
<211> LENGTH: 833
<212> TYPE: PRT
<213> ORGANISM: Artificial sequence
<220> FEATURE:
<223> OTHER INFORMATION: Mutant taq polymerase

```
<400> SEQUENCE: 78

Met Ala Met Leu Pro Leu Phe Glu Pro Lys Gly Arg Val Leu Leu Val
1               5                   10                  15

Asp Gly His His Leu Ala Tyr Arg Thr Phe Ala Leu Lys Gly Leu
            20                  25                  30

Ile Thr Ser Arg Gly Glu Pro Val Gln Ala Val Tyr Gly Phe Ala Lys
        35                  40                  45

Ser Leu Leu Lys Ala Leu Lys Glu Asp Gly Tyr Lys Ala Val Phe Val
    50                  55                  60

Val Phe Asp Ala Lys Ala Pro Ser Phe Arg His Glu Ala Tyr Glu Ala
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Phe Thr Arg Leu Glu
            100                 105                 110

Val Gln Gly Tyr Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Asp
    130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asp Asn
            180                 185                 190

Leu Pro Gly Val Lys Gly Ile Gly Glu Lys Thr Ala Leu Lys Leu Leu
        195                 200                 205

Lys Glu Trp Gly Ser Leu Glu Asn Leu Leu Lys Asn Leu Asp Arg Val
    210                 215                 220

Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
                245                 250                 255

Val Asp Leu Ala Gln Gly Arg Glu Pro Asp Arg Glu Gly Leu Arg Ala
            260                 265                 270

Phe Leu Glu Arg Leu Glu Phe Gly Ser Leu Leu His Glu Phe Gly Leu
        275                 280                 285

Leu Glu Ser Pro Lys Ala Leu Glu Glu Ala Pro Trp Pro Pro Pro Glu
    290                 295                 300

Gly Ala Phe Val Gly Phe Val Leu Ser Arg Lys Glu Pro Met Trp Ala
305                 310                 315                 320

Asp Leu Leu Ala Leu Ala Ala Ala Arg Gly Gly Arg Val His Arg Ala
                325                 330                 335

Pro Glu Pro Tyr Lys Ala Leu Arg Asp Leu Lys Glu Ala Arg Gly Leu
            340                 345                 350

Leu Ala Lys Asp Leu Ser Val Leu Ala Leu Arg Glu Gly Leu Gly Leu
        355                 360                 365

Pro Pro Gly Asp Asp Pro Met Leu Leu Ala Tyr Leu Leu Asp Pro Ser
    370                 375                 380

Asn Thr Thr Pro Glu Gly Val Ala Arg Arg Tyr Gly Gly Glu Trp Thr
385                 390                 395                 400

Glu Glu Ala Gly Glu Arg Ala Ala Leu Ser Glu Arg Leu Phe Ala Asn
                405                 410                 415
```

-continued

```
Leu Trp Gly Arg Leu Glu Gly Glu Arg Leu Leu Trp Leu Tyr Arg
            420                 425                 430

Glu Val Asp Arg Pro Leu Ser Ala Val Leu Ala His Met Glu Ala Thr
        435                 440                 445

Gly Val Arg Leu Asp Val Ala Tyr Leu Arg Ala Leu Ser Leu Glu Val
450                 455                 460

Ala Glu Glu Ile Ala Arg Leu Glu Ala Glu Val Phe Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Arg Thr Gly Lys
            500                 505                 510

Arg Ser Thr Ser Ala Ala Val Leu Glu Ala Leu Arg Glu Ala His Pro
        515                 520                 525

Ile Val Glu Lys Ile Leu Gln Tyr Arg Glu Leu Thr Lys Leu Lys Ser
    530                 535                 540

Thr Tyr Ile Asp Pro Leu Pro Asp Leu Ile His Pro Arg Thr Gly Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590

Gln Arg Ile Arg Arg Ala Phe Ile Ala Glu Glu Gly Trp Leu Leu Val
        595                 600                 605

Ala Leu Asp Tyr Ser Gln Ile Glu Leu Arg Val Leu Ala His Leu Ser
    610                 615                 620

Gly Asp Glu Asn Leu Ile Arg Val Phe Gln Glu Gly Arg Asp Ile His
625                 630                 635                 640

Thr Glu Thr Ala Ser Trp Met Phe Gly Val Pro Pro Glu Ala Val Asp
                645                 650                 655

Pro Leu Met Arg Arg Ala Ala Lys Thr Val Asn Phe Gly Val Leu Tyr
            660                 665                 670

Gly Met Ser Ala His Arg Leu Ser Gln Glu Leu Ser Ile Pro Tyr Glu
        675                 680                 685

Glu Ala Val Ala Phe Ile Glu Arg Tyr Phe Gln Ser Phe Pro Lys Val
    690                 695                 700

Arg Ala Trp Ile Glu Lys Thr Leu Glu Glu Gly Arg Lys Arg Gly Tyr
705                 710                 715                 720

Val Glu Thr Leu Phe Gly Arg Arg Arg Tyr Val Pro Asp Leu Asn Ala
                725                 730                 735

Arg Val Lys Ser Val Arg Glu Ala Ala Glu Arg Met Ala Phe Asn Met
            740                 745                 750

Pro Val Gln Gly Thr Ala Ala Asp Leu Met Lys Leu Ala Met Val Lys
        755                 760                 765

Leu Phe Pro Arg Leu Arg Glu Met Gly Ala Arg Met Leu Leu Gln Val
    770                 775                 780

His Asp Glu Leu Leu Leu Glu Ala Pro Gln Ala Arg Ala Glu Glu Val
785                 790                 795                 800

Ala Ala Leu Ala Lys Glu Ala Met Glu Lys Ala Tyr Pro Leu Ala Val
                805                 810                 815

Pro Leu Glu Val Glu Val Gly Ile Gly Glu Asp Trp Leu Ser Ala Lys
            820                 825                 830
```

Glu

<210> SEQ ID NO 79
<211> LENGTH: 2502
<212> TYPE: DNA
<213> ORGANISM: Artificial sequence
<220> FEATURE:
<223> OTHER INFORMATION: Mutant Taq polymerase coding sequence

<400> SEQUENCE: 79

```
atggcgatgc ttcccctctt tgagcccaag ggccgcgtcc tcctggtgga cggccaccac     60
ctggcctacc gcaccttctt cgccctgaag ggccccacca cgagccgggg cgaaccggtg    120
caggtggtct acggcttcgc caagagcctc ctcaaggccc tgaaggagga cgggtacaag    180
gccgtcttcg tggtctttga cgccaaggcc cctcattcc gccacaaggc ctacgaggcc     240
tacagggcgg ggagggcccc gacccccgag gacttccccc ggcagctcgc cctcatcaag    300
gagctggtgg acctcctggg gtttacccgc ctcgaggtcc ccggctacga ggcggacgac    360
gttctcgcca ccctggccaa gaaggcggaa aaggaggggt acgaggtgcg catcctcacc    420
gccgaccgcg cctctacca actcgtctct gaccgcgtcg ccgtcctcca ccccgagggc    480
cacctcatca ccccggagtg gctttgggag aagtacggcc tcaggccgga gcagtgggtg    540
gacttccgcg ccctcgtggg ggaccccctcc gacaacctcc ccggggtcaa gggcatcggg    600
gagaagaccg cccctcaagct cctcaaggag tggggaagcc tggaaaacct cctcaagaac    660
ctggaccggg taaagccaga aaacgtccgg gagaagatca ggccccacct ggaagacctc    720
aggctctcct ggagctctcc ccgggtgcgc accgacctcc cctggaggt ggacctcgcc     780
caggggcggg agcccgaccg ggagaggctt agggccttc tggagaggct tgagtttggc    840
ggcctcctcc acgagttcgg ccttctggaa agccccaagg ccctggagga ggcccctgg     900
cccccgccgg aaggggcctt cgtgggcttt gtgctttccc gcaaggagcc catgtgggcc    960
gatcttctgg ccctggccgc cgccaggggt ggtcggtcc accggccccc cgagccttat   1020
aaagccctca gggacttgaa ggaggcgcgg gggcttctcg ccaaagacct gagcgttctg   1080
gccctgaggg aaggccttgg cctcccgccc ggcgacgacc ccatgctcct cgcctacctc   1140
ctggaccctt ccaacaccac ccccgagggg gtggcccggc gctacggcgg ggagtggacg   1200
gaggaggcgg gggagcgggc cgcccttttcc gagaggctct cgccaacct gtggggagg   1260
cttgaggggg aggagaggct cctttggctt taccgggagg tggagaggcc ccttttccgtt   1320
gtcctggccc acatggaggc cacaggggtg cgcctggacg tggcctatct cagggccttg   1380
tccctggagg tggccgagga tcgcccgc ctcgaggccg aggtcttccg cctggccggc   1440
caccccttca acctcaactc ccgggaccag ctggaaaggg tcctctttga cgagctaggg   1500
cttccccgcca tcggcaagac ggagaagacc ggcaagcgct ccaccggcgc cgccgtcctg   1560
gaggccctcc gcgaggccca ccccatcgtg gagaagatcc tgcagtaccg ggagctcacc   1620
aagctgaaga gcacctacat tgacccttg ccggacctca tccacccag acgggccgc   1680
ctccacaccc gcttcaacca gacggccacg gccacgggca ggctaagtag ctccgacccc   1740
aacctcccag aacatccccgt ccgcacccg ctcgggcaga ggatccgcgc ggccttcatc   1800
gccgaggagg ggtggctatt ggtggtcctg gactatagcc agatagagct cagggtgctg   1860
gcccacctct ccggcgacga gaacctgatc cgggtcttcc aggagggggcg ggacatccac   1920
acggaaaccg ccagctggat gttcggcgtc cccggggag ccgtgaccc ctaatgcgc     1980
cgggcggcca agaccatcaa cttcgggt ctctacggca tgtcggccca ccgcctctcc   2040
```

```
caggagctag ccatcccttc cgaggaggcc caggccttca ttgagcgcta cattcagagc    2100
ttccccaagg tgcgggcctg gattgagaag accctggagg agggcaggag gcggggtac     2160 gtggagaccc tcttcggccg ccgtcgctac gtgccagacc tagaggcccg ggtgaagagc    2220
gtgcgggagg cggccgagcg catggccttc aacatgcccg tccagggcac cgccgccgac   2280
ctcatgaagc tggctatggt gaagctcttc cccaggctgg aagaaacggg ggccaggatg    2340
ctccttcagg tccacgacga gctggtcctc gaggccccaa agagagggc ggaggccgtg    2400 gcccggctgg ccaaggaggc catggagggg gtgtatcccc tggccgtgcc cctggaggtg    2460
gaggtgggga tagggagga ctggctctcc gccaaggagt ga                        2502
```

<210> SEQ ID NO 80
<211> LENGTH: 833
<212> TYPE: PRT
<213> ORGANISM: Artificial sequence
<220> FEATURE:
<223> OTHER INFORMATION: Mutant Taq polymerase

<400> SEQUENCE: 80

```
Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Pro
            20                  25                  30

Thr Thr Ser Arg Gly Glu Pro Val Gln Val Val Tyr Gly Phe Ala Lys
        35                  40                  45

Ser Leu Leu Lys Ala Leu Lys Glu Asp Gly Tyr Lys Ala Val Phe Val
    50                  55                  60

Val Phe Asp Ala Lys Ala Pro Ser Phe Arg His Lys Ala Tyr Glu Ala
65                  70                  75                  80

Tyr Arg Ala Gly Arg Ala Pro Thr Pro Glu Asp Phe Pro Arg Gln Leu
                85                  90                  95

Ala Leu Ile Lys Glu Leu Val Asp Leu Leu Gly Phe Thr Arg Leu Glu
            100                 105                 110

Val Pro Gly Tyr Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Gly
    130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asp Asn
            180                 185                 190

Leu Pro Gly Val Lys Gly Ile Gly Glu Lys Thr Ala Leu Lys Leu Leu
        195                 200                 205

Lys Glu Trp Gly Ser Leu Glu Asn Leu Leu Lys Asn Leu Asp Arg Val
    210                 215                 220

Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
                245                 250                 255

Val Asp Leu Ala Gln Gly Arg Glu Pro Asp Arg Glu Arg Leu Arg Ala
            260                 265                 270

Phe Leu Glu Arg Leu Glu Phe Gly Gly Leu Leu His Glu Phe Gly Leu
```

```
                275                 280                 285
Leu Glu Ser Pro Lys Ala Leu Glu Glu Ala Pro Trp Pro Pro Glu
            290                 295                 300
Gly Ala Phe Val Gly Phe Val Leu Ser Arg Lys Glu Pro Met Trp Ala
305                 310                 315                 320
Asp Leu Leu Ala Leu Ala Ala Arg Gly Arg Val His Arg Ala
                325                 330                 335
Pro Glu Pro Tyr Lys Ala Leu Arg Asp Leu Lys Glu Ala Arg Gly Leu
            340                 345                 350
Leu Ala Lys Asp Leu Ser Val Leu Ala Leu Arg Glu Gly Leu Gly Leu
            355                 360                 365
Pro Pro Gly Asp Asp Pro Met Leu Leu Ala Tyr Leu Leu Asp Pro Ser
370                 375                 380
Asn Thr Thr Pro Glu Gly Val Ala Arg Arg Tyr Gly Gly Glu Trp Thr
385                 390                 395                 400
Glu Glu Ala Gly Glu Arg Ala Ala Leu Ser Glu Arg Leu Phe Ala Asn
                405                 410                 415
Leu Trp Gly Arg Leu Glu Gly Glu Arg Leu Leu Trp Leu Tyr Arg
            420                 425                 430
Glu Val Glu Arg Pro Leu Ser Val Val Leu Ala His Met Glu Ala Thr
            435                 440                 445
Gly Val Arg Leu Asp Val Ala Tyr Leu Arg Ala Leu Ser Leu Glu Val
450                 455                 460
Ala Glu Glu Ile Ala Arg Leu Glu Ala Glu Val Phe Arg Leu Ala Gly
465                 470                 475                 480
His Pro Phe Asn Leu Asn Ser Arg Asp Gln Leu Glu Arg Val Leu Phe
                485                 490                 495
Asp Glu Leu Gly Leu Pro Ala Ile Gly Lys Thr Glu Lys Thr Gly Lys
            500                 505                 510
Arg Ser Thr Gly Ala Ala Val Leu Glu Ala Leu Arg Glu Ala His Pro
            515                 520                 525
Thr Val Glu Lys Ile Leu Gln Tyr Arg Glu Leu Thr Lys Leu Lys Ser
            530                 535                 540
Thr Tyr Ile Asp Pro Leu Pro Asp Leu Ile His Pro Arg Thr Gly Arg
545                 550                 555                 560
Leu His Thr Arg Phe Asn Gln Thr Ala Thr Ala Thr Gly Arg Leu Ser
                565                 570                 575
Ser Ser Asp Pro Asn Leu Gln Asn Ile Pro Val Arg Thr Pro Leu Gly
            580                 585                 590
Gln Arg Ile Arg Arg Ala Phe Ile Ala Glu Glu Gly Trp Leu Leu Val
            595                 600                 605
Val Leu Asp Tyr Ser Gln Ile Glu Leu Arg Val Leu Ala His Leu Ser
            610                 615                 620
Gly Asp Glu Asn Leu Ile Arg Val Phe Gln Glu Gly Arg Asp Ile His
625                 630                 635                 640
Thr Glu Thr Ala Ser Trp Met Phe Gly Val Pro Arg Glu Ala Val Asp
                645                 650                 655
Pro Leu Met Arg Arg Ala Ala Lys Thr Ile Asn Phe Gly Val Leu Tyr
            660                 665                 670
Gly Met Ser Ala His Arg Leu Ser Gln Glu Leu Ala Ile Pro Tyr Glu
            675                 680                 685
Glu Ala Gln Ala Phe Ile Glu Arg Tyr Ile Gln Ser Phe Pro Lys Val
            690                 695                 700
```

```
Arg Ala Trp Ile Glu Lys Thr Leu Glu Glu Gly Arg Arg Arg Gly Tyr
705                 710                 715                 720
Val Glu Thr Leu Phe Gly Arg Arg Tyr Val Pro Asp Leu Glu Ala
            725                 730                 735
Arg Val Lys Ser Val Arg Glu Ala Ala Glu Arg Met Ala Phe Asn Met
        740                 745                 750
Pro Val Gln Gly Thr Ala Ala Asp Leu Met Lys Leu Ala Met Val Lys
    755                 760                 765
Leu Phe Pro Arg Leu Glu Glu Thr Gly Ala Arg Met Leu Leu Gln Val
770                 775                 780
His Asp Glu Leu Val Leu Glu Ala Pro Lys Glu Arg Ala Glu Ala Val
785                 790                 795                 800
Ala Arg Leu Ala Lys Glu Ala Met Glu Gly Val Tyr Pro Leu Ala Val
            805                 810                 815
Pro Leu Glu Val Glu Val Gly Ile Gly Glu Asp Trp Leu Ser Ala Lys
        820                 825                 830
Glu

<210> SEQ ID NO 81
<211> LENGTH: 2505
<212> TYPE: DNA
<213> ORGANISM: Artificial sequence
<220> FEATURE:
<223> OTHER INFORMATION: Mutant Taq polymerase coding sequence

<400> SEQUENCE: 81
atgcgtggta tgcttcctct ttttgagccc aagggccgcg tcctcctggt ggacggccac     60
cacctggcct accgcacctt cttcgccctg aagggcccca ccacgagccg gggcgaaccg    120
gtgcaggcgg tctacggctt cgccaagagc ctcctcaagg ccctgaagga ggacgggtac    180
aaggccgcct tcgtggtctt tgacgccaag gccccctcct tcgccacga ggcctacgag    240 gcctacaagg cggggagggc cccgaccccc gaggacttcc cccggcagct cgccctcatc    300
aaggagctgg tggaccttct ggggtttacc cgcctcgagg tcctggcta cgaggcggac    360 gacgtcctcg ccaccctggc caagaaggcg aaaaggagg ggtacgaggt gcgcatcctc    420
accgccgacc gcgacctcta ccaactcgtc tccgaccgcg tcgccgtcct ccaccccgag    480
ggccacctca tcccccgga gtggctttgg agaagtacg gctcaggcc ggagcagtgg    540 gtggacttcc gcgccctcgt gggggacccc tccgacaacc tccccggggt caagggcatc    600
ggggagaaga ccgccctcaa gctcctcaag gagtggggaa gcctggaaaa cctcctcaag    660
aacctggacc gggtaaagcc agaaaacgtc cgggagaaga tcaaggccca cctggaagac    720
ctcaggctct ccttggagct ctcccggggtg cgcaccgacc tccccctgga ggtggacctc    780
gcccaggggc gggagcccga ccgggagagg cttagggcct ttctggagag gcttgagttt    840
ggcggcctcc tccacgagtt cggccttctg gaaagcccca aggccctgga ggaggccccc    900
tggcccccgc cggaaggggc cttcgtgggc tttgtgcttt cccgcaagga gcccatgtgg    960
gccgatcttc tggccctggc cgccgccagg ggtggtcggg tccaccgggc cccgagcct   1020 tataaagccc tcagggactt gaaggaggcg cgggggcttc tcgccaaaga cctgagcgtt   1080
ctggccctaa gggaaggcct tggcctcccg cccggcgacg accccatgct cctcgcctac   1140
ctcctggacc cttccaacac cacccccgag ggggtggccc ggcgctacgg cggggagtgg   1200
acggaggagg cggggagcg gccgccctt tccgagaggc tcttcgccaa cctgtgggg   1260
```

```
aggcttgagg gggaggagag gctcctttgg ctttaccggg aggtggatag gcccctttcc    1320
gctgtcctgg cccacatgga ggccacaggg gtacggctgg acgtggcctg cctgcaggcc    1380
ctttccctgg agcttgcgga ggagatccgc cgcctcgagg aggaggtctt ccgcttggcg    1440
ggccacccct tcaacctcaa ctcccgggac cagctggaaa gggtcctctt tgacgagcta    1500
gggcttcccg ccatcggcaa gacggagaag accggcaagc gctccaccag cgccgccatc    1560
ctggaggccc tccgcgaggc ccaccccatc gtggagaaga tcctgcagta ccggagctc    1620
accaagctga gagcaccta cattgacccc ttgccggacc tcatccaccc caggacgggc    1680
cgcctccaca cccgcttcaa ccagacggcc acggccacgg gcaggctaag tagctccgat    1740
cccaacctcc agaacatccc cgtccgcacc ccgctcgggc agaggatccg ccgggccttc    1800
atcgccgagg aggggtggct attggtggtc ctggactata gccagataga gctcaggg     1860
ctggcccacc tctccggcga cgagaacctg acccgggtct tccaggaggg gcgggacatc    1920
cacacggaaa ccgccagctg gatgttcggc gtcccccggg aggccgtgga cccctgatg    1980
cgccgggcgg ccaagaccat caacttcggg gttctctacg gcatgtcggc ccaccgcctc    2040
tcccaggagc tggccatccc ttacgaggag gcccaggcct tcatagagcg ctacttccaa    2100
agcttccccca aggtgcgggc ctggatagaa aagaccctgg aggaggggag gaagcggggc    2160
tacgtggaaa ccctcttcgg aagaaggcgc tacgtgcccg acctcaacgc ccgggtgaag    2220
agtgtcaggg aggccgcgga gcgcatggcc ttcaacatgc ccgtccaggg caccgccgcc    2280
gaccttatga agctcgccat ggtgaagctc ttcccccgcc tccgggagat ggggggcccgc   2340
atgctcctcc aggtccacga cgagctcctc ctggaggccc ccaagcgcg gcccgaggag     2400
gtggcggctt tggccaagga ggccatggag aaggcctatc ccctcgccgt accctggag    2460
gtgaaggtgg ggatcgggga ggactggctc tccgccaagg agtga                    2505
```

<210> SEQ ID NO 82
<211> LENGTH: 834
<212> TYPE: PRT
<213> ORGANISM: Artificial sequence
<220> FEATURE:
<223> OTHER INFORMATION: Mutant Taq polymerase

<400> SEQUENCE: 82

```
Met Arg Gly Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Pro Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Ala Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140
```

-continued

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Arg Leu Arg
            260                 265                 270

Ala Phe Leu Glu Arg Leu Glu Phe Gly Ser Leu Leu His Glu Phe Gly
        275                 280                 285

Leu Leu Glu Ser Pro Lys Ala Leu Glu Glu Ala Pro Trp Pro Pro Pro
    290                 295                 300

Glu Gly Ala Phe Val Gly Phe Val Leu Ser Arg Lys Glu Pro Met Trp
305                 310                 315                 320

Ala Asp Leu Leu Ala Leu Ala Ala Ala Arg Gly Gly Arg Val His Arg
                325                 330                 335

Ala Pro Glu Pro Tyr Lys Ala Leu Arg Asp Leu Lys Glu Ala Arg Gly
            340                 345                 350

Leu Leu Ala Lys Asp Leu Ser Val Leu Ala Leu Arg Glu Gly Leu Gly
        355                 360                 365

Leu Pro Pro Gly Asp Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Glu Ala Gly Glu Arg Ala Ala Leu Ser Glu Arg Leu Phe Ala
                405                 410                 415

Asn Leu Trp Gly Arg Leu Glu Gly Glu Glu Arg Leu Leu Trp Leu Tyr
            420                 425                 430

Arg Glu Val Asp Arg Pro Leu Ser Ala Val Leu Ala His Met Glu Ala
        435                 440                 445

Thr Gly Val Arg Leu Asp Val Ala Cys Leu Gln Ala Leu Ser Leu Glu
    450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Gly Leu Pro Ala Ile Gly Lys Thr Glu Lys Thr Gly
            500                 505                 510

Lys Arg Ser Thr Ser Ala Ala Ile Leu Glu Ala Leu Arg Glu Ala His
        515                 520                 525

Pro Ile Val Glu Lys Ile Leu Gln Tyr Arg Glu Leu Thr Lys Leu Lys
    530                 535                 540

Ser Thr Tyr Ile Asp Pro Leu Pro Asp Leu Ile His Pro Arg Thr Gly
545                 550                 555                 560

Arg Leu His Thr Arg Phe Asn Gln Thr Ala Thr Ala Thr Gly Arg Leu

```
                565                 570                 575
Ser Ser Ser Asp Pro Asn Leu Gln Asn Ile Pro Val Arg Thr Pro Leu
            580                 585                 590

Gly Gln Arg Ile Arg Arg Ala Phe Ile Ala Glu Gly Trp Leu Leu
        595                 600                 605

Val Val Leu Asp Tyr Ser Gln Ile Glu Leu Arg Val Leu Ala His Leu
        610                 615                 620

Ser Gly Asp Glu Asn Leu Thr Arg Val Phe Gln Glu Gly Arg Asp Ile
625                 630                 635                 640

His Thr Glu Thr Ala Ser Trp Met Phe Gly Val Pro Arg Glu Ala Val
                645                 650                 655

Asp Pro Leu Met Arg Arg Ala Ala Lys Thr Ile Asn Phe Gly Val Leu
                660                 665                 670

Tyr Gly Met Ser Ala His Arg Leu Ser Gln Glu Leu Ala Ile Pro Tyr
            675                 680                 685

Glu Glu Ala Gln Ala Phe Ile Glu Arg Tyr Phe Gln Ser Phe Pro Lys
        690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
                725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
        755                 760                 765

Lys Leu Phe Pro Arg Leu Arg Glu Met Gly Ala Arg Met Leu Leu Gln
770                 775                 780

Val His Asp Glu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Lys Val Gly Ile Gly Glu Asp Trp Leu Ser Ala
            820                 825                 830

Lys Glu

<210> SEQ ID NO 83
<211> LENGTH: 2502
<212> TYPE: DNA
<213> ORGANISM: Artificial sequence
<220> FEATURE:
<223> OTHER INFORMATION: Mutant Taq polymerase coding sequence

<400> SEQUENCE: 83
atggcgatgc ttccctctct tgagcccaag ggccgtgtcc tcctggtgga cggccaccac      60
ctggcctacc gcaccttctt cgccctgaag ggccccacca cgagccgggg cgaaccggtg     120
caggtggtct acggcttcgc caagagcctc ctcaaggccc tgaaggagga cgggtacaag     180
gccgtcttcg tggtctttga cgccaaggcc cccccattcc gccacaaggc ctacgaggcc     240 tacaggcgg ggagggcccc gaccccgag gacttccccc ggcagctcgc cctcatcaag     300
gagctggtgg acctcctggg gtttacccgc tcgaggtcc ccggctacga ggcggacgac     360
gttctcgcca ccctggccaa gaaggcggaa aaggagggt acgaggtgcg catcctcacc     420
gccgaccgcg gctctacca actcgtgtct gaccgcgtcg ccgtcctcca ccccgagggc     480 caccctcatca ccccggagtg gctttgggag aagtacggcc tcaggccgga gcagtgggtg     540
```

```
gacttccgcg ccctcgtggg ggaccccctcc gacaacctcc ccggggtcaa gggcatcggg      600
gagaagaccg ccctcaagct cctcaaggag tggggaagcc tggaaaacct cctcaagaac      660
ctggaccggg taaagccaga aaacgtccgg gagaagatca aggcccacct ggaagatctc      720
aggctctcct tggagctctc ccgggtgcgc accgacctcc cctggaggt ggacctcgcc       780 caggggcggg agcccgaccg ggaggggctt agggcctttc tggagaggct gagtttggc       840 agcctcctcc acgagttcgg ccttctggaa agccccaagg ccctggagga ggcccctgg       900 ccccccgccgg aagggccctt cgtgggcttt gtgctttccc gcaaggagcc catgtgggcc    960
gatcttctgg ccctggccgc cgccaggggt ggtcgagtcc accgggcccc cgagccttat     1020
aaagccctca gggacctgaa ggaggcgcgg gggcttctcg ccaaagacct gagcgttctg     1080
gccctaaggg aaggccttgg cctcccgccc ggcgacgacc ccatgctcct cgcctacctc     1140
ctggaccctt ccaacaccac ccccgagggg gtggcccggc gctacggcgg ggagtggacg     1200
gaggaggcgg gggagcgggc cgccctttcc gagaggctct cgccaacct gtggggagg      1260 cttgaggggg aggagaggct cctttggctt taccgggagg tggagaggcc ccctttccgct    1320 gtcctggccc acatggaggc cacggggtg cgcctggacg tggcctatct cagggccttg     1380
tccctggagg tggccgagga gatcgcccgc ctcgaggccg aggtcttccg cctggccggc     1440
caccccttca acctcaactc ccgggaccag ctggaaatgg tgctctttga cgagcttagg     1500
cttcccgcct tggggaagac gcaaaagacg ggcaagcgct ccaccagcgc cgccgtcctg     1560 gaggcccctcc gcgaggccca ccccatcgtg gagaagatcc tgcagtaccg ggagctcacc    1620
aagctgaaga gcacctacat tgacccctgg tcggacctca tccaccccag gacggggcgc    1680
ctccacaccc gcttcaacca gacggccacg gccacgggca ggctaagtag ctccgatccc    1740
aacctccaga acatccccgt ccgcacccccg cttgggcaga ggatccgccg ggccttcatc    1800
gccgaggagg ggtggctact ggtggtcctg gactatagcc agatagagct cagggtgctg    1860
gcccacctct ccggcgacga aaacctgatc agggtcttcc aggagggggcg ggacatccac    1920 acggagaccg ccagctggat gttcggcgtc cccggggagg ccgtggaccc cctgatgcgc     1980
cgggcggcca agaccatcaa cttcgggtc ctctacggca tgtcggccca ccgcctctcc      2040
caggagctag ccatcccctta cgaggaggcc caggccttca ttgagcgcta ctttcagagc    2100 ttcccccaagg tgcgggcctg gattgagaag accctggagg agggcaggag gcgggggtac    2160
gtggagaccc tcttcggccg ccgccgctac gtgccagacc tagaggcccg ggtgaagagc    2220
gtgcgggagg cggccgagcg catggccttc aacatgcccg tccagggcac cgccgccgac     2280
ctcatgaagc tggctatggt gaagctcttc cccaggctgg aggaaatggg ggccaggatg    2340
ctccttcagg tccacgacga gctggtcctc gaggccccaa aagagagggc ggaggccgtg     2400
gcccggctgg ccaaggaggt catggaggggg gtgtatcccc tggccgtgcc cctggaggtg    2460
gaggtgggga tagggagga ctggctctcc gccaaggagt ga                         2502
```

<210> SEQ ID NO 84
<211> LENGTH: 833
<212> TYPE: PRT
<213> ORGANISM: Artificial sequence
<220> FEATURE:
<223> OTHER INFORMATION: Mutant Taq polymerase

<400> SEQUENCE: 84

Met Ala Met Leu Pro Leu Phe Glu Pro Lys Gly Arg Val Leu Leu Val
1               5                   10                  15

```
Asp Gly His His Leu Ala Tyr Arg Thr Phe Phe Ala Leu Lys Gly Pro
                20                  25                  30

Thr Thr Ser Arg Gly Glu Pro Val Gln Val Val Tyr Gly Phe Ala Lys
            35                  40                  45

Ser Leu Leu Lys Ala Leu Lys Glu Asp Gly Tyr Lys Ala Val Phe Val
50                  55                  60

Val Phe Asp Ala Lys Ala Pro Pro Phe Arg His Lys Ala Tyr Glu Ala
65                  70                  75                  80

Tyr Arg Ala Gly Arg Ala Pro Thr Pro Glu Asp Phe Pro Arg Gln Leu
                85                  90                  95

Ala Leu Ile Lys Glu Leu Val Asp Leu Leu Gly Phe Thr Arg Leu Glu
            100                 105                 110

Val Pro Gly Tyr Glu Ala Asp Asp Val Leu Ala Thr Leu Ala Lys Lys
        115                 120                 125

Ala Glu Lys Glu Gly Tyr Gly Val Arg Ile Leu Thr Ala Asp Arg Gly
    130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asp Asn
            180                 185                 190

Leu Pro Gly Val Lys Gly Ile Gly Glu Lys Thr Ala Leu Lys Leu Leu
        195                 200                 205

Lys Glu Trp Gly Ser Leu Glu Asn Leu Leu Lys Asn Leu Asp Arg Val
    210                 215                 220

Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
                245                 250                 255

Val Asp Leu Ala Gln Gly Arg Glu Pro Asp Arg Glu Gly Leu Arg Ala
            260                 265                 270

Phe Leu Glu Arg Leu Glu Phe Gly Ser Leu Leu His Glu Phe Gly Leu
        275                 280                 285

Leu Glu Ser Pro Lys Ala Leu Glu Glu Ala Pro Trp Pro Pro Pro Glu
    290                 295                 300

Gly Ala Phe Val Gly Phe Val Leu Ser Arg Lys Glu Pro Met Trp Ala
305                 310                 315                 320

Asp Leu Leu Ala Leu Ala Ala Ala Arg Gly Gly Arg Val His Arg Ala
                325                 330                 335

Pro Glu Pro Tyr Lys Ala Leu Arg Asp Leu Lys Glu Ala Arg Gly Leu
            340                 345                 350

Leu Ala Lys Asp Leu Ser Val Leu Ala Leu Arg Glu Gly Leu Gly Leu
        355                 360                 365

Pro Pro Gly Asp Asp Pro Met Leu Leu Ala Tyr Leu Leu Asp Pro Ser
    370                 375                 380

Asn Thr Thr Pro Glu Gly Val Ala Arg Arg Tyr Gly Gly Glu Trp Thr
385                 390                 395                 400

Glu Glu Ala Gly Glu Arg Ala Ala Leu Ser Glu Arg Leu Phe Ala Asn
                405                 410                 415

Leu Trp Gly Arg Leu Glu Gly Glu Glu Arg Leu Leu Trp Leu Tyr Arg
            420                 425                 430
```

Glu Val Glu Arg Pro Leu Ser Ala Val Leu Ala His Met Glu Ala Thr
            435                 440                 445

Gly Val Arg Leu Asp Val Ala Tyr Leu Arg Ala Leu Ser Leu Glu Val
450                 455                 460

Ala Glu Glu Ile Ala Arg Leu Glu Ala Glu Val Phe Arg Leu Ala Gly
465                 470                 475                 480

His Pro Phe Asn Leu Asn Ser Arg Asp Gln Leu Glu Met Val Leu Phe
                485                 490                 495

Asp Glu Leu Arg Leu Pro Ala Leu Gly Lys Thr Gln Lys Thr Gly Lys
            500                 505                 510

Arg Ser Thr Ser Ala Ala Val Leu Glu Ala Leu Arg Glu Ala His Pro
            515                 520                 525

Ile Val Glu Lys Ile Leu Gln Tyr Arg Glu Leu Thr Lys Leu Lys Ser
            530                 535                 540

Thr Tyr Ile Asp Pro Leu Ser Asp Leu Ile His Pro Arg Thr Gly Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590

Gln Arg Ile Arg Arg Ala Phe Ile Ala Glu Glu Gly Trp Leu Leu Val
            595                 600                 605

Val Leu Asp Tyr Ser Gln Ile Glu Leu Arg Val Leu Ala His Leu Ser
            610                 615                 620

Gly Asp Glu Asn Leu Ile Arg Val Phe Gln Glu Gly Arg Asp Ile His
625                 630                 635                 640

Thr Glu Thr Ala Ser Trp Met Phe Gly Val Pro Arg Glu Ala Val Asp
                645                 650                 655

Pro Leu Met Arg Arg Ala Ala Lys Thr Ile Asn Phe Gly Val Leu Tyr
            660                 665                 670

Gly Met Ser Ala His Arg Leu Ser Gln Glu Leu Ala Ile Pro Tyr Glu
            675                 680                 685

Glu Ala Gln Ala Phe Ile Glu Arg Tyr Phe Gln Ser Phe Pro Lys Val
            690                 695                 700

Arg Ala Trp Ile Glu Lys Thr Leu Glu Glu Gly Arg Arg Arg Gly Tyr
705                 710                 715                 720

Val Glu Thr Leu Phe Gly Arg Arg Arg Tyr Val Pro Asp Leu Glu Ala
                725                 730                 735

Arg Val Lys Ser Val Arg Glu Ala Ala Glu Arg Met Ala Phe Asn Met
            740                 745                 750

Pro Val Gln Gly Thr Ala Ala Asp Leu Met Lys Leu Ala Met Val Lys
            755                 760                 765

Leu Phe Pro Arg Leu Glu Glu Met Gly Ala Arg Met Leu Leu Gln Val
770                 775                 780

His Asp Glu Leu Val Leu Glu Ala Pro Lys Glu Arg Ala Glu Ala Val
785                 790                 795                 800

Ala Arg Leu Ala Lys Glu Val Met Glu Gly Val Tyr Pro Leu Ala Val
                805                 810                 815

Pro Leu Glu Val Glu Val Gly Ile Gly Glu Asp Trp Leu Ser Ala Lys
            820                 825                 830

Glu

<210> SEQ ID NO 85

<211> LENGTH: 2502
<212> TYPE: DNA
<213> ORGANISM: Artificial sequence
<220> FEATURE:
<223> OTHER INFORMATION: Mutant Taq polymerase coding sequence

<400> SEQUENCE: 85

| | | | | | |
|---|---|---|---|---|---|
| atggcgatgc | ttccctctct | tgagcccaaa | ggccgggtcc | tcctggtgga | cggccaccac | 60 |
| ctggcctacc | gcaccttctt | cgccctgaag | ggcctcacca | cgagccgggg | cgaaccggtg | 120 |
| caggtggtct | acggcttcgc | caagagcctc | ctcaaggccc | tgaaggagga | cgggtacaag | 180 |
| gccgtcttcg | tggtctttga | cgccaaggcc | cctcattcc | gccacaaggc | ctacgaggcc | 240 |
| tacagggcgg | ggagggcccc | gacccccag | gacttcccc | ggcagctcgc | cctcatcaag | 300 |
| gagctggtgg | acctcctggg | gtttacccgc | ctcgaggtcc | ccggctacga | ggcggacgac | 360 |
| gttctcgcca | ccctggccaa | gaaggcggaa | aaggaggggt | acgaggtgcg | catcctcacc | 420 |
| gccgaccgcg | cctctacca | actcgtctcc | gaccgcgtcg | ccgtcctcca | ccccgagggc | 480 |
| cacctcatca | ccccggagtg | gctttgggag | aagtacggcc | tcaggccgga | gcagtgggtg | 540 |
| gacttccgcg | ccctcgtggg | ggaccccctc | gacaacctcc | ccggggtcaa | gggcatcggg | 600 |
| gagaagaccg | ccctcaagct | cctcaaggag | tggggaagc | tggaaaacct | cctcaagaac | 660 |
| ctggaccggg | taaagccaga | aaacgtccgg | gagaagatca | aggcccacct | ggaagacctc | 720 |
| aggctctcct | tggagctctc | ccgggtgcgc | accgacctcc | cctggaggt | ggacctcgcc | 780 |
| caggggcggg | agcccgaccg | ggaggggctt | agggcctttc | tggagaggct | tgagtttggc | 840 |
| agcctcctcc | acgagttcgg | ccttctggaa | agccccaagg | ccctggagga | ggcccctgg | 900 |
| ccccgccgg | aagggggcctt | cgtgggcttt | gtgctttcc | gcaaggagcc | catgtgggcc | 960 |
| gatcttctgg | ccctggccgc | cgccaggggt | ggtcgagtcc | accaggcccc | cgagccttat | 1020 |
| aaagccctca | gggacctgaa | ggaggcgcgg | gggcttctcg | ccaaagacct | gagcgttctg | 1080 |
| gccctaaggg | aaggccttgg | cctcccgccc | ggcgacgacc | ccatgctcct | cgcctacctc | 1140 |
| ctggaccctt | ccaacaccac | ccccgagggg | gtggcccggc | gctacggcgg | ggagtggacg | 1200 |
| gaggaggcgg | gggagcgggc | cgcccttttcc | gagaggctct | tcgccaacct | gtggggagg | 1260 |
| cttgaggggg | aggagaggct | cctttggctt | taccgggagg | tggagaggcc | cctttccgct | 1320 |
| gtcctggccc | acatggagac | cacggggtg | cgcctggacg | tggcctatct | cagggccttg | 1380 |
| tccctggagg | tggccgagga | gatcgcccgc | ctcgaggccg | aggtcttccg | cctggccggc | 1440 |
| cgccccttca | acctcaactc | ccgagaccag | ctggaaaggg | tcctctttga | cgagctaggg | 1500 |
| cttcccgcca | tcggcaagac | ggagaagacc | ggcaagcgct | ccaccagcgc | cgccgtcctg | 1560 |
| gaggccctcc | gcgaggccca | ccccatcgtg | gagaagatcc | tgcagtaccg | ggagctcacc | 1620 |
| aagctgaaga | gcacctacat | tgaccccttg | ccggacctca | tccacccag | acgggccgc | 1680 |
| ctccacaccc | gcttcaacca | gacggccacg | gccacgggca | ggctaagtag | ctccgatccc | 1740 |
| aacctccaga | acatccccgt | ccgcaccccg | cttgggcaga | ggatccgccg | ggccttcatc | 1800 |
| gccgaggagg | ggtggctatt | ggtggtcctg | gactatagcc | agatggagct | cagggtgctg | 1860 |
| gcccacctct | ccggcgacga | gaacctgatc | agggtcttcc | aggaggggaa | ggacatccac | 1920 |
| acccagaccg | caagctggat | gttcggtgtc | ccccggagg | ccgtggaccc | cctgatgcgc | 1980 |
| cggggcgcca | agacggtgaa | cttcggcgtc | ctctacggca | tgtccgccca | taggctctcc | 2040 |
| caggagcttt | ccatcccta | cgaggaggcg | gtggccttca | tagagcgcta | cttccaaagc | 2100 |
| ttccccaagg | tgcgggcctg | gattgagaag | acctggagg | agggcaggag | gcggggtac | 2160 |

-continued

```
gtggagaccc tcttcggccg ccgccgctac gtgcccgacc tcaacgcccg gatgaagagc    2220
gtcagggggg ccgcggagcg catggccttc aacatgcccg tccagggcac cgccgccgac    2280
ctcatgaagc tcgccatggt gaagctcttc ccccgcctcc gggagatggg ggcccgcatg    2340
ctcctccagg tccacgacga gctcctcctg gaggccccc  aagcgcgggc cgaggaggtg    2400
gcggctttgg ccaaggaggc catggagaag gcctatcccc tcgccgtacc cctggaggtg    2460
gaggtgggga tcggggagga ctggctctcc gccaaggagt ga                      2502
```

<210> SEQ ID NO 86
<211> LENGTH: 833
<212> TYPE: PRT
<213> ORGANISM: Artificial sequence
<220> FEATURE:
<223> OTHER INFORMATION: Mutant Taq polymerase

<400> SEQUENCE: 86

```
Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Leu
            20                  25                  30

Thr Thr Ser Arg Gly Glu Pro Val Gln Val Val Tyr Gly Phe Ala Lys
        35                  40                  45

Ser Leu Leu Lys Ala Leu Lys Glu Asp Gly Tyr Lys Ala Val Phe Val
    50                  55                  60

Val Phe Asp Ala Lys Ala Pro Ser Phe Arg His Lys Ala Tyr Glu Ala
65                  70                  75                  80

Tyr Arg Ala Gly Arg Ala Pro Thr Pro Gln Asp Phe Pro Arg Gln Leu
                85                  90                  95

Ala Leu Ile Lys Glu Leu Val Asp Leu Leu Gly Phe Thr Arg Leu Glu
            100                 105                 110

Val Pro Gly Tyr Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Gly
    130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asp Asn
            180                 185                 190

Leu Pro Gly Val Lys Gly Ile Gly Glu Lys Thr Ala Leu Lys Leu Leu
        195                 200                 205

Lys Glu Trp Gly Ser Leu Glu Asn Leu Leu Lys Asn Leu Asp Arg Val
    210                 215                 220

Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
                245                 250                 255

Val Asp Leu Ala Gln Gly Arg Glu Pro Asp Arg Glu Gly Leu Arg Ala
            260                 265                 270

Phe Leu Glu Arg Leu Glu Phe Gly Ser Leu Leu His Glu Phe Gly Leu
        275                 280                 285

Leu Glu Ser Pro Lys Ala Leu Glu Glu Ala Pro Trp Pro Pro Pro Glu
    290                 295                 300
```

```
Gly Ala Phe Val Gly Phe Val Leu Ser Arg Lys Glu Pro Met Trp Ala
305                 310                 315                 320

Asp Leu Leu Ala Leu Ala Ala Arg Gly Arg Val His Gln Ala
                325                 330                 335

Pro Glu Pro Tyr Lys Ala Leu Arg Asp Leu Lys Glu Ala Arg Gly Leu
            340                 345                 350

Leu Ala Lys Asp Leu Ser Val Leu Ala Leu Arg Glu Gly Leu Gly Leu
                355                 360                 365

Pro Pro Gly Asp Asp Pro Met Leu Leu Ala Tyr Leu Leu Asp Pro Ser
370                 375                 380

Asn Thr Thr Pro Glu Gly Val Ala Arg Arg Tyr Gly Gly Glu Trp Thr
385                 390                 395                 400

Glu Glu Ala Gly Glu Arg Ala Ala Leu Ser Glu Arg Leu Phe Ala Asn
                405                 410                 415

Leu Trp Gly Arg Leu Glu Gly Glu Arg Leu Leu Trp Leu Tyr Arg
                420                 425                 430

Glu Val Glu Arg Pro Leu Ser Ala Val Leu Ala His Met Glu Thr Thr
                435                 440                 445

Gly Val Arg Leu Asp Val Ala Tyr Leu Arg Ala Leu Ser Leu Glu Val
450                 455                 460

Ala Glu Glu Ile Ala Arg Leu Glu Ala Glu Val Phe Arg Leu Ala Gly
465                 470                 475                 480

Arg Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
                500                 505                 510

Arg Ser Thr Ser Ala Ala Val Leu Glu Ala Leu Arg Glu Ala His Pro
                515                 520                 525

Ile Val Glu Lys Ile Leu Gln Tyr Arg Glu Leu Thr Lys Leu Lys Ser
                530                 535                 540

Thr Tyr Ile Asp Pro Leu Pro Asp Leu Ile His Pro Arg Thr Gly Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
                580                 585                 590

Gln Arg Ile Arg Arg Ala Phe Ile Ala Glu Glu Gly Trp Leu Leu Val
                595                 600                 605

Val Leu Asp Tyr Ser Gln Met Glu Leu Arg Val Leu Ala His Leu Ser
                610                 615                 620

Gly Asp Glu Asn Leu Ile Arg Val Phe Gln Glu Gly Lys Asp Ile His
625                 630                 635                 640

Thr Gln Thr Ala Ser Trp Met Phe Gly Val Pro Pro Glu Ala Val Asp
                645                 650                 655

Pro Leu Met Arg Arg Ala Ala Lys Thr Val Asn Phe Gly Val Leu Tyr
                660                 665                 670

Gly Met Ser Ala His Arg Leu Ser Gln Glu Leu Ser Ile Pro Tyr Glu
                675                 680                 685

Glu Ala Val Ala Phe Ile Glu Arg Tyr Phe Gln Ser Phe Pro Lys Val
                690                 695                 700

Arg Ala Trp Ile Glu Lys Thr Leu Glu Glu Gly Arg Arg Arg Gly Tyr
705                 710                 715                 720
```

```
Val Glu Thr Leu Phe Gly Arg Arg Arg Tyr Val Pro Asp Leu Asn Ala
            725                 730                 735

Arg Met Lys Ser Val Arg Gly Ala Ala Glu Arg Met Ala Phe Asn Met
            740                 745                 750

Pro Val Gln Gly Thr Ala Ala Asp Leu Met Lys Leu Ala Met Val Lys
            755                 760                 765

Leu Phe Pro Arg Leu Arg Glu Met Gly Ala Arg Met Leu Leu Gln Val
            770                 775                 780

His Asp Glu Leu Leu Leu Glu Ala Pro Gln Ala Arg Ala Glu Glu Val
785                 790                 795                 800

Ala Ala Leu Ala Lys Glu Ala Met Glu Lys Ala Tyr Pro Leu Ala Val
                805                 810                 815

Pro Leu Glu Val Glu Val Gly Ile Gly Glu Asp Trp Leu Ser Ala Lys
            820                 825                 830

Glu

<210> SEQ ID NO 87
<211> LENGTH: 2502
<212> TYPE: DNA
<213> ORGANISM: Artificial sequence
<220> FEATURE:
<223> OTHER INFORMATION: Mutant Taq polymerase coding sequence

<400> SEQUENCE: 87
atggcgatgc ttcccctctt tgagcccaag ggccgtgtcc tcctggtgga cggccaccac      60
ctggcctacc gcacctcctt cgccctgaag ggccccacca cgagccgggg cgaaccggtg     120
caggtggtct acggcttcgc caagagcctc ctcaaggccc tgaaggagga cgggtacaag     180
gccgtcttcg tggtctttga cgccaaggcc cccccattcc gccacaaggc ctacgaggcc     240
tacagggcgg ggagggcccc gaccccgag gacttccccc ggcagctcgc cctcgtcaag     300
gagctggtgg acctcctggg gtttacccgc ctcgaggtcc ccggctacga ggcggacgac     360
gttctcgcca ccctggccaa gaaggcggaa aaggagggt acgaggtgcg catcctcacc     420
gccgaccgcg cctctacca actcgtctct gaccgcgtcg ccgtcctcca ccccgagggc     480
cacctcatca ccccggagtg gctttgggag aagtacggcc tcaggccgga gcagtgggtg     540
gacttccgcg ccctcgtggg ggaccccctcc gacaacctcc ccggggtcaa gggcatcggg     600
gagaagaccg cctcaagct cctcaaggag tggggaagcc tggaaaacct cctcaagaac     660
ctggaccggg taaagccaga aaacgtccgg gagaagatca ggcccacct ggaagacctc     720 aggctctcct ggagctctc ccgggtgcgc accgacctcc cctggaggt ggacctcgcc     780 caggggcggg agcccgaccg ggaaaggctt agggcctttc tggagaggct tgagtttggc     840
agcctcctcc atgagttcgg ccttctggaa agccccaagg ccctggagga ggcccctgg     900 cccccgccgg aagggggcctt cgtgggcttt gtgctttccc gcaaggcgcc catgtgggcc     960
gatcttctgg ccctggccgc cgccaggggt ggtcggtct accggccccc cgagccttat    1020
aaagccctca gggacttgaa ggaggcgcgg gggcttctcg ccaaagacct gagcgttctg    1080
gccctaaggg aaggccttgg cctcccgccc ggcgacgacc ccatgctcct cgcctacctc    1140
ctggaccctt ccaacaccac ccccgagggg gtggcccggc gctacggcgg ggagtggacg    1200
gaggaggcgg gggagcgggc cgccctttcc gagaggctct tcgccaacct gtggggagg    1260 cttgagggg aggagaggct cctttggctt accggagg tggataggcc cctttccgct    1320
gtcctggccc acatggaggc cacaggggta cggctggacg tggcctgcct gcaggccctt    1380
```

```
tccctggagc ttgcggagga gatccgccgc ctcgaggagg aggtcttccg cttggcgggc    1440
cacaccttca acctcaactc ccgggaccag ctggaaaggg tcctctttga cgagctaggg    1500
cttcccgcca tcggcaagac ggagaagacc ggcaagcgct ccaccagcgc cgccatcctg    1560
gaggccctcc gcgaggccca ccccatcgtg gagaagatcc tgcagtaccg ggagctcacc    1620
aagctgaaga gcacctacat tgaccccttg ccggacctca tccaccccag gacgggccgc    1680
ctccacaccc gcttcaacca gacggccacg gccacgggca ggctaagtag ctccgatccc    1740
aacctccaga acatccccgt ccgcacccct cttgggcaga ggatccgccg ggccttcatc    1800
gccgaggagg ggtggctact ggtggtcctg gactatagcc agatagagct cagggtgctg    1860
gctcacctct ccggcgacga aaacctgatc agggtcttcc aggaggggcg ggacatccac    1920
acggagaccg ccagctggat gttcggcgtc ccccgggagg ccgtggaccc cctgatgcgc    1980
cgggcggcca agaccatcaa cttcggggtc ctctacggca tgtcggccca ccgcctctcc    2040
caggagctag ccatcccttta cgaggaggcc caggccttca ttgagcgcta ctttcagagc    2100
ttccccaagg tgcgggcctg gattgagaag gccctggagg agggcaggag gcgggggtac    2160
gtggagaccc tcttcggaag aaggcgctac gtgcccgacc tcaacgcccg ggtgaagagt    2220
gtcagggagg ccgcggagcg catggccttc aacatgcccg tccagggcac cgccgccgac    2280
cttatgaagc tcgccatggt gaagctcttc ccccgcctcc gggagatggg ggcccgcatg    2340
ctcctccagg tccacgacga gctcctcctg gaggccccca agcgcgggc cgaggaggtg    2400 gcggctttgg ccaaggaggc catggagaag gcctatcccc tcgccgtacc cctggaggtg    2460
aaggtgggga tcggggagga ctggctctcc gccaaggagt ga                      2502
```

<210> SEQ ID NO 88
<211> LENGTH: 833
<212> TYPE: PRT
<213> ORGANISM: Artificial sequence
<220> FEATURE:
<223> OTHER INFORMATION: Mutant Taq polymerase

<400> SEQUENCE: 88

Met Ala Met Leu Pro Leu Phe Glu Pro Lys Gly Arg Val Leu Leu Val
1               5                   10                  15

Asp Gly His His Leu Ala Tyr Arg Thr Ser Phe Ala Leu Lys Gly Pro
            20                  25                  30

Thr Thr Ser Arg Gly Glu Pro Val Gln Val Val Tyr Gly Phe Ala Lys
        35                  40                  45

Ser Leu Leu Lys Ala Leu Lys Glu Asp Gly Tyr Lys Ala Val Phe Val
    50                  55                  60

Val Phe Asp Ala Lys Ala Pro Pro Phe Arg His Lys Ala Tyr Glu Ala
65                  70                  75                  80

Tyr Arg Ala Gly Arg Ala Pro Thr Pro Glu Asp Phe Pro Arg Gln Leu
                85                  90                  95

Ala Leu Val Lys Glu Leu Val Asp Leu Leu Gly Phe Thr Arg Leu Glu
            100                 105                 110

Val Pro Gly Tyr Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Gly
    130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro

```
                    165                 170                 175
Glu Gln Trp Val Asp Phe Arg Ala Leu Val Gly Asp Pro Ser Asp Asn
                180                 185                 190

Leu Pro Gly Val Lys Gly Ile Gly Glu Lys Thr Ala Leu Lys Leu Leu
                195                 200                 205

Lys Glu Trp Gly Ser Leu Glu Asn Leu Leu Lys Asn Leu Asp Arg Val
            210                 215                 220

Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
                245                 250                 255

Val Asp Leu Ala Gln Gly Arg Glu Pro Asp Arg Glu Arg Leu Arg Ala
                260                 265                 270

Phe Leu Glu Arg Leu Glu Phe Gly Ser Leu Leu His Glu Phe Gly Leu
                275                 280                 285

Leu Glu Ser Pro Lys Ala Leu Glu Glu Ala Pro Trp Pro Pro Pro Glu
                290                 295                 300

Gly Ala Phe Val Gly Phe Val Leu Ser Arg Lys Ala Pro Met Trp Ala
305                 310                 315                 320

Asp Leu Leu Ala Leu Ala Ala Ala Arg Gly Gly Arg Val Tyr Arg Ala
                325                 330                 335

Pro Glu Pro Tyr Lys Ala Leu Arg Asp Leu Lys Glu Ala Arg Gly Leu
                340                 345                 350

Leu Ala Lys Asp Leu Ser Val Leu Ala Leu Arg Glu Gly Leu Gly Leu
                355                 360                 365

Pro Pro Gly Asp Asp Pro Met Leu Leu Ala Tyr Leu Leu Asp Pro Ser
370                 375                 380

Asn Thr Thr Pro Glu Gly Val Ala Arg Arg Tyr Gly Gly Glu Trp Thr
385                 390                 395                 400

Glu Glu Ala Gly Glu Arg Ala Ala Leu Ser Glu Arg Leu Phe Ala Asn
                405                 410                 415

Leu Trp Gly Arg Leu Glu Gly Glu Glu Arg Leu Leu Trp Leu Tyr Arg
                420                 425                 430

Glu Val Asp Arg Pro Leu Ser Ala Val Leu Ala His Met Glu Ala Thr
                435                 440                 445

Gly Val Arg Leu Asp Val Ala Cys Leu Gln Ala Leu Ser Leu Glu Leu
                450                 455                 460

Ala Glu Glu Ile Arg Arg Leu Glu Glu Glu Val Phe Arg Leu Ala Gly
465                 470                 475                 480

His Thr Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
                500                 505                 510

Arg Ser Thr Ser Ala Ala Ile Leu Glu Ala Leu Arg Glu Ala His Pro
            515                 520                 525

Ile Val Glu Lys Ile Leu Gln Tyr Arg Glu Leu Thr Lys Leu Lys Ser
            530                 535                 540

Thr Tyr Ile Asp Pro Leu Pro Asp Leu Ile His Pro Arg Thr Gly Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590
```

```
Gln Arg Ile Arg Arg Ala Phe Ile Ala Glu Glu Gly Trp Leu Leu Val
            595                 600                 605
Val Leu Asp Tyr Ser Gln Ile Glu Leu Arg Val Leu Ala His Leu Ser
        610                 615                 620
Gly Asp Glu Asn Leu Ile Arg Val Phe Gln Glu Gly Arg Asp Ile His
625                 630                 635                 640
Thr Glu Thr Ala Ser Trp Met Phe Gly Val Pro Arg Glu Ala Val Asp
                645                 650                 655
Pro Leu Met Arg Arg Ala Ala Lys Thr Ile Asn Phe Gly Val Leu Tyr
            660                 665                 670
Gly Met Ser Ala His Arg Leu Ser Gln Glu Leu Ala Ile Pro Tyr Glu
        675                 680                 685
Glu Ala Gln Ala Phe Ile Glu Arg Tyr Phe Gln Ser Phe Pro Lys Val
    690                 695                 700
Arg Ala Trp Ile Glu Lys Ala Leu Glu Glu Gly Arg Arg Arg Gly Tyr
705                 710                 715                 720
Val Glu Thr Leu Phe Gly Arg Arg Tyr Val Pro Asp Leu Asn Ala
                725                 730                 735
Arg Val Lys Ser Val Arg Glu Ala Ala Glu Arg Met Ala Phe Asn Met
            740                 745                 750
Pro Val Gln Gly Thr Ala Ala Asp Leu Met Lys Leu Ala Met Val Lys
        755                 760                 765
Leu Phe Pro Arg Leu Arg Glu Met Gly Ala Arg Met Leu Leu Gln Val
    770                 775                 780
His Asp Glu Leu Leu Leu Glu Ala Pro Gln Ala Arg Ala Glu Glu Val
785                 790                 795                 800
Ala Ala Leu Ala Lys Glu Ala Met Glu Lys Ala Tyr Pro Leu Ala Val
                805                 810                 815
Pro Leu Glu Val Lys Val Gly Ile Gly Glu Asp Trp Leu Ser Ala Lys
            820                 825                 830
Glu

<210> SEQ ID NO 89
<211> LENGTH: 2502
<212> TYPE: DNA
<213> ORGANISM: Artificial sequence
<220> FEATURE:
<223> OTHER INFORMATION: Mutant Taq polymerase coding sequence

<400> SEQUENCE: 89
atggcgatgc ttccctctt tgagcccaag ggccgcgtcc tcctggtgga cggccaccac      60
ctggcctacc gcgccttctt cgccctgaag ggcctcacca cgagccgggg cgaaccggtg     120
caggcggtct acggcttcgc caagagcctc ctcaaggccc tgaaggagga cgggtacaag     180
gccgtcttcg tggtctttga cgccaaggcc cctccttcc gccacgaggc ctacgaggcc      240
tacaaggcgg ggagggcccc gaccccgag gacttccccc ggcagctcgc cctcatcaag     300
gagctggtgg acctcctggg gtttacccgc ctcgaggtcc aaggctacga ggcggacgac     360
gtcctcgcca cctggccaa gaaggcgaa aaagaagggt acgaggtgcg catcctcacc      420
gccgaccggg acctctacca gctcgtctcc gaccgcgtcg ccgtcctcca ccccgagggc     480
cacctcatca ccccggagtg gctttgggag aagtacggcc tcaggccgga gcagtgggtg     540
gacttccgcg ccctcgtggg ggaccctcc aacaacctcc ccggggtcaa gggcatcggg     600
gagaagaccg ccctcaagct cctcaaggag tggggaagcc tggaaaacct cctcaagaac     660
```

```
ctggaccggg taaagccaga aaacgtccgg gagaagatca aggcccacct ggaagacctc    720
aggctctcct tggagctctc ccgggtgcgc accgacctcc cctggaggt ggacctcgcc    780 caggggcggg agctcgaccg ggagaggctt agggcctttc tggagaggct tgagtttggc    840
ggcctcctcc acgagttcgg ccttctggaa agccccaagg ccctggagga ggcccccagg    900 ccccgccgg aagggccctt cgtgggcttt gtgctttccc gcaaggagcc catgtgggcc     960
gatcttctgg ccctggccgc cgccaggggt ggtcgggtcc accgggcccc cgagccttat   1020
aaagccctca gggacttgaa ggaggcgcgg gggcttctcg ccaaagacct gagcgttctg   1080
gccctaaggg aaggccttgg cctcccgccc ggcgacgacc ccatgctcct cgcctacctc   1140
ctggacccct ccaacaccgc ccccgagggg gtggcccggc gctacggcgg ggagtggacg   1200
gaggaggcgg gggagcgggc cgccctttcc gagaggctct cgccaacct gtgggggagg    1260 cttgaggggg aggagaggct cctttggctt taccgggagg tggataggcc cctttccgct   1320
gtcctggccc acatggaggc cacaggggta cggctgacg tggcctatct cagggccttg    1380
tccctggagg tggccgagga gatcgcgcgc ctcgaggccg aggtcttccg cctggccggc   1440
caccccttca acctcaactc ccgagaccag ctggaaaggg tcctctttga cgagctaggg   1500
cttcccgcca tcggcaagac ggagaagacc ggcaagcgct ccaccagcgc cgccgtcctg   1560
gaggccctcc gcgaggccca ccccatcgtg gagaagatcc tgcagtaccg ggagctcacc   1620
aagctgaaga gcacctacat tgacccttg ccgaacctca tccatcccag gacgggccgc   1680
ctccacaccc gcttcaacca gacggccacg gccacgggca ggctaagtag ctccgatccc   1740
aacctccaga acatccccgt ccgcaccccg ctcgggcaga ggatccgccg ggccttcatc   1800
gccgaggagg ggtggctatt ggtggtcctg gactatagcc agatagagct cagggtgctg   1860
gcccacctct ccggcgacga gaacctgatc cgggtcttcc aggaggggcg ggacatccac   1920
acggaaaccg ccagctggat gttcggcgtc cccgggagg ccgtggaccc cctgatgcgc   1980
cgggcggcca agaccatcaa cttcgggtt ctctacggca tgtcggccca ccgcctctcc   2040
caggagctag ccatcccta cgaggaggcc caggccttca ttgagcgcta ctttcagagc   2100
ttccccaagg tgcgggcctg gatagaaaag acctggagg aggggaggaa gcggggctac   2160
gtggaaaccc tcttcggaag aaggcgctac gtgcccgacc tcaacgcccg ggtgaagggc   2220
gtcagggagg ccgcggagcg catggccttc aacatgccg tccagggcac cgccgccgac   2280
ctcatgaagc tcgccatggt gaagctcttc ccccgcctcc gggagatggg ggcccgcatg   2340
ctcctccagg tccacgacga gctcctcctg gagccccca agcgcgggc cggggaggtg   2400 gcggctttgg ccaaggaggc catggagaag gcctatcccc tcgccgtacc cctggaggtg   2460
aaggtgggga tcggggagga ctggctctcc gccaaggagt ga                     2502
```

<210> SEQ ID NO 90
<211> LENGTH: 833
<212> TYPE: PRT
<213> ORGANISM: Artificial sequence
<220> FEATURE:
<223> OTHER INFORMATION: Mutant Taq polymerase

<400> SEQUENCE: 90

Met Ala Met Leu Pro Leu Phe Glu Pro Lys Gly Arg Val Leu Leu Val
1               5                   10                  15

Asp Gly His His Leu Ala Tyr Arg Ala Phe Phe Ala Leu Lys Gly Leu
            20                  25                  30

-continued

```
Thr Thr Ser Arg Gly Glu Pro Val Gln Ala Val Tyr Gly Phe Ala Lys
         35                  40                  45

Ser Leu Leu Lys Ala Leu Lys Glu Asp Gly Tyr Lys Ala Val Phe Val
 50                  55                  60

Val Phe Asp Ala Lys Ala Pro Ser Phe Arg His Glu Ala Tyr Glu Ala
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Leu Gly Phe Thr Arg Leu Glu
            100                 105                 110

Val Gln Gly Tyr Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Asp
    130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asn Asn
            180                 185                 190

Leu Pro Gly Val Lys Gly Ile Gly Glu Lys Thr Ala Leu Lys Leu Leu
        195                 200                 205

Lys Glu Trp Gly Ser Leu Glu Asn Leu Leu Lys Asn Leu Asp Arg Val
    210                 215                 220

Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
                245                 250                 255

Val Asp Leu Ala Gln Gly Arg Glu Leu Asp Arg Glu Arg Leu Arg Ala
            260                 265                 270

Phe Leu Glu Arg Leu Glu Phe Gly Gly Leu Leu His Glu Phe Gly Leu
        275                 280                 285

Leu Glu Ser Pro Lys Ala Leu Glu Glu Ala Pro Trp Pro Pro Pro Glu
    290                 295                 300

Gly Ala Phe Val Gly Phe Val Leu Ser Arg Lys Glu Pro Met Trp Ala
305                 310                 315                 320

Asp Leu Leu Ala Leu Ala Ala Ala Arg Gly Gly Arg Val His Arg Ala
                325                 330                 335

Pro Glu Pro Tyr Lys Ala Leu Arg Asp Leu Lys Glu Ala Arg Gly Leu
            340                 345                 350

Leu Ala Lys Asp Leu Ser Val Leu Ala Leu Arg Glu Gly Leu Gly Leu
        355                 360                 365

Pro Pro Gly Asp Asp Pro Met Leu Leu Ala Tyr Leu Leu Asp Pro Ser
    370                 375                 380

Asn Thr Ala Pro Glu Gly Val Ala Arg Arg Tyr Gly Gly Glu Trp Thr
385                 390                 395                 400

Glu Glu Ala Gly Glu Arg Ala Ala Leu Ser Glu Arg Leu Phe Ala Asn
                405                 410                 415

Leu Trp Gly Arg Leu Glu Gly Glu Glu Arg Leu Leu Trp Leu Tyr Arg
            420                 425                 430

Glu Val Asp Arg Pro Leu Ser Ala Val Leu Ala His Met Glu Ala Thr
        435                 440                 445

Gly Val Arg Leu Asp Val Ala Tyr Leu Arg Ala Leu Ser Leu Glu Val
```

```
                    450                 455                 460
Ala Glu Glu Ile Ala Arg Leu Glu Ala Glu Val Phe Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
            500                 505                 510

Arg Ser Thr Ser Ala Ala Val Leu Glu Ala Leu Arg Glu Ala His Pro
        515                 520                 525

Ile Val Glu Lys Ile Leu Gln Tyr Arg Glu Leu Thr Lys Leu Lys Ser
    530                 535                 540

Thr Tyr Ile Asp Pro Leu Pro Asn Leu Ile His Pro Arg Thr Gly Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590

Gln Arg Ile Arg Arg Ala Phe Ile Ala Glu Glu Gly Trp Leu Leu Val
        595                 600                 605

Val Leu Asp Tyr Ser Gln Ile Glu Leu Arg Val Leu Ala His Leu Ser
    610                 615                 620

Gly Asp Glu Asn Leu Ile Arg Val Phe Gln Glu Gly Arg Asp Ile His
625                 630                 635                 640

Thr Glu Thr Ala Ser Trp Met Phe Gly Val Pro Arg Glu Ala Val Asp
                645                 650                 655

Pro Leu Met Arg Arg Ala Ala Lys Thr Ile Asn Phe Gly Val Leu Tyr
            660                 665                 670

Gly Met Ser Ala His Arg Leu Ser Gln Glu Leu Ala Ile Pro Tyr Glu
        675                 680                 685

Glu Ala Gln Ala Phe Ile Glu Arg Tyr Phe Gln Ser Phe Pro Lys Val
    690                 695                 700

Arg Ala Trp Ile Glu Lys Thr Leu Glu Glu Gly Arg Lys Arg Gly Tyr
705                 710                 715                 720

Val Glu Thr Leu Phe Gly Arg Arg Arg Tyr Val Pro Asp Leu Asn Ala
                725                 730                 735

Arg Val Lys Gly Val Arg Glu Ala Ala Glu Arg Met Ala Phe Asn Met
            740                 745                 750

Pro Val Gln Gly Thr Ala Ala Asp Leu Met Lys Leu Ala Met Val Lys
        755                 760                 765

Leu Phe Pro Arg Leu Arg Glu Met Gly Ala Arg Met Leu Leu Gln Val
    770                 775                 780

His Asp Glu Leu Leu Leu Glu Ala Pro Gln Ala Arg Ala Gly Glu Val
785                 790                 795                 800

Ala Ala Leu Ala Lys Glu Ala Met Glu Lys Ala Tyr Pro Leu Ala Val
                805                 810                 815

Pro Leu Glu Val Lys Val Gly Ile Gly Glu Asp Trp Leu Ser Ala Lys
            820                 825                 830

Glu

<210> SEQ ID NO 91
<211> LENGTH: 2499
<212> TYPE: DNA
<213> ORGANISM: Artificial sequence
<220> FEATURE:
```

-continued

<223> OTHER INFORMATION: Mutant Taq polymerase coding sequence

<400> SEQUENCE: 91

```
atggcgatgc ttcccctctt tgagcccaaa ggccgggtcc tcctggtgga cggccaccac      60
ctggcctacc gcaccttctt cgccctgaag ggcctcacca cgagccgggg cgaaccggtg     120
caggtggtct acggcttcgc caagagcctc ctcaaggccc tgaaggagga cgggtacaag     180
gccgtcttcg tggtctttga cgccaaggcc ccctccctcc gccacgaggc ctacgaggcc     240
tacaaggcgg ggagggcccc gaccccgag gacttcctcc ggcagctcgc cctcatcaag     300
gagctggtgg acctcctggg gtttacccgc ctcgaggtcc aaggctacga ggcggacgac     360
gtcctcgcca ccctggccaa gaaggcggaa aagaagggt acgaggtgcg catcctcacc     420
gccgaccggg acctctacca gctcgtctcc gaccgcgtcg ccgtcctcca ccccgagggc     480
cacctcatca ccccggagtg gctttgggag aagtacggcc tcaggccgga cagtgggtg     540
gacttccgcg ccctcgtggg ggaccccctc gacaacctcc ccggggtcaa gggcatcggg     600
gagaagaccg ccctcaagct cctcaaggag tggggaagcc tggaaaacct cctcaagaac     660
ctggaccggc tgaagcccgc catccggag aagatcctgg cccacatgga cgatctgaag     720
ctctcctggg acctggccaa ggtgcgcacc gacctgcccc tagaggtgga cttcgccaaa     780
aggcgggagc ccgaccggga gaggcttagg gcctttctgg agaggcttga gcttggcagc     840
ctcctccacg agttcggcct tctgaaaagc cccaagaccc tggaggaggc ctcctggccc     900
ccgccggaag gggccttcgt gggctttgtg cttttcccgca aggagcccat gtgggccgat     960
cttctggccc tggccgccgc cagggggggc cgggtccacc gggccccga gccttataaa    1020
gccctcaggg acctgaagga ggcgcggggg cttctcgcca agacctgag cgttctggcc    1080
ctaagggaag gccttggcct cccgcccggc gacgacccca tgctcctcgc ctacctcctg    1140
gacccttcca acaccacccc cgaggggtg gcccggcgct acggcgggga gtggacgaag    1200
gaggcggggg agcgggccgc cctttccgag aggctcttcg ccaacctgtg gggaggctt    1260
gaggggagg agaggctcct ttggctttac cgggaggtgg ataggcccct ttccgctgtc    1320
ctggcccaca tggaggccac aggggtgcgc ttggacgtgg cctatctcag gccttgtcc    1380
ctggaggtgg ccgaggagat cgcccgcctc gaggccgagg tcttccgcct ggccggccat    1440
cccttcaacc tcaactcccg ggaccagctg gaaagggtcc tctttgacga gctagggctt    1500
cccgccatcg gcaagacgga gaagaccggc aagcgctcca ccagcgccgc cgtcctggag    1560
gccctccgcg aggcccaccc catcgtggag aagatcctgc agtaccggga gctcaccaag    1620
ctgaagagca cctacattga ccccttgccg gacctcatcc accccaggac gggccgcctc    1680
cacacccgct caaccagac ggccacggcc acgggcaggc taagtagctc cgatcccaac    1740
ctccagaaca tccccgtccg caccccgctc gggcagagga tccgccgggc cttcgtcgcc    1800
gaggaggggt ggctattggt ggtcctggac tatagccaga tagagctcag ggtgctggcc    1860
cacctctccg gcgacgagaa cctgacccgg gtcttcctgg aggggcggga catccacacg    1920
gaaaccgcca gctggatgtt cggcgtcccc cgggaggccg tggacccct gatgcgccgg    1980
gcggccaaga ccatcaactt cggggttctc tacggcatgt cggcccaccg cctctcccag    2040
gagctggcca tcccttacga ggaggccag gccttcatag agcgctactt ccaaagcttc    2100
cccaaggtgc gggcctggat agaaaagacc ctggaggagg gaggaagcg gggctacgtg    2160
gaaaccctct cggaagaag cgcctacgtg cccgacctca cgcccggggt gaagagtgtc    2220
agggaggccg cggagcgcat ggccttcaac atgcccgtcc agggcaccgc cgccgacctt    2280
```

```
atgaagctcg ccatggtgaa gctcttcccc cgcctccggg agatgggggc ccgcatgctc    2340
ctccaggtcc acgacgagct cctcctggag gccccccaag cgcgggccga ggaggtggcg    2400
gctttggcca aggaggccat ggagaaggcc tatcccctcg ccgtacccct ggaggtgaag    2460
gaggggatcg gggaggactg gctctccgcc aaggagtga                          2499
```

<210> SEQ ID NO 92
<211> LENGTH: 832
<212> TYPE: PRT
<213> ORGANISM: Artificial sequence
<220> FEATURE:
<223> OTHER INFORMATION: Mutant Taq polymerase

<400> SEQUENCE: 92

```
Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Leu
            20                  25                  30

Thr Thr Ser Arg Gly Glu Pro Val Gln Val Val Tyr Gly Phe Ala Lys
        35                  40                  45

Ser Leu Leu Lys Ala Leu Lys Glu Asp Gly Tyr Lys Ala Val Phe Val
    50                  55                  60

Val Phe Asp Ala Lys Ala Pro Ser Leu Arg His Glu Ala Tyr Glu Ala
65                  70                  75                  80

Tyr Lys Ala Gly Arg Ala Pro Thr Pro Glu Asp Phe Leu Arg Gln Leu
                85                  90                  95

Ala Leu Ile Lys Glu Leu Val Asp Leu Leu Gly Phe Thr Arg Leu Glu
            100                 105                 110

Val Gln Gly Tyr Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Asp
    130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asp Asn
            180                 185                 190

Leu Pro Gly Val Lys Gly Ile Gly Glu Lys Thr Ala Leu Lys Leu Leu
        195                 200                 205

Lys Glu Trp Gly Ser Leu Glu Asn Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Leu Gly Ser Leu Leu His Glu Phe Gly Leu Leu
        275                 280                 285

Glu Ser Pro Lys Thr Leu Glu Glu Ala Ser Trp Pro Pro Glu Gly
    290                 295                 300

Ala Phe Val Gly Phe Val Leu Ser Arg Lys Glu Pro Met Trp Ala Asp
305                 310                 315                 320
```

-continued

```
Leu Leu Ala Leu Ala Ala Arg Gly Gly Arg Val His Arg Ala Pro
            325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Glu Trp Thr Lys
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Arg Leu Leu Trp Leu Tyr Arg Glu
            420                 425                 430

Val Asp Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
            580                 585                 590

Arg Ile Arg Arg Ala Phe Val Ala Glu Glu Gly Trp Leu Leu Val Val
            595                 600                 605

Leu Asp Tyr Ser Gln Ile Glu Leu Arg Val Leu Ala His Leu Ser Gly
            610                 615                 620

Asp Glu Asn Leu Thr Arg Val Phe Leu Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Lys Arg Gly Tyr Val
705                 710                 715                 720

Glu Thr Leu Phe Gly Arg Arg Arg Tyr Val Pro Asp Leu Asn Ala Arg
            725                 730                 735

Val Lys Ser Val Arg Glu Ala Ala Glu Arg Met Ala Phe Asn Met Pro
```

```
                740                 745                 750
Val Gln Gly Thr Ala Ala Asp Leu Met Lys Leu Ala Met Val Lys Leu
            755                 760                 765

Phe Pro Arg Leu Arg Glu Met Gly Ala Arg Met Leu Leu Gln Val His
        770                 775                 780

Asp Glu Leu Leu Leu Glu Ala Pro Gln Ala Arg Ala Glu Glu Val Ala
785                 790                 795                 800

Ala Leu Ala Lys Glu Ala Met Glu Lys Ala Tyr Pro Leu Ala Val Pro
                805                 810                 815

Leu Glu Val Lys Glu Gly Ile Gly Glu Asp Trp Leu Ser Ala Lys Glu
            820                 825                 830

<210> SEQ ID NO 93
<211> LENGTH: 2550
<212> TYPE: DNA
<213> ORGANISM: Artificial sequence
<220> FEATURE:
<223> OTHER INFORMATION: Mutant Taq polymerase coding sequence

<400> SEQUENCE: 93
atggcgatgc ttcccctctt tgagcccaag ggccgcgtcc tcctggtgga cggccaccac     60
ctggcctacc gcaccttctt cgccctgaag ggccccacca cgagccgggg cgaaccggtg    120
caggtggtct acggcttcgc caagagcctc ctcaaggccc tgaaagagga cgggtacaag    180
gccgtcttcg tggtctttga cgccaaggcc ccctcattcc gccacaaggc ctacgaggcc    240
tacagggcgg ggagggcccc gaccccgag  gacttccccc ggcagctcgc cctcatcaag    300
gagctggtgg acctcctggg gtttaccgc  ctcgaggtcc ccggctacga ggcggacgac    360
gttctcgcca ccctggccaa gaaggcgaaa aggagggggt acgaggtgcg catcctcacc    420
gccgaccgcg ccctctacca actcgtctct gaccgcgtcg ccgtcctcca ccccgagggc    480
cacctcatca cccccggagtg gctttgggag aagtacggcc tcaggccgga gcagtgggtg    540
gacttccgcg ccctcgtggg ggaccctcc  gacaacctcc ccggggtcaa gggcatcggg    600
gagaagaccg ccctcaagct cctcaaggag tggggaagcc tggaaaacct cctcaagaac    660
ctggaccggg taaagccaga aaacgtccgg gagaagatca aggcccacct ggaagacctc    720
aggctctcct ggagctctc  ccgggtgcgc accgacctcc ccctggaggt ggacctcgcc    780
caggggcggg agcccgaccg ggagaggctt agggcctttc tggagaggct tgagtttggc    840
ggcctcctcc acgagttcgg ccttctggaa agccccaagg ccctggagga ggcccctgg     900
ccccccgccg aaggggcctt cgtgggcttt gtgctttccc gcaaggagcc catgtgggcc    960
gatcttctgg ccctggccgc cgccaggggt ggtcgggtcc accgggcccc tgagccttat   1020
aaagccctca gggacttgaa ggaggcgcgg gggcttctcg ccaaagacct gagcgttctg   1080
gccctgaggg aaggccttgg cctcccgccc ggcgacgacc ccatgctcct cgcctacctc   1140
ctggaccctt ccaacaccac ccccgagggg gtggcccggc gctacggcgg gagtggacg    1200
gaggaggcgg gggagcgggc cgccctttcc gagaggctct cgccaacct  gtggggagg    1260
cttgaggggg aggagaggct cctttggctt taccgggagg tggagagacc cctttccgct   1320
gtcctggccc acatggaggc cacggggtg  cgcctggacg tggcctatct cagggccttg   1380
tccctggagg tggccgagga gatcgcccgc ctcgaggccg aggtcttccg cctggccggc   1440
caccccttca acctcaactc ccgagaccag ctggaaaggg tcctctttga cgagctaggg   1500
cttcccgcca tcggcaagac ggagaagacc ggcaagcgct ccaccagcgc cgccgtcctg   1560
```

```
gaggccctcc gcgaggccca ccccatcgtg agaagatcc tgcagtaccg ggagctcacc      1620
aagctgaaga gcacctacat tgaccccttg ccggaccaca tccacccag acgggccgc       1680 ctccacaccc gcttcaacca gacggccacg gccacgggca ggctaagtag ctccgatccc     1740
aacctccaga acatccccgt ccgcacccc ctcgggcaga ggatccgccg ggccttcatc     1800
gccgaggagg ggtggctatt ggtggtcctg gactatagcc agatagagct cagggtgctg     1860
gcccacctct ccggcgacga gaacctgacc cgggtcttcc aggaggggcg ggacatccac     1920
acggaaaccg ccagctggat gttcggcgtc ccccggggagg ccgtggaccc cctgatgcgc     1980
cgggcggcca agaccatcaa cttcgggggtt ctctacggca tgtcggccca ccgcctctcc     2040
caggagctgg ccatcccctta cgaggaggcc caggccttca tagagcgcta cttccaaagc     2100
ttccccaagg tgcgggcctg gatagaaaag accctggagg aggggaggaa gcggggctac     2160
gtggaaaccc tcttcggaag aaggcgctac gtgcccgacc tcaacgcccg ggtgaagagt     2220
gtcagggagg ccgcggagcg catggccttc aacatgcccg tccagggcac cgccgccgac     2280
cttatgaagc tcgccatggt gaagctctac ccccgcctcc gggagatggg ggcccgcatg     2340
ctcctccagg tccacgacga gctcctcctg gaggcccccc aagcgcgggc cgaggaggtg     2400 gcggcttttgg ccaaggaggc catggagaag gcctatcccc tcgccgtacc cctggaggtg     2460
aaggtgggga tcgggagga ctggctctcc gcccaaggag tgagtcgacc tgcaggcagc     2520
gcttggcgtc acccgcagtt cggtggttaa                                     2550
```

<210> SEQ ID NO 94
<211> LENGTH: 849
<212> TYPE: PRT
<213> ORGANISM: Artificial sequence
<220> FEATURE:
<223> OTHER INFORMATION: Mutant Taq polymerase

<400> SEQUENCE: 94

```
Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Pro
                20                  25                  30

Thr Thr Ser Arg Gly Glu Pro Val Gln Val Val Tyr Gly Phe Ala Lys
            35                  40                  45

Ser Leu Leu Lys Ala Leu Lys Glu Asp Gly Tyr Lys Ala Val Phe Val
        50                  55                  60

Val Phe Asp Ala Lys Ala Pro Ser Phe Arg His Lys Ala Tyr Glu Ala
65                  70                  75                  80

Tyr Arg Ala Gly Arg Ala Pro Thr Pro Glu Asp Phe Pro Arg Gln Leu
                85                  90                  95

Ala Leu Ile Lys Glu Leu Val Asp Leu Leu Gly Phe Thr Arg Leu Glu
                100                 105                 110

Val Pro Gly Tyr Glu Ala Asp Asp Val Leu Ala Thr Leu Ala Lys Lys
            115                 120                 125

Ala Glu Lys Glu Gly Tyr Glu Val Arg Ile Leu Thr Ala Asp Arg Gly
        130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asp Asn
                180                 185                 190
```

```
Leu Pro Gly Val Lys Gly Ile Gly Glu Lys Thr Ala Leu Lys Leu Leu
        195                 200                 205

Lys Glu Trp Gly Ser Leu Glu Asn Leu Leu Lys Asn Leu Asp Arg Val
        210                 215                 220

Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
                245                 250                 255

Val Asp Leu Ala Gln Gly Arg Glu Pro Asp Arg Glu Arg Leu Arg Ala
                260                 265                 270

Phe Leu Glu Arg Leu Glu Phe Gly Gly Leu Leu His Glu Phe Gly Leu
                275                 280                 285

Leu Glu Ser Pro Lys Ala Leu Glu Glu Ala Pro Trp Pro Pro Pro Glu
                290                 295                 300

Gly Ala Phe Val Gly Phe Val Leu Ser Arg Lys Glu Pro Met Trp Ala
305                 310                 315                 320

Asp Leu Leu Ala Leu Ala Ala Arg Gly Gly Arg Val His Arg Ala
                325                 330                 335

Pro Glu Pro Tyr Lys Ala Leu Arg Asp Leu Lys Glu Ala Arg Gly Leu
                340                 345                 350

Leu Ala Lys Asp Leu Ser Val Leu Ala Leu Arg Glu Gly Leu Gly Leu
                355                 360                 365

Pro Pro Gly Asp Asp Pro Met Leu Leu Ala Tyr Leu Leu Asp Pro Ser
                370                 375                 380

Asn Thr Thr Pro Glu Gly Val Ala Arg Arg Tyr Gly Gly Glu Trp Thr
385                 390                 395                 400

Glu Glu Ala Gly Glu Arg Ala Ala Leu Ser Glu Arg Leu Phe Ala Asn
                405                 410                 415

Leu Trp Gly Arg Leu Glu Gly Glu Glu Arg Leu Leu Trp Leu Tyr Arg
                420                 425                 430

Glu Val Glu Arg Pro Leu Ser Ala Val Leu Ala His Met Glu Ala Thr
                435                 440                 445

Gly Val Arg Leu Asp Val Ala Tyr Leu Arg Ala Leu Ser Leu Glu Val
                450                 455                 460

Ala Glu Glu Ile Ala Arg Leu Glu Ala Glu Val Phe Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
                500                 505                 510

Arg Ser Thr Ser Ala Ala Val Leu Glu Ala Leu Arg Glu Ala His Pro
                515                 520                 525

Ile Val Glu Lys Ile Leu Gln Tyr Arg Glu Leu Thr Lys Leu Lys Ser
                530                 535                 540

Thr Tyr Ile Asp Pro Leu Pro Asp His Ile His Pro Arg Thr Gly Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
                580                 585                 590

Gln Arg Ile Arg Arg Ala Phe Ile Ala Glu Glu Gly Trp Leu Leu Val
                595                 600                 605
```

```
Val Leu Asp Tyr Ser Gln Ile Glu Leu Arg Val Leu Ala His Leu Ser
    610                 615                 620

Gly Asp Glu Asn Leu Thr Arg Val Phe Gln Gly Arg Asp Ile His
625                 630                 635                 640

Thr Glu Thr Ala Ser Trp Met Phe Gly Val Pro Arg Glu Ala Val Asp
                645                 650                 655

Pro Leu Met Arg Arg Ala Ala Lys Thr Ile Asn Phe Gly Val Leu Tyr
            660                 665                 670

Gly Met Ser Ala His Arg Leu Ser Gln Glu Leu Ala Ile Pro Tyr Glu
            675                 680                 685

Glu Ala Gln Ala Phe Ile Glu Arg Tyr Phe Gln Ser Phe Pro Lys Val
690                 695                 700

Arg Ala Trp Ile Glu Lys Thr Leu Glu Glu Gly Arg Lys Arg Gly Tyr
705                 710                 715                 720

Val Glu Thr Leu Phe Gly Arg Arg Arg Tyr Val Pro Asp Leu Asn Ala
                725                 730                 735

Arg Val Lys Ser Val Arg Glu Ala Ala Glu Arg Met Ala Phe Asn Met
            740                 745                 750

Pro Val Gln Gly Thr Ala Ala Asp Leu Met Lys Leu Ala Met Val Lys
            755                 760                 765

Leu Tyr Pro Arg Leu Arg Glu Met Gly Ala Arg Met Leu Leu Gln Val
770                 775                 780

His Asp Glu Leu Leu Leu Glu Ala Pro Gln Ala Arg Ala Glu Glu Val
785                 790                 795                 800

Ala Ala Leu Ala Lys Glu Ala Met Glu Lys Ala Tyr Pro Leu Ala Val
                805                 810                 815

Pro Leu Glu Val Lys Val Gly Ile Gly Glu Asp Trp Leu Ser Ala Gln
            820                 825                 830

Gly Val Ser Arg Pro Ala Gly Ser Ala Trp Arg His Pro Gln Phe Gly
            835                 840                 845

Gly

<210> SEQ ID NO 95
<211> LENGTH: 2502
<212> TYPE: DNA
<213> ORGANISM: Artificial sequence
<220> FEATURE:
<223> OTHER INFORMATION: Mutant Taq polymerase coding sequence

<400> SEQUENCE: 95
atggcgatgc ttcccctctt tgagcccaag ggccgcgtcc tcctggtgga cggccaccac      60
ctggcctacc gcaccttctt cgccctgaag ggccccacca cgagccgggg cgaaccggtg     120
caggtggtct acggcttcgc caagagcctc ctcaaggccc tgaaggagga cgggtacaag     180
gccgtcttcg tggtctttga cgccaaggcc cctcattcc gccacaaggc ctacgaggcc      240 tacaggcgg ggaggccccc gacccccgag gacttccccc ggcagctcgc cctcatcaag     300
gagctggtgg acctcctggg gtttaccccgc ctcgaggtcc ccggctacga ggcggacgac     360
gttctcgcca ccctggccaa gaaggcgaa aaggaggggt acgaggtgcg catcctcacc      420
gccgaccgcg gcctctacca actcgtctct gaccgcgtcg ccgtcctcca ccccgagggc     480
cacctcatca cccggagtg gctttgggag aagtacggcc tcaggccgga gcagtgggta     540
gacttccgcg ccctcgtggg ggaccccctcc gacaacctcc ccgggggtcaa gggcatcggg     600 gagaagaccg ccctcaagct cctcaaggag tggggaagcc tggaaaacct cctcaagaac     660
```

```
ctggaccggg taaagccaga aaacgtccgg gagaagatca aggcccacct ggaagacctc    720
aggctctcct tggagctctc ccgggtgcgc accgacctcc ccctggaggt ggacctcgcc    780
caggggcggg agcccgaccg ggaggggctt agggcctttc tggagaggct tgagtttggc    840
agcctcctcc acgagttcgg ccttctggaa agccccaagg ccctggagga ggcccccctgg   900
cccccgccgg aaggggcctt cgtgggcttt gtgctttcac gcaaggagcc catgtgggcc    960
gatcttctgg ccctggccgc cgccaggggg ggtcgggtcc accgggcccc cgagccttat   1020
aaagccctca gggacttgaa ggaggcgcgg gggcttctcg ccaaagacct gagcgttctg   1080
gccctaaggg aaggccttgg cctcccgccc ggcgacgacc ccatgctcct cgcctacctc   1140
ctggacccct tccaacaccgc ccccgagggg gtggcccggc gctacggcgg ggagtggacg   1200
gaggaggcgg gggagcgggc cgcccttttcc gagaggctct tcgccaacct gtggggggagg  1260
cttgaggggg aggagaggct cctttggctt taccgggagg tggataggcc cctttccgct   1320
gtcctggccc acatggaggc cacaggggta cggctggacg tggcctgcct gcaggccctt   1380
tccctggagc ttgcggagga gatccgccgc ctcgaggagg aggtcttccg cttggcgggc   1440
caccccttca acctcaactc ccgggaccag ctggaaaggg tcctctttga cgagctaggg   1500
cttcccgcca tcggcaagac ggagaagacc ggcaagcgct ccaccagcgc cgccatcctg   1560
gaggccctcc gcgaggccca cccatcgtg gagaagatcc tgcagtaccg ggagctcacc   1620
aagctgaaga gcacctacat tgacccttg ccggacctca tccacccag acgggccgc    1680
ctccacaccc gcttcaacca gacggccacg gccacgggca ggctaagtag ctccggtccc   1740
aacctccaga acatccccgt ccgcacccgg ctcgggcaga ggatccgccg ggccttcgtc   1800
gccgaggagg ggtggctatt ggtggtcctg gactatagcc agatagagct cagggtgctg   1860
gcccacctct ccggcgacga gaacctgacc cgggtcttcc tggagggggg ggacatccac   1920
acggaaaccg ccagctggat gttcggcgtc ccccgggagg ccgtggaccc cctgatgcgc   1980
cgggcggcca agaccatcaa cttcgggttt ctctacggca tgtcggccca ccgcctctcc   2040
caggagctgg ccatcccttta cgaggaggcc caggccttca tagagcgcta cttccaaagc   2100
ttccccaagg tgcgggcctg gatagaaaag accctggagg aggggaggaa gcgggggctac  2160
gtggaaaccc tcttcggaag aaggcgctac gtgcccgacc tcaacgcccg ggtgaagagt   2220
gtcagggagg ccgcggagcg catggccttc aacatgcccg tccagggcac cgccgccgac   2280
cttatgaagc tcgccatggt gaagctcttc ccccgcctcc gggagatggg ggcccgcatg   2340
ctcctccagg tccacgacga gctcctcctg gaggcccccc aagcgcgggc cgaggaagtg   2400
gcggctttgg ccaaggaggc catggagaag gcctatcccc tcgccgtacc cctggaggtg   2460
aaggtgggga tcggggagga ctggctctcc gccaaggagt ga                      2502
```

<210> SEQ ID NO 96
<211> LENGTH: 833
<212> TYPE: PRT
<213> ORGANISM: Artificial sequence
<220> FEATURE:
<223> OTHER INFORMATION: Mutant Taq polymerase

<400> SEQUENCE: 96

Met Ala Met Leu Pro Leu Phe Glu Pro Lys Gly Arg Val Leu Leu Val
 1               5                  10                  15

Asp Gly His His Leu Ala Tyr Arg Thr Phe Phe Ala Leu Lys Gly Pro
             20                  25                  30

Thr Thr Ser Arg Gly Glu Pro Val Gln Val Val Tyr Gly Phe Ala Lys

```
                35                  40                  45
Ser Leu Leu Lys Ala Leu Lys Glu Asp Gly Tyr Lys Ala Val Phe Val
 50                  55                  60

Val Phe Asp Ala Lys Ala Pro Ser Phe Arg His Lys Ala Tyr Glu Ala
 65                  70                  75                  80

Tyr Arg Ala Gly Arg Ala Pro Thr Pro Glu Asp Phe Pro Arg Gln Leu
                 85                  90                  95

Ala Leu Ile Lys Glu Leu Val Asp Leu Gly Phe Thr Arg Leu Glu
                100                 105                 110

Val Pro Gly Tyr Glu Ala Asp Asp Val Leu Ala Thr Leu Ala Lys Lys
                115                 120                 125

Ala Glu Lys Glu Gly Tyr Glu Val Arg Ile Leu Thr Ala Asp Arg Gly
                130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asp Asn
                180                 185                 190

Leu Pro Gly Val Lys Gly Ile Gly Glu Lys Thr Ala Leu Lys Leu Leu
                195                 200                 205

Lys Glu Trp Gly Ser Leu Glu Asn Leu Leu Lys Asn Leu Asp Arg Val
210                 215                 220

Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
                245                 250                 255

Val Asp Leu Ala Gln Gly Arg Glu Pro Asp Arg Glu Gly Leu Arg Ala
                260                 265                 270

Phe Leu Glu Arg Leu Glu Phe Gly Ser Leu Leu His Glu Phe Gly Leu
                275                 280                 285

Leu Glu Ser Pro Lys Ala Leu Glu Glu Ala Pro Trp Pro Pro Pro Glu
290                 295                 300

Gly Ala Phe Val Gly Phe Val Leu Ser Arg Lys Glu Pro Met Trp Ala
305                 310                 315                 320

Asp Leu Leu Ala Leu Ala Ala Arg Gly Gly Arg Val His Arg Ala
                325                 330                 335

Pro Glu Pro Tyr Lys Ala Leu Arg Asp Leu Lys Glu Ala Arg Gly Leu
                340                 345                 350

Leu Ala Lys Asp Leu Ser Val Leu Ala Leu Arg Glu Gly Leu Gly Leu
                355                 360                 365

Pro Pro Gly Asp Asp Pro Met Leu Leu Ala Tyr Leu Leu Asp Pro Ser
370                 375                 380

Asn Thr Ala Pro Glu Gly Val Ala Arg Arg Tyr Gly Gly Glu Trp Thr
385                 390                 395                 400

Glu Glu Ala Gly Glu Arg Ala Ala Leu Ser Glu Arg Leu Phe Ala Asn
                405                 410                 415

Leu Trp Gly Arg Leu Glu Gly Glu Glu Arg Leu Leu Trp Leu Tyr Arg
                420                 425                 430

Glu Val Asp Arg Pro Leu Ser Ala Val Leu Ala His Met Glu Ala Thr
                435                 440                 445

Gly Val Arg Leu Asp Val Ala Cys Leu Gln Ala Leu Ser Leu Glu Leu
450                 455                 460
```

```
Ala Glu Glu Ile Arg Arg Leu Glu Glu Val Phe Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
            500                 505                 510

Arg Ser Thr Ser Ala Ala Ile Leu Glu Ala Leu Arg Glu Ala His Pro
        515                 520                 525

Ile Val Glu Lys Ile Leu Gln Tyr Arg Glu Leu Thr Lys Leu Lys Ser
530                 535                 540

Thr Tyr Ile Asp Pro Leu Pro Asp Leu Ile His Pro Arg Thr Gly Arg
545                 550                 555                 560

Leu His Thr Arg Phe Asn Gln Thr Ala Thr Ala Thr Gly Arg Leu Ser
                565                 570                 575

Ser Ser Gly Pro Asn Leu Gln Asn Ile Pro Val Arg Thr Pro Leu Gly
            580                 585                 590

Gln Arg Ile Arg Arg Ala Phe Val Ala Glu Glu Gly Trp Leu Leu Val
        595                 600                 605

Val Leu Asp Tyr Ser Gln Ile Glu Leu Arg Val Leu Ala His Leu Ser
610                 615                 620

Gly Asp Glu Asn Leu Thr Arg Val Phe Leu Glu Gly Arg Asp Ile His
625                 630                 635                 640

Thr Glu Thr Ala Ser Trp Met Phe Gly Val Pro Arg Glu Ala Val Asp
                645                 650                 655

Pro Leu Met Arg Arg Ala Ala Lys Thr Ile Asn Phe Gly Val Leu Tyr
            660                 665                 670

Gly Met Ser Ala His Arg Leu Ser Gln Glu Leu Ala Ile Pro Tyr Glu
        675                 680                 685

Glu Ala Gln Ala Phe Ile Glu Arg Tyr Phe Gln Ser Phe Pro Lys Val
690                 695                 700

Arg Ala Trp Ile Glu Lys Thr Leu Glu Glu Gly Arg Lys Arg Gly Tyr
705                 710                 715                 720

Val Glu Thr Leu Phe Gly Arg Arg Arg Tyr Val Pro Asp Leu Asn Ala
                725                 730                 735

Arg Val Lys Ser Val Arg Glu Ala Ala Glu Arg Met Ala Phe Asn Met
            740                 745                 750

Pro Val Gln Gly Thr Ala Ala Asp Leu Met Lys Leu Ala Met Val Lys
        755                 760                 765

Leu Phe Pro Arg Leu Arg Glu Met Gly Ala Arg Met Leu Leu Gln Val
770                 775                 780

His Asp Glu Leu Leu Leu Glu Ala Pro Gln Ala Arg Ala Glu Glu Val
785                 790                 795                 800

Ala Ala Leu Ala Lys Glu Ala Met Glu Lys Ala Tyr Pro Leu Ala Val
                805                 810                 815

Pro Leu Glu Val Lys Val Gly Ile Gly Glu Asp Trp Leu Ser Ala Lys
            820                 825                 830

Glu

<210> SEQ ID NO 97
<211> LENGTH: 2502
<212> TYPE: DNA
<213> ORGANISM: Artificial sequence
<220> FEATURE:
<223> OTHER INFORMATION: Mutant Taq polymerase coding sequence
```

<400> SEQUENCE: 97

```
atggcgatgc ttccctctct tgagcccaag ggccgcgtcc tcctggtgga cggccaccac    60
ctggcctacc gcaccttctt cgccctgaag ggccccacca cgagccgggg cgaaccggtg   120
caggtggtct acggcttcgc caagagcctc ctcaaggccc tgaaggagga cgggtacaag   180
gccgtcttcg tggtctttga cgccaaggcc ccctcattcc gccacaaggc ctacgaggcc   240
tacagggcgg ggagggcccc gacccccgag gacttccccc ggcagctcgc cctcatcaag   300
gagctggtgg aacctcctggg gtttacccgc ctcgaggtcc ccggctacga ggcggacgac   360
gttctcgcca ccctggccaa gaaggcggaa aaggaggggt acgaggtgcg catcctcacc   420
gccgaccgcg gcctctacca actcgtctct gaccgcgtcg ccgtcctcca ccccgagggc   480
cacctcatca ccccggagtg gctttgggag aagtacggcc tcaggccgga gcagtgggtg   540
gacttccgcg ccctcgtggg ggacccctcc gacaacctcc ccggggtcaa gggcatcggg   600
gagaagaccg ccctcaagct cctcaaggag tggggaagcc tggaaaacct cctcaagaac   660
ctggaccggg taaagccaga aaacgtccgg gagaagatca aggcccacct ggaagacctc   720
aggctctcct tggagctctc ccgggtgcgc accgacctcc cctggaggt ggacctcgcc   780
cagaggcggg agcccgaccg ggaggggctt agggcctttc tggagaggct tgagtttggc   840
agcctcttcc acgagttcgg ccttctggaa agccccaagg ccctggagga ggcccccctgg   900
cccccgccgg aaggggcctt cgtgggcttt gtgctttccc gcaaggagcc catgtgggcc   960
gatcttctgg ccctggccgc cgccaggggt ggtcgagtcc accggccccc cgagccttat  1020
aaagccctca gggacctgaa ggaggcgcgg gggcttctcg ccaaagacct gagcgttctg  1080
gccctaaggg aaggccttgg cctcccgccc ggcgacgacc ccatgctcct cgcctacctc  1140
ctggacccctt ccaacaccac ccccgagggg gtggcccggc gctacggcgg ggagtggacg  1200
gaggaggcgg gggagcgggc cgcccttttcc gagaggctct cgccaacctt gtggggggagg  1260
cttgaggggg aggagaggct cctttggctt taccgggagg tggagaggcc cctttccgct  1320
gtcctggccc acatggaggc cacgggggtg cgcctggacg tggcctatct cagggccttg  1380
tccctggagg tggccgagga gatcgcccgc ctcgaggccc aggtcttccg cctggccggc  1440
caccccttca acctcaactc ccgggaccag ctggaaatgg tgctctttga cgagcttagg  1500
cttcccgcct tggggaagac gcaaaagacg ggcaagcgct ccaccagcgc cgccgtcctg  1560
gaggccctcc gcgaggccca ccccatcgtg gagaagatcc tgcagtaccg ggagctcacc  1620
aagctgaaga gcacctacat tgacccccttg tcggacctca tccacccccag gacgggccgc  1680
ctccacaccc gcttcaacca gacggccacg gccacgggca ggctaagtag ctccgatccc  1740
aacctccaga acatccccgt ccgcacccccg cttgggcaga ggatccgccg ggccttcatc  1800
gccgaggagg ggtggctact ggtggtcctg gactatagcc agatagagct cagggtgctg  1860
gcccacctct ccggcgacga aaacctgatc agggtcttcc aggagggggcg ggacatccac  1920
acggagaccg ccagctggat gttcggcgtc cccgggagg ccgtggaccc cctgatgcgc  1980
cgggcggcca agaccatcaa cttcggggtc ctctacggca tgtcggccca ccgcctctcc  2040
caggagctag ccatccctta cgaggaggcc caggccttca ttgagcgcta ctttcagagc  2100
ttccccaagg tgcgggcctg gattgagaag accctggagg agggcaggag gcgggggtac  2160
gtggagaccc tcttcggccg ccgccgctac gtgccagacc tagaggcccg ggtgaagagc  2220
gtgcgggagg cggccgagcg catggccttc aacatgcccg tccagggcac cgccgccgac  2280
```

```
ctcatgaagc tggctatggt gaagctcttc cccaggctgg agaaacgggg ggccaggatg    2340
ctccttcagg tccacgacga gctggtcctc gaggccccaa agagagggc ggaggccgtg     2400 gcccggctgg ccaaggaggc catggagggg gtgtatcccc tggccgtgcc cctggaggtg    2460
gaggtgggga tagggagga ctggctctcc gccaagggtt ag                        2502
```

```
<210> SEQ ID NO 98
<211> LENGTH: 833
<212> TYPE: PRT
<213> ORGANISM: Artificial sequence
<220> FEATURE:
<223> OTHER INFORMATION: Mutant Taq polymerase

<400> SEQUENCE: 98
```

```
Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Pro
            20                  25                  30

Thr Thr Ser Arg Gly Glu Pro Val Gln Val Val Tyr Gly Phe Ala Lys
        35                  40                  45

Ser Leu Leu Lys Ala Leu Lys Glu Asp Gly Tyr Lys Ala Val Phe Val
    50                  55                  60

Val Phe Asp Ala Lys Ala Pro Ser Phe Arg His Lys Ala Tyr Glu Ala
65                  70                  75                  80

Tyr Arg Ala Gly Arg Ala Pro Thr Pro Glu Asp Phe Pro Arg Gln Leu
                85                  90                  95

Ala Leu Ile Lys Glu Leu Val Asp Leu Leu Gly Phe Thr Arg Leu Glu
            100                 105                 110

Val Pro Gly Tyr Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Gly
    130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asp Asn
            180                 185                 190

Leu Pro Gly Val Lys Gly Ile Gly Glu Lys Thr Ala Leu Lys Leu Leu
        195                 200                 205

Lys Glu Trp Gly Ser Leu Glu Asn Leu Leu Lys Asn Leu Asp Arg Val
    210                 215                 220

Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
                245                 250                 255

Val Asp Leu Ala Gln Arg Arg Glu Pro Asp Arg Glu Gly Leu Arg Ala
            260                 265                 270

Phe Leu Glu Arg Leu Glu Phe Gly Ser Leu Phe His Glu Phe Gly Leu
        275                 280                 285

Leu Glu Ser Pro Lys Ala Leu Glu Glu Ala Pro Trp Pro Pro Pro Glu
    290                 295                 300

Gly Ala Phe Val Gly Phe Val Leu Ser Arg Lys Glu Pro Met Trp Ala
305                 310                 315                 320

Asp Leu Leu Ala Leu Ala Ala Ala Arg Gly Gly Arg Val His Arg Ala
```

```
                     325                 330                 335
Pro Glu Pro Tyr Lys Ala Leu Arg Asp Leu Lys Glu Ala Arg Gly Leu
                 340                 345                 350

Leu Ala Lys Asp Leu Ser Val Leu Ala Leu Arg Glu Gly Leu Gly Leu
                 355                 360                 365

Pro Pro Gly Asp Asp Pro Met Leu Leu Ala Tyr Leu Leu Asp Pro Ser
370                 375                 380

Asn Thr Thr Pro Glu Gly Val Ala Arg Arg Tyr Gly Gly Glu Trp Thr
385                 390                 395                 400

Glu Glu Ala Gly Glu Arg Ala Ala Leu Ser Glu Arg Leu Phe Ala Asn
                 405                 410                 415

Leu Trp Gly Arg Leu Glu Gly Glu Glu Arg Leu Leu Trp Leu Tyr Arg
                 420                 425                 430

Glu Val Glu Arg Pro Leu Ser Ala Val Leu Ala His Met Glu Ala Thr
                 435                 440                 445

Gly Val Arg Leu Asp Val Ala Tyr Leu Arg Ala Leu Ser Leu Glu Val
                 450                 455                 460

Ala Glu Glu Ile Ala Arg Leu Glu Ala Glu Val Phe Arg Leu Ala Gly
465                 470                 475                 480

His Pro Phe Asn Leu Asn Ser Arg Asp Gln Leu Glu Met Val Leu Phe
                 485                 490                 495

Asp Glu Leu Arg Leu Pro Ala Leu Gly Lys Thr Gln Lys Thr Gly Lys
                 500                 505                 510

Arg Ser Thr Ser Ala Ala Val Leu Glu Ala Leu Arg Glu Ala His Pro
                 515                 520                 525

Ile Val Glu Lys Ile Leu Gln Tyr Arg Glu Leu Thr Lys Leu Lys Ser
530                 535                 540

Thr Tyr Ile Asp Pro Leu Ser Asp Leu Ile His Pro Arg Thr Gly Arg
545                 550                 555                 560

Leu His Thr Arg Phe Asn Gln Thr Ala Thr Ala Thr Gly Arg Leu Ser
                 565                 570                 575

Ser Ser Asp Pro Asn Leu Gln Asn Ile Pro Val Arg Thr Pro Leu Gly
                 580                 585                 590

Gln Arg Ile Arg Arg Ala Phe Ile Ala Glu Glu Gly Trp Leu Leu Val
                 595                 600                 605

Val Leu Asp Tyr Ser Gln Ile Glu Leu Arg Val Leu Ala His Leu Ser
                 610                 615                 620

Gly Asp Glu Asn Leu Ile Arg Val Phe Gln Glu Gly Arg Asp Ile His
625                 630                 635                 640

Thr Glu Thr Ala Ser Trp Met Phe Gly Val Pro Arg Glu Ala Val Asp
                 645                 650                 655

Pro Leu Met Arg Arg Ala Ala Lys Thr Ile Asn Phe Gly Val Leu Tyr
                 660                 665                 670

Gly Met Ser Ala His Arg Leu Ser Gln Glu Leu Ala Ile Pro Tyr Glu
                 675                 680                 685

Glu Ala Gln Ala Phe Ile Glu Arg Tyr Phe Gln Ser Phe Pro Lys Val
                 690                 695                 700

Arg Ala Trp Ile Glu Lys Thr Leu Glu Glu Gly Arg Arg Arg Gly Tyr
705                 710                 715                 720

Val Glu Thr Leu Phe Gly Arg Arg Arg Tyr Val Pro Asp Leu Glu Ala
                 725                 730                 735

Arg Val Lys Ser Val Arg Glu Ala Ala Glu Arg Met Ala Phe Asn Met
                 740                 745                 750
```

-continued

```
Pro Val Gln Gly Thr Ala Ala Asp Leu Met Lys Leu Ala Met Val Lys
        755                 760                 765
Leu Phe Pro Arg Leu Gly Glu Thr Gly Ala Arg Met Leu Leu Gln Val
    770                 775                 780
His Asp Glu Leu Val Leu Glu Ala Pro Lys Glu Arg Ala Glu Ala Val
785                 790                 795                 800
Ala Arg Leu Ala Lys Glu Ala Met Glu Gly Val Tyr Pro Leu Ala Val
            805                 810                 815
Pro Leu Glu Val Glu Val Gly Ile Gly Glu Asp Trp Leu Ser Ala Lys
                820                 825                 830
Gly
```

<210> SEQ ID NO 99
<211> LENGTH: 20
<212> TYPE: DNA
<213> ORGANISM: Artificial sequence
<220> FEATURE:
<223> OTHER INFORMATION: Primer for analysis of mutant polymerase

<400> SEQUENCE: 99
cgtggtcgcg acggatgccg                                           20

<210> SEQ ID NO 100
<211> LENGTH: 51
<212> TYPE: DNA
<213> ORGANISM: Artificial sequence
<220> FEATURE:
<223> OTHER INFORMATION: Template for mutant polymerase analysis

<400> SEQUENCE: 100
agctaccatg cctgcacgaa ttcggcatcc gtcgcgacca cggtcgcagc g         51

<210> SEQ ID NO 101
<211> LENGTH: 51
<212> TYPE: DNA
<213> ORGANISM: Artificial sequence
<220> FEATURE:
<223> OTHER INFORMATION: Template for analysis of mutant polymerases
<220> FEATURE:
<221> NAME/KEY: misc_feature
<222> LOCATION: (22)..(22)
<223> OTHER INFORMATION: n is an abasic site

<400> SEQUENCE: 101
agctaccatg cctgcacgac ancggcatcc gtcgcgacca cggtcgcagc g         51

<210> SEQ ID NO 102
<211> LENGTH: 40
<212> TYPE: DNA
<213> ORGANISM: Artificial sequence
<220> FEATURE:
<223> OTHER INFORMATION: Primer for selection of polymerase able to
      replicate 5-nitroindol
<220> FEATURE:
<221> NAME/KEY: misc_feature
<222> LOCATION: (40)..(40)
<223> OTHER INFORMATION: n is 5-nitroindol

<400> SEQUENCE: 102
caggaaacag ctatgacaaa aatctagata acgagggcan                     40

<210> SEQ ID NO 103
<211> LENGTH: 45
<212> TYPE: DNA

```
<213> ORGANISM: Artificial sequence
<220> FEATURE:
<223> OTHER INFORMATION: Primer for selection of polymerase able to
      replicate 5-nitroindol
<220> FEATURE:
<221> NAME/KEY: misc_feature
<222> LOCATION: (45)..(45)
<223> OTHER INFORMATION: n is 5-nitroindol

<400> SEQUENCE: 103
gtaaaacgac ggccagtacc accgaactgc gggtgacgcc aagcn              45

<210> SEQ ID NO 104
<211> LENGTH: 40
<212> TYPE: DNA
<213> ORGANISM: Artificial sequence
<220> FEATURE:
<223> OTHER INFORMATION: Primer used to select polymerases able to
      replicate 5-nitroindol
<220> FEATURE:
<221> NAME/KEY: misc_feature
<222> LOCATION: (31)..(31)
<223> OTHER INFORMATION: n is 5-nitroindol
<220> FEATURE:
<221> NAME/KEY: misc_feature
<222> LOCATION: (40)..(40)
<223> OTHER INFORMATION: n is 5-nitroindol

<400> SEQUENCE: 104
caggaaacag ctatgacaaa aatctagata ncgagggcan                    40

<210> SEQ ID NO 105
<211> LENGTH: 45
<212> TYPE: DNA
<213> ORGANISM: Artificial sequence
<220> FEATURE:
<223> OTHER INFORMATION: Primer used to select polymerase able to
      replicate 5-nitroindol
<220> FEATURE:
<221> NAME/KEY: misc_feature
<222> LOCATION: (22)..(22)
<223> OTHER INFORMATION: n is 5-nitroindol
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (45)..(45)
<223> OTHER INFORMATION: n is 5-nitroindol

<400> SEQUENCE: 105
gtaaaacgac ggccagtacc acngaactgc gggtgacgcc aagcn              45

<210> SEQ ID NO 106
<211> LENGTH: 2502
<212> TYPE: DNA
<213> ORGANISM: Artificial sequence
<220> FEATURE:
<223> OTHER INFORMATION: Mutant Taq polymerase coding sequence

<400> SEQUENCE: 106
atggcgatgc ttcccctctt tgagcccaaa ggccgggtcc tcctggtgga cggccaccac    60
ctggcctacc gcaccttctt cgccctgaag ggcctcacca cgagccgggg cgaaccggtg   120
caggcggttt acggcttcgc caagagcctc ctcaaggccc tgaaggagga cgggtacaag   180
gccgtcttcg tggtctttga cgccaaggcc ccctccttcc gccacgaggc ctacgaggcc   240
tacaaggcgg ggagggcccc gacccccgag gacttccccc ggcagctcgc cctcatcaag   300
```

```
gagctggtgg acctcctggg gtttacccgc ctcgaggtcc aaggctacga ggcggacgac    360
gtcctcgcca ccctggccaa gaaggcggaa aaagaagggt acgaggtgcg catcctcacc    420
gccgaccggg acctctacca gctcgtctcc gaccgcgtcg ccgtcctcca ccccgagggc    480
cacctcatca ccccggagtg gctttgggag aagtacggcc tcaggccgga gcagtgggtg    540
gacttccgcg ccctcgtggg ggaccctcc gacaacctcc ccgggatcaa gggcatcggg    600
gagaagaccg ccctcaagct cctcaaggag tggggaagcc tggaaaacct cctcaagaac    660
ctggaccggg taaagccaga aaatgtccgg gagaagatca aggcccacct ggaagacctc    720
aggctctcct tggagctctc ccgggtgcgc accgacctcc ccctggaggt ggacttcgcc    780
aaaaggcggg agcccgaccg ggagaggctt agggccttc tggagaggct tgagtttggc    840
agcctcctcc acgagttcgg ccttctggaa agccccaagg ccctggagga ggcccctgg    900
ccccgccgg aagggccctt cgtgggcttt gtgctttccc gcaaggagcc catgtgggcc    960
gatcttctgg ccctggccgc cgccaagggt ggccgggtcc accgggcccc cgagccttat    1020
aaagccctca gggacttgaa ggaggcgcgg gggcttctcg ccaaagacct gagcgttctg    1080
gccctaaggg aaggccttgg cctcccgccc ggcgacgacc ccatgctcct cgcctacctc    1140
ctggacccctt ccaacaccac ccccgagggg gtggcccggc gctacggcgg ggagtggacg    1200
gaggaggcgg gggagcgggc cgccctttcc gagaggctct cgccaacct gtggggagg    1260
cttgaggggg aggagaggct ccttggctt accggagg tggagaggcc cctttccgct    1320
gtcctggccc acatggaggc cacggggtg cgcctggacg tggcctatct cagggccttg    1380
tccctggagg tggccgagga gatcgcccgc ctcgaggccg aggtcttccg cctggccggc    1440
cacccttca acctcaactc ccgagaccag ctggaaaggg tcctctttga cgagctaggg    1500
cttccccgcca tcggcaagac ggagaagacc ggcaagcgct ccaccagcgc cgccgtcctg    1560
gaggccctcc gcgaggccca ccccatcgtg gagaagatcc tgcagtaccg ggagctcacc    1620
aagctgaaga gcacctacat tgacccctg ccggacctca tccaccccag gacgggccgc    1680
ctccacaccc gcttcaacca gacggccacg gccacgggca ggctaagtag ctccgatccc    1740
aacctccaga acatccccgt ccgcaccccg ctcgggcaga ggatccgccg ggccttcatc    1800
gccgagggg ggtggctatt ggtggtcctg gactatagcc agatggagct cagggtgctg    1860
gcccacctct ccggcgacga gaacctgatc cgggtcttcc aggagggcg ggacatccac    1920
acggaaaccg ccagctggat gttcggcgtc ccccgggagg ccgtggaccc cctgatgcgc    1980
cgggcggcca agaccatcaa cttcgggtt tctctacggca tgtcggccca ccgcctctcc    2040
caggagctag ccatccctta cgaggaggcc caggccttca ttgagcgcta ctttcagagc    2100
ttccccaagg tgcgggcctg gattgagaag accctggagg agggcaggag gcgggggtac    2160
gtggagaccc tcttcggccg ccgccgctac gtgccagacc tagaggcccg ggtgaagagc    2220
gtgcgggagg cggccgagcg catggccttc aacatgccg tccagggcac cgccgccgac    2280
ctcatgaagc tggctatggt gaagctcttc ccaggctgg aggaaacggg ggccaggatg    2340
ctccttcagg tccacgacga gctggtcctc gaggccccaa aagagagggc ggaggccgtg    2400
gcccggctgg ccaaggaggt catggaggg gtgtatcccc tggccgtgcc cctggaggtg    2460
gaggtgggga taggggagga ctggctctcc gccaaggagt ga                      2502
```

<210> SEQ ID NO 107
<211> LENGTH: 833
<212> TYPE: PRT
<213> ORGANISM: Artificial sequence
<220> FEATURE:
<223> OTHER INFORMATION: Mutant Taq polymerase

<400> SEQUENCE: 107

```
Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Leu
            20                  25                  30

Thr Thr Ser Arg Gly Glu Pro Val Gln Ala Val Tyr Gly Phe Ala Lys
        35                  40                  45

Ser Leu Leu Lys Ala Leu Lys Glu Asp Gly Tyr Lys Ala Val Phe Val
    50                  55                  60

Val Phe Asp Ala Lys Ala Pro Ser Phe Arg His Glu Ala Tyr Glu Ala
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Phe Thr Arg Leu Glu
            100                 105                 110

Val Gln Gly Tyr Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Asp
    130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asp Asn
            180                 185                 190

Leu Pro Gly Ile Lys Gly Ile Gly Glu Lys Thr Ala Leu Lys Leu Leu
        195                 200                 205

Lys Glu Trp Gly Ser Leu Glu Asn Leu Leu Lys Asn Leu Asp Arg Val
    210                 215                 220

Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
                245                 250                 255

Val Asp Phe Ala Lys Arg Arg Glu Pro Asp Arg Glu Arg Leu Arg Ala
            260                 265                 270

Phe Leu Glu Arg Leu Glu Phe Gly Ser Leu Leu His Glu Phe Gly Leu
        275                 280                 285

Leu Glu Ser Pro Lys Ala Leu Glu Glu Ala Pro Trp Pro Pro Pro Glu
    290                 295                 300

Gly Ala Phe Val Gly Phe Val Leu Ser Arg Lys Glu Pro Met Trp Ala
305                 310                 315                 320

Asp Leu Leu Ala Leu Ala Ala Lys Gly Gly Arg Val His Arg Ala
                325                 330                 335

Pro Glu Pro Tyr Lys Ala Leu Arg Asp Leu Lys Glu Ala Arg Gly Leu
            340                 345                 350

Leu Ala Lys Asp Leu Ser Val Leu Ala Leu Arg Glu Gly Leu Gly Leu
        355                 360                 365

Pro Pro Gly Asp Asp Pro Met Leu Leu Ala Tyr Leu Leu Asp Pro Ser
    370                 375                 380

Asn Thr Thr Pro Glu Gly Val Ala Arg Arg Tyr Gly Gly Glu Trp Thr
385                 390                 395                 400
```

```
Glu Glu Ala Gly Glu Arg Ala Ala Leu Ser Glu Arg Leu Phe Ala Asn
            405                 410                 415

Leu Trp Gly Arg Leu Glu Gly Glu Glu Arg Leu Leu Trp Leu Tyr Arg
            420                 425                 430

Glu Val Glu Arg Pro Leu Ser Ala Val Leu Ala His Met Glu Ala Thr
            435                 440                 445

Gly Val Arg Leu Asp Val Ala Tyr Leu Arg Ala Leu Ser Leu Glu Val
            450                 455                 460

Ala Glu Glu Ile Ala Arg Leu Glu Ala Glu Val Phe Arg Leu Ala Gly
465                 470                 475                 480

His Pro Phe Asn Leu Asn Ser Arg Asp Gln Leu Glu Arg Val Leu Phe
            485                 490                 495

Asp Glu Leu Gly Leu Pro Ala Ile Gly Lys Thr Glu Lys Thr Gly Lys
            500                 505                 510

Arg Ser Thr Ser Ala Ala Val Leu Glu Ala Leu Arg Glu Ala His Pro
            515                 520                 525

Ile Val Glu Lys Ile Leu Gln Tyr Arg Glu Leu Thr Lys Leu Lys Ser
            530                 535                 540

Thr Tyr Ile Asp Pro Leu Pro Asp Leu Ile His Pro Arg Thr Gly Arg
545                 550                 555                 560

Leu His Thr Arg Phe Asn Gln Thr Ala Thr Ala Thr Gly Arg Leu Ser
            565                 570                 575

Ser Ser Asp Pro Asn Leu Gln Asn Ile Pro Val Arg Thr Pro Leu Gly
            580                 585                 590

Gln Arg Ile Arg Arg Ala Phe Ile Ala Glu Gly Gly Trp Leu Leu Val
            595                 600                 605

Val Leu Asp Tyr Ser Gln Met Glu Leu Arg Val Leu Ala His Leu Ser
            610                 615                 620

Gly Asp Glu Asn Leu Ile Arg Val Phe Gln Glu Gly Arg Asp Ile His
625                 630                 635                 640

Thr Glu Thr Ala Ser Trp Met Phe Gly Val Pro Arg Glu Ala Val Asp
            645                 650                 655

Pro Leu Met Arg Arg Ala Ala Lys Thr Ile Asn Phe Gly Val Leu Tyr
            660                 665                 670

Gly Met Ser Ala His Arg Leu Ser Gln Glu Leu Ala Ile Pro Tyr Glu
            675                 680                 685

Glu Ala Gln Ala Phe Ile Glu Arg Tyr Phe Gln Ser Phe Pro Lys Val
            690                 695                 700

Arg Ala Trp Ile Glu Lys Thr Leu Glu Glu Gly Arg Arg Arg Gly Tyr
705                 710                 715                 720

Val Glu Thr Leu Phe Gly Arg Arg Arg Tyr Val Pro Asp Leu Glu Ala
            725                 730                 735

Arg Val Lys Ser Val Arg Glu Ala Ala Glu Arg Met Ala Phe Asn Met
            740                 745                 750

Pro Val Gln Gly Thr Ala Ala Asp Leu Met Lys Leu Ala Met Val Lys
            755                 760                 765

Leu Phe Pro Arg Leu Glu Glu Thr Gly Ala Arg Met Leu Leu Gln Val
            770                 775                 780

His Asp Glu Leu Val Leu Glu Ala Pro Lys Glu Arg Ala Glu Ala Val
785                 790                 795                 800

Ala Arg Leu Ala Lys Glu Val Met Glu Gly Val Tyr Pro Leu Ala Val
            805                 810                 815
```

Pro Leu Glu Val Glu Val Gly Ile Gly Glu Asp Trp Leu Ser Ala Lys
        820                 825                 830

Glu

<210> SEQ ID NO 108
<211> LENGTH: 2499
<212> TYPE: DNA
<213> ORGANISM: Artificial sequence
<220> FEATURE:
<223> OTHER INFORMATION: Mutant Taq polymerase coding sequence

<400> SEQUENCE: 108

| | | | | |
|---|---|---|---|---|
| atggcgatgc | ttcccctctt | tgagcccaaa | ggccgggtcc | tcctggtgga cggccaccac | 60 |
| ctggcctacc | gcaccttctt | cgccctgaag | ggcctcacca | cgagtcgggg cgaaccggtg | 120 |
| caggcggtct | acggcttcgc | caagagcctc | ctcaaggccc | tgaaggagga cgggtacaag | 180 |
| gccatcttcg | tggtctttga | cgccaaggcc | cctccttcc | gccacgaggc ccacgaggcc | 240 |
| tacaaggcgg | ggagggcccc | gagccccgag | gacttccccc | ggcagctcgc cctcatcaag | 300 |
| gagctggtgg | acctcctggg | gtttacccgc | ctcgaggtcc | aaggctacga ggcggacgac | 360 |
| gtcctcgcca | ccctggccaa | gaaggcgaa | aaagaagggt | acgaggtgcg catcctcacc | 420 |
| gccgaccggg | acctctacca | gctcgtctcc | gaccgcgtcg | ccgtcctcca ccccgagggc | 480 |
| cacctcatca | ccccggagtg | gctttgggag | aagtacggcc | tcaggccgga gcagtgggtg | 540 |
| gacttccgcg | ccctcgtggg | ggaccctcc | gacaacctcc | ccggggtcaa gggcatcggg | 600 |
| gagaagaccg | ccctcaagct | cctcaaggag | tggggaagcc | tggaaaacct cctcaagaac | 660 |
| ctggaccggc | tgaagcccgc | catccgggag | aagatcctgg | cccacatgga cgatctgaag | 720 |
| ctctcctggg | acctggccaa | ggtgcgcacc | gacctgcccc | tggaggtgga cttcgccaaa | 780 |
| aggcgggagt | ccgatcggga | gaggcttagg | gcctttctgg | agaggcttga gtttggcagc | 840 |
| ctcctccacg | agttcggcct | tctggaaagc | cccaaggccc | tggaggaggc ccctggggcc | 900 |
| ccgccggtag | gggccttcgt | gggctttgtg | ctttccccgca | aggagcccat gtgggccgat | 960 |
| cttctggccc | tggccgccgc | caggggtggt | cgggtccacc | gggcccccga gccttataaa | 1020 |
| gccctcagag | acctgaagga | ggcgcggggg | cttctcgcca | aagacctgag cgttctggcc | 1080 |
| ctgagggaag | gccttggcct | cccgcccggc | gacgacccca | tgctcctcgc ctacctcctg | 1140 |
| gaccctccca | acaccacccc | cgaggtggtg | gcccggcgct | acggcgggga gtggacggag | 1200 |
| gaggcggggg | agcgggccgc | ctttccgag | aggctcttcg | ccaacctgtg ggggaggctt | 1260 |
| gagggggagg | ggaggctcct | ttggctttac | cggggggtgg | agaggccct tccgctgtc | 1320 |
| ctggcccaca | tggaggccac | aggggtgcgc | ctggacgtgg | cctatctcag ggccttgtcc | 1380 |
| ctggaggtgg | ccgaggagat | cgcccgcctc | gaggccgagg | tcttccgcct ggccggccac | 1440 |
| cccttcaacc | tcaactcccg | ggaccagctg | gaaagggtcc | tctttgacga gctagggctt | 1500 |
| cccgccatcg | gcaagacgga | gaagaccggc | aagcgctcca | ccagcgccgc cgtcctggag | 1560 |
| gccctccgcg | aggcccaccc | catcgtggag | aagatcctgc | agtaccggga gctcaccaag | 1620 |
| ctgaagagca | cttacattga | ccccttgccg | gacctcatcc | accccaggac gggccgcctc | 1680 |
| cacacccgct | tcaaccagac | ggccacggcc | acgggcaggc | taagtagctc cgatcccaac | 1740 |
| ctccagaaca | tccccgtccg | caccccgctc | gggcagagga | tccgccgggc cttcatcgcc | 1800 |
| gagggggggt | ggctattggt | ggtcctggac | tatagccaga | tggagctcag ggtgctggcc | 1860 |
| cacctctccg | gcgacgagaa | cctgatccgg | gtcttccagg | aggggcggga catccacacg | 1920 |

```
gaaaccgcca gctggatgtt cggcgtcccc cgggaggccg tggaccccct gatgcgccgg    1980
gcggccaaga ccatcaactt cggggttctc tacggcatgt cggcccaccg cctctcccag    2040
gagctagcca tcccttacga ggaggcccag gccttcattg agcgctactt ccaaagcttc    2100
cccaaggtgc gggcctggat agaaaagacc ctggaggagg ggaggaagcg gggctacgtg    2160
gaaaccctct tcggaagaag gcgctacgtg cccgacctca cgcccgggt gaagagcgtc     2220 agggaggccg cggagcgcat ggccttcaac atgcccgtcc agggcaccgc cgccgacctc    2280
acgaagctgg ctatggtgaa gctcttcccc aggctggagg aaacgggggc caggatgctc    2340
cttcaggtcc acgacgagct ggtcctcgag gccccaaaag agagggcgga ggccgtggcc    2400
cggctggcca aggaggtcat ggaggggtg tatcccctgg ccgtgcccct ggaggtggag     2460
gtggggatag ggaggactg gctttccgcc aagggttag                            2499
```

<210> SEQ ID NO 109
<211> LENGTH: 832
<212> TYPE: PRT
<213> ORGANISM: Artificial sequence
<220> FEATURE:
<223> OTHER INFORMATION: Mutant Taq polymerase

<400> SEQUENCE: 109

```
Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Leu
            20                  25                  30

Thr Thr Ser Arg Gly Glu Pro Val Gln Ala Val Tyr Gly Phe Ala Lys
        35                  40                  45

Ser Leu Leu Lys Ala Leu Lys Glu Asp Gly Tyr Lys Ala Ile Phe Val
    50                  55                  60

Val Phe Asp Ala Lys Ala Pro Ser Phe Arg His Glu Ala His Glu Ala
65                  70                  75                  80

Tyr Lys Ala Gly Arg Ala Pro Ser Pro Glu Asp Phe Pro Arg Gln Leu
                85                  90                  95

Ala Leu Ile Lys Glu Leu Val Asp Leu Leu Gly Phe Thr Arg Leu Glu
            100                 105                 110

Val Gln Gly Tyr Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Asp
    130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asp Asn
            180                 185                 190

Leu Pro Gly Val Lys Gly Ile Gly Glu Lys Thr Ala Leu Lys Leu Leu
        195                 200                 205

Lys Glu Trp Gly Ser Leu Glu Asn Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Ser Asp Arg Glu Arg Leu Arg Ala Phe
```

```
                260               265                 270
Leu Glu Arg Leu Glu Phe Gly Ser Leu Leu His Glu Phe Gly Leu Leu
            275                 280                 285
Glu Ser Pro Lys Ala Leu Glu Ala Pro Trp Pro Pro Val Gly
290                 295                 300
Ala Phe Val Gly Phe Val Leu Ser Arg Lys Glu Pro Met Trp Ala Asp
305                 310                 315                 320
Leu Leu Ala Leu Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
            340                 345                 350
Ala Lys Asp Leu Ser Val Leu Ala Leu Arg Glu Gly Leu Gly Leu Pro
            355                 360                 365
Pro Gly Asp Asp Pro Met Leu Leu Ala Tyr Leu Leu Asp Pro Ser Asn
        370                 375                 380
Thr Thr Pro Glu Val Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu Gly Val
                420                 425                 430
Val Glu Arg Pro Leu Ser Ala Val Leu Ala His Met Glu Ala Thr Gly
            435                 440                 445
Val Arg Leu Asp Val Ala Tyr Leu Arg Ala Leu Ser Leu Glu Val Ala
            450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
                500                 505                 510
Ser Thr Ser Ala Ala Val Leu Glu Ala Leu Arg Glu Ala His Pro Ile
            515                 520                 525
Val Glu Lys Ile Leu Gln Tyr Arg Glu Leu Thr Lys Leu Lys Ser Thr
            530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
            580                 585                 590
Arg Ile Arg Arg Ala Phe Ile Ala Glu Gly Gly Trp Leu Leu Val Val
            595                 600                 605
Leu Asp Tyr Ser Gln Met Glu Leu Arg Val Leu Ala His Leu Ser Gly
            610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
                660                 665                 670
Met Ser Ala His Arg Leu Ser Gln Glu Leu Ala Ile Pro Tyr Glu Glu
            675                 680                 685
```

```
Ala Gln Ala Phe Ile Glu Arg Tyr Phe Gln Ser Phe Pro Lys Val Arg
        690                 695                 700

Ala Trp Ile Glu Lys Thr Leu Glu Glu Gly Arg Lys Arg Gly Tyr Val
705                 710                 715                 720

Glu Thr Leu Phe Gly Arg Arg Arg Tyr Val Pro Asp Leu Asn Ala Arg
                    725                 730                 735

Val Lys Ser Val Arg Glu Ala Ala Glu Arg Met Ala Phe Asn Met Pro
                740                 745                 750

Val Gln Gly Thr Ala Ala Asp Leu Thr Lys Leu Ala Met Val Lys Leu
            755                 760                 765

Phe Pro Arg Leu Glu Glu Thr Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Gly
            820                 825                 830

<210> SEQ ID NO 110
<211> LENGTH: 59
<212> TYPE: DNA
<213> ORGANISM: Artificial sequence
<220> FEATURE:
<223> OTHER INFORMATION: Hairpin primer for polymerase assay
<220> FEATURE:
<221> NAME/KEY: misc_feature
<222> LOCATION: (37)..(37)
<223> OTHER INFORMATION: n is dU-biotin

<400> SEQUENCE: 110
tagctcggta acgccggctt ccgtcgcgac cacgttnttc gtggtcgcga cggaagccg      59

<210> SEQ ID NO 111
<211> LENGTH: 61
<212> TYPE: DNA
<213> ORGANISM: Artificial sequence
<220> FEATURE:
<223> OTHER INFORMATION: Hairpin primer for polymerase assays
<220> FEATURE:
<221> NAME/KEY: misc_feature
<222> LOCATION: (39)..(39)
<223> OTHER INFORMATION: n is dU-biotin

<400> SEQUENCE: 111
tagctcggat tttcgccggc ttccgtcgcg accacgttnt tcgtggtcgc gacggaagcc     60
g                                                                    61

<210> SEQ ID NO 112
<211> LENGTH: 60
<212> TYPE: DNA
<213> ORGANISM: Artificial sequence
<220> FEATURE:
<223> OTHER INFORMATION: Hairpin primer for polymerase assay
<220> FEATURE:
<221> NAME/KEY: misc_feature
<222> LOCATION: (38)..(38)
<223> OTHER INFORMATION: n is dU-biotin

<400> SEQUENCE: 112
tagctaccag ggctccggct tccgtcgcga ccacgttntt cgtggtcgcg acggaagccg     60
```

```
<210> SEQ ID NO 113
<211> LENGTH: 67
<212> TYPE: DNA
<213> ORGANISM: Artificial sequence
<220> FEATURE:
<223> OTHER INFORMATION: Hairpin primer for polymerase assays
<220> FEATURE:
<221> NAME/KEY: misc_feature
<222> LOCATION: (22)..(22)
<223> OTHER INFORMATION: n is an abasic site
<220> FEATURE:
<221> NAME/KEY: misc_feature
<222> LOCATION: (45)..(45)
<223> OTHER INFORMATION: n is dU-biotin

<400> SEQUENCE: 113
agctaccatg cctgcacgca gncggcatcc gtcgcgacca cgttnttcgt ggtcgcgacg    60
gatgccg                                                             67

<210> SEQ ID NO 114
<211> LENGTH: 23
<212> TYPE: DNA
<213> ORGANISM: Artificial sequence
<220> FEATURE:
<223> OTHER INFORMATION: Primer for polymerase extension assay

<400> SEQUENCE: 114
taatacgact cactataggg aga                                           23

<210> SEQ ID NO 115
<211> LENGTH: 30
<212> TYPE: DNA
<213> ORGANISM: Artificial sequence
<220> FEATURE:
<223> OTHER INFORMATION: Template for polymerase extension assay
<220> FEATURE:
<221> NAME/KEY: misc_feature
<222> LOCATION: (24)..(24)
<223> OTHER INFORMATION: n is 5-nitroindol

<400> SEQUENCE: 115
attatgctga gtgatatccc tctnatcgat                                    30

<210> SEQ ID NO 116
<211> LENGTH: 28
<212> TYPE: DNA
<213> ORGANISM: Artificial sequence
<220> FEATURE:
<223> OTHER INFORMATION: Template for polymerase extension assay
<220> FEATURE:
<221> NAME/KEY: misc_feature
<222> LOCATION: (24)..(24)
<223> OTHER INFORMATION: n is any of G, A, T, and C

<400> SEQUENCE: 116
attatgctga gtgatatccc tctngtca                                      28

<210> SEQ ID NO 117
<211> LENGTH: 23
<212> TYPE: DNA
<213> ORGANISM: Artificial sequence
<220> FEATURE:
<223> OTHER INFORMATION: Primer for polymerase extension assay
```

```
<400> SEQUENCE: 117
gcggtgtaga gacgagtgcg gag                                            23

<210> SEQ ID NO 118
<211> LENGTH: 50
<212> TYPE: DNA
<213> ORGANISM: Artificial sequence
<220> FEATURE:
<223> OTHER INFORMATION: Template for polymerase extension assay

<400> SEQUENCE: 118
ctctcacaag cagccaggca agctccgcac tcgtctctac accgctccgc              50
```

DNA POLYMERASE

RELATED APPLICATIONS

This application is a continuation of Ser. No. 12/538,392 filed Aug. 10, 2009, which is a divisional of U.S. application Ser. No. 11/417,403, which was filed on May 3, 2006, which is a continuation of Application No. PCT/GB04/004643, which was filed on 3 Nov. 2004, which designated the United States and was published in English, and which claims the benefit of United Kingdom Applications GB0410871.8, filed 14 May 2004, and GB0325650.0, filed 3 Nov. 2003. The entire teachings of the above applications are incorporated herein by reference.

FIELD OF INVENTION

The present invention relates to DNA polymerases. In particular the invention relates to a method for the generation of DNA polymerases which exhibit a relaxed substrate specificity. Uses of engineered polymerases produced using the methods of the invention are also described.

BACKGROUND

Accurate DNA replication is of fundamental importance to all life ensuring the maintenance and transmission of the genome and limiting tumorigenesis in higher organisms. High-fidelity DNA polymerases perform an astonishing feat of molecular recognition, incorporating the correct nucleotide triphosphate (dNTP) substrate molecules as specified by the template base with minimal error rates. For example, even without exonucleolytic proofreading, the replicative DNA polymerase III from *E. coli* on average only makes one error in ~$10^5$ base pairs (Schaaper JBC 1993).

As energetic differences between correctly and mispaired nucleotides per se are much too small to give rise to a $10^5$ fold discrimination, the structure of the polymerase active site in high-fidelity polymerases has evolved to enhance those differences. Recent structural studies of the A-family (Pol I-like) DNA polymerases from *Thermus aquaticus* (Taq) (Li 98), phage T7 (Ellenberger) and *B. stearothermophilus* (Bst) (Beese) in particular have revealed how conformational changes during the catalytic cycle may exclude non-cognate base-pairing geometries because of steric clashes within the closed active site. As a result of these tight steric constraints, not only are mismatched nucleotides excluded but catalysis becomes exquisitely sensitive to even slight distortions in the primer-template duplex. This precludes or greatly diminishes the replication of modified or damaged DNA templates, the incorporation of modified or unnatural deoxinucleotide triphosphates (dNTP) and the extension of mismatched or unnatural 3' termini.

While desirable in nature, such stringent substrate discrimination is limiting for many applications in biotechnology. Specifically, it restricts the use of unnatural or modified nucleotide bases and the applications they enable. It also precludes the efficient PCR amplification of damaged DNA templates.

Some other naturally occurring polymerases are less stringent with regard to their substrate specificity. For example, viral reverse transcriptases like HIV-1 reverse transcriptase or AMV reverse transcriptase and polymerases capable of translesion synthesis such as polY-family polymerases, pol X (Vaisman et al, 2001, JBC) or pol X (Washington (2002), PNAS; or the unusual polB-family polymerase pol X (Johnson, Nature), all extend 3' mismatches with elevated efficiency compared to high fidelity polymerases. The disadvantage of the use of translesion synthesis polymerases for biotechnological uses is that they depend on cellular processivity factors for their activity, such as PCNA. Moreover such polymerases are not stable at the temperatures at which certain biotechnological techniques are performed, such as PCR. Furthermore most Translesion synthesis polymerases have a much reduced fidelity, which would severely compromise their utility for cloning.

Using another approach, the availability of high-resolution structures has guided efforts to rationally alter the substrate specificity of high fidelity DNA polymerases by site-directed mutagenesis e.g. to increase acceptance of dideoxi- (ddNTPs) (Li 99) or ribonucleotides (rNTPs) (Astatke 98). In vivo complementation followed by screening has also yielded polymerase variants with increased rNTP incorporation and limited bypass of template lesions (Patel 01). Recently, two different in vitro strategies for selection of polymerase activity have been described (Jestin 00, Ghadessy 01, Xia 02). One is based on the proximal attachent of polymerase and template-primer duplex on the same phage particle and has allowed the isolation mutants of Taq polymerase, which incorporate rNTPs and dNTPs with comparable efficiency (Xia 02). However, such methods are complex, prone to error and are laborious.

Recently, the technique of compartmentalized self-replication (CSR) (Ghadessy 01), which is based on the self-replication of polymerase genes by the encoded polymerases within discrete, non-communicating compartments has allowed the selection of mutants of Taq polymerase with increased thermostability and/or resistance to the potent inhibitor heparin (Ghadessy et al 01).

However, there still remains a need in the art for an efficient and simple method for relaxing the substrate specificity of high fidelity DNA polymerases whilst maintaining high catalytic turnover and processivity of DNA fragments up to several tens of kb. Such polymerases will be of particular use in applications such as PCR amplification and sequencing of damaged DNA templates, for the incorporation of unnatural base analogues into DNA (such as is required for sequencing or array labelling) and as a starting point for the creation of novel polymerase activities using compartmentalised self replication or other methods.

SUMMARY OF THE INVENTION

The present inventors modified the principles of directed evolution, (in particular compartmentalised self replication) described in GB97143002, 986063936 and GB 01275643 in the name of the present inventors, to relax the steric control of high fidelity DNA polymerases and consequently to expand the substrate range of such polymerases. All of the documents listed above are herein incorporated by reference.

They surprisingly found that by performing the technique of compartmentalised self replication referenced above, using repertoires of randomly mutated Taq genes, and flanking primers bearing the mismatches A*G and C*C at their 3' terminus/end, then mutants were generated which not only exhibited the ability to extend the A*G and C*C tranversion mismatches used in the CSR selection, but also surprisingly exhibited a generic ability to extend mispaired 3' termini. This finding is especially significant since Taq polymerase is not able to extend 3' mismatches (Kwok wt al, (1990), Huang (1992).

The mutant polymerases generated also exhibit high catalytic turnover, concomitant with other high fidelity polymerases and are capable of efficient amplification of DNA fragments up to 26 kb.

Thus in a first aspect the present invention provides a method for the generation of an engineered DNA polymerase with an expanded substrate range which comprises the step of preparing and expressing nucleic acid encoding an engineered DNA polymerase utilising template nucleic acid and flanking primers which bear one or more distorting 3' termini/ends.

As herein defined 'flanking primers which bear a 3' distorting terminus/end' refer to those primers which possess at their 3' ends one or more group/s, preferably nucleotide group/s which deviate from cognate base-pairing geometry. Such deviations from cognate base-pairing geometry includes but is not limited to: nucleotide mismatches, base lesions (i.e. modified or damaged bases) or entirely unnatural, synthetic base substitutes. According to the above aspects of the invention, advantageously, the flanking primer/s bear one or more nucleotide mismatches at their 3' end/terminus.

Advantageously, according to the above aspects of the invention the flanking primers may have one, two, three, four, or five or more nucleotide mismatches at the 3' primer end. More advantageously, the one or more nucleotide mismatches are consecutive mismatches. More advantageously, according to the above aspects of the invention, the flanking primers have one or two nucleotide mismatches at the 3' primer end. Most preferably according to the above aspects of the invention, the flanking primers have one nucleotide mismatch at their 3' primer end.

More specifically the term 'distorting 3' termini/ends' includes within its scope the phenomenon whereby, for example, either the 3' terminal base (1-mismatch) or the 3' terminal and upstream base (2-mismatch, 3-mismatch, 4-mismatch and so on) are not complementary to the template base. Preferably mismatches are transversion mismatches i.e. apposing purines with purines and pyrimidines with pyrimidines. Preferably transversion mismatches are G.A and C.C. This type of primer terminus distortion is referred to herein as 'primer mismatch distortion'.

In addition, and as eluded to above, the term 'flanking primers bearing distorting 3' termini/ends' includes within its scope flanking primers bearing one or more unatural base analogues at the 3' termini/end of the one or more flanking primers so that distortion of the cognate DNA duplex geometry is created.

The method of the invention may be used to expand the substrate range of any DNA polymerase which lacks an intrinsic 3-5' exonuclease proofreading activity or where a 3-5' exonuclease proofreading activity has been disabled, e.g. through mutation. Suitable DNA polymerases include polA, polB (see e.g. Patrel & Loeb, Nature Struc Biol 2001) polC, polD, polY, polX and reverse transcriptases (RT) but preferably are processive, high-fidelity polymerases.

Advantageously, an engineered DNA polymerase with an expanded substrate range according to the invention is generated from a pol A-family DNA polymerase. Advantageously, the DNA polymerase is generated from a repertoire of pol A DNA polymerase nucleic acid as template nucleic acid. Preferably the pol A polymerase is Taq polymerase and the flanking primers used in the generation of the polymerase are one or more of those primers selected from the group consisting of the following: 5'-CAG GAA ACA GCT ATG ACA AAA ATC TAG ATA ACG AGG GA-3';A•G mismatch; SEQ ID NO: 3); 5'GTA AAA CGA CGG CCA GTA CCA CCG AAC TGC GGG TGA CGC CAA GCC-3' C*C mismatch (SEQ ID NO: 4).

More advantageously, according to the above aspect of the invention, the nucleic acid encoding the engineered polymerase according to the invention is generated using PCR using one or more flanking primers listed herein.

Advantageously, the method of the present invention involves the use of compartmentalised self replication, and consists of the steps listed below:
  (a) preparing nucleic acid encoding a engineered DNA polymerase, wherein the polymerase is generated using a repertoire of nucleic acid molecules encoding one or more DNA polymerases and flanking primers which bears a 3' distorting end.
  (b) compartmentalising the nucleic acid of step (a) into microcapsules;
  (c) expressing the nucleic acid to produce their respective DNA polymerase within the microcapsules;
  (d) sorting the nucleic acid encoding the engineered DNA polymerase which exhibits an expanded substrate range; and
  (e) expressing the engineered DNA polymerase which exhibits an expanded substrate range.

Most advantageously, the method of the invention comprises the use of one or more DNA polymerases and flanking primers which bears one or more nucleotide mismatches at their 3' primer ends.

According to the above aspects of the invention, the term 'engineered DNA polymerase' refers to a DNA polymerase which has a nucleic acid sequence which is not 100% identical at the nucleic acid level to the one or more DNA polymerase/s or fragments thereof, from which it is derived, and which is synthetic. According to the invention, an engineered DNA polymerase may belong to any family of DNA polymerase.

Advantageously, an engineered DNA polymerase according to the invention is a pol A DNA polymerase. As referred to above the term 'engineered DNA polymerase' also includes within its scope fragments, derivatives and homologues of an 'engineered DNA polymerase' as herein defined so long as it exhibits the requisite property of possessing an expanded substrate range as defined herein. In addition, it is an essential feature of the present invention that an engineered DNA polymerase according to the invention does not include a polymerase with a 3-5' exonuclease activity under the conditions used for the polymerisation reaction. (This definition includes polymerases in which the 3-5' exonuclease is not part of the polymerase polypeptide chain but is associated non-covalently with the active polymerase). Such a proofreading activity would remove any 3' mismatches incorporated according to the method of the invention, and thus would prevent a polymerase according to the invention possessing an expanded substrate range as defined herein.

As defined herein the term 'expanded substrate range' (of an engineered DNA polymerase) means that substrate range of an engineered DNA polymerase according to the present invention is broader than that of the one or more DNA polymerases, or fragments thereof from which it is derived. The term 'a broader substrate range' refers to the ability of an engineered polymerase according to the present invention to extend one or more 3' distorting ends, advantageously transversion mismatches (purine*purine, pyrimidine*pyrimidine) for example A*A, C*C, G*G, T*T and G*A, which the one or more polymerase/s from which it is derived cannot extend. That is, essentially, a DNA polymerase which exhibits a relaxed substrate range as herein defined has the ability not only to extend the 3' distorting endsused in its generation, IE those of the flanking primers) but also exhibits a generic ability to extend 3' distorting ends (for example A*G, A*A, G*G mismatches). Preferably, 'expanded substrate range' (of an engineered DNA polymerase) includes a wider spectrum of unnatural nucleotide substrates including αS dNTPs, dye-labelled nucleotides, damaged DNA templates and so on. More details are given in the Examples.

According to the above aspect of the invention advantageously the DNA polymerase generated using CSR technology is a pol A polymerase and it is generated using flanking primers selected from the group consisting of the following: 5'-CAG GAA ACA GCT ATG ACA AAA ATC TAG ATA ACG AGG GA-3';A•G mismatch; SEQ ID NO: 3); 5'GTA AAA CGA CGG CCA GTA CCA CCG AAC TGC GGG TGA CGC CAA GCC-3' C*C mismatch (SEQ ID NO: 4).

One skilled in the art will appreciate that in essence, any DNA polymerase flanking primer which incorporates a 3' mismatch will work with any suitable repertoire. The process of mismatch extension will vary in characteristics from polymerase to polymerase, and will also vary according to the experimental conditions. For example, G*A and C*C are the most disfavoured mismatches for extension by Taq polymerase (Huang et al, 92). Other mismatches are favoured for extension by other polymerases and this can be routinely determined by the skilled person.

One skilled in the art will also appreciate that it is an essential feature of the present invention that the methods described herein will only work for polymerases which are devoid of 3-5' exonuclease activity proofreading under the conditions used for the polymerisation reaction, as such activity would result in the removal of the incorporated mismatches.

Using the method of the invention, the present inventors generated a number of pol A polymerase mutants. Two of the mutants named M1 and M4 not only exhibit the ability to extend the G*A and C*C transversion mismatches used in the CSR selection, but also surprisingly exhibit a generically enhanced ability to extend 3' mismatched termini.

Thus in a further aspect the present invention provides an engineered DNA polymerase which exhibits an expanded substrate range. Preferably such an engineered polymerase is obtainable using one or more method/s of the present invention.

According to the above aspect of the invention, preferably the DNA polymerase is a pol A polymerase.

According to the above aspect of the invention, preferably the engineered DNA polymerase is obtained using the method of the invention.

In a further aspect still, the present invention provides a pol A DNA polymerase with an expanded substrate range, or the nucleic acid encoding it, wherein the DNA polymerase is designated M1 or M4 as shown in FIG. 1 and FIG. 2 respectively and depicted as SEQ No 1 and SEQ No 2 respectively.

According to the above aspect of the invention, preferably the engineered DNA polymerase as herein defined is that polymerase designated M1 in FIG. 1 and depicted SEQ No 1.

In yet a further aspect the invention provides a pol A DNA polymerase with an expanded substrate range, wherein the polymerase exhibits at least 95% identity to one or more of the amino acid sequences designated M1 and M4 as shown in FIG. 1 and FIG. 2 respectively and depicted SEQ No 1 and SEQ No 2 respectively and which comprises any one or more of the following mutations: E520G, D144G, L254P, E520G, E524G, N583S, 1.1-D144G, L254P, E520G, E524G, N583S, V113I, A129V, L245R, E315K, G364D, G403R, E432D, P481A, I614M, R704W, D144G, G370D, E742G, K56E, I63T, K127R, M317I, Q680R, R343G, G370D, E520G, G12A, A109T, D251E, P387L, A608V, R617K, D655E, T710N, E742G, A109T, D144G, V155I, P298L, G370D, I614M, E694K, R795G, E39K, R343G, G370D, E520G, T539A, M747V, K767R, G84A, D144G, K314R, E520G, F598L, A608V, E742G, D58G, R74P, A109T, L245R, R343G, G370D, E520G, N583S, E694K, A743P.

Advantageously, the invention provides a pol A DNA polymerase with an expanded substrate range, or the nucleic acid encoding it, wherein the polymerase exhibits at least 95% identity to one or more of the amino acid sequences designated M1 and M4 as shown in FIG. 1 and FIG. 2 respectively and depicted SEQ 1 and 2 respectively and which comprises any one or more of the following mutations: G84A, D144G, K314R, E520G, F598L, A608V, E742G, D58G, R74P, A109T, L245R, R343G, G370D, E520G, N583S, E694K, A743P.

Most advantageously, the invention provides a pol A DNA polymerase with an expanded substrate range, or the nucleic acid encoding it, wherein the polymerase exhibits at least 95% identity to one or more of the amino acid sequences designated M1 and M4 as shown in FIG. 1 and FIG. 2 respectively and depicted SEQ 1 and 2 respectively and which comprises any one or more of the following mutations: G84A, D144G, K314R, E520G, F598L, A608V, E742G.

According to the above aspect of the invention the mutation 'E520G' describes a DNA polymerase according to the invention in which glycine is present at position 520 of the amino acid sequence. The present inventors were surprised to find that E520, which is located at the tip of the thumb domain at a distance 20 A from the 3'OH of the mismatched primer terminus, would be involved in mismatch recognition or extension. The mutation of E520 to G520 is clearly important in such roles however as the present inventors have demonstrated. This aspect of the invention is described further in the detailed description of the invention.

The present inventors consider that the method of the invention is applicable to the generation of 'blends' of engineered DNA polymerases with an expanded substrate range. According to the present invention the term a 'blend' of more than one polymerase refers to a mixture of 2 or more, 3 or more 4 or more, 5 or more engineered polymerases. Preferably the term 'blends' refers to a mixture of 6, 7, 8, 9 or 10 or more 'engineered polymerases'.

It is important to note that the extension of mismatched 3' primer termini is a feature of naturally occurring polymerases. Viral reverse transcriptases (RT) like HIV-1 RT or AMV RT and polymerases capable of translesion synthesis (TLS) such as the polY-family polymerases pol ι (Vaisman 2001JBC) or pol κ (Washington 2002 PNAS) or the unusual polB-family polymerase polζ (Johnson Nature), all extend 3' mismatches with elevated efficiency compared to high-fidelity polymerases. Thus, the mutant polA polymerases according to the present invention share significant functional similarities with other polymerases found in nature but so far represent, the only known member of the polA-family polymerases that are proficient in mismatch extension (ME) and translesion synthesis (TLS).

In contrast to TLS polymerases, which are distributive and depend on cellular processivity factors such as PCNA, M1 and M4 combine mismatch extension (ME) and translesion synthesis (TLS) with high processivity and in the case of M1 are capable of efficient amplification of DNA fragments of up to 26 kb.

In a further aspect still the present invention provides a nucleic acid construct which is capable of encoding a pol A DNA polymerase which exhibits an expanded substrate range, wherein said pol A DNA polymerase is depicted in FIG. 1 and FIG. 2 as SEQ No 1 or SEQ No 2 and is designated M1 and M4 respectively.

According to the above aspect of the invention, preferably the nucleic acid construct encodes the M1 pol A polymerase as described herein.

In a further aspects the invention provides a pol A DNA polymerase with an expanded substrate range, in particular which is capable of mismatch extension, wherein the DNA polymerase comprises, preferably consists of the amino acid sequence of any one or more of the clones designated herein as 3B5, 3B8, 3C12 and 3D1.

In yet a further aspect the invention provides a pol A DNA polymerase with an expanded substrate range, in particular which is capable of abasic site bypass, wherein the DNA polymerase comprises, preferably consists of the amino acid sequence of any one or more of the clones designated herein as 3A10, 3B6 and 3B11.

In a further aspect still the invention provides a pol A DNA polymerase with an expanded substrate range, in particular which is capable of DNA replication involving the incorporation of unatural base analogues into the newly replicated DNA, wherein the pol A DNA polymerase comprises, preferably consists of the amino acid sequence of any one or more of the clones designated herein as 4D11 and 5D4.

In a further aspect the present invention provides a pol A DNA polymerase with an expanded substrate range, wherein the polymerase exhibits at least 95% identity to one or more of the amino acid sequences designated 3B5, 3B8, 3C12, 3D1, 3A10, 3B6, 3B11, 4D11 and 5D4. which comprises any one or more of the mutations (with respect to either of the three parent genes Taq, Tth, Tfl) or gene segments found in clones 3B5, 3B8, 3C12, 3D1, 3A10, 3B6, 3B11, 4D11 and 5D4.

In a further aspect still, the present invention provides a vector comprising a nucleic acid construct according to the present invention.

In a further aspect still the present invention provides the use of a DNA polymerase according to the present invention in any one or more of the following applications selected from the group consisting of the following: PCR amplification, sequencing of damaged DNA templates, the incorporation of unnatural base analogues into DNA and the creation of novel polymerase activities.

According to the above aspect of the invention, preferably the use is of a 'blend' of DNA polymerases according to the invention or selected according to the method of the invention. The use of blends of polymerases will be familiar to those skilled in the art and is described in Barnes, W. M. (1994) *Proc. Natl. Acad. Sci. USA* 91, 2216-2220 which is herein incorporated by reference.

According to the above aspect of the invention, preferably the DNA polymerase is a pol A DNA polymerase. Advantageously, it is generated using CSR technology using flanking primers bearing one or more 3' mismatch pairs of interest as described herein. Other suitable methods include screening after activity preselection (see Patel & Loeb 01) and phage display with proximity coupled template-primer duplex substrate (Jestin 01, Xue, 02. CST is also ideally suited as the present inventors have demonstrated.

According to the above aspect of the invention, preferably the use of a polymerase according to the invention is in PCR amplification and the polymerase is M1 as herein described.

According to the above aspect of the invention, advantageously, the creation of novel polymerase activities is produced using the technique of compartmentalised self replication as described herein.

DEFINITIONS

The term 'engineered DNA polymerase' refers to a DNA polymerase which has a nucleic acid sequence which is not 100% identical at the nucleic acid level to the one or more DNA polymerase/s or fragments thereof, from which it is derived, and which has been generated using one or more biotechnological methods. Advantageously, an engineered DNA polymerase according to the invention is a pol-A family DNA polymerase or a pol-B family DNA polymerase. More advantageously, an engineered DNA polymerase according to the invention is a pol-A family DNA polymerase. As referred to above the term 'engineered DNA polymerase' also includes within its scope fragments, derivatives and homologues of an 'engineered DNA polymerase' as herein defined so long as it exhibits the requisite property of possessing an expanded substrate range as defined herein. In addition, it is an essential feature of the present invention that an engineered DNA polymerase according to the invention does not include a polymerase with a 3-5' exonuclease activity under the conditions used for the polymerisation reaction. Such a proofreading activity would remove any 3' mismatches incorporated according to the method of the invention, and thus would prevent a polymerase according to the invention possessing an expanded substrate range as defined herein.

As herein defined 'flanking primers which bear a 3' distorting terminus' refer to those DNA polymerase primers which possess at their 3' ends one or more group/s, preferably nucleotide group/s which deviate from cognate base-pairing geometry. Such deviations from cognate base-pairing geometry includes but is not limited to: nucleotide mismatches, base lesions (i.e. modified or damaged bases) or entirely unnatural, synthetic base substitutes at the 3 end of a flanking primer used according to the methods of the invention. According to the above aspects of the invention, advantageously, the flanking primer/s bear one or more nucleotide mismatches at their 3' end. Advantageously, according to the above aspects of the invention the flanking primers may have one, two, three, four, or five or more nucleotide mismatches at the 3' primer end. Preferably according to the above aspects of the invention, the flanking primers have one or two nucleotide mismatches at the 3' primer end. Most preferably according to the above aspects of the invention, the flanking primers have one nucleotide mismatch at their 3' primer end.

As defined herein the term 'expanded substrate range' (of an engineered DNA polymerase) means that substrate range of an engineered DNA polymerase according to the present invention is broader than that of the one or more DNA polymerases, or fragments thereof from which it is derived. The term 'a broader substrate range' refers to the ability of an engineered polymerase according to the present invention to extend one or more 3' distorting ends, advantageously transversion mismatches (purine*purine, pyrimidine*pyrimidine) for example A*A, C*C, G*G, T*T and G*A, which the one or more polymerase/s from which it is derived cannot extend. That is, essentially, a DNA polymerase which exhibits a relaxed substrate range as herein defined has the ability not only to extend the 3' distorting ends used in its generation, IE those of the flanking primers) but also exhibits a generic ability to extend 3' distorting ends (for example A*G, A*A, G*G mismatches).

BRIEF DESCRIPTION OF THE FIGURES

FIG. 1 shows the M1 nucleic acid (a; SEQ ID NO: 5) and amino acid sequence (b; SEQ ID NO: 1).

FIG. 2 shows the M4 nucleic acid (a; SEQ ID NO: 6) amino acid sequence (b; SEQ ID NO 2).

FIG. 14. Polymerases selected for replication of 5NI were tested for activity with a range of substrates using the hairpin ELISA assay described in example 8. See example 16 for details. Sample 366 is from the Herdengel cave (Austria) and is 60 000 years old. Sample GS 3-7 is from the Gamsulzen cave (Austria) and is between 25 000 and 45 000 years old.

In eight out of a total of nine uncontaminated experiments, the blend of mismatch polymerases produced more successful (positive) amplifications than SuperTaq. The odds of this occurring by chance are $(9!/(8!1!))*(0.5)^8(0.5)^1=1.76\%$, as determined by binomial distribution analysis. Given the heterogenity of aDNA samples, it is not surprising that in one case SuperTaq performed better than the blend. Experiment 5 is depicted in FIG. 35.

The experiments are listed in chronological order and it is noteworthy that the difference in performance between SuperTaq and the blend became less pronounced as time passed. This may be due to freeze/thawing further damaging the aDNA as well as to loss of activity in the blend which less pure than SuperTaq.

Figure 15:
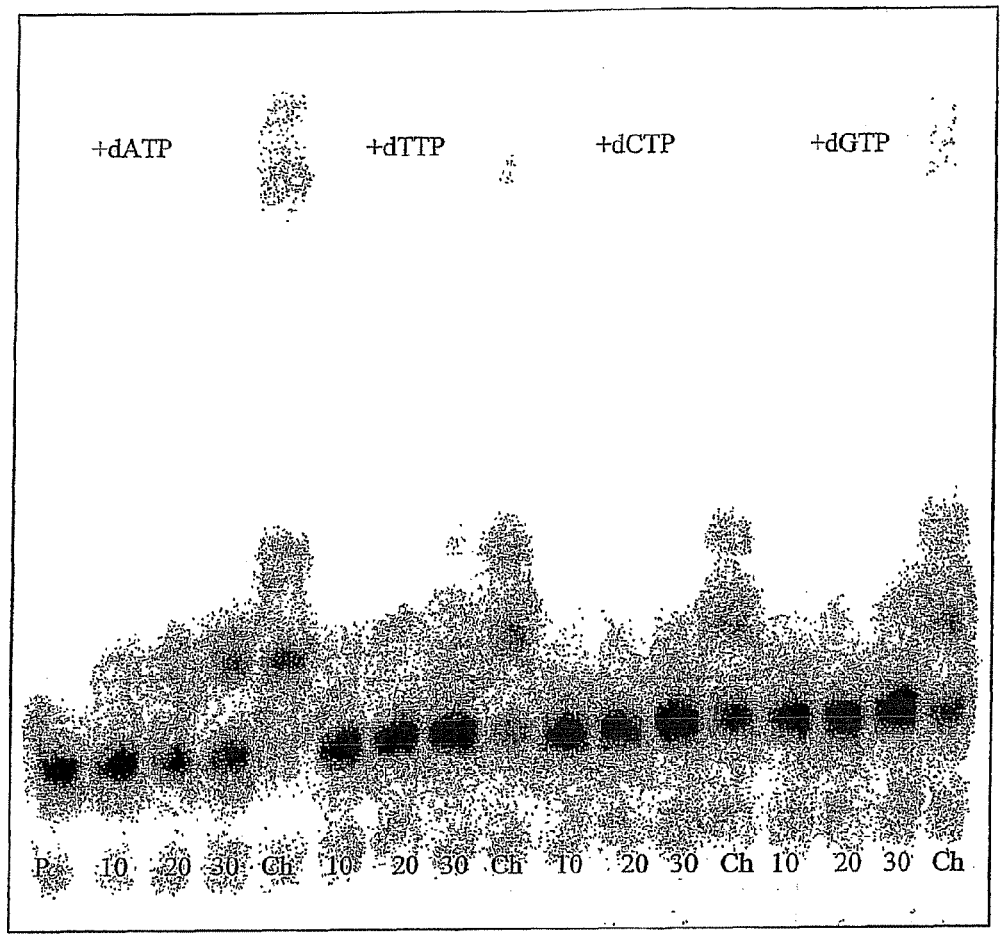

FIG. 15. Polymerases selected for replication of 5NI were tested for activity with a range of substrates. Polymerase 4D11. P is primer, Ch is the chase reaction. Reaction times in minutes. See example 16 for details.

Figure 16:
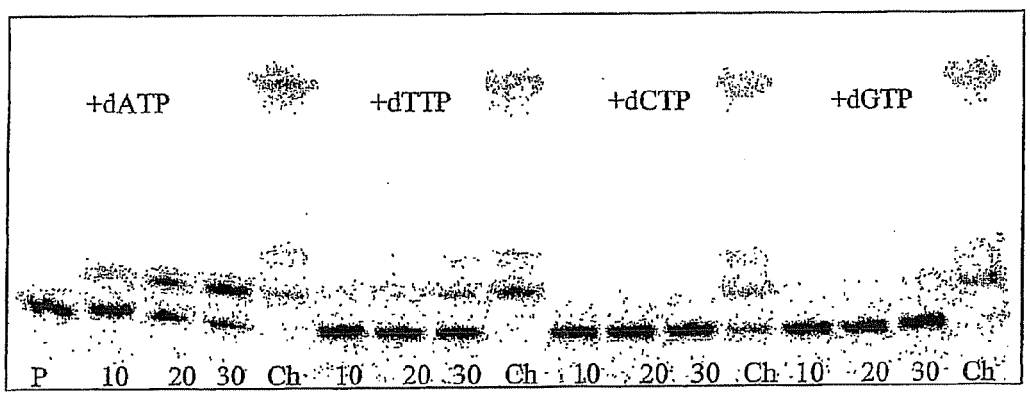

FIG. 16. Polymerases selected for replication of 5NI were tested for activity with a range of substrates Polymerase 5D4. P is primer, Ch is the chase reaction. Reaction times in minutes. See example 16 for details.

Figure 17:
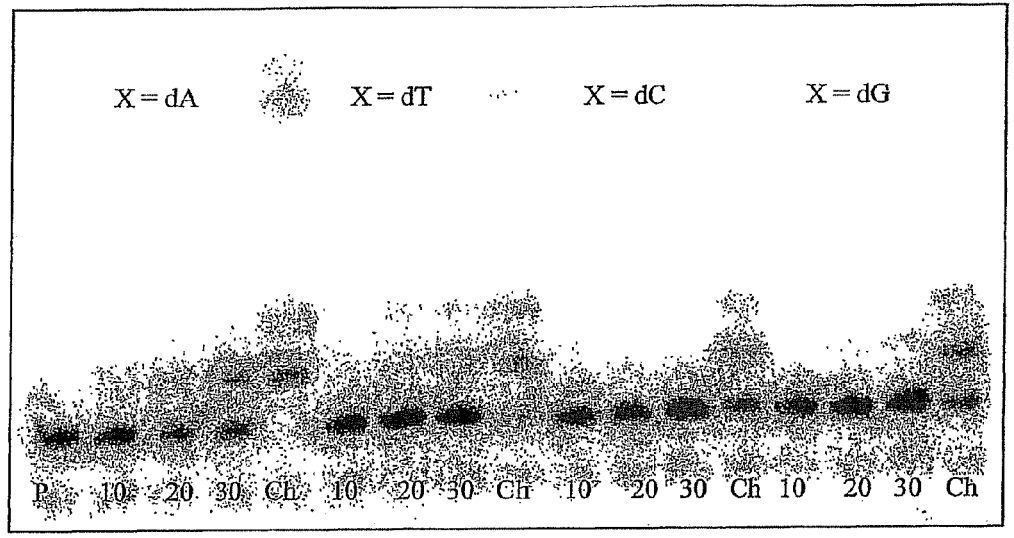

FIG. 17. Polymerases selected for replication of 5NI were tested for activity with a range of substrates Polymerase 4D11. P is primer, Ch is the chase reaction. Reaction times in minutes. See example 16 for details.

Figure 18:
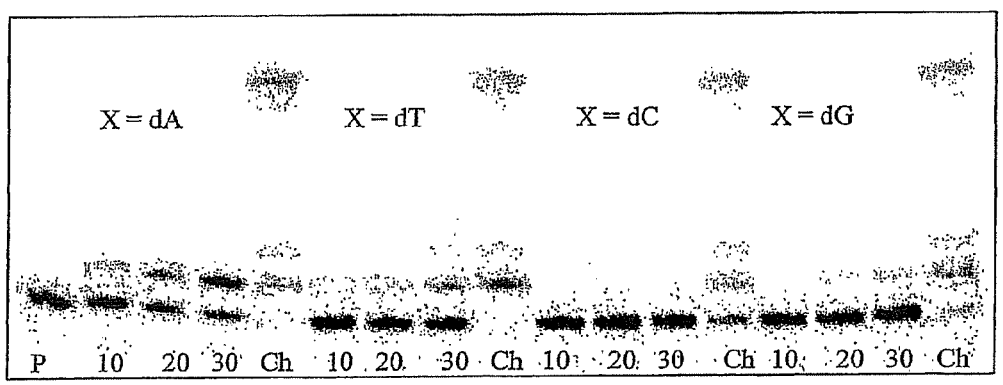

FIG. 18. Polymerases selected for replication of 5NI were tested for activity with a range of substrates Polymerase 5D4. P is primer, Ch is the chase reaction. Reaction times in minutes. See example 16 for details.

Figure 19:
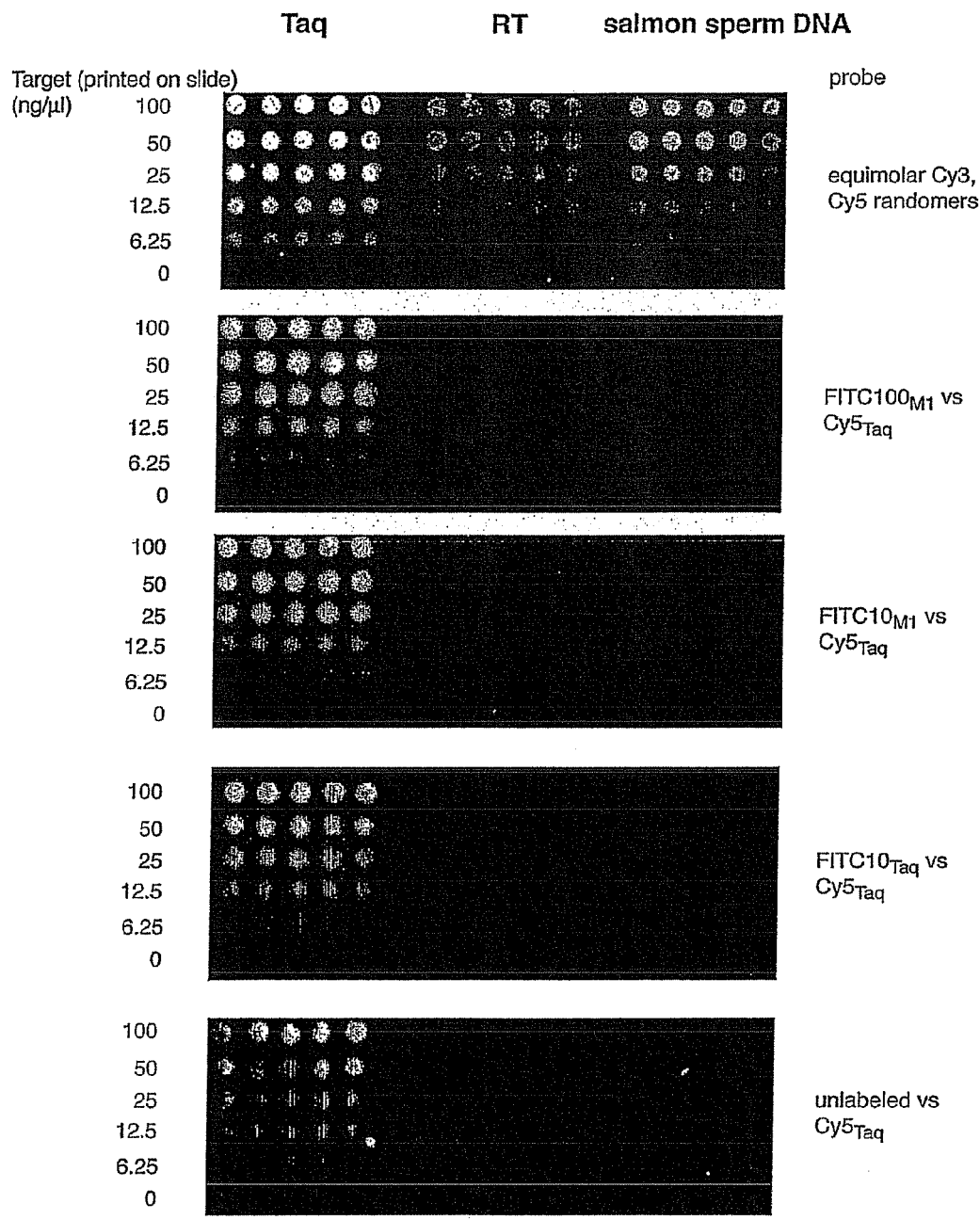

FIG. 19. Microarray hybridisations of FITC-labelled probes. Microarrays contained 5 replicate features of serial dilutions of Taq, RT and genomic salmon sperm DNA target sequences, as indicated. Labelled randomers were used to visualise the microarray and assess the availability of target sequences for hybridisation. Array co-hybridisations were performed with a Cy5-labelled Taq probe ($Cy5_{Taq}$), as a reference, and equivalent unlabelled or FITC-labelled probes ($FITC10_{Taq}$, $FITC10_{M1}$, $FITC100_{M1}$). Single examples from 3 replicate experiments are displayed for each co-hybridisation.

Figure 20:
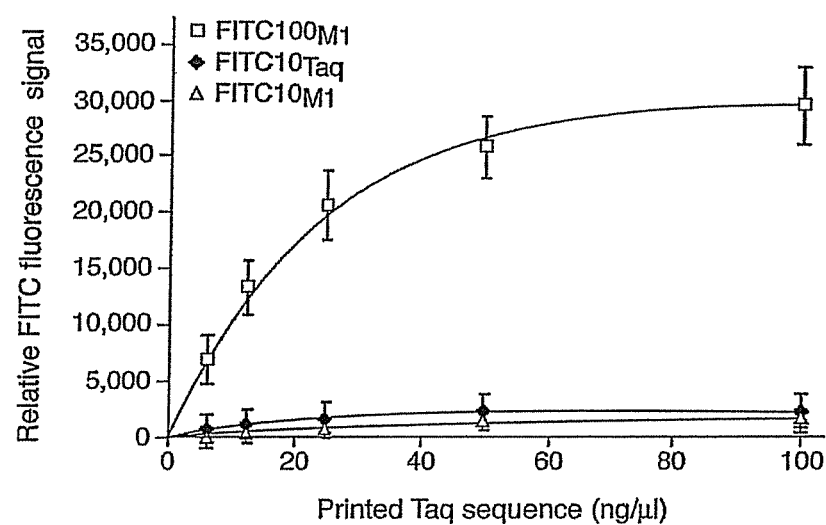

FIG. 20, FIG. 21. Microarray signals from FITC-labelled probes. Mean FITC fluorescence signal of FITC-labelled probes ($FITC10_{Taq}$, $FITC10_{M1}$, $FITC100_{M1}$) for each co-hybridisation is plotted against the Cy5 fluorescence signal of the reference probe ($Cy5_{Taq}$) for A) Taq, B) RT and C) genomic salmon sperm DNA target sequences, as indicated. D) Microarray background signals from FITC-labelled probes are determined using 3 replicate microarrays for each co-hybridisation experiment of a Cy5-labelled Taq probe ($Cy5_{Taq}$), as a reference, and unlabeled or FITC-labelled probes ($FITC10_{Taq}$, $FITC10_{M1}$, $FITC100_{M1}$). Background information was generated by measuring fluorescence signal from 12 non-feature areas of each microarray. Mean pixel intensities were generated and used to derive a ratiometric value for each non-feature area. A mean of the mean ratio+/−1 standard deviation is displayed for each co-hybridisation experiment.

Figure 22:
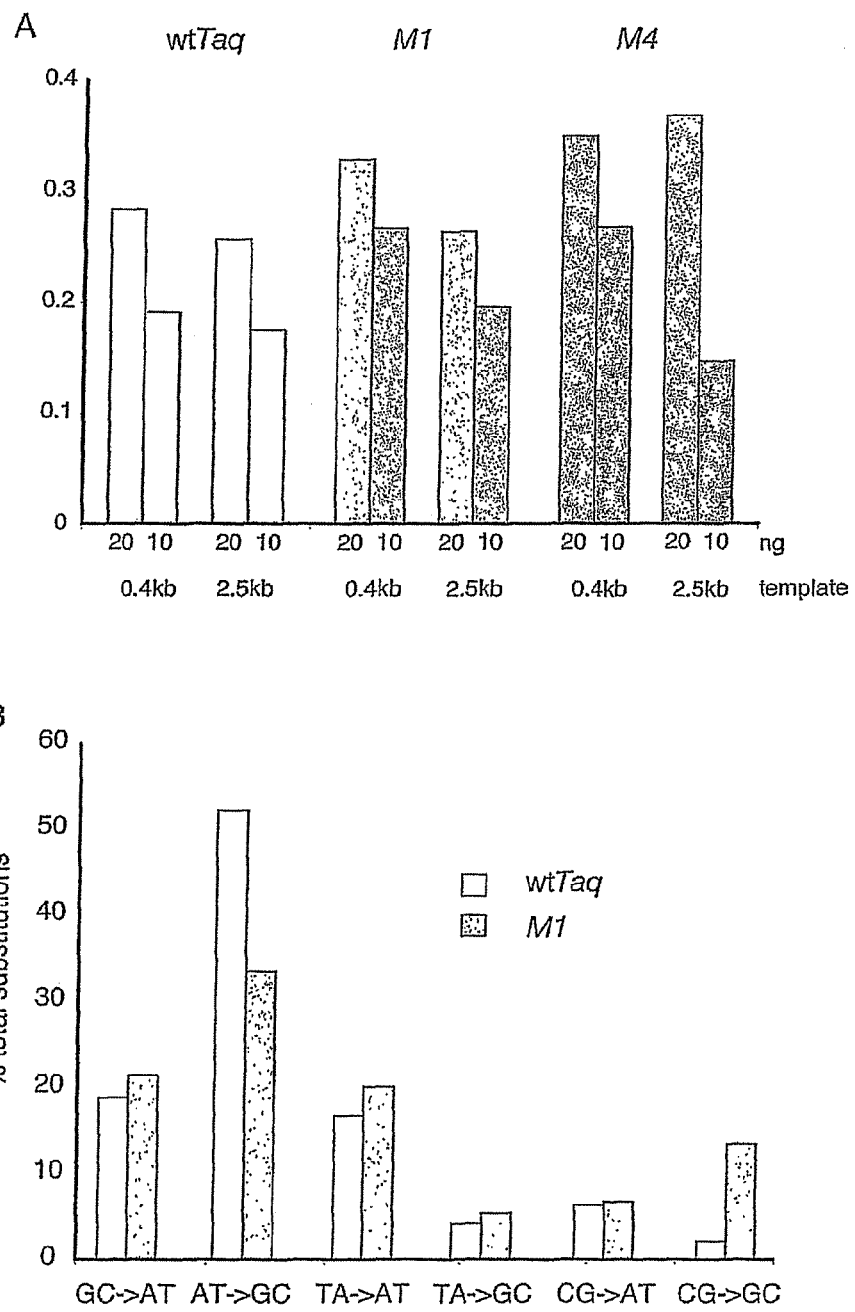

FIG. 22. Fidelity. (A) MutS ELISA. Relative replication fidelity of wtTaq, M1 and M4 was determined using mutS ELISA of two different DNA fragments (either a 0.4 kb or 2.5 kb region of the cloned Taq gene) obtained by PCR and probed at two different concentrations. (B) Spectra of nucleotide substitutions observed in PCR fragments amplified with either wtTaq or M1. Types of substitutions are given as % of total substitutions (wtTaq: 48, M1: 74). Equivalent substitutions on either strand (e.g. G→A, C→T) were added together (GC→AT). Observed −1 deletions (wtTaq: 3, M1: 1) are not shown.

FIG. 23. Processivity of wtTaq, M1 and M4 was measured at three different polymerase concentrations in the absence (A) or presence (B) of trap DNA. The processivity for nucleotide incorporation at each position was variable but essentially identical for all three polymerases. For example, the probability of enzyme dissociation is higher at positions 2-5 compared to positions 6 and 7 for all three polymerases. In the presence of trap DNA (to ensure all primer extension is the result of a single DNA binding event) 13% of bound wtTaq, 28% of M1 and 15% of M4 extended primers to the end of the template. The termination probabilities for positions 2 through 5 varied from 15-25% for wtTaq and M1 and from 13-35% for M4, while at positions 6 and 7 the termination probability was 5% for wtTaq, 1% for M1, and 2-4% for M4. DNA replication has been characterized as low processive when the termination probability reaches 40-80%[15]. Our results suggest that M1 and M4 are both processive polymerases, with processivity equal or higher than wtTaq, arguing against a mechanistic interdependence of low processivity and translesion synthesis.

DETAILED DESCRIPTION OF THE INVENTION (A) Principles Underlying CST Technology According to the Invention.

In a preferred embodiment the present invention provides a method for the generation of an engineered DNA polymerase with an expanded substrate range which comprises the steps of:
  (a) preparing nucleic acid encoding a mutant DNA polymerase, wherein the polymerase is generated using flanking primers which bear a 3' distorting end
  (b) compartmentalising the nucleic acid of step (a) into microcapsules;
  (c) expressing the nucleic acid to produce their respective DNA polymerase within the microcapsules;
  (d) sorting the nucleic acid encoding the mutant DNA polymerase which exhibits an expanded substrate range; and
  (e) expressing the mutant DNA polymerase which exhibits an expanded substrate range.

The techniques of directed evolution and compartmentalised self replication are detailed in GB 97143002 and GB 98063936 and GB 01275643, in the name of the present inventors. These documents are herein incorporated by reference.

The inventors modified the methods of compartmentalised self replication and surprisingly generated DNA polymerases which exhibited an expanded substrate range as herein defined.

In particular, the inventors realised that for self-replication of Taq polymerase, compartments must remain stable at the high temperatures of PCR thermocycling. Encapsulation of PCRs has been described previously for lipid vesicles (Oberholzer, T., Albrizio, M. & Luisi, P. L. (1995) *Chem. Biol.* 2, 677-82 and fixed cells and tissues (Haase, A. T., Retzel, E. F. & Staskus, K. A. (1990) *Proc. Natl. Acad. Sci. USA* 87, 4971-5; Embleton, M. J., Gorochov, G., Jones, P. T. & Winter, G. (1992) *Nucleic Acids*) but with low efficiencies.

The present inventors used recently developed oil in water emulsions but modified the composition of the surfactant as well as the oil to water ratio. Details are given in Example 1. These modifications greatly increased the heat stability of the compartments and allowed PCR yields in the emulsion to approach those of PCR in solution. Further details of the method of compartmentalised self replication are given below.

Microcapsules

The microcapsules used according to the method of the invention require appropriate physical properties to allow the working of the invention.

First, to ensure that the nucleic acids and gene products may not diffuse between microcapsules, the contents of each microcapsule must be isolated from the contents of the surrounding microcapsules, so that there is no or little exchange of the nucleic acids and gene products between the microcapsules over the timescale of the experiment.

Second, the method of the present invention requires that there are only a limited number of nucleic acids per microcapsule. This ensures that the gene product of an individual nucleic acid will be isolated from other nucleic acids. Thus, coupling between nucleic acid and gene product will be highly specific. The enrichment factor is greatest with on average one or fewer nucleic acids per microcapsule, the linkage between nucleic acid and the activity of the encoded gene product being as tight as is possible, since the gene product of an individual nucleic acid will be isolated from the products of all other nucleic acids. However, even if the theoretically optimal situation of, on average, a single nucleic acid or less per microcapsule is not used, a ratio of 5, 10, 50, 100 or 1000 or more nucleic acids per microcapsule may prove beneficial in sorting a large library. Subsequent rounds of sorting, including renewed encapsulation with differing nucleic acid distribution, will permit more stringent sorting of the nucleic acids. Preferably, there is a single nucleic acid, or fewer, per microcapsule.

Third, the formation and the composition of the microcapsules must not abolish the function of the machinery the expression of the nucleic acids and the activity of the gene products.

Consequently, any microencapsulation system used must fulfil these three requirements. The appropriate system(s) may vary depending on the precise nature of the requirements in each application of the invention, as will be apparent to the skilled person.

A wide variety of microencapsulation procedures are available (see Benita, 1996) and may be used to create the microcapsules used in accordance with the present invention. Indeed, more than 200 microencapsulation methods have been identified in the literature (Finch, 1993).

These include membrane enveloped aqueous vesicles such as lipid vesicles (liposomes) (New, 1990) and non-ionic surfactant vesicles (van Hal et al., 1996). These are closed-membranous capsules of single or multiple bilayers of non-covalently assembled molecules, with each bilayer separated from its neighbour by an aqueous compartment. In the case of liposomes the membrane is composed of lipid molecules; these are usually phospholipids but sterols such as cholesterol may also be incorporated into the membranes (New, 1990). A variety of enzyme-catalysed biochemical reactions, including RNA and DNA polymerisation, can be performed within liposomes (Chakrabarti et al., 1994; Oberholzer et al., 1995a; Oberholzer et al., 1995b; Walde et al., 1994; Wick & Luisi, 1996).

With a membrane-enveloped vesicle system much of the aqueous phase is outside the vesicles and is therefore non-compartmentalised. This continuous, aqueous phase should be removed or the biological systems in it inhibited or destroyed (for example, by digestion of nucleic acids with DNase or RNase) in order that the reactions are limited to the microcapsules (Luisi et al., 1987).

Enzyme-catalysed biochemical reactions have also been demonstrated in microcapsules generated by a variety of other methods. Many enzymes are active in reverse micellar solutions (Bru & Walde, 1991; Bru & Walde, 1993; Creagh et al., 1993; Haber et al., 1993; Kumar et al., 1989; Luisi & B., 1987; Mao & Walde, 1991; Mao et al., 1992; Perez et al., 1992; Walde et al., 1994; Walde et al., 1993; Walde et al., 1988) such as the AOT-isooctane-water system (Menger & Yamada, 1979).

Microcapsules can also be generated by interfacial polymerisation and interfacial complexation (Whateley, 1996). Microcapsules of this sort can have rigid, nonpermeable membranes, or semipermeable membranes. Semipermeable microcapsules bordered by cellulose nitrate membranes, polyamide membranes and lipid-polyamide membranes can all support biochemical reactions, including multienzyme systems (Chang, 1987; Chang, 1992; Lim, 1984). Alginate/polylysine microcapsules (Lim & Sun, 1980), which can be formed under very mild conditions, have also proven to be very biocompatible, providing, for example, an effective method of encapsulating living cells and tissues (Chang, 1992; Sun et al., 1992).

Non-membranous microencapsulation systems based on phase partitioning of an aqueous environment in a colloidal system, such as an emulsion, may also be used.

Preferably, the microcapsules of the present invention are formed from emulsions; heterogeneous systems of two immiscible liquid phases with one of the phases dispersed in the other as droplets of microscopic or colloidal size (Becher, 1957; Sherman, 1968; Lissant, 1974; Lissant, 1984).

Emulsions

Emulsions may be produced from any suitable combination of immiscible liquids. Preferably the emulsion of the present invention has water (containing the biochemical components) as the phase present in the form of finely divided droplets (the disperse, internal or discontinuous phase) and a hydrophobic, immiscible liquid (an 'oil') as the matrix in which these droplets are suspended (the nondisperse, continuous or external phase). Such emulsions are termed 'water-in-oil' (W/O). This has the advantage that the entire aqueous phase containing the biochemical components is compartmentalised in discreet droplets (the internal phase). The external phase, being a hydrophobic oil, generally contains none of the biochemical components and hence is inert.

The emulsion may be stabilised by addition of one or more surface-active agents (surfactants). These surfactants are termed emulsifying agents and act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash and Ash, 1993). Suitable oils include light white mineral oil and non-ionic surfactants (Schick, 1966) such as sorbitan monooleate (Span™80; ICI) and polyoxyethylenesorbitan monooleate (Tween™ 80; ICI) and Triton-X-100.

The use of anionic surfactants may also be beneficial. Suitable surfactants include sodium cholate and sodium taurocholate. Particularly preferred is sodium deoxycholate, preferably at a concentration of 0.5% w/v, or below. Inclusion of such surfactants can in some cases increase the expression of the nucleic acids and/or the activity of the gene products. Addition of some anionic surfactants to a non-emulsified reaction mixture completely abolishes translation. During emulsification, however, the surfactant is transferred from the aqueous phase into the interface and activity is restored. Addition of an anionic surfactant to the mixtures to be emulsified ensures that reactions proceed only after compartmentalisation.

Creation of an emulsion generally requires the application of mechanical energy to force the phases together. There are a variety of ways of doing this which utilise a variety of mechanical devices, including stirrers (such as magnetic stirbars, propeller and turbine stirrers, paddle devices and whisks), homogenisers (including rotor-stator homogenisers, high-pressure valve homogenisers and jet homogenisers), colloid mills, ultrasound and 'membrane emulsification' devices (Becher, 1957; Dickinson, 1994).

Aqueous microcapsules formed in water-in-oil emulsions are generally stable with little if any exchange of nucleic acids or gene products between microcapsules. Additionally, we have demonstrated that several biochemical reactions proceed in emulsion microcapsules. Moreover, complicated biochemical processes, notably gene transcription and translation are also active in emulsion microcapsules. The technology exists to create emulsions with volumes all the way up to industrial scales of thousands of liters (Becher, 1957; Sherman, 1968; Lissant, 1974; Lissant, 1984).

The preferred microcapsule size will vary depending upon the precise requirements of any individual selection process that is to be performed according to the present invention. In all cases, there will be an optimal balance between gene library size, the required enrichment and the required concentration of components in the individual microcapsules to achieve efficient expression and reactivity of the gene products.

Details of one example of an emulsion used when performing the method of the present invention are given in Example 1.

Expression within Microcapsules

The processes of expression must occur within each individual microcapsule provided by the present invention. Both in vitro transcription and coupled transcription-translation become less efficient at sub-nanomolar DNA concentrations. Because of the requirement for only a limited number of DNA molecules to be present in each microcapsule, this therefore sets a practical upper limit on the possible microcapsule size. Preferably, the mean volume of the microcapsules is less that $5.2 \times 10^{-16}$ m$^3$, (corresponding to a spherical microcapsule of diameter less than 10 μm, more preferably less than $6.5 \times 10^{-17}$ m$^3$ (5 μm), more preferably about $4.2 \times 10^{-18}$ m$^3$ (2 μm) and ideally about $9 \times 10^{-18}$ m$^3$ (2.6 μm).

The effective DNA or RNA concentration in the microcapsules may be artificially increased by various methods that will be well-known to those versed in the art. These include, for example, the addition of volume excluding chemicals such as polyethylene glycols (PEG) and a variety of gene amplification techniques, including transcription using RNA polymerases including those from bacteria such as *E. coli* (Roberts, 1969; Blattner and Dahlberg, 1972; Roberts et al., 1975; Rosenberg et al., 1975), eukaryotes e. g. (Weil et al., 1979; Manley et al., 1983) and bacteriophage such as T7, T3 and SP6 (Melton et al., 1984); the polymerase chain reaction (PCR) (Saiki et al., 1988); Qβ replicase amplification (Miele et al., 1983; Cahill et al., 1991; Chetverin and Spirin, 1995; Katanaev et al., 1995); the ligase chain reaction (LCR) (Landegren et al., 1988; Barany, 1991); and self-sustained sequence replication system (Fahy et al., 1991) and strand displacement amplification (Walker et al., 1992). Even gene amplification techniques requiring thermal cycling such as PCR and LCR could be used if the emulsions and the in vitro transcription or coupled transcription-translation systems are thermostable (for example, the coupled transcription-translation systems could be made from a thermostable organism such as *Thermus aquaticus*).

Increasing the effective local nucleic acid concentration enables larger microcapsules to be used effectively. This allows a preferred practical upper limit to the microcapsule volume of about $5.2 \times 10^{-16}$ m$^3$ (corresponding to a sphere of diameter 10 um).

The microcapsule size must be sufficiently large to accommodate all of the required components of the biochemical reactions that are needed to occur within the microcapsule. For example, in vitro, both transcription reactions and coupled transcription-translation reactions require a total nucleoside triphosphate concentration of about 2 mM.

For example, in order to transcribe a gene to a single short RNA molecule of 500 bases in length, this would require a minimum of 500 molecules of nucleoside triphosphate per microcapsule ($8.33 \times 10^{-22}$ moles). In order to constitute a 2 mM solution, this number of molecules must be contained within a microcapsule of volume $4.17 \times 10^{-19}$ liters ($4.17 \times 10^{-22}$ m$^3$ which if spherical would have a diameter of 93 nm.

Furthermore, particularly in the case of reactions involving translation, it is to be noted that the ribosomes necessary for the translation to occur are themselves approximately 20 nm in diameter. Hence, the preferred lower limit for microcapsules is a diameter of approximately 100 nm.

Therefore, the microcapsule volume is preferably of the order of between $5.2 \times 10^{-22}$ m$^3$ and $5.2 \times 10^{-16}$ m$^3$ corresponding to a sphere of diameter between 0.1 um and 10 um, more preferably of between about $5.2 \times 10^{-19}$ m$^3$ and $6.5 \times 10^{-17}$ m$^3$ (1 um and 5 um). Sphere diameters of about 2.6 um are most advantageous.

It is no coincidence that the preferred dimensions of the compartments (droplets of 2.6 um mean diameter) closely resemble those of bacteria, for example, *Escherichia* are 1.1-1.5×2.0-6.0 um rods and *Azotobacter* are 1.5-2.0 um diameter ovoid cells. In its simplest form, Darwinian evolution is based on a 'one genotype one phenotype' mechanism. The concentration of a single compartmentalised gene, or genome, drops from 0.4 nM in a compartment of 2 um diameter, to 25 pM in a compartment of 5 um diameter. The prokaryotic transcription/translation machinery has evolved to operate in compartments of ~1-2 um diameter, where single genes are at approximately nanomolar concentrations. A single gene, in a compartment of 2.6 um diameter is at a concentration of 0.2 nM. This gene concentration is high enough for efficient translation. Compartmentalisation in such a volume also ensures that even if only a single molecule of the gene product is formed it is present at about 0.2 nM, which is important if the gene product is to have a modifying activity of the nucleic acid itself. The volume of the microcapsule should thus be selected bearing in mind not only the requirements for transcription and translation of the nucleic acid/nucleic acid, but also the modifying activity required of the gene product in the method of the invention.

The size of emulsion microcapsules may be varied simply by tailoring the emulsion conditions used to form the emulsion according to requirements of the selection system. The larger the microcapsule size, the larger is the volume that will be required to encapsulate a given nucleic acid/nucleic acid library, since the ultimately limiting factor will be the size of the microcapsule and thus the number of microcapsules possible per unit volume.

The size of the microcapsules is selected not only having regard to the requirements of the transcription/translation system, but also those of the selection system employed for the nucleic acid/nucleic acid construct. Thus, the components of the selection system, such as a chemical modification system, may require reaction volumes and/or reagent concentrations which are not optimal for transcription/translation. As set forth herein, such requirements may be accommodated by a secondary re-encapsulation step; moreover, they may be accommodated by selecting the microcapsule size in order to maximise transcription/translation and selection as a whole. Empirical determination of optimal microcapsule volume and reagent concentration, for example as set forth herein, is preferred.

A "nucleic acid/nucleic acid" in accordance with the present invention is as described above. Preferably, a nucleic acid is a molecule or construct selected from the group consisting of a DNA molecule, an RNA molecule, a partially or wholly artificial nucleic acid molecule consisting of exclusively synthetic or a mixture of naturally-occurring and synthetic bases, any one of the foregoing linked to a polypeptide, and any one of the foregoing linked to any other molecular group or construct. Advantageously, the other molecular group or construct may be selected from the group consisting of nucleic acids, polymeric substances, particularly beads, for example polystyrene beads, magnetic substances such as magnetic beads, labels, such as fluorophores or isotopic labels, chemical reagents, binding agents such as macrocycles and the like.

The nucleic acid portion of the nucleic acid may comprise suitable regulatory sequences, such as those required for efficient expression of the gene product, for example promoters, enhancers, translational initiation sequences, polyadenylation sequences, splice sites and the like.

Product Selection

Details of a preferred method of performing the method of the invention are given in Example 1. However, those skilled in the art will appreciate that the examples given are non-limiting and methods for product selection are discussed in more general terms below.

A ligand or substrate can be connected to the nucleic acid by a variety of means that will be apparent to those skilled in the art (see, for example, Hermanson, 1996). Any tag will suffice that allows for the subsequent selection of the nucleic acid. Sorting can be by any method which allows the preferential separation, amplification or survival of the tagged nucleic acid. Examples include selection by binding (including techniques based on magnetic separation, for example using Dynabeads™), and by resistance to degradation (for example by nucleases, including restriction endonucleases).

One way in which the nucleic acid molecule may be linked to a ligand or substrate is through biotinylation. This can be done by PCR amplification with a 5'-biotinylation primer such that the biotin and nucleic acid are covalently linked.

The ligand or substrate to be selected can be attached to the modified nucleic acid by a variety of means that will be apparent to those of skill in the art. A biotinylated nucleic acid may be coupled to a polystyrene microbead (0.035 to 0.2 um in diameter) that is coated with avidin or streptavidin, that will therefore bind the nucleic acid with very high affinity. This bead can be derivatised with substrate or ligand by any suitable method such as by adding biotinylated substrate or by covalent coupling.

Alternatively, a biotinylated nucleic acid may be coupled to avidin or streptavidin complexed to a large protein molecule such as thyroglobulin (669 Kd) or ferritin (440 Kd). This complex can be derivatised with substrate or ligand, for example by covalent coupling to the alpha-amino group of lysines or through a non-covalent interaction such as biotin-avidin. The substrate may be present in a form unlinked to the nucleic acid but containing an inactive "tag" that requires a further step to activate it such as photoactivation (e.g. of a "caged" biotin analogue, (Sundberg et al., 1995; Pirrung and Huang, 1996)). The catalyst to be selected then converts the substrate to product. The "tag" could then be activated and the "tagged" substrate and/or product bound by a tag-binding molecule (e.g. avidin or streptavidin) complexed with the nucleic acid. The ratio of substrate to product attached to the nucleic acid via the "tag" will therefore reflect the ratio of the substrate and product in solution.

When all reactions are stopped and the microcapsules are combined, the nucleic acids encoding active enzymes can be enriched using an antibody or other molecule which binds, or reacts specifically with the "tag". Although both substrates and product have the molecular tag, only the nucleic acids encoding active gene product will co-purify.

The terms "isolating", "sorting" and "selecting", as well as variations thereof, are used herein. Isolation, according to the present invention, refers to the process of separating an entity from a heterogeneous population, for example a mixture, such that it is free of at least one substance with which it was associated before the isolation process. In a preferred embodiment, isolation refers to purification of an entity essentially to homogeneity. Sorting of an entity refers to the process of preferentially isolating desired entities over undesired entities. In as far as this relates to isolation of the desired entities, the terms "isolating" and "sorting" are equivalent. The method of the present invention permits the sorting of desired nucleic acids from pools (libraries or repertoires) of nucleic acids which contain the desired nucleic acid. Selecting is used to refer to the process (including the sorting process) of isolating an entity according to a particular property thereof.

Initial selection of a nucleic acid/nucleic acid from a nucleic acid library (for example a mutant taq library) using the present invention will in most cases require the screening of a large number of variant nucleic acids. Libraries of nucleic acids can be created in a variety of different ways, including the following.

Pools of naturally occurring nucleic acids can be cloned from genomic DNA or cDNA (Sambrook et al., 1989); for example, mutant Taq libraries or other DNA polymerase libraries, made by PCR amplification repertoires of taq or other DNA polymerase genes have proved very effective sources of DNA polymerase fragments. Further details are given in the examples.

Libraries of genes can also be made by encoding all (see for example Smith, 1985; Parmley and Smith, 1988) or part of genes (see for example Lowman et al., 1991) or pools of genes (see for example Nissim et al., 1994) by a randomised or doped synthetic oligonucleotide. Libraries can also be made by introducing mutations into a nucleic acid or pool of nucleic acids 'randomly' by a variety of techniques in vivo, including; using 'mutator strains', of bacteria such as E. coli mutD5 (Liao et al., 1986; Yamagishi et al., 1990; Low et al., 1996). Random mutations can also be introduced both in vivo and in vitro by chemical mutagens, and ionising or UV irradiation (see Friedberg et al., 1995), or incorporation of mutagenic base analogues (Freese, 1959; Zaccolo et al., 1996). 'Random' mutations can also be introduced into genes in vitro during polymerisation for example by using error-prone polymerases (Leung et al., 1989). In a preferred embodiment of the method of the invention, the repertoire of nucleic fragments used is a mutant Taq repertoire which has been mutated using error prone PCR. Details are given in Examples 1. According to the method of the invention, the term 'random' may be in terms of random positions with random repertoire of amino acids at those positions or it may be selected (predetermined) positions with random repertoire of amino acids at those selected positions.

Further diversification can be introduced by using homologous recombination either in vivo (see Kowalczykowski et al., 1994 or in vitro (Stemmer, 1994a; Stemmer, 1994b)).

Microcapsules/Sorting

In addition to the nucleic acids described above, the microcapsules according to the invention will comprise further components required for the sorting process to take place. Other components of the system will for example comprise those necessary for transcription and/or translation of the nucleic acid. These are selected for the requirements of a specific system from the following; a suitable buffer, an in vitro transcription/replication system and/or an in vitro translation system containing all the necessary ingredients, enzymes and cofactors, RNA polymerase, nucleotides, nucleic acids (natural or synthetic), transfer RNAs, ribosomes and amino acids, and the substrates of the reaction of interest in order to allow selection of the modified gene product.

A suitable buffer will be one in which all of the desired components of the biological system are active and will therefore depend upon the requirements of each specific reaction system. Buffers suitable for biological and/or chemical reactions are known in the art and recipes provided in various laboratory texts, such as Sambrook et al., 1989.

The in vitro translation system will usually comprise a cell extract, typically from bacteria (Zubay, 1973; Zubay, 1980; Lesley et al., 1991; Lesley, 1995), rabbit reticulocytes (Pelham and Jackson, 1976), or wheat germ (Anderson et al., 1983). Many suitable systems are commercially available (for example from Promega) including some which will allow coupled transcription/translation (all the bacterial systems and the reticulocyte and wheat germ TNT™ extract systems from Promega). The mixture of amino acids used may include synthetic amino acids if desired, to increase the possible number or variety of proteins produced in the library. This can be accomplished by charging tRNAs with artificial amino acids and using these tRNAs for the in vitro translation of the proteins to be selected (Ellman et al., 1991; Benner, 1994; Mendel et al., 1995).

After each round of selection the enrichment of the pool of nucleic acids for those encoding the molecules of interest can be assayed by non-compartmentalised in vitro transcription/replication or coupled transcription-translation reactions. The selected pool is cloned into a suitable plasmid vector and RNA or recombinant protein is produced from the individual clones for further purification and assay.

Microcapsule Identification

Microcapsules may be identified by virtue of a change induced by the desired gene product which either occurs or manifests itself at the surface of the microcapsule or is detectable from the outside as described in section iii (Microcapsule Sorting). This change, when identified, is used to trigger the modification of the gene within the compartment. In a preferred aspect of the invention, microcapsule identification relies on a change in the optical properties of the microcapsule resulting from a reaction leading to luminescence, phosphorescence or fluorescence within the microcapsule. Modification of the gene within the microcapsules would be triggered by identification of luminescence, phosphorescence or fluorescence. For example, identification of luminescence, phosphorescence or fluorescence can trigger bombardment of the compartment with photons (or other particles or waves) which leads to modification of the nucleic acid. A similar procedure has been described previously for the rapid sorting of cells (Keij et al., 1994). Modification of the nucleic acid may result, for example, from coupling a molecular "tag", caged by a photolabile protecting group to the nucleic acids: bombardment with photons of an appropriate wavelength leads to the removal of the cage. Afterwards, all microcapsules are combined and the nucleic acids pooled together in one environment. Nucleic acids encoding gene products exhibiting the desired activity can be selected by affinity purification using a molecule that specifically binds to, or reacts specifically with, the "tag".

Multi Step Procedure

It will be also be appreciated that according to the present invention, it is not necessary for all the processes of transcription/replication and/or translation, and selection to proceed in one single step, with all reactions taking place in one microcapsule. The selection procedure may comprise two or more steps. First, transcription/replication and/or translation of each nucleic acid of a nucleic acid library may take place in a first microcapsule. Each gene product is then linked to the nucleic acid which encoded it (which resides in the same microcapsule). The microcapsules are then broken, and the nucleic acids attached to their respective gene products optionally purified. Alternatively, nucleic acids can be attached to their respective gene products using methods which do not rely on encapsulation. For example phage display (Smith, G. P., 1985), polysome display (Mattheakkis et al., 1994), RNA-peptide fusion (Roberts and Szostak, 1997) or lac repressor peptide fusion (Cull, et al., 1992).

In the second step of the procedure, each purified nucleic acid attached to its gene product is put into a second microcapsule containing components of the reaction to be selected. This reaction is then initiated. After completion of the reactions, the microcapsules are again broken and the modified nucleic acids are selected. In the case of complicated multistep reactions in which many individual components and reaction steps are involved, one or more intervening steps may be performed between the initial step of creation and linking of gene product to nucleic acid, and the final step of generating the selectable change in the nucleic acid.

Amplification

In all the above configurations, genetic material comprised in the nucleic acids may be amplified and the process repeated in iterative steps. Amplification may be by the polymerase chain reaction (Saiki et al., 1988) or by using one of a variety of other gene amplification techniques including; Qβ replicase amplification (Cahill, Foster and Mahan, 1991; Chetverin and Spirin, 1995; Katanaev, Kurnasov and Spirin, 1995); the ligase chain reaction (LCR) (Landegren et al., 1988; Barany, 1991); the self-sustained sequence replication system (Fahy, Kwoh and Gingeras, 1991) and strand displacement amplification (Walker et al., 1992).

(B) DNA Polymerases According to the Invention.

(i) General

High fidelity DNA polymerases such as Pol A (like Taq polymerase) and Pol-B family polymerases which lack a 3'-5' exonuclease proofreading capability show a strict blockage to the extension of distorted or mismatched 3' primer termini to avoid propagation of misincorporations. While the degree of blockage varies considerably depending on the nature of the mismatch, some transversion (purine•purine/pyrimidine•pyrimidine) mismatches are extended up to $10^6$-fold less efficiently than matched termini (Huang 92). Likewise, many unnatural base analogues, while incorporated efficiently, act as strong terminators (Kool, Loakes).

The present inventors have modified the principles described in Ghadessy, F. G et al (2001) Proc. Nat. Acad. Sci, USA, 93, 4552-4557 (compartmentalised self replication) and Ghadessy 2003, and outlined above. Both these documents are herein incorporated by reference. The present inventors have used these modified techniques to develop a method by which the substrates specificity of high fidelity DNA polymerases may be expanded in a generic way.

The inventors have exemplified the technique by expanding the substrate specificity of the high-fidelity pol-A family polymerases. In particular, the present inventors created two repertoires of randomly mutated Taq genes, as described in Ghadessy, F. G et al (2001) referred to above. Three cycles of mismatch extension CSR was performed using flanking primers bearing the mismatches A*G and C*C at their 3' ends. Selected clones were ranked using a PCR extension assay described herein.

Selected mutants exhibited the ability to extend the G*A and C*C tranversion mismatches used in the CSR selection, but also exhibited a generic ability to extend mispaired 3' termini. These results are surprising, especially since Taq polymerase is unable to extend such mismatches (Kwok et al, (1990); Huang (1992).

Thus, using this approach, the inventors have generated DNA polymerases which exhibit a relaxed substrate specificity/expanded substrate range.

According to the present invention, the term 'expanded substrate range' (of an engineered DNA polymerase) means that substrate range of an engineered DNA polymerase according to the present invention is broader than that of the one or more DNA polymerases, or fragments thereof from which it is derived. The term 'a broader substrate range' refers to the ability of an engineered polymerase according to the present invention to extend one or more 3' mismatches, for example A*A, G*A, G*G, T*T, C*C, which the one or more polymerase/s from which it is derived cannot extend. That is, essentially, a DNA polymerase which exhibits a relaxed substrate range as herein defined has the ability not only to extend the 3' mismatches used in its generation, (IE those of the flanking primers), but also exhibits a generic ability to extend 3' mismatches (for example A*G, A*A, G*G).

The two best mutants M1 (G84A, D144G, K314R, E520G, F598L, A608V, E742G) and M4 (D58G, R74P, A109T, L245R, R343G, G370D, E520G, N583S, E694K, A743P) were chosen for further investigation.

M1 and M4 not only had greatly increased ability to extend the G•A and C•C transversion mismatches used in the CSR selection, but appeared to have acquired a more generic ability to extend 3' mispaired termini, including other strongly disfavoured transversion mismatches (such as A•G, A•A, G•G) (FIG. 1B), which wtTaq polymerase was unable to extend, as previously reported (Kwok et al 1990, Huang 92).

(ii) M1 and M4 Mutants According to the Invention.

Nucleic acid sequences encoding M1 and M4 pol A DNA polymerase mutants are depicted SEQ No 1 and SEQ No 2 respectively and are shown in FIG. 1 and FIG. 2 respectively.

Despite very similar properties, M1 and M4 (and indeed other selected clones) have few mutations in common, suggesting there are multiple molecular solutions to the mismatch extension phenotype. One exception was E520G, a mutation that is shared by all but one of the four best clones of the final selection. Curiously, E520 is located at the very tip of the thumb domain at a distance of 20 Å from the 3' OH of the mismatched primer terminus and its involvement in mismatch recognition or extension is unclear. However, E520G is clearly important for mismatch extension as backmutation reduces mismatch extension in both M1 and M4 to near wt levels (FIG. 2).

The only other feature clearly shared by both M1 and M4 are mutations targeting residues, which may be involved in flipping out the +1 template base. Residue E742 mutated in M1 (E742G) forms a direct contact with the flipped out +1 base on the template strand (Li et al), while in M4 the adjacent residue A743 is mutated to proline (A743P), which may disrupt interactions by distorting local backbone conformation. Back mutation of E742G in M1 reduced mismatch extension, but only by ca. 20% indicating that it does not contribute decisively to mismatch extension.

Figure 3:
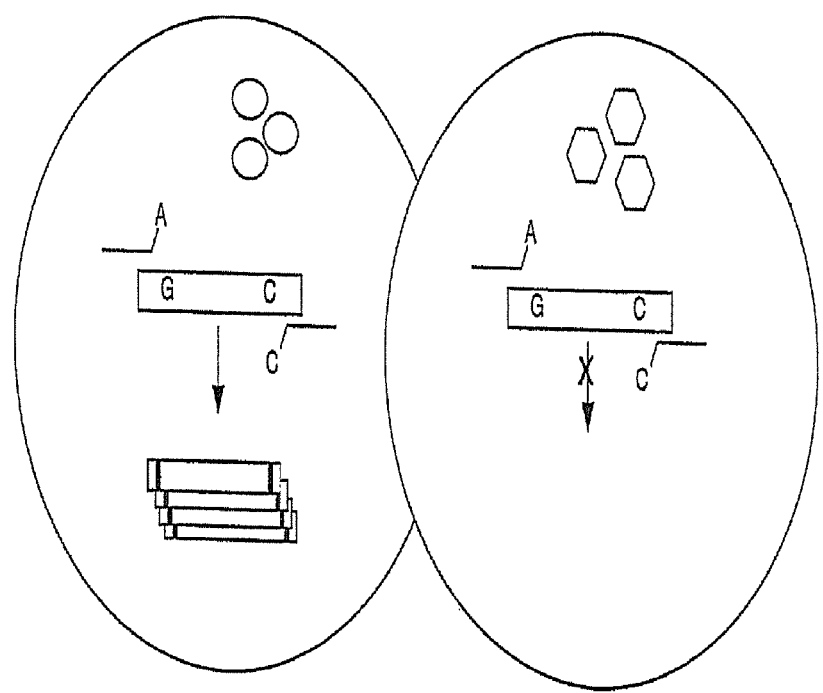
FIG. 3 shows the general scheme of mismatch extension CSR selection. Self-replication of the pol gene by the encoded polymerase requires extension of flanking primers bearing G•A and C•C 3' mismatches. Polymerases capable of mismatch extension (Pol*) replicate their own encoding gene (pol*), while Pol$^x$ cannot extend mismatches and fails to self-replicate. Black bars denote incorporation of the mismatch into replication products.
Figure 4A:
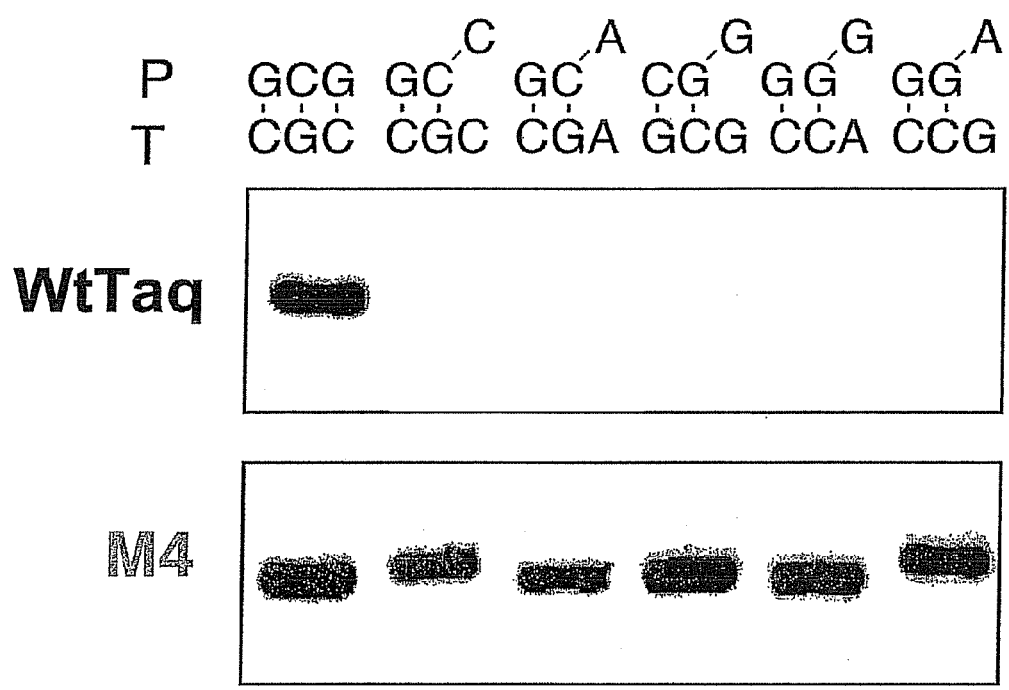
FIG. 4. Mismatch extension properties of selected polymerases. (a) Polymerase activity in PCR for matched 3' ends and mismatches. Only mutant polymerases M4 and M1 (not shown) generate amplification products using primers with 3' transversion mismatches. (b) Mismatch extension PCR assay. Mismatch extension capability is expressed as arbitrary mismatch extension units (ratio of polymerase activity in PCR with matched vs. mismatched flanking primers). Different polymerases (black diamonds) and derivatives (open squares, triangles) are shown in separate columns.
Figure 4B:
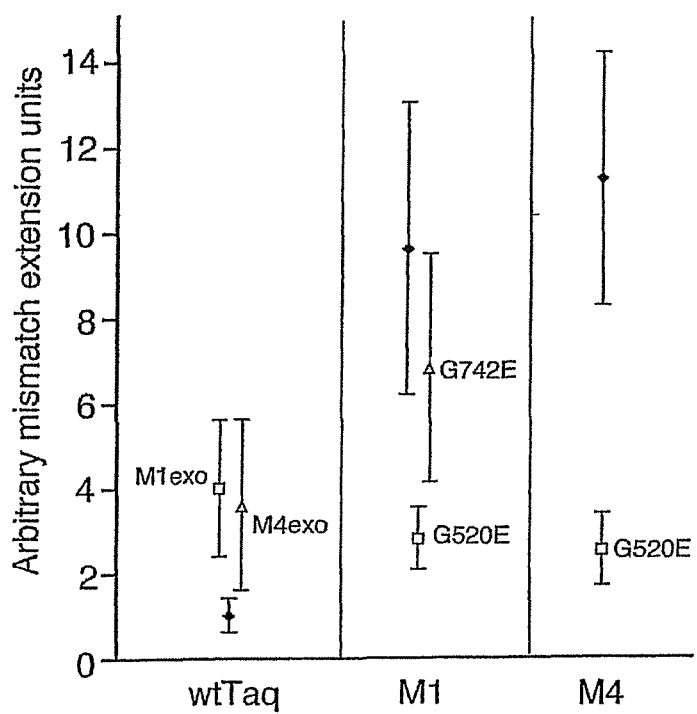

Surprisingly, mutations in the N-terminal 5'-3' exonuclease domain (53exoD) also appear to be contributing to mismatch extension as suggested by the 2-4 fold increased mismatch extension ability of chimeras of the 53exoD of M1, M4 and polD of wtTaq (FIG. 4). How they promote mismatch extension is unclear but given the apparent distance of the 53exoD from the active site (Utz 99, Eom 96) is unlikely to involve direct effects on extension catalysis. Increased affinity for primer-template duplex could also increase mismatch extension (Huang 92) but dissociation constants of wtTaq, M1 and M4 for matched and mismatched primer-template duplex were indistinguishable as judged by an equilibrium binding assay (Huang 92) (not shown).

The Relationship of M1 and M4 with Other Naturally Occurring DNA Polymerases

Extension of mismatched 3' primer termini is a feature of naturally occurring polymerases. Viral reverse transcriptases (RT) like HIV-1 RT or AMV RT and polymerases capable of translesion synthesis (TLS) such as the polY-family polymerases pol ι (Vaisman 2001JBC) or pol κ (Washington 2002 PNAS) or the unusual polB-family polymerase polζ (Johnson Nature), all extend 3' mismatches with elevated efficiency compared to high-fidelity polymerases. Thus, the selected polymerases share significant functional similarities with preexisting polymerases but represent, to our knowledge, the only known polA-family polymerases that are proficient in mismatch extension (ME) and translesion synthesis (TLS). In contrast to TLS polymerases, which are distributive and depend on cellular processivity factors such as PCNA (Prakash refs for eta/kappa and iota), M1 and M4 combine ME and TLS with high processivity and in the case of M1 are capable of efficient amplification of DNA fragments of up to 26 kb.

In the case of viral RTs, ME may play a crucial role in allowing error-prone yet processive replication of a multi-kb viral genome. For TLS polymerases, proficient mismatch extension is also a necessary prerequisite for their biological function as unpaired and distorted primer termini necessarily occur opposite lesions in the DNA template strand. The ability of TLS polymerases to traverse replication blocking lesions in DNA is thought to arise from a relaxed geometric selection in the active site (Goodman 02). The ability of M1 and M4 to process both bulky mispairs and a distorting CPD (cys-syn thymidine-thymidine dimer) dimer makes it plausible that, in analogy to TLS polymerases, they also have acquired a more open active site. Indeed, modelling showed that a CPD dimer can not be accommodated in the wtTaq polymerase active site without mayor steric clashes (Trincao01).

M1 (and to a lesser degree M4) also display a much increased ability to incorporate extend and replicate different types of unnatural nucleotide substrates that deviate to varying degrees from the canonical nucleobase structure. Of these the αS substitution is the most conservative. However, the sulfur anion is significantly larger than oxygen anion and coordinates cations poorly, which may be among the reasons why the wt enzyme will not tolerate full αS substitution. Fluorescently-labelled nucleotides like aS nucleotides retain base-pairing potential but include a bulky and hydrophobic substituent that must be accomodated by the polymerase active site. Steric clashes in the active site are allieviated by the presence of a long, flexible linker. Indeed, we find biotin-16-dUTP a much better substrate for M1 than biotin-11-dUTP, while wtTaq cannot utilize either. The hydrophobic analogue 5NI represents the most drastic departure from standard nucleotide chemistry we investigated. Comparable in size to a purine base, 5NI completely lacks any hydrogen bonding potential but like the natural bases, favours the anti-position with respect to the ribose sugar as judged by NMR (J. Gallego, D. L. and P. H., unpublished results). Therefore, a 5NI•A or 5NI•G basepair would closely resemble a purine-purine transversion mismatch and may cause similar distortions to the canonical DNA duplex geometry. Elegant experiments using isosteric non-hydrogen bonding base analogues have shown that Watson-Crick hydrogen bonding per se is not required for efficient insertion or replication (reviewed by Kool 02). However, while many non-hydrogen-bonding hydrophobic base analogues are efficiently incorporated, they subsequently lead to termination, both at the 3' end and as a template base (Kool, Romesberg).

Structural and biochemical studies have previously identified regions of the polymerase structure that are important for mismatch discrimination such as motif A (involved in binding the incoming dNTP), the 0-helix (motif B) and residues involved in minor groove hydrogen bonding (24, 25). Inspection of the sequence of M1 and M4 reveals a conspicuous absence of mutations in these regions. Rather mutations in M1 and M4 implicate regions of the polymerase not previously associated with substrate recognition such as the tip of the thumb subdomain (E520), the +1 template base-flipping function (E742, A743) in the finger subdomain and the 5-3' exonuclease domain (53exoD).

Figure 5:
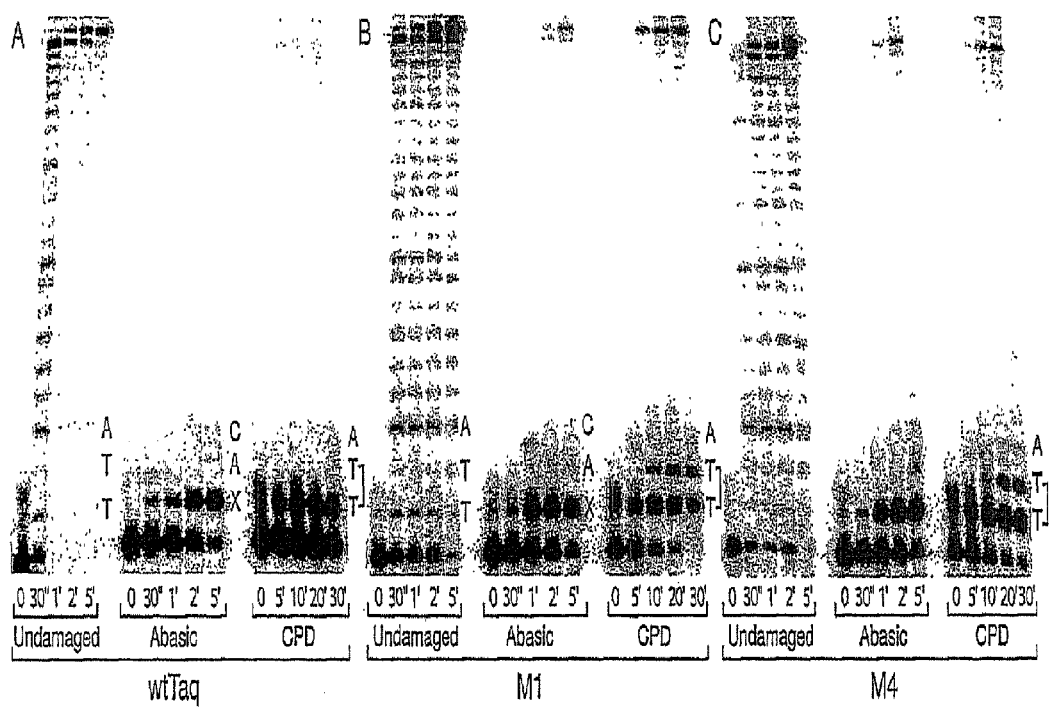
FIG. 5. Lesion bypass activity (A) wtTaq, (B) M1, (C) M4. Each polymerase was assayed over time for its ability to extend a radiolabeled primer annealed to either an undamaged template, or a template containing an abasic site or a cis-syn cyclobutane thymine-thymine dimer (CPD). Template sequence was identical except for three bases located immediately downstream of the primer (N1-3). The local sequence context in the N1-3 region is given on the right hand side of each respective panel. X=abasic site; T-T=CPD.

The 53exoD is too distant from the active site to have direct effects on mismatch extension. It is, however, thought to be crucial for polymerase processivity and may thus influence mismatch extension (24). Indeed, the Stoffel fragment of Taq polymerase (26), which lacks the 53exoD, displays both reduced processivity and more stringent mismatch discrimination (27). Mutations in the 53exoD of M1 and M4 may therefore contribute to mismatch extension by enhancing polymerase processivity. Together with the ability to bypass abasic sites (generated in large DNA fragments during thermocycling) this may also contribute to the proficiency of M1 at long PCR (FIG. 5). E520 is located at the very tip of the thumb domain at the end of the H2 helix at a distance of 20 Å from the 3' OH of the mismatched primer terminal base (P1) (2). Mechanistic aspects of the involvement of the E520G mutation in mismatch recognition or extension are therefore not obvious either. It is worth noting though that adjacent regions, especially the preceding loop connecting helices H1 and H2 and parts of helix I, make extensive contacts with the template-primer duplex between P3-P7 (2). It has previously been observed that mismatch incorporation affects extension kinetics up to the P4 position (24). E520G may modify the structure of these regions to ease passage of mismatches and increase elongation efficiency post incorporation. Base flipping, i.e. rotation of the designated base out of the DNA helix axis is a common mechanism among DNA modifying enzymes (e.g. glycosylases) but its precise role for polymerase function is less clear. It has been speculated that flipping out of the +1 template base may contribute to polymerase fidelity by preventing out-of-register base-pairing (25) of the 3' nucleotide to cognate upstream template bases. Interference with this mechanism therefore might promote apparent mismatch extension but would produce −1 base deletions. However, neither primer extensions nor sequencing of PCR products generated with M1 or M4 using primers with 3' G•A and C•C mismatches revealed any template slippage but on the contrary, confirmed in-register extension of the mismatches (not shown). The utility of reduced base-flipping in the context of the TLS capability of M1 and M4 is easier to understand, especially on the CPD dimer, as the two covalently linked thymine template bases would be refractory to flipping out. Indeed, TLS polymerases, which are naturally able to bypass CPD dimers, appear to lack a base-flipping function (28).

Extension and Incorporation Kinetics of Polymerases According to the Invention.

Examination of the extension and incorporation kinetics of the mutant polymerases suggests that they have a significantly increased propensity to not only extend but also incorporate transversion mispairs and consequently should have a significantly increased mutation rate compared to the wt enzyme. More relaxed geometric selection in the active site might also be expected to come at the price of significantly reduced fidelity as indeed is the case for TLS polymerases (23). However, measurement of the overall mutation rate using the MutS assay (not shown) and sequencing of PCR products generated by M1 indicated only a modest (<2-fold) increase in the mutation rate (Table 1) mostly due to an increased propensity for transversions. As discussed previously (10), CSR should select for optimal self-mutation rates within the error threshold (31). A change in the mutation spectrum towards a more even distribution of transition and transversion mutations may be an effective solution to accelerate adaptation, while maintaining a healthy distance from the error threshold. This may also make M1 a useful tool for protein engineering as the bias of Taq (and other DNA polymerases) for transition mutations limits the regions of sequence space that can be accessed effectively using PCR mutagenesis

TABLE 1

Mutation spectrum of wtTaq and M1 in PCR

| | Transitions | | Transversions | | | | |
|---|---|---|---|---|---|---|---|
| | AT->GC | GC->AT | AT->TA | AT->CG | GC->TA | GC->CG | Deletions |
| WtTaq* | 25 | 9 | 8 | 2 | 3 | 1 | 3 |
| M1* | 25 | 16 | 15 | 4 | 5 | 10 | 1 |

*Mutations derived from sequencing of 40 clones (800 bp) each.

In summary DNA polymerases according to the present invention, in particular M1 and M4 respectively as depicted in SEQ No 1 and SEQ No 2 possess the following properties:
(1) DNA Translesion synthesis
(2) A generic ability to incorporate unnatural base analogues into DNA.
(3) M1 has the ability to efficiently amplify DNA targets up to 26 kb.

Uses of DNA Polymerases According to the Invention.

Directed evolution towards extension of distorting transversion mismatches like G•A or C•C by CSR yields novel, "unfussy" polymerases with an ability to perform not only efficient mismatch extension and TLS but also accept a range of unnatural nucleotide substrates. The present inventors have shown that the evolution of TLS from a high-fidelity, polA-family, pol B family or other polymerases requires but few mutations, suggesting that TLS and relaxed substrate recognition are functionally connected and may represent a default state of polymerase function rather than a specialization.

The unusual properties of the DNA polymerases according to the present invention, in particular M1 and M4 may have immediate uses for example for the improved incorporation of dye-modified nucleotides in sequencing and array labelling and/or the amplification of ultra-long DNA targets. They may prove useful in the amplification of damaged DNA templates in forensics or paelobiology, may permit an expansion of the chemical repertoire of aptamers or deoxi-ribozymes (Benner, Barbas, ribozyme review) and may aid efforts to expand the genetic alphabet (Benner, Schultz). The altered mutation spectrum of M1 may make a useful tool in random mutagenesis experiments as the strong bias of Taq and other polymerases towards (A→G, T→C) transitions limits the combinatorial diversity accessible through PCR mutagenesis. Furthermore, the ability of M1 & M4 to extend 3' ends in which the last base is mismatched with the template strand and the ability of H10 (see example 6) to extend 3' ends in which the last two bases are mismatched with the template strand may extend the scope of DNA shuffling methods (Stemmer) by allowing to recombine more distantly related sequences.

In addition, DNA polymerases according to the invention, in particular pol A polymerases, for example M1 and M4 pol A polymerases as herein described may serve as a useful framework for mutagenesis and evolution towards polymerases capable of utilizing an ever wider array of modified nucleotide substrates. The inventors anticipate that directed evolution may ultimately permit modification of polymerase chemistry itself, allowing the creation of amplifiable DNA-like polymers of defined sequence thus extending molecular evolution to material science.

The invention will now be described by the following examples which are in no way limiting of the invention claimed herein.

Example 1

General Methods

List of Primers:

```
 1: 5'-CAG GAA ACA GCT ATG ACA AAA ATC TAG ATA ACG AGG GA-3';
    A·G mismatch (SEQ ID NO: 3)

2: 5'-GTA AAA CGA CGG CCA GTA CCA CCG AAC TGC GGG TGA CGC CAA GCC-3';
    C·C mismatch (SEQ ID NO: 4)

3: 5'-AAA AAT CTA GAT AAC GAG GGC AA-3' (SEQ ID NO: 13)

4: 5'-ACC ACC GAA CTG CGG GTG ACG CCA AGC G-3' (SEQ ID NO: 14)

5: 5'-GAA CTG CGG GTG ACG CCA AGC GCA 3'; A·A mismatch (SEQ ID NO: 15)

6: 5'-CC GAA CTG CGG GTG ACG CCA AGC GG 3'; G·G mismatch (SEQ ID NO: 16)

7: 5'-GAA CTG CGG GTG ACG CCA AGC GCG-3'; G·A mismatch (SEQ ID NO: 17)

8: 5'-AAA AAT CTA GAT AAC GAG GGC AA-3' (SEQ ID NO: 18)

9: 5'-CCG ACT GGC CAA GAT TAG AGA GTA TGG-3' (SEQ ID NO: 19)

10: 5'-GAT TTC CAC GGA TAA GAC TCC GCA TCC-3' (SEQ ID NO: 20)

11: 5'-GGC AGA CGA TGA TGC AGA TAA CCA GAG C-3' (SEQ ID NO: 21)

12: 5'-GCC GAT AGA TAG CCA CGG ACT TCG TAG-3' (SEQ ID NO: 22)

13: 5'-GGA GTA GAT GCT TGC TTT TCT GAG CC-3' (SEQ ID NO: 23)

14: 5'-GAG TTC GTG CTT ACC GCA GAA TGC AG-3' (SEQ ID NO: 24)

15: 5'-ACC GAA CTG CGG GTG ACG CCA AGC G 3' (SEQ ID NO: 25)

16: 5'-ACC GAA CTG CGG GTG ACG CCA AGC C 3' (SEQ ID NO: 26)

17: 5'-ACC GAA CTG CGG GTG ACG CCA AGC A 3' (SEQ ID NO: 27)

18: 5'-AAA CAG CGC TTG GCG TCA CCC GCA GTT CGG T-3' (SEQ ID NO: 28)

19: 5'-AAA CAG GGC TTG GCG TCA CCC GCA GTT CGG T-3' (SEQ ID NO: 29)

20: 5'-AAA CAG AGC TTG GCG TCA CCC GCA GTT CGG T-3' (SEQ ID NO: 30)

21: 5'-AAA CAC CGC TTG GCG TCA CCC GCA GTT CGG T-3' (SEQ ID NO: 31)

22: 5'-AGC TAC CAT GCC TGC ACG AAT TCG GCA TCC GTC GCG ACC ACG GTC GCA
    GCG-3' (undamaged) (SEQ ID NO: 32)

23: 5'-AGC TAC CAT GCC TGC ACG ACA XCG GCA TCC GTC GCG ACC ACG
    GTC GCA GCG-3'; X = abasic site (SEQ ID NO: 33)
```

-continued

24: 5'-AGC TAC CAT GCC TGC ACG AAX XCG GCA TCC GTC GCG ACC ACG GTC GCA GCG-3', XX = CPD dimer (SEQ ID NO: 34)

25: 5'-CGT GGT CGC GAC GGA TGC CG-3' (SEQ ID NO: 35)

26: 5'-TAA TAC GAC TCA CTA TAG GGA GA-3' (SEQ ID NO: 36)

27: 5'-ACT GXT CTC CCT ATA GTG AGT CGT ATT A-3'; X = 5NI (SEQ ID NO: 37)

Materials and Methods

DNA Manipulation and Protein Expression.

Expression of Taq clones for screening and CSR selection was as described (10). For kinetic measurements and gel extension assays, polymerases were purified as described (32) using a Biorex70 ion exchange resin (BioRad). All PCR and primer extensions were performed in 1× Taq buffer (50 mM KCl/10 mM Tris.HCl (pH 9.0)/0.1% Triton X-100/1.5 mM $MgCl_2$), with dNTPs (0.25 mM (Amersham Pharmacia Biotech, NJ)) and appropriate primers unless specified otherwise. Primer sequences are provided in Supplementary information. Primer extension reactions were terminated by addition of 95% formamide/10 mM EDTA and analysed on 20% polyacrylamide/7 M Urea gels.

CSR Selection.

Activity preselected libraries L1* and L2* (10) were combined and 3 rounds of CSR selection carried out as described (10) except using primers 1: (A•G mismatch) and 2: (C•C mismatch) and 15 cycles of (94° C. 1 min, 55° C. 1 min, 72° C. 8 min). Round 2 clones were recombined by staggered extension process (StEP) PCR shuffling (33) as described. For round 3, CSR cycles were reduced to 10 and annealing times to 30 sec.

PCR.

A PCR assay was used to screen and rank clones. Briefly, clones were normalized for activity in PCR with matched primers 3, 4 and activity with mismatched primers 1 and 2 (1 μM each) determined at minimal cycle number (15-25 cycles). Extension capability for different mismatches was determined by the same assay using mismatch primers 2 (C•C mismatch), 5 (A•A mismatch), 6 (G•G mismatch), 7 (G•A mismatch) with matched primer 3 or primer 1 (A•G mismatch) with matched primer 4. Incorporation of unnatural substrates in 50 cycle PCR was carried out using standard conditions and 50 μM c'S dNTPs (Promega) or 50 μM FITC-12-dATP (Perkin-Elmer), Rhodamine-5-dUTP (Perkin-Elmer) or Biotin-16-dUTP (Roche) with equivalent amounts of the other 3 dNTPs (all 50 μM). Long PCR was carried out using a two-step cycling protocol as described (22) 94° C. for 2 minutes, followed by 20 cycles of (94° C. 15 sec, 68° C. 30 min) using 5 ng of phage λ DNA (New England Biolabs) template and either primers 9, 10, 11 with primer 12 or primer 13 with primers 10, 14.

Single Nucleotide Incorporation/Extension Kinetics.

Kinetic parameters were determined using a gel-based assay essentially as described (16). Primers 15, 16, 17 (3' base=G, C, A respectively) were $^{32}$P-labeled and annealed to one of template strands 18, 19, 20 (template base=C, G, A respectively) or 21 (template base C different context). Duplex substrates were used at 50 nM final concentration in 1× Taq buffer with various concentrations of enzyme and dNTP. Reactions were carried out at 60° C. for times whereby <20% of primer-template was utilized at the highest concentration of dNTP.

Template Affinity Assays.

An equilibrium binding assay (12) was used to determine relative affinity of polymerases for the mismatched primer-templates used in the kinetics assays. Polymerases were pre-incubated at 60° C. in 1× Taq buffer with 50 nM $^{32}$P-labeled matched primer-template and 50 nM unlabeled mismatched competitor primer-templates. Reactions were initiated by simultaneous addition of dCTP (200 μM) and trap DNA (XbaI/SalI-restricted sheared salmon sperm DNA, 4.5 mg/ml). Prior experiments demonstrated trap-effectiveness over the time period used (15 seconds).

Translesion Replication Assay.

Template primers 22 (undamaged) or 23 (containing a synthetic abasic site) were synthesized by Lofstrand Laboratories (Gaithersburg, Md.). Template primer 24 (containing a single cis-syn thymine dimer), was synthesized as described (34). Primer 25 was $^{32}$P-labeled and annealed to one of the three templates 22, 23, 24 (at a primer template ratio of molar 1:1.5) and extended in 40 mM Tris.HCl at pH 8.0, 5 mM $MgCl_2$, 100 μM of each dNTP, 10 mM DTT, 250 μg/ml BSA, 2.5% glycerol, 10 nM primer-template DNA and 0.1 Unit of polymerase at 60° C. for various times.

5N1 Replication Assay.

Primer 26 was $^{32}$P-labeled and annealed to template primer 27 (containing a single 5-nitroindole) in 1× Taq buffer, 0.1 or 0.5 U of the polymerase was added and reactions incubated at 60° C. for 15 mins, after which 40 μM of each dNTP were added and incubation at 60° C. continued for various times.

Fidelity Assays.

Mutation rates were determined using the mutS ELISA assay (Genecheck, Ft. Collins, Colo.) or by performing 2×50 cycles of PCR on three different templates and sequencing the cloned products.

Example 2

Kinetic Analysis

Extension and incorporation kinetics of M1 and M4 for a selection of mismatches were measured using a gel-based steady-state kinetic assay (Goodman) (Tables 1 & 2). M1 and M4 respectively extend a C•C mispair 390 and 75-fold more efficiently than wtTaq. Examination of the other most disfavored mismatches (G•A, A•G, A•A, G•G) reveals generic, although less pronounced, increases of extension efficiencies, as suggested by the PCR assay (FIG. 4, FIG. 5). The gain in extension efficiency derives predominantly from increased relative Vmax values for the mutant polymerases, while Km for nucleotide substrates remains largely unchanged. For most DNA polymerases the relative efficiency of extending a given mispair (f0ext) is similar to the relative efficiency of forming it (finc) (Goodman 1993, Goodman 1990, Washington 2001). Indeed, M1 and M4 respectively incorporate dCTP opposite template base C 206- and 29-fold more efficiently than wtTaq (Table 2).

TABLE 2

Steady-state kinetic parameters for extension kinetics by wtTaq and mutant polymerases.

| 3'-Terminal Base pair* | Polymerase | $V_{max}$ (% Min$^{-1}$) | $K_m$ (μM) | f† | $f_{ext}$‡ | Ratio of $f_{ext}$§ |
|---|---|---|---|---|---|---|
| C · G | WtTaq | 1477.0 | 0.016 | 92312.5 | — | — |
|       | M1    | 308.0  | 0.02  | 15400   | — | — |
|       | M4    | 817.0  | 0.012 | 68083   | — | — |
| C · C | WtTaq | 0.2    | 39.9  | 0.00546 | $5.9 \times 10^{-8}$ | 1.0 |
|       | M1    | 9.2    | 25.8  | 0.356   | $2.3 \times 10^{-5}$ | 390.0 |
|       | M4    | 11.1   | 36.6  | 0.303   | $4.5 \times 10^{-6}$ | 75.3 |
| G · A | WtTaq | 1.6    | 32.8  | 0.05    | $5.4 \times 10^{-7}$ | 1.0 |
|       | M1    | 2.4    | 22.0  | 0.111   | $7.2 \times 10^{-6}$ | 13.3 |
|       | M4    | 7.5    | 29.0  | 0.26    | $3.8 \times 10^{-6}$ | 7.0 |
| A · G | WtTaq | 28.0   | 45.2  | 0.02    | $2.1 \times 10^{-7}$ | 1.0 |
|       | M1    | 44.6   | 280.2 | 0.02    | $1.3 \times 10^{-6}$ | 6.2 |
|       | M4    | 50.0   | 259.0 | 0.1     | $1.5 \times 10^{-6}$ | 7.0 |
| A · A | WtTaq | 1.7    | 27.3  | 0.062   | $6.7 \times 10^{-7}$ | 1.0 |
|       | M1    | 1.5    | 40.9  | 0.037   | $2.4 \times 10^{-6}$ | 3.6 |
|       | M4    | 8.5    | 32.9  | 0.259   | $3.8 \times 10^{-6}$ | 5.7 |
| G · G | WtTaq | 20.4   | 174.0 | 0.117   | $1.3 \times 10^{-6}$ | 1.0 |
|       | M1    | 29.6   | 67.0  | 0.44    | $2.9 \times 10^{-5}$ | 22.5 |
|       | M4    | 70.6   | 107.0 | 0.66    | $9.7 \times 10^{-6}$ | 7.6 |

*Template base: 3' primer base; Incorporated base is dCTP
†f, enzyme efficiency = $V_{max}/K_m$
‡$f_{ext}$, f (mismatched 3'terminus)/f (matched terminus)
§$f_{ext}$ (mutant polymerase)/$f_{ext}$ (wtTaq)

TABLE 2

Steady-state kinetic parameters for incorporation kinetics by wtTaq and mutant polymerases.

| Base pair* | Polymerase | $V_{max}$ (% Min$^{-1}$) | $K_m$ (μM) | f† | $f_{inc}$‡ | Ratio of $f_{inc}$§ |
|---|---|---|---|---|---|---|
| G: dCTP | WtTaq | 1477    | 0.016   | 92312.5  | — | — |
|         | M1    | 308     | 0.02    | 15400    | — | — |
|         | M4    | 817     | 0.012   | 68083    | — | — |
| G: dGTP | WtTaq | 57.47   | 365.27  | 0.157    | $1.7 \times 10^{-6}$ | 1 |
|         | M1    | 215.98  | 377.1   | 0.573    | $3.72 \times 10^{-5}$ | 21.88 |
|         | M4    | 656.46  | 82.34   | 7.97     | $1.17 \times 10^{-4}$ | 68.82 |
| G: dATP | WtTaq | 1973.68 | 258.53  | 7.63     | $8.27 \times 10^{-5}$ | 1 |
|         | M1    | 681.82  | 257.2   | 2.65     | $1.72 \times 10^{-4}$ | 2.08 |
|         | M4    | 1935.48 | 157.77  | 12.27    | $1.80 \times 10^{-4}$ | 2.18 |
| G: dTTP | WtTaq | 25.08   | 1.64    | 15.29    | $1.65 \times 10^{-4}$ | 1 |
|         | M1    | 10.19   | 1.65    | 6.18     | $4.01 \times 10^{-4}$ | 2.43 |
|         | M4    | 63.20   | 5.10    | 12.39    | $1.82 \times 10^{-4}$ | 1.1 |
| C: dGTP | WtTaq | 2356.02 | 0.0366  | 64285.69 | — | — |
|         | M1    | 111.66  | 0.0387  | 2884.55  | — | — |
|         | M4    | 335.42  | 0.01    | 33542    | — | — |
| C: dCTP | WtTaq | 3.3     | 1330.89 | 0.0025   | $3.86 \times 10^{-8}$ | 1 |
|         | M1    | 6.08    | 264.14  | 0.023    | $7.97 \times 10^{-6}$ | 206.74 |
|         | M4    | 52.63   | 1390.63 | 0.0378   | $1.13 \times 10^{-6}$ | 29.22 |

*Template base: incoming nucleotide
†f, enzyme efficiency = $V_{max}/K_m$
‡$f_{inc}$, f (incorrect dNTP)/f (correct dNTP)
§$f_{inc}$ (mutant polymerase)/$f_{inc}$ (wtTaq)

Example 3

Translesion Synthesis

Transversion mispairs represent distorting deviations from the cognate duplex structure. We therefore investigated if M1 and M4 were capable of processing other deviations of the DNA structure such as lesions in the template strand. Using a gel-extension assay we investigated their ability to traverse an abasic site and a cis-syn thymine pyrmidine dimer (CPD) template strand lesion. In control assays using an undamaged template, wtTaq, M1 and M4 efficiently and rapidly extended primers to the end of the template (FIG. 5). On the template containing an abasic site, wtTaq efficiently inserts a base opposite the lesion but, further extension is largely abolished. In contrast, both M1 and M4 are able to extend past the lesion and to the end of the template. The size of the final product is similar to that observed on the undamaged template indicating that bypass occurred without deletions. Perhaps the most striking example of the proficiency of M1 and M4 to bypass template lesions is observed on the CPD-containing template (FIG. 5). Under the assay conditions, wtTaq utilizes a fraction of the available template and is only able to insert a base opposite the 3'T of the dimer after prolonged reaction conditions. In contrast, both M1 and M4 are able to readily extend all of the primer to the 3'T of the dimer. In addition, there is also considerable extension of these primers to the 5'T of the CPD. As with the abasic template, a significant fraction of these primers are subsequently fully extended to the end of the template in an error-free manner without deletions. We estimate that trans-lesion synthesis (TLS) by M1 and M4 may only be 2-5 fold less efficient than that observed with a naturally occurring TLS polymerase, Dpo4 from *S. solfataricus* (Boudsocq et al (2001), Nucleic Acid Res, 29, 46072001) on the same template.

Example 4

Unnatural Substrates

Figure 6A:
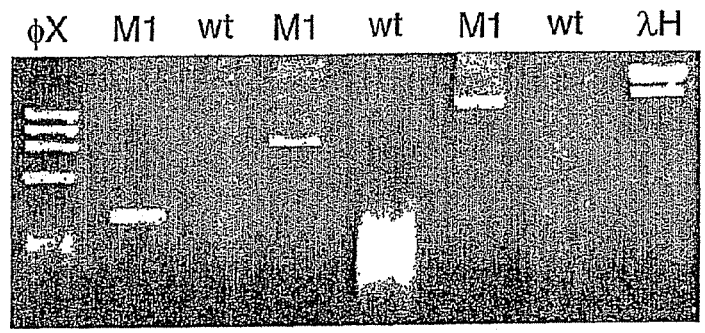
FIG. 6. Polymerase activity on unnatural substrates. (A) Polymerase activity in PCR using all αS dNTPs. αS DNA amplification products of 0.4 kb, 0.8 kb and 2 kb, are obtained with M1 but not with wtTaq (wt). φX, HaeIII-digested phage φX174 DNA marker. λH, HindIII-digested phage λ DNA marker. (B) Polymerase activity in PCR with complete replacement of dATP with FITC-12-dATP (left) or dTTP with Biotin-16-dUTP (right). Only M1 yields amplification products. M, 1 kb DNA ladder (Invitrogen). (C) Bypass of a 5-nitroindol template (5NI) base. Polymerase activity was assayed over time for its ability to extend a radiolabeled primer annealed to a template containing a 5NI template base.
Figure 6B:
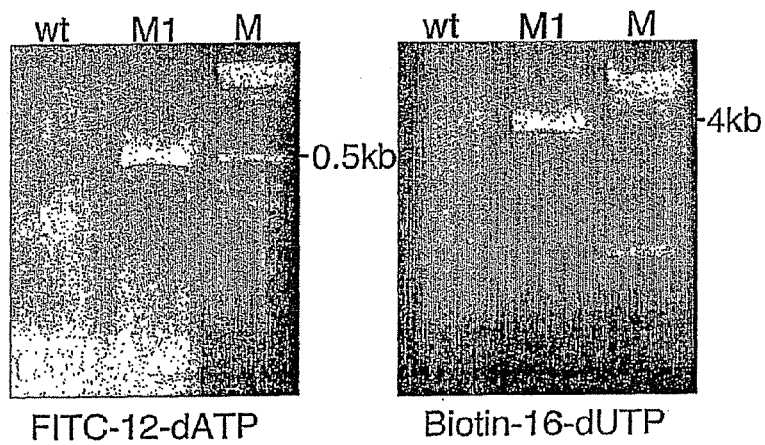
Figure 6C:
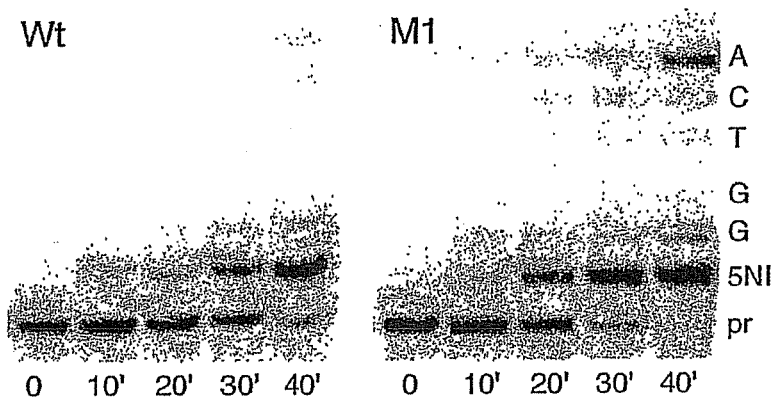

We reasoned that relaxed geometric selection might also aid the incorporation of unnatural base analogues, some of which inhibit or arrest polymerase activity due to poor geometric fit or lack of interaction with either polymerase or template strand. A first, conservative example are phosphothioate nucleotide triphosphates (αS dNTPs), in which one of the oxygen atoms in the cc phosphate group is replaced by sulfur. As part of a dNTP mixture, αS dNTPs are generally well accepted as substrates by DNA polymerases but when we replaced all four dNTPs with their αS counterparts in PCR wtTaq failed to generate any amplification products, while M1 (and to lesser extent M4) were able to generate PCR products of up to 2 kbp, indicating that they could utilize αS dNTPs with much increased efficiency compared to the wt enzyme (FIG. 6). As expected, the resulting αS DNA was completely resistant to cleavage by DNA endonucleases (not shown). Nucleotides bearing bulky adducts such as fluorescent dyes are widely used in applications such as dye terminator sequencing or array labelling. Although generally well tolerated they are incorporated considerably less efficiently than the natural dNTP substrates and can cause permature termination in homopolymeric runs, presumably because of steric crowding due to the bulky dye molecules. In PCR the effect is potentiated because both template and product strands are labelled. When we replaced dUTP with Biotin-16-dUTP or dATP with FITC-12-dATP in PCR, wtTaq was unable to generate any amplification products, while M1 was able to generate 2.7 kb amplification products fully labelled with Biotin-16-dUTP or a 0.4 kb fully labelled with FITC-12-dATP (FIG. 6). Recently, there has been significant interest in hydrophobic, non-hydrogen bonding base-analogues and the applications they may enable. One of these is the candidate "universal base" 5-nitroindole (5NI) (Loakes & Brown 96), which, like other hydrophobic, strongly stacking base analogues, is readily accepted as a substrate, but once incorporated, acts as a strong terminator both at the 3' end and as a template base. In contrast, M4 and in particular M1 efficiently bypass template strand 5NI (FIG. 6) and to a lesser degree, extend 5NI at the 3' end (not shown).

Example 5

Long PCR

Figure 7:
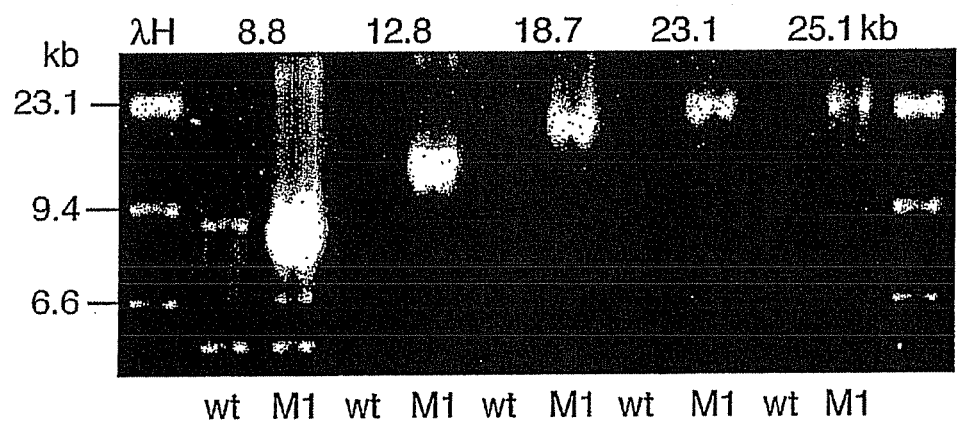
FIG. 7. Long range PCR. PCR amplification of fragments of increasing length from a phage λ DNA template. WtTaq (wt) fails to generate amplification products larger than 8.8 kb while M1 is able to amplify fragments of >25 kb. λH, HindIII-digested phage λ DNA marker.
Figure 8A:
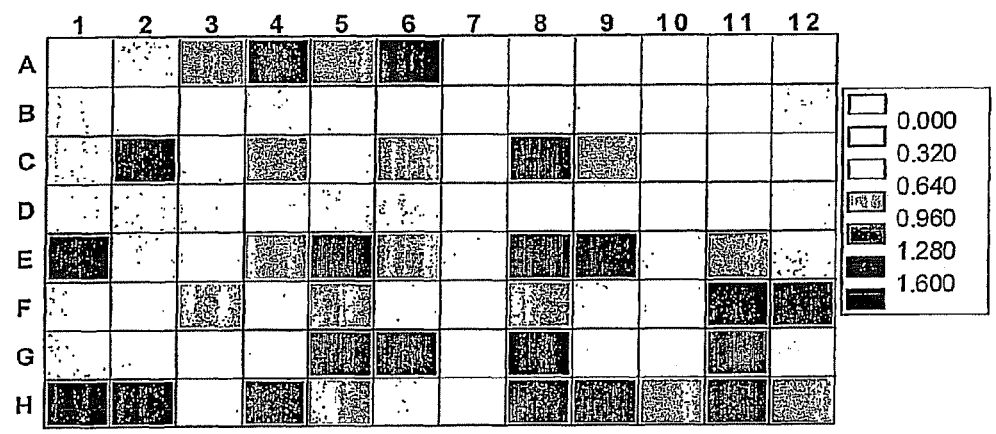
FIG. 8. Hairpin-ELISAs to test nucleotide analogue incorporation by mismatch extension clones. (a) shows assay using primer FITC4 (SEQ ID NO: 7); (b) shows assay using primer FITC102 (SEQ ID NO: 8); (c) shows assay using primer ELISAC4P (SEQ ID NO: 9); (d) shows assay using primer ELISAT3P (SEQ ID NO: 10); (e) shows assay using hairpin primer bearing an abasic site (SEQ ID NO: 11).
Figure 8B:
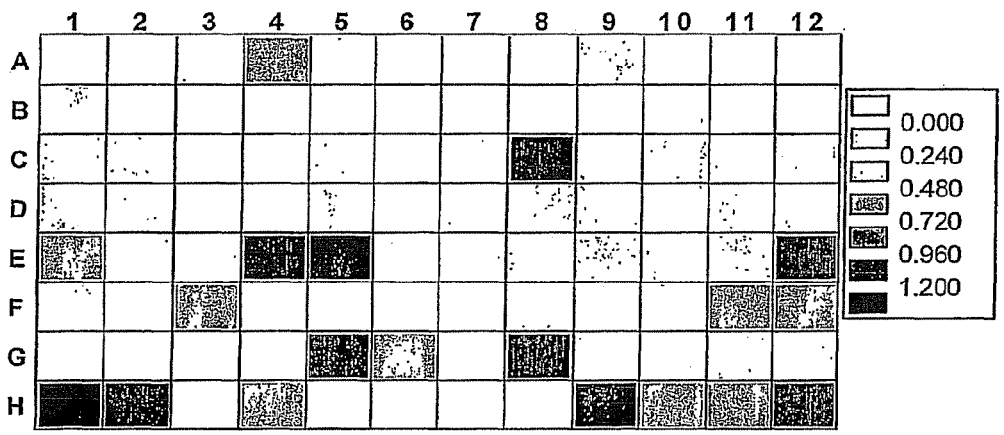
Figure 8C:
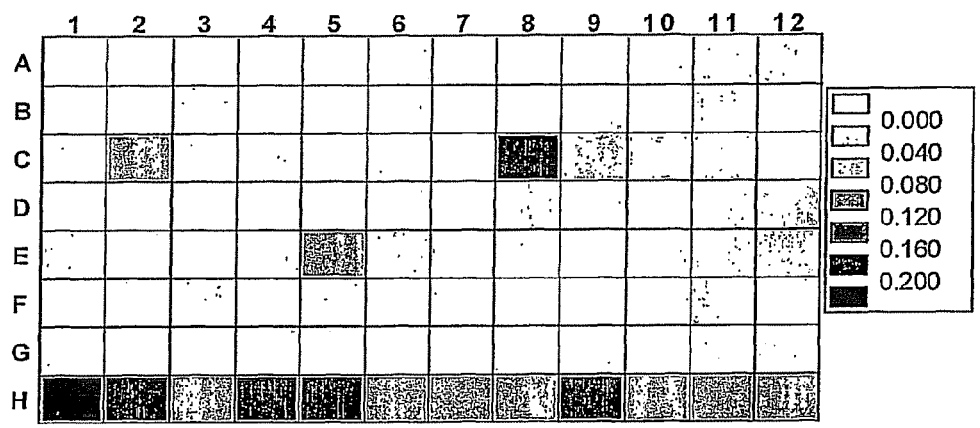
Figure 8D:
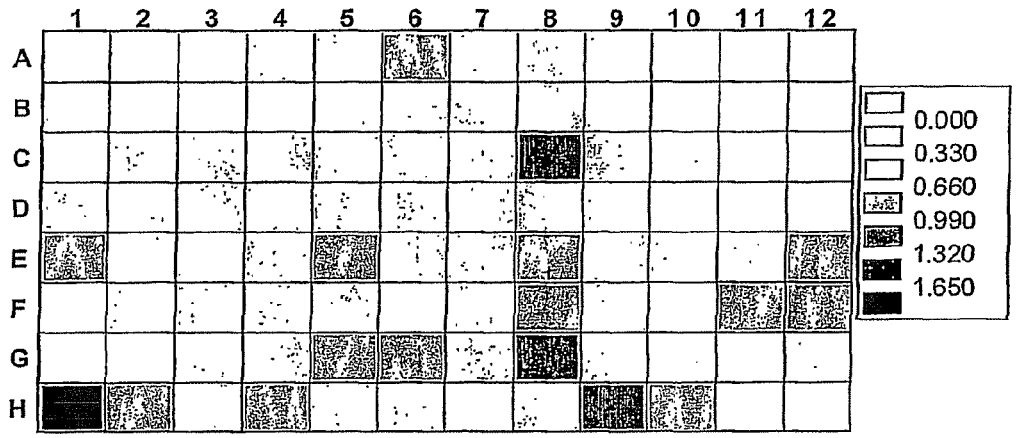
Figure 8E:
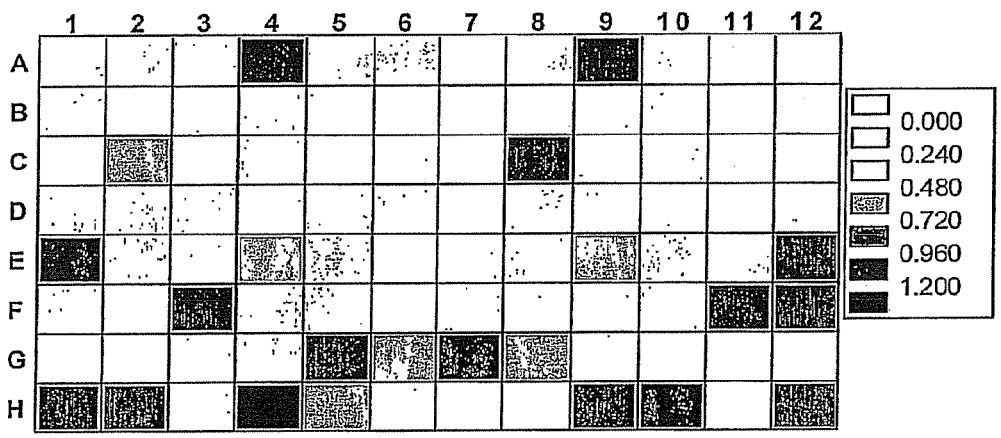

Amplification product size with wtTaq is generally limited to fragments a few kb long but can be extended to much longer targets by inclusion of a proofreading polymerase (Barnes 92). We found that the selected polymerases, in particular M1 was able to efficiently amplify of targets up to 26 kb (FIG. 7), using standard PCR conditions in the absence of auxiliary polymerases or other processivity factors. Under the same conditions wtTaq enzyme failed to amplify targets >9 kb. The molecular basis for the product size limitation in the wt enzyme is thought to be premature termination due to an inability to extend mismatches following nucleotide misin-corporation. These are thought to be removed by the proofreading polymerase allowing extension to resume. Our results that a generic mismatch extension ability to results in a similarly extended amplification range supports this concept.

Example 6

Libraries of Polymerase Chimeras

Libraries of chimeric polymerase gene variants were constructed using a gene shuffling technique called Staggered extension protocol (StEP, (Zhao, Giver et al. 1998)). This technique allows two or more genes of interest from different species to be randomly recombined to produce chimeras, the sequence of which contains parts of the original input parent genes.

*Thermus aquaticus* (Taq) wild type and T8 (a previously selected 11 fold more thermostable Taq variant (Ghadessy, Ong et al. 2001)), *Thermus thermophilus* (Tth) and *Thermus flavus* (Tfl) polymerases had previously been amplified from genomic DNA and cloned into pASK75 (Skerra 1994) and tested for activity. These genes were then shuffled using the staggered extension protocol (StEP) as described (Zhao, Giver et al. 1998) with (CAG GAA ACA GCT ATG ACA AAA ATC TAG ATA ACG AGG GCA A (SEQ ID NO: 38) and GTA AAA CGA CG G CCA GTA CCA CCG AAC TGC GGG TGA CGC CAA GCG (SEQ ID NO: 39)), recloned into pASK75 and transformed into *E. coli* TG1. The library size was scored by dilution assays and determining the ratio of clones containing insert using PCR screening and was approximately $10^8$. A diagnostic restriction digest of 20 clones produced 20 unique restriction patterns, indicating that the library was diverse. Subsequent sequencing of selected chimeras showed an average of 4 to 6 crossovers per gene.

Example 7

Selection of Two Mismatch Extension Polymerase

CSR emulsification and selection was performed on the StEP Taq, Tth and Tfl library essentially as described (Ghadessy, Ong et al. 2001). Mismatch primers with two mismatches at their 3' end (5'-GTA AAA CGA CGG CCA GTT TAT TAA CCA CCG AAC TGC-3' (SEQ ID NO: 40), 5'-CAG GAA ACA GCT ATG ACT CGA CAA AAA TCT AGA TAA CGA CC-3' (SEQ ID NO: 41)) were in the emulsion as the source of selective pressure. The aqueous phase was ether extracted, PCR purified (Qiagen, Chatsworth, Calif.) with an additional 35% GnHC1, digested with DpnI to remove methylated plasmid DNA, treated with ExoSAP (USB) to remove residual primers, reamplified with outnested primers and recloned and transformed into *E. coli* as above.

The resultant clones were screened and ranked by PCR assay. Briefly, 2 μL of induced cells were added to 20 μL of PCR mix with the relevant mismatch primers. Clones that produced a band were then subjected to further analysis and the most active clones were sequenced.

In particular, clone H10 has significant activity on the primers with two mismatches. H10 is a chimera of *T. aquaticus* wild type (residues 4 to 20 and 221 to 640), T8 (residues 1 to 3 and 641 to 834) and *T. thermophilus* (residues 21 to 220). H10 has five detectable crossover sites and 13 point mutations, of which 4 are silent (F74III, F28II0L, P300IIS, T387IIA, A441IIV, A519IIV Q536IIR, R679IIG, F699IIL).

Example 8

Selecting for a 4 Mismatch Extension Polymerase

CSR emulsification and selection was performed on the StEP Taq, Tth and Tfl library essentially as described (Ghadessy, Ong et al. 2001). The library had previously been cloned into pASK75 (see example 6). The aqueous phase was ether extracted and replication products were purified using a PCR purification kit (Qiagen, Chatsworth, Calif.) including a wash with an 35% GnHCl. 7 µl of purified replication products (from 48) were digested with 1 µl DpnI (20 Units) to remove plasmid DNA and treated with 2 µl ExoSAP (USB) to remove residual primers for 1 h at 37° C. and reamplified with outnested primers (GTAAAACGACGGCCAGT (SEQ ID NO: 42) and CAGGAAACAGCTATGAC (SEQ ID NO: 43), 94° C. 2 minutes, and then 30 cycles of 94° C. 30 seconds, 50° C. for 30 seconds and 72° C. for 5 minutes with a final 65° C. for 10 minutes). Reamplification products were digested with XbaI and SalI, recloned into pASK75 and transformed into *E. coli* as above.

In parallel an alternative selection approach was used: the induced library was emulsified as above with the additional presence of biotinylated dUTP and incubated at 94° C. 5 minutes, 50° C. 1 minute and 72° C. 1 minute. The aqueous phase was ether extracted, the DNA in the aqueous phase was precipitated by addition of ¹/₁₀ volume of 3M NaAc, 1 glycogen and 2.5 volumes of 100% ethanol. This was then incubated for 1 hour at −20° C., spun for at 13000 rpm for 30 minutes in a benchtop microcentrifuge, washed with 70% ethanol and resuspended in 50 µl buffer EB (Qiagen). 20 µl of Dynabeads (DynaL Biotech) were washed twice and resuspended in 20 µl of bead buffer (10 mM Tris pH 7.5, 1 mM EDTA, 0.2M NaCl) The washed beads were then mixed with the selection in a total volume of 0.5 ml bead buffer and then incubated overnight under constant agitation at room temperature to capture biotinylated products. Beads were washed twice in bead buffer, twice in buffer EB and finally resuspended in 50 µl bead buffer. The resuspended beads were reamplified with outnested primers (sequences and programme as above) and recloned and transformed into *E. coli* as above.

Two sets of mismatch primers with four mismatches at their 3' end (underlined) (5'-CAG GAA ACA GCT ATG ACA AAA GTG AAA TGA ATA GTT CGA CTTTT-3' (SEQ ID NO: 44) and 5'-GTA AAA CGA CGG CCA GTC TTC ACA GGT CAA GCT TAT TAA GGTG-3' (SEQ ID NO: 45) as the first set and 5'-CAG GAA ACA GCT ATG ACC ATT GAT AGA GTT ATT TTA CCA CAGGG-3' (SEQ ID NO: 46) and 5'-GTA AAA CGA CGG CCA GTC TTC ACA GGT CAA GCT TAT TAA GGTG-3' (SEQ ID NO: 47) as the second set) were used in the emulsion as two separate sources source of selective pressure.

The resultant clones from both CSR and CST were screened and ranked by PCR assay. Briefly, 2 µl of induced cells were added to 20 µl of PCR mix with the relevant 4 mismatch primers. Clones that produced a band were then subjected to further analysis and their activity on single, double and quadruple mismatch primers (single mismatch primers: 5'-CAG GAA ACA GCT ATG ACA AAA ATC TAG ATA ACG AGG GA-3' (SEQ ID NO: 48) and 5'-GTA AAA CGA CGG CCA GTA CCA CCG AAC TGC GGG TGA CGC CAA GCC 3' (SEQ ID NO: 49); double mismatch primers: CAG GAA ACA GCT ATG ACT CGA CAA AAA TCT AGA TAA CGA CC (SEQ ID NO: 50) and GTA AAA CGA CGG CCA GTT TAT TAA CCA CCG AAC TGC (SEQ ID NO: 51); four mismatch primers above.) was investigated. Polymerases that could extend all of these mismatches were found, though many polymerases could do only one of the mismatches and none could do all.

The plasmid DNA of the ten best clones was then purified and shuffled as described above (StEP, (Zhao, Giver et al. 1998)). This was then purified, cut and cloned and the resultant library was subjected to another round of CSR as described (Ghadessy, Ong et al. 2001). The same two sets of mismatch primers with four mismatches at their 3' end were used in the emulsion as two separate sources source of selective pressure. This was then dealt with as above and the resultant clones were screened and ranked by PCR assay (as above). Once again, polymerases that could extend all of these mismatches were found (see Table), though many polymerases could do only one of the mismatches and none could do all. There was a notable increase in clones displaying mismatch activity over the first round.

The best clones from the second round were combined with the best clones from the first round on a 96 well plate and were subjected to further screening.

The following table is a summary of the results.

|   | 1 | 2 | 3 | 4 | 5 | 6 | 7 | 8 | 9 | 10 | 11 | 12 |
|---|---|---|---|---|---|---|---|---|---|----|----|----|
| A | −,−,− | −,−,− | −,−,− | +,−,− | +,−,− | +,+,− | +,−,− | +,−,− | +,−,− | −,−,− | −,−,− | −,−,− |
| B | +,−,− | −,−,− | −,−,− | −,−,− | −,−,− | +,−,− | +,−,− | −,−,− | +,−,− | −,−,− | −,−,− | −,−,− |
| C | −,−,− | +,−,− | +,−,− | −,−,− | +,−,− | +,−,− | −,−,− | +,−,− | +,−, | +,−,− | −,−,− | +,−,+ |
| D | +,−,− | −,−,− | −,−,− | −,+,− | +,−,− | +,−,− | +,−,− | +,−,− | −,−,+ | −,−,− | −,−,− | −,−,− |
| E | +,−,− | +,+,− | +,+,− | +,+,− | +,+,− | +,+,− | +,+,− | +,−,− | +,+,− | +,−,− | +,+,− | +,−,− |
| F | −,−,− | +,−,− | +,+,− | +,−,− | +,+,− | +,−,− | +,−,− | +,−,− | +,−,− | +,+,− | +,−,− | +,+,− |
| G | +,−,− | +,−,− | +,−,− | +,−,− | +,−,− | +,+,− | +,−,− | +,−,− | +,−,− | +,−,− | +,−,− | +,−,− |
| H | +,−,− | +,−,− | −,−,− | +,−,− | +,−,− | +,−,− | −,−,− | +,−,− | +,−,− | +,−,− | +,−,− | +,−,− |

A1 is Tth polymerase; A2 Tfl; A3 Taq; A4 M1; A5 M4; A6 H10 (see previous example. 1A7 to 1D12 are first round clones (where 1 indicates that these are first round clones), 2E1 to 2H12 are second round clones (where 2 indicates that these are second round clones)

Figure 9:
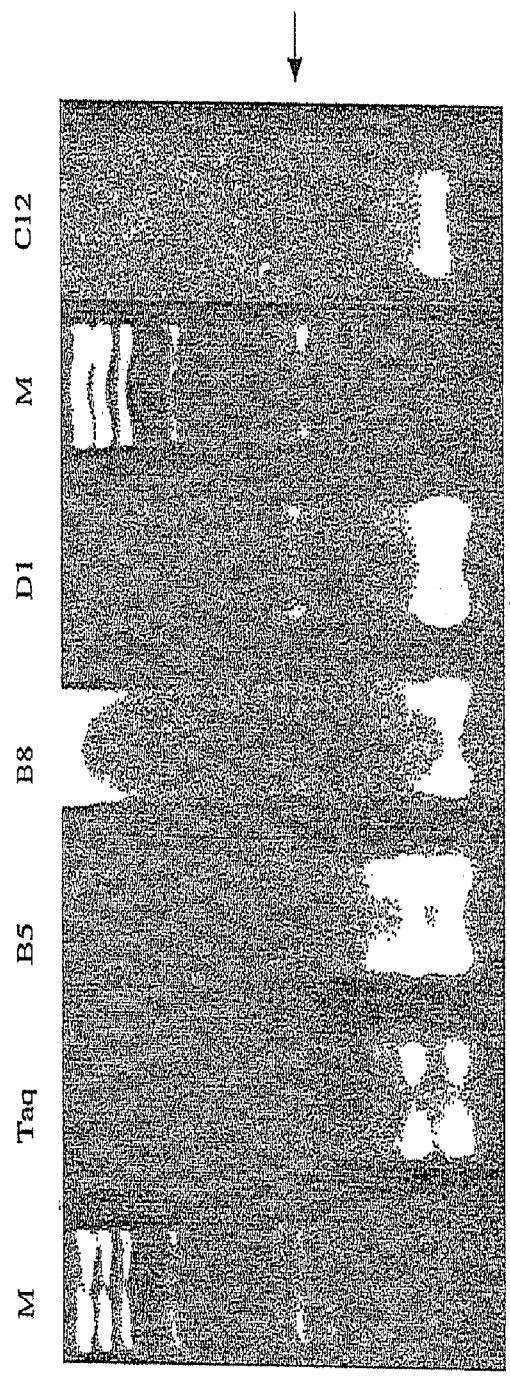
FIG. 9. Clones 3B5. 3B8, 3C12 and 3D1 (where 3 indicates that these are third round clones) were able to extend primers containing four mismatches. The 292 base pair product is indicated with an arrow and was produced after 50 cycles of PCR. It is noteworthy that significant amount of non-specific products are produced in all cases, although the amount of non-specific product varies from polymerase to polymerase. The C12 lane has been appended from another gel. Lane M: markers, Hae III digest of ΦX174.

The best first and second round clones were shuffled as described above and subjected to another round of CSR. The same two sets of mismatch primers with four mismatches at their 3' end were used in the emulsion as two separate sources of selective pressure. This was then dealt with as above and the resultant clones were screened and ranked by PCR assay (as above). Once again, polymerases that could extend all of these mismatches were found. In particular, clones 3B5. 3B8, 3C12 and 3D1 (where 3 indicates that these are third round clones) were able to extend primers containing four mismatches. See FIG. 9

Some promising clones were sequenced. All of the polymerases displayed a similar composition: the first part of the protein, roughly corresponding to the 5-3 exonuclease domain of the polymerase, was derived from Tth, whilst the remaining part of the protein was derived from Taq. Four point mutations (L33→P, E78→K, D145→G and E822→K) re-occurred in the majority of sequenced mutants and one (B10) had acquired an extra 16 amino acids at its C terminus through a frame shift at position 2499. Tfl was highly under-represented, although some of its sequence was present.

Example 9

Hairpin ELISA to Measure Polymerase Activity

The below protocol is a sensitive method to measure polymerase activity both for the incorporation of unnatural nucleotide substrates (added to the reaction mixture) or the extension or replication of unnatural nucleotide substrates (incorporated as part of the hairpin oligo).

The assay comprises a hairpin oligonucleotide which constitutes both primer and template in one. In contains as part of the hairpin a biotinylated dU residue, which allows capture of the hairpin oligonucleotide on streptavidin-coated surfaces.

The oligonucleotide folds up into a hairpin with a 5' overhang, which serves as the template strand for the polymerase (typical sequence: 5'-AGC TAC CAT GCC TGC ACG CAG TCGGCATCCGTCGCGACCACG TT5 TT CGTGGTCGCGACGGATGCCG-3' (SEQ ID NO: 52), bases involved in hairpin formation are underlined, 3' base is in bold, 5=dU-biotin).

Extension reactions are carried out in the presence of small amounts of a labelled nucleotide typically DIG-16-dUTP. Product is captured (for example on a streptavidin coated ELISA plate) and incorporation of labelled nucleotide into the product strand is measured (using for example an anti-DIG antibody) and taken as a measure of polymerase activity.
Method:

Extension reactions are carried out in 1× Taq buffer including 1-100 nM of hairpin primer and 100 µM dNTP mixture (comprising 0.3-30% dUTP-DIG), typically incubated at 94° C. for 1-5 min, followed by incubation at 50° C. for 1-5 min, followed by incubation at 72° C. for 1-5 min. (1-10 µl) Reaction products are added to Streptavidin coated ELISA plates (Streptawell, Roche) in 200 µl PBS, 0.2% Tween20 (PBST) and incubated at room temperature for 10 min to 1 h. ELISA plates are washed 3× in PBST and 200 µl of anti-DIG-POD Fab2 fragment (Roche) diluted 1/2000 in PBST is added and the plate is incubated at room temperature for 10 min to 1 h. The plate is washed 3-4× in PBST and developed with an appropriate POD substrate.

Example 10

Hairpin-ELISAs to Test Nucleotide Analogue Incorporation by Mismatch Extension Clones Clones previously selected for their ability to extend from a 4 basepair mismatch were assayed for their ability to incorporate a variety of nucleotide analogues.

Clones were grown at 30° C. overnight in 200 µl 2XTY+ ampicillin (100 µg/ml).

A 150 µl (2xTY+ampicillin 100 µg/ml) overday culture was started from the overnight and grown for 3 hours at 37° C. After 3 hours protein expression was induced by the addition of 50 µl of 2XTY+anhydrous tetracycline (8 ng/ml) to the culture which was then allowed to grow for a further 3 h at 37° C. The cells were pelleted at 2254×g for 5 minutes and the growth medium removed by aspiration after which the cell pellet was resuspended in 100 µl×Taq buffer (10 mM Tris-HCl, pH 9.0, 1.5 mM $MgCl_2$, 50 mM KCl, 0.1% Triton X-100, 0.01% (w/v) stabiliser; HT Biotechnology Ltd). Resuspended cells were lysed by incubation at 85° C. for 10 minutes and the cell debris was pelleted at 2254×g for 5 minutes.
ELISA Protocol:
Extension Reaction.

Reactions were performed in a final volume of 12.5 µl comprising:
1× Taq buffer (10 mM Tris-HCl, pH 9.0, 1.5 mM $MgCl_2$, 50 mM KCl, 0.1% Triton X-100, 0.01% (w/v) stabiliser; HT Biotechnology Ltd).
50 pmoles of primer.
25 µM of each dNTP (minus the nucleotide analogue) of which 10% (2.5 µM) of the dTTP is digoxigenin-11-dUTP and 90% (22.5 µM) is dTTP.
25 µM the nucleotide analogue.
2.5 µl of cell lysate.
The reaction conditions were:
95° C. 5 minutes; 50° C. 5 minutes; 72° C. 5 minutes.
Detection Reaction:

5 µl of the extension reaction was added to 200 µl of PBS-Tween (lx PBS; 0.2% Tween 20) in StreptaWell high bind plates (Roche) and allowed to bind for 30 minutes at room temperature. The plate was washed 3× in PBS-Tween after which was added 200 µl PBS-Tween+anti-digioxigenin-POD Fab fragments (antibody diluted 1/2000; Roche). The antibody was allowed to bind for 30 minutes at room temperature.

The plate was washed 3× in PBS-Tween and 200 µl of the substrate added (per ml 100 µl of 1M NaAc pH 6.0, 10 µl of DAB, 1 µl of $H_2O_2$, the reaction was allowed to develop after which it was stopped by adding 100 µl of 1M $H_2SO_4$.

Experiment I

ELISA with Fluorescein 12-dATP

The ability of clones selected for 4-mismatch extension to incorporate Fluorescein 12-dATP (Perkin Elmer) was assayed using the primer FITC4. The lysates used were concentrated 4-fold.

Experiment II

ELISA with Biotin 11-dATP

The ability of clones selected for 4-mismatch extension to incorporate Biotin 11-dATP (Perkin Elmer) was assayed using the primer FITC10. The lysates used were concentrated 4-fold.

Experiment III

ELISA with CyDye 5-dCTP

The ability of clones selected for 4-mismatch extension to incorporate Cy5-dCTP (Amersham Biosciences) was assayed using the primer ELISAC4P. The lysates used were concentrated 4-fold.

Experiment IV

ELISA with CyDye 3-dUTP

The ability of clones selected for 4-mismatch extension to incorporate CyDye 3-dUTP (Amersham Biosciences) was assayed using the primer ELISAT3P. The lysates used were concentrated 4-fold. The DIG labelled dUTP in the extension reaction was replaced with Fluorescein 12-dATP and the incorporation of Fluorescein 12-dATP was detected by anti-Fluorescein-POD Fab fragments (Roche).

Experiment V

Abasic Site ELISA

The ability of clones selected for 4-mismatch extension to bypass abasic sites was assayed using the primer Pscreen1Abas (AGC TAC CAT GCC TGC ACG CAG 1 CG GCA TCC GTC GCG ACC ACG TT5 TTC GTG GTC GCG ACG GAT GCC G (SEQ ID NO: 53), 1=abasic site 5=dU biotin). The lysates used were concentrated 4-fold.

Clones selected for 4-mismatch extension were assayed for activity with different substrates using an ELISA assay.
A1=Tth Wild-type
A2=Tfl Wild-type
A3=Taq Wild-type
A4=Taq mutant M1
A5=Taq mutant M4
A6=Taq mutant H10
Rows A-D Clones isolated after 1 round of 4-mismatch selection
Rows E-H Clones isolated after 2 rounds of 4-mismatch selection
The results are shown in FIG. 8.

Experiment V

Abasic Site and 5-hydroxyhydantoin Bypass

Polymerases 3A10 and 3D1 were investigated further for their ability to bypass abasic sites and 5-hydroxy hydantoins, which are both known to exist in damaged DNA such as found in ancient samples, using the ELISA based activity screen as described above. Both polymerases were more proficient at lesion bypass than wild type Taq by up to two orders of magnitude.

The hydantion phosphoramidite was synthesised by standard procedures starting from the hydantoin free base. Glycosylation of the silylated hydantoin base in the presence of tin(IV) chloride with the ditoluoyl (alpha) chlorosugar gave rise to two N-glycosylated products which were separated and characterised by 2D-NMR experiments. The tolyl groups were removed with ammonia to yield the free nucleoside which was dimethoxytritylated and phosphytylated in the usual manner. The hairpin primer to assay hydantoin bypass was: 5'-AGC TAC CAT GCC TGC ACG CAG XCG GCA TCC GTC GCG ACC ACG TTY TTC GTG GTC GCG ACG GAT GCC G-3' (SEQ ID NO: 54), X=hydantoin, Y=Biotin-dU.

The sequences of the clones referred to in Examples are shown below: For the avoidance of any doubt, the first sequence provided in each section is the nucleic acid sequence. The second sequence provided is the corresponding amino acid sequence of the clone.

2F3:

(SEQ ID NO: 55)

```
ATGGCGATGCTTCCCCTCTTTGAGCCCAAGGGCCGCGTCCTCCTGGTGGACGGCCACCACCTGGCCTACCGCACCTTCTT

CGCCCTGAAGGGCCCCACCACGAGCCGGGGCGAACCGGTGCAGGTGGTCTACGGCTTCGCCAAGAGCCTCCTCAAGGCC

CTGAAGGAGGACGGGTACAAGGCCGTCTTCGTGGTCTTTGACGCCAAGGCCCCCTCATTCCGCCACAAGGCCTACGAGG

CCTACAGGGCGGGGAGGGCCCCGACCCCCGAGGACTTCCCCCGGCAGCTCGCCCTCATCAAGGAGCTGGTGGACCTCCT

GGGGTTTACCCGCCTCGAGGTCCCCGGCTACGAGGCGGACGACGTTCTCGCCACCGTGGCCAAGAAGGCGGAAAAGGA

GGGGTACGAGGTGGGCATCCTCACCGCCGACCGCGGCCTCTACCAACTCGTCTCTGACCGCGTCGCCGTCCTCCACCCCG

AGGGCCACCTCATCACCCCGGAGTGGCTTTGGGAGAAGTACGGCCTCAGGCCGGAGCAGTGGGTGGACTTCCGCGCCCT

CGTGGGGGACCCCTCCGACAACCTCCCCGGGGTCAAGGGCATCGGGGAGAAGACCGCCCTCAAGCTCCTCAAGGAGTG

GGGAAGCCTGGAAAACCTCCTCAAGAACCTGGACCGGGTAAAGCCAGAAAACGTCCGGGAGAAGATCAAGGCCCACCT

GGAAGACCTCAGGCTCTCCTTGGAGCTCTCCCGGGTGCGCACCGACCTCCCCCTGGAGGTGGACCTCGCCCAGGGGCGG

GAGCCCGACCGGAGGGGCTTAGGGCCTTTCTGGAGAGGCTTGAGTTTGGCAGCCTCCTCCACGAGTTCGGCCTTCTGG

AAAGCCCCAAGGCCCTGGAGGAGGCCCCCTGGCCCCCGCCGGAAGGGGCCTTCGTGGGCTTTGTGCTTTCCCGCAAGGA

GCCCATGTGGGCCGATCTTCTGGCCCTGGCCGCCGCCAGGGGGGGCCGGGTCCACCGGGCCCCCGAGCCTTATAAAGCC

CTCAGAGACCTGAAGGAGGCGCGGGGGCTTCTCGCCAAAGACCTGAGCGTTCTGGCCCTGAGGGAAGGCCTTGGCCTCC

CGCCCGGCGACGACCCCATGCTCCTCGCCTACCTCCTGGACCCTTCCAACACCACCCCCGAGGGGTGGCCCGGCGCTA

CGGCGGGGAGTGGACGGAGGAGGCGGGGAGCGGGCCGCCCTTTCCGAGAGGCTCTTCGCCAACCTGTGGGGAGGCT

TGAGGGGAGGAGAGGCTCCTTTGGCTTTACCGGGAGGTGGAGAGGCCCCTTTCCGTTGTCCTGGCCCACATGGAGGCC

ACAGGGGTGCGCCTGGACGTGGCCTATCTCAGGGCCTTGTCCCTGGAGGTGGCCGAGGAGATCGCCCGCCTCGAGGCCG

AGGTCTTCCGCCTGGCCGGCCACCCCTTCAACCTCAACTCCCGGGACCAGCTGGAAAGGGTCCTCTTTGACGAGCTAGG

GCTTCCCGCCATCGGCAAGACGGAGAAGACCGGCAAGCGCTCCACCGGCGCCGCCGTCCTGGAGGCCCTCCACGAGGC

CCACCCCATCGTGGAGAAGATCCTGCAGTACCGGGAGCTCACCAAGCTGAAGAGCACCTACATTGACCCCTTGCCGGAC
```

```
CTCATCCACCCCAGGACGGGCCGCCTCCACACCCGCTTCAACCAGACGGCCACGGCCACGGGCAGGCTAAGTAGCTCCG

ATCCCAACCTCCAGAACATCCCCGTCCGCACCCAGCTTGGGCAGAGGATCCGCCGGGCCTTCATCGCCGAGGAGGGGTG

GCTATTGGTGGTCCTGGACTATAGCCAGATAGAGCTCAGGGTGCTGGCCCACCTCTCCGGCGACGAGAACCTGATCCGG

GTCTTCCAGGAGGGCGGGACATCCACACGGAAACCGCCAGCTGGATGTTCGGCGTCCCCCAGGAGGCCGTGGACCCCC

TGATGCGCCGGGCGGCCAAGACCATCAACTTCGGGGTTCTCTACGGCATGTCGGCCTACCGCCTCTCCCAGGAGCTAGC

CATCCCTTACGAGGAGCCCAGGCCTTCATTGAGCGCTACTTTCAGAGCTTCCCCAAGGTGCGGGCCTGGATTGGGAAG

ACCCTGGAGGAGGGCAGGAGGCGGGGGTACGTGGAGACCCTCTTCGGCCGCCGCCGCTACGTGCCAGACCTAGAGGCC

CGGGTGAAGAGCGTGCGGGAGGCGGCCGAGCGCATGGCCTTCAACACGCCCGTCCAGGGCACCGCCGCCGACCTCATG

AAGCTAGCTATGGTGAAGCTCTTCCCCAGGCTGGAGGAAATGGGGGCCAGGATGCTCCTTCAGGTCCACGACGAGCTGG

TCCTCGAGGCCCCAAAAGAGAGGGCGGAGGCCGTGGCCCGGCTGGCCAAGGAGGTCATGGAGGGGGTGTATCCCCTGG

CCGTGCCCCTGGAGGTGGAGGTGGGGATAGGGGAGGACTGGCTCTCCGCCAAGGAGTGA
```

(SEQ ID NO: 56)
MAMLPLFEPKGRVLLVDGHHLAYRTFFALKGPTTSRGEPVQVVYGFAKSLLKALKEDGYKAVFVVFDAKAPSFRHKAYEAY
RAGRAPTPEDFPRQLALIKELVDLLGFTRLEVPGYEADDVLATVAKKAEKEGYEVGILTADRGLYQLVSDRVAVLHPEGHLIT
PEWLWEKYGLRPEQWVDFRALVGDPSDNLPGVKGIGEKTALKLLKEWGSLENLLKNLDRVKPENVREKIKAHLEDLRLSLE
LSRVRTDLPLEVDLAQGREPDREGLRAFLERLEFGSLLHEFGLLESPKALEEAPWPPPEGAFVGFVLSRKEPMWADLLALAAA
RGGRVHRAPEPYKALRDLKEARGLLAKDLSVLALREGLGLPPGDDPMLLAYLLDPSNTTPEGVARRYGGEWTEEAGERAAL
SERLFANLWGRLEGEERLLWLYREVERPLSVVLAHMEATGVRLDVAYLRALSLEVAEEIARLEAEVERLAGHPFNLNSRDQL
ERVLFDELGLPAIGKTEKTGKRSTGAAVLEALHEAHPIVEKILQYRELTKLKSTYIDPLPDLIHPRTGRLHTRFNQTATATGRLS
SSDPNLQNIEVRTQLGQRIRRAFIAEEGWLLVVLDYSQIELRVLAHLSGDENLIRVFQEGRDEFITETASWMFGVPQEAVDPLMR
RAAKTINFGVLYGMSAYRLSQELAIPYEEAQAFIERYFQSFPKVRAWIGKTLEEGRRRGYVETLFGRRRYVPDLEARVKSVRE
AAERMAFNTPVQGTAADLMKLAMVKLEPRLEEMGARMLLQVHDELVLEAPKERAEAVARLAKEVMEGVYPLAVPLEVEV
GIGEDWLSAKE*

1A10:

(SEQ ID NO: 57)
```
ATGCGTGGTATGCCTCCTCTTTTTGAGCCCAAGGGCCGCGTCCTCCTGGTGGACGGCCACCTGGCCTACCGCACCTTCTT

CGCCCTGAAGGGCCCCACCACGAGCCGGGGCGAACCGGTGCAGGCGGTCTACGGCTTCGCCAAGAGCCTCCTCAAGGC

CCTGAAGGAGGACGGGTACAAGGCCGTCTTCGTGGTCTTTGACGCCAAGGCCCCCTCCCTCCGCCACGAGGCCTACGAG

GCCTACAAGGCGGGGAGGGCCCCGACCCCCGAGGACTTCCCCCGGCAGCTCGCCCTCATCAAGGAGCTGGTGGACCTCC

TGGGGTTTACCCGCCTCGAGGTCCCCGGCTACGAGGCGGACGACGTTCTCGCCACCGTGGCCAAGAAGGCGGAAAAGGA

GGGGTACGAGGTGCGCATCCTCACCGCCGACCGCGACCTCTACCAACTCGTCTCCGACCGCGTCGCCGTCCTCCACCCCG

AGGGCCACCTCATCACCCCGGAGTGGCTTTGGGAGAAGTACGGCCTCAGGCCGGAGCAGTGGGTGGACTTCCGCGCCCT

CGTGGGGGACCCCTCCGACAACCTCCCCGGGGTCAAGGGCATCGGGGAGAGGACCGCCCTCAAGCTCCTCAAGGAGTG

GGGAAGCCTGGAAAACCTCCTCAAGAACCTGGACCGGGTAAAGCCAGAAAACGTCCGGGAGAAGATCAAGGCCCACCT

GGAAGACCTCAGGCTCTCCTTGGAGCTCTCCCGGGTGCGCACCGACCTCCCCCTGGAGGTGGACCTCGCCCAGGGGCGG

GAGCCCGACCGGGAGAGGCTTAGGGCCTTTCTGGAGAGGCTTGAGTTTGGCAGCCTCCTCCACGAGTTCGGCCTTCTGG

AAAGCCCCAAGGCCCTGGAGGAGGCCCCTGGCCCCCGCCGGAAGGGGCCTTCGTGGGCTTTGTGCTTTCCCGCAAGGA

GCCCATGTGGGCCGATCTTCTGGCCCTGGCCGCCGCCAGGGGTGGTCGGGTCCACCGGGCCCCCGAGCCTTATAAAGCC

CTCAGGGACTTGAAGGAGGCGCGGGGCTTCTCGCCAAAGACCTGAGCGTTCTGGCCCTAAGGGAAGGCCTTGGCCTCC

CGCCCGGCGACGACCCCATGCTCCTCGCCTACCTCCTGGACCCTTCCAACACCACCCCCGAGGGGGTGGCCCGGCGCTA

CGGCGGGGAGTGGACGGAGGAGGCGGGGGAGCGGGCCGCCCTTTCCGAGAGGCTCTTCGCCAACCTGTGGGGGAAGCT

TGAGGGGGAGGAGAGGCTCCTTTGGCTTTACCGGGAGGTGGATAGGCCCCTTTCCGCTGTCCTGGCCCACATGGAGGCC
```

-continued

ACAGGGGTGCGCCTGGACGTGGCCTATCTCAGGGCCTCGTCCCTGGAGGTGGCCGAGGAGATCGCCCGCCTCGAGGCCG

AGGTCTTCCGCCTGGCCGGCCACCCCTTCAACCTCAACTCCCGGGACCAGCTGGAAAGGGTCCTCTTTGACGAGCTAGG

GCTTCCCGCCATCGGCAAGACGGAGAAGACCGGCAAGCGCTCCACCAGCGCCGCCGTCCTGGAGGCCCTCCGCGAGGC

CCACCCCATCGTGGAGAAGATCCTGCAGTACCGGGAGCTCACCAAGCTGAAGAGCACCTACATTGACCCCTTGCCGGAC

CTCATCCACCCCAGGACGGGCCGCCTCCACACCCGCTTCAACCAGACGGCCACGGCCACAGGCAGGCTAAGTAGCTCCG

ATCCCAACCTCCAGAACATCCCCGTCCGCACCCCGCTTGGGCAGAGGATCCGCCGGGCCTTCATCGCCGAGGAGGGGTG

GCTATTGGTGGCCCTGGACTATAGCCAGATAGAGCTCAGGGTGCTGGCCCACCTCTCCGGCGACGAGAACCTGATCCGG

GTCTTCCAGGAGGGGCGGGACATCCACACGGAGACCGCCAGTTGGATGTTCGGCGTCCCCGGGAGGCCGTGGACCCCC

TGATGCGCCGGGCGGCCAAGACCATCAACTTCGGGGTCCTCTACGGCATGTCGGCCCGCCGCCTCTCCCAGGAGCTAGC

CATCCCTTACGAGGAGGCCCAGGCCTTCATTGAGCGCTACTTTCAGAGCTTCCCCAAGGTGCGGGCCTGGATTGAGAAG

ACCCTGGAGGAGGGCAGGAGGCGGGGGTACGTGGAGACCCTCTTCGGCCGCCGCCGCTACGTGCCAGACCTAGAGGCC

CGGGTGAAGAGCGTGCGGGAGGCGGCCGAGCGCATGGCCTTCAACATGCCCGTCCAGGGCACCGCCGCCGACCTCATG

AAGCTGGCTATGGTGAAGCTCTTCCCCAGGCTGGAGGAAATGGGGGCCAGGATGCTCCTTCAGGTCCACGACGAGCTGG

TCCTCGAGGCCCCAAAAGAGAGGGCGGAGGCCGTGGCCCGGCTGGCCAAGGAGGTCATGGAGGGGGTGTATCCCCTGG

CCGTGCCCCTGGAGGTGGAGGTGGGGATAGGGGAGGACTGGCTCTCCGCCAAGGAGTGA (SEQ ID NO: 58)
MRGMPPLFEPKGRVLLVDGHLAYRTFFALKGPTTSRGEPVQAVYGFAKSLLKALKEDGYKAVFVVFDAKAPSLRHEAYEAY

KAGRAPTPEDFPRQLALIKELVDLLGFTRLEVPGYEADDVLATLAKKAEKEGYEVRILTADRDLYQLVSDRVAVLHPEGHLIT

PEWLWEKYGLRPEQWVDFRALVGDPSDNLPGVKGIGERTALKLLKEWGSLENLLKNLDRVKPENVREKIAHLEDLRLSLE

LSRVRTDLPLEVDLAQGREPDRERLRAFLERLEFGSLLHEFGLLESPKALEEAPWPPPEGAFVGFVLSRKEPMWADLLALAAA

RGGRVHRAPEPYKALRDLKEARGLLAKDLSVLALREGLGLPPGDDPMLLAYLLDPSNTTPEGVARRYGGEWTEEAGERAAL

SERLFANLWGKLEGEERLLWLYREVDRPLSAVLAHMEATGVRLDVAYLRASSLEVAEEIARLEAEVERLAGHPFNLNSRDQL

ERVLFDELGLPAIGKTEKTGKRSTSAAVLEALREAHPIVEKILQYRELTKLKSTYIDPLPDLITIPRTGRLHTRFNQTATATGRLS

SSDPNLQNIPVRTPLGQRIRRAFIAEEGWLLVALDYSQIELRVLAHLSGDENLIRVFQEGRDIHTETASWMFGVPREAVDPLMR

RAAKTINFGVLYGMSARRLSQELAIPYEEAQAFIERYFQSFPKVRAWIEKTLEEGRRRGYVETLFGRRRYVPDLEARVKSVRE

AAERMAFNMPVQGTAADLMKLAMVKLEPRLEEMGARMLLQVHDELVLEAPKERAEAVARLAKEVMEGVYPLAVPLEVEV

GIGEDWLSAKE*

1A9:
(SEQ ID NO: 59)
ATGCGTGGTATGCATCCTCTTTTTGAGCCCAAGGGCGCGTCCTCCTGGTGGACGGCCACCACCTGGCCTACCGCACCTT

CCACGCCCTGAAGGGGCTCACCACCAGCCGGGGGGAGCCGGTGCGGCGGTCCACGGCTTCGCCAAGAGCCTCCTCAA

GGCCCTGAAGGAGGACGGGTACAAGGCCGTCTTCGTGGTCTTTGACGCCAAGGCCCCCTCCTTCCGCCACGAGGCCTAC

GAGGCCTACAAGGCGGGGAGGGCCCCGACCCCCGAGGACTTCCCCCGGCAGCTCGCCCTCATCAAGGAGCTGGTGGAC

CTCCTGGGGTTTACCCGCCTCGAGGTCCCCGGCTACGAGGCGGACGACGTTCTCGCCACCCTGGCCAAGAAGGCGGAAA

AGGAGGGGTACGAGGTGCGCATCCTCACCGCCGACCGCGACCTCTACCAACTCGTCTCCGACCGCGTCGCCGTCCTCCA

CCCCGAGGGCCACCTCATCACCCCGGAGTGGCTTTGGGAGAAGTACGGCCTCAGGCCGGAGCAGTGGGTGGACTTCCGC

GCCCTCGTGGGGGACCCCTCCGACAACCTCCCCGGGGTCAAGGGCATCGGGGAGAAGACCGCCCTCAAGCTCCTCAAGG

AGTGGGGAAGCCTGGAAAACCTCCTCAAGAACCTGGACCGGCTGAAGCCCGCCATCGGGAGAAGATCCTGGCCCACA

TGGACGATCTGAAGCTCTCCTGGGACCTGGCCAAGGTGCGCACCGACCTGCCCCTAGAGGTGGACTTCGCCAAAAGGCG

GGAGCCCGACCGGGAGAGGCTTAGGGCCTTTCTGGAGAGGCTTGAGCTTGGCAGCCTCCTCCACGAGTTCGGCCTTCTG

GAAAGCCCCAAGACCCTGGAGGAGGCCTCCTGGCCCCGCCGGAAGGGGCCTTCGTGGGCTTTGTGCTTTCCCGCAAGG

AGCCCATGTGGGCCGATCTTCTGGCCCTGGCCGCCGCCAGGGGGGGCCGGGTCCACCGGGCCCCCGAGCCTTATAAAGC

-continued

```
CCTCAGAGACCTGAAGGAGGCGCGGGGGCTTCTCGCCAAAGACCTGAGCGTTCTGGCCCTGAGGGAAGGCCTTGGCCTC

CCGCCCGGCGACGACCCCATGCTCCTCGCCTACCTCCTGGACCCTTCCAACACCACCCCCGAGGGGTGGCCCGGCGCT

ACGGCGGGGAGTGGACGGAGGAGGCGGGGGAGCGGGCCGCCCTTTCCGAGAGGCTCTTCGCCAACCTGTGGGGGAGGC

TTGAGGGGAGGAGAGGCTCCTTTGGCTTTACCGGGAGGTGGAGAGGCCCCTTTCCGTTGTCCTGGCCCACATGGAGGC

CACAGGGGTGCGCCTGGACGTGGCCTATCTCAGGGCCTTGTCCCTGGAGGTGGCCGAGGAGATCGCCCGCCTCGAGGCC

GAGGTCTTCCGCCTGGCCGGCCACCCCTTCAACCTCAACTCCCGGGACCAGCTGGAAAGGGTCCTCTTTGACGAGCTAG

GGCTTCCCGCCATCGGCAAGACGGAGAAGACCGGCAAGCGCTCCACCGGCGCCGCCGTCCTGGAGGCCCTCCGCGAGG

CCCACCCCATCGTGGAGAAGATCCTGCAGTACCGGGAGCTCACCAAGCTGAAGAGCACCTACATTGACCCCTTGCCGGA

CCTCATCCACCCCAGGACGGGCCGCCTCCACACCCGCTTCAACCAGACGGCCACGGCCACGGGCAGGCTAAGTAGCTCC

GATCCCAACCTCCAGAACATCCCCGTCCGCACCCAGCTTGGGCAGAGGATCCGCCGGGCCTTCATCGCCGAGGAGGGGT

GGCTATTGGTGGTCCTGGACTATAGCCAGATAGAGCTCAGGGTGCTGGCCCACCTCTCCGGCGACGAGAACCTGATCCG

GGTCTTCCAGGAGGGCGGGACATCCACACGGAAACCGCCAGCTGGATGTTCGGCGTCCCCAGGAGGCCGTGGACCCC

CTGATGCGCCGGGCGGCCAAGACCATCAACTTCGGGGTTCTCTACGGCATGTCGGCCTACCGCCTCTCCCAGGAGCTAG

CCATCCCTTACGAGGAGGCCCAGGCCTTCATTGAGCGCTACTTTCAGAGCTTCCCCAAGGTGCGGGCCTGGATTGGGAA

GACCCTGGAGGAGGGCAGGAGGCGGGGGTACGTGGAGACCCTCTTCGGCCGCCGCCGCTACGTGCCAGACCTAGAGGC

CCGGGTGAAGAGCGTGCGGGAGGCGGCCGAGCGCATGGCCTTCAACACGCCCGTCCAGGGCACCGCCGCCGACCTCAT

GAAGCTGGCTATGGTGAAGCTCTTCCCCAGGCTGGAGGAAATGGGGGCCAGGATGCTCCTTCAGGTCCACGACGAGCTA

GTCCTCGAGGCCCCAAAAGAGAGGGCGGAGGCCGTGGCCCGGCTGGCCAAGGAGGTCATGGAGGGGGTGTATCCCCTG

GCCGTGCCCCTGGAGGTGGAGGTGGGGATAGGGGAGGACTGGCTCTCCGCCAAGGAGTGA
```

(SEQ ID NO: 60)
MRGMHPLFEPKGRVLLVDGHHLAYRTFHALKGLTTSRGEPVRAVHGFAKSLLKALKEDGYKAVFVVFDAKAPSFRHEAYEA

YKAGRAPTPEDFPRQLALIKELVDLLGFTRLEVPGYEADDVLATLAKKAEKEGYEVRILTADRDLYQLVSDRVAVLHPEGHLI

TPEWLWEKYGLRPEQWVDFRALVGDPSDNLPGVKGIGEKTALKLLKEWGSLENLLKNLDRLKPAIREKILAHMDDLKLSWD

LAKVRTDLPLEVDFAKRREPDRERLRAFLERLELGSLLHEFGLLESPKTLEEASWPPPEGAFVGFVLSRKEPMWADLLALAAA

RGGRVHRAPEPYKALRDLKEARGLLAKDLSVLALREGLGLPPGDDPMLLAYLLDPSNTTPEGVARRYGGEWTEEAGERAAL

SERLFANLWGRLEGEERLLWLYREVERPLSVVLAHMEATGVRLDVAYLRALSLEVAEEIARLEAEVERLAGHPFNLNSRDQL

ERVLFDELGLPAIGKTEKTGKRSTGAAVLEALREAHPIVEKILQYRELTKLKSTYIDPLPDLIHPRTGRLHTRFNQTATATGRLS

SSDPNLQNIEVRTQLGQRIRRAFIAEEGWLLVVLDYSQIELRVLAHLSGDENLIRVFQEGRDEFITETASWMFGVPQEAVDPLMR

RAAKTINFGVLYGMSAYRLSQELAIPYEEAQAFIERYFQSFPKVRAWIGKTLEEGRRRGYVETLFGRRRYVPDLEARVKSVRE

AAERMAFNTPVQGTAADLMKLAMVKLFPRLEEMGARMLLQVHDELVLEAPKERAEAVARLAKEVMEGVYPLAVPLEVEV

GIGEDWLSAKE*

2F12:

(SEQ ID NO: 61)
```
ATGCGTGGTATGCTTCCTCTTTTTGAGCCCAAGGGCGCGTCCTCCTGGTGGACGGCCACCACCTGGCCTACCGCACCTT

CTTCGCCCTGAAGGGCCTCACCACGAGCCGGGGCGAACCGGTGCAGGCGGTCTACGGCTTCGCCAAGAGCCTCCTCAAG

GCCCTGAAGGAGGACGGGTACAAGGCCGTCTTCGTGGTCTTTGACGCCAAGGCCCCCTCCCTCCGCCACGAGGCCTACG

AGGCCTACAAGGCGGGGAGGCCCCGACCCCCGAGGACTTCCCCCGGCAGCTCGCCCTCATCAAGGAGCTGGTGGACCT

CCTGGGGTTTACCCGCCTCGAGGTCCCCGGCTACGAGGCGGACGACGTTCTCGCCACCCTGGCCAAGAAGGCGGAAAAG

GAGGGGTACGAGGTGCGCATCCTCACCGCCGACCGCGACCTCTACCAACTCGTCTCCGACCGCGTCGCCGTCCTCCACC

CCGAGGGCCACCTCATCACCCCGGAGTGGCTTTGGGAGAAGTACGGCCTCAGGCCGGAGCAGTGGGTGGACTTCCGCGC

CCTCGTGGGGACCCCTCCGACAACCTCCCCGGGGTCAAGGGCATCGGGGAGAAGACCGCCCTCAAGCTCCTCAAGGAG

TGGGGAAGCCTGGAAAACCTCCTCAAGAACCTGGACCGGCTGAAGCCCGCCATCCGGGAGAAGATCCTGGCCCACATG
```

-continued

```
GACGATCTGAAGCTCTCCTGGGACCTGGCCAAGGTGCGCACCGACCTGCCCCTGGAGGTGGACTTCGCCAAAAGGCGGG
AGCCCGACCGGGAGAGGCTTAGGGCCTTTCTGGAGAGGCTTGAGCTTGGCAGCCTCCTCCACGAGTTCGGCCTTCTGGA
AAGCCCCAAGGCCCTGGAGGAGGCCTCCTGGCCCCCGCCGGAAGGGGCCTTCGTGGGCTTTGTGCTTACCCGCAAGGAG
CCCATGTGGGCCGATCTTCTGGCCCTGGCCGCCGCCAGGGGGGCCGGGTCCACCGGGCCCCGAGCCTTATAAAGCCC
TCAGGGACCTGAAGGAGGCGCGGGGGCTTCTCGCCAAAGACCTGAGCGTTCTGGCCCTGAGGGAAGGCCTTGGCCTCCC
GCCCGGCGACGACCCCATGCTCCTCGCCTACCTCCTGGACCCTTCCAACACCACCCCCGAGGGGTGGCCCGGCGCTAC
GGCGGGGAGTGGACGGAGGAGGCGGGGAGCGGGCCGCCCTTTCCGAGAGGCTCTTCGCCAACCTGTGGGGGAGGCTT
GAGGGGGAGGAGAGGCTCCTTTGGCTTTACCGGGAGGTGGAGAGACCCCTTTCCGCTGTCCTGGCCCACATGGAGGCCA
CGGGGGTGCGCCTGGACGTGGCCTATCTCAGGGCCTTGTCCCTGGAGGTGGCCGAGGAGATCGCCCGCCTCGAGGCCGA
GGTCTTCCGCCTGGCCGGCCACCCCCTTCAACCTCAACTCCCGAGACCAGCTGGAAAGGGTCCTCTTTGACGAGCTAGGGC
TTCCCGCCATCGGCAAGACGGAGAAGACCGGCAAGCGCTCCACCAGCGCCGCCGTCCTGGAGGCCCTCCGCGAGGCCC
ACCCCATCGTGGAGAAGATCCTGCAGTACCGGGAGCTCACCAAGCTGAAGAGCACCTACATTGACCCCTTGCCGGACCT
CATCCACCCCAGGACGGGCCGCCTCCACACCCGCTTCAACCAGACGGCCACGGCCACGGGCAGGCTAAGTAGCTCCGAT
CCCAACCTCCAGAACATCCCCGTCCGCACCCCGCTTGGGCAGAGGATCCGCCGGGCCTTCATCGCCGAGGAGGGGTGGC
TATTGGTGGCCCTGGACTATAGCCAGATAGAGCTCAGGGTGCTGGCCCACCTCTCCGGCGACGAGAACCTGATCCGGGT
CTTCCAGGAGGGGCGGGACATCCACACGGAGACCGCCAGCTGGATGTTCGGCGTCCCCGGGAGGCCGTGGACCCCCTG
ATGCGCCGGGCGGCCAAGACCATCAACTTCGGGGTCCTCTACGGCATGTCGGCCCACCGCCTCTCCCAGGAGCTAGCCA
TCCCTTACGAGGAGGCCCAGGCCTTCATTGAGCGCTACTTTCAGAGCTTCCCCAAGGTGCGGGCCTGGATTGAGAAGAC
CCTGGAGGAGGGCAGGAGGCGGGGGTACGTGGAGACCCTCTTCGGCCGCCGCCGCTACGTGCCAGACCTAGAGGCCCG
GGTGAAGAGCGTGCGGGAGGCGGCCGAGCGCATGGCCTTCAACATGCCCGTCCAGGGCACCGCCGCCGACCTTATGAA
GCTCGCCATGGTGAAGCTCTTCCCCCGCCTCCGGGAGATGGGGGCCCGCATGCTCCTCCAGGTCCACGACGAGCTCCTCC
TGGAGGCCCCCCAAGCGCGGGCCGAGGAGGTGGCGGCTTTGGCCAAGGAGGCCATGGAGAAGGCCTATCCCCTCGCCG
TACCCCTGGAGGTGAAGGTGGGGATCGGGGAGGACTGGCTCTCCGCCAAGGAGTGA
```

(SEQ ID NO: 62)
MRGMLPLFEPKGRVLLVDGHHLAYRTFFALKGLTTSRGEPVQAVYGFAKSLLKALKEDGYKAVFVVFDAKAPSLRHEAYEA
YKAGRAPTPEDFPRQLALIKELVDLLGFTRLEVPGYEADDVLATLAKKAEKEGYEVRILTADRDLYQLVSDRVAVLHPEGHLI
TPEWLWEKYGLRPEQWVDFRALVGDPSDNLPGVKGIGEKTALKLLKEWGSLENLLKNLDRLKPAIREKILAHMDDLKLSWD
LAKVRTDLPLEVDFAKRREPDRERLRAFLERLELGSLLHEFGLLESPKALEEASWPPPEGAFVGFVLTRKEPMWADLLALAAA
RGGRVHRAPEPYKALRDLKEARGLLAKDLSVLALREGLGLPPGDDPMLLAYLLDPSNTTPEGVARRYGGEWTEEAGERAAL
SERLFANLWGRLEGEERLLWLYREVERPLSAVLAHMEATGVRLDVAYLRALSLEVAEEIARLEAEVERLAGHPFNLNSRDQL
ERVLFDELGLPAIGKTEKTGKRSTSAAVLEALREAHPIVEKILQYRELTKLKSTYIDPLPDLIHPRTGRLHTRFNQTATATGRLS
SSDPNLQNIPVRTPLGQRIRRAFIAEEGWLLVALDYSQIELRVLAHLSGDENLIRVFQEGRDIHTETASWMFGVPREAVDPLMR
RAAKTINFGVLYGMSAHRLSQELAIPYEEAQAFIERYFQSFPKVRAWIEKTLEEGRRGYVETLFGRRRYVPDLEARVKSVRE
AAERMAFNMPVQGTAADLMKLAMVKLFPRLREMGARMLLQVHDELLLEAPQARAEEVAALAKEAMEKAYPLAVPLEVKV
GIGEDWLSAKE*

1C2:

(SEQ ID NO: 63)
```
ATGGCGATGCTTCCCCTCTTTGAGCCCAAGGGCCGCGTCCTCCTGGTGGACGGCCACCACCTGGCCTACCGCACCTTCTT
CGCCCTGAAGGGCCCCACCACGAGCCGGGGCGAACCGGTGCAGGTGGTCTACGGCTTCGCCAAGAGCCTCCTCAAGGCC
CTGAAGGAGGACGGGTACAAGGCCGTCTTCGTGGTCTTTGACGCCAAGGCCCCTCATTCCGCCACAAGGCCTACGAGG
CCTACAGGGCGGGGAGGGCCCCGACCCCCGAGGACTTCCCCCGGCAGCTCGCCCTCATCAAGGAGCTGGTGGACCTCCT
GGGGTTTACCCGCCTCGAGGTCCCCGGCTACGAGGCGGACGACGTTCTCGCCACCCTGGCCAAGAAGGCGGAAAAGGA
```

-continued

```
GGGGTACGAGGTGCGCATCCTCACCGCCGACCGCGGCCTATACCAACTCGTCTATGACCGCGTCGCCGTCCTCCACCCC

GAGGGCCACCTCATCACCCCGGAGTGGCTTTGGGAGAAGTACGGCCTCAGGCCGGAGCAGTGGGTGGACTTCCGCGCCC

TCGTGGGGACCCCTCCGACAACCTCCCCGGGGTCAAGGGCATCGGGGAGAAGACCGCCCTCAAGCTCCTCAAGGAGTG

GGGAAGCCTGGAAAACCTCCTCAAGAACCTGGACCGGGTAAAGCCAGAAAACGTCCGGGAGAAGATCAAGGCCCACCT

GGAAGACCTCAGGCTCTCCTTGGAGCTCTCCCGGGTGCGCACCGACCTCCCCCTGGAGGTGGACCTCGCCCAGGGGCGG

GAGCCCGACCGGGAGGGGCTTAGGGCCTTTCTGGAGAGGCTTGAGTTTGGCAGCCTCCTCCACGAGTTCGGCCTTCTGG

AAAGCCCCAAGGCCCTGGAGGAGGCCCCCTGGCCCCCGCCGGAAGGGGCCTTCGTGGGCTTTGTGCTTTCCCGCAAGGA

GCCCATGTGGGCCGATCTTCTGGCCCTGGCCGCCGCCAGGGGTGGTCGAGTCCACCGGGCCCCCGAGCCTTATAAAGCC

CTCAGGGACCTGAAGGAGGCGCGGGGGCTTCTCGCCAAAGACCTGAGCGTTCTGGCCCTAAGGGAAGGCCTTGGCCTCC

CGCCCGGCGACGACCCCATGCTCCTCGCCTACCTCCTGGACCCTTCCAACACCACCCCCGAGGGGGTGGCCCGGCGCTA

CGGCGGGGAGTGGACGGAGGAGGCGGGGGAGCGGGCCGCCCTTTCCGAGAGGCTCTTCGCCAACCTGTGGGGGAGGCT

TGAGGGGGAGGAGAGGCTCCTTTGGCTTTACCGGGAGGTGGAGAGGCCCCTTTCCGCTGTCCTGGCCCACATGGAGGCC

ACGGGGGTGCGCCTGGACGTGGCCTATCTCAGGGCCTTGTCCCTGGAGGTGGCCGAGGAGATCGCCCGCCTCGAGGCCG

AGGTCTTCCGCCTGGCCGGCCACCCCTTCAACCTCAACTCCCGGGACCAGCTGGAAATGGTGCTCTTTGACGAGCTTAGG

CTTCCCGCCTTGGGGAAGACGCAAAAGACGGGCAAGCGCTCCACCAGCGCCGCCGTCCTGGAGGCCCTCCGCGAGGCCC

ACCCCATCGTGGAGAAGATCCTGCAGTACCGGGAGCTCACCAAGCTGAAGAGCACCTACATTGACCCCTTGTCGGACCT

CATCCACCCCAGGACGGGCCGCCTCCACACCCGCTTCAACCAGACGGCCACGGCCACGGGCAGGCTAAGTAGCTCCGAT

CCCAACCTCCAGAACATCCCCGTCCGCACCCCGCTTGGGCAGAGGATCCGCCGGGCCTTCATCGCCGAGGAGGGTGGC

TACTGGTGGTCCTGGACTATAGCCAGATAGAGCTCAGGGTGCTGGCCCACCTCTCCGGCGACGAAAACCTGATCAGGGT

CTTCCAGGAGGGGCGGGACATCCACACGGAGACCGCCAGCTGGATGTTCGGCGTCCCCGGGAGGCCGTGGACCCCCTG

ATGCGCCGGGCGGCCAAGACCATCAACTTCGGGGTCCTCTACGGCATGTCGGCCCACCGCCTCTCCCAGGAGCTAGCCA

TCCCTTACGAGGAGGCCCAGGCCTTCATTGAGCGCTACTTTCAGAGCTTCCCCAAGGTGCGGGCCTGGATTGAGAAGAC

CCTGGAGGAGGGCAGGAGGCGGGGGTACGTGGAGACCCTCTTCGGCCGCCGCCGCTACGTGCCAGACCTAGAGGCCCG

GGTGAAGAGCGTGCGGGAGGCGGCCGAGCGCATGGCCTTCAACATGCCCGTCCAGGGCACCGCCGCCGACCTCATGAA

GCTGGCTATGGTGAAGCTCTTCCCCAGGCTGGAGGAAATGGGGGCCAGGATGCTCCTTCAGGTCCACGACGAGCTGGTC

CTCGAGGCCCCAAAAGAGAGGGCGGAGGCCGTGGCCCGGCTGGCCAAGGAGGTCATGGAGGGGGTGTATCCCCTGGCC

GTGCCCCTGGAGGTGGAGGTGGGGATAGGGGAGGACTGGCTCTCCGCCAAGGAGTGA
```

(SEQ ID NO: 64)

```
MAMLPLFEPKGRVLLVDGHHLAYRTFFALKGPTTSRGEPVQVVYGFAKSLLKALKEDGYKAVFVVFDAKAPSFRHKAYEAY

RAGRAPTPEDFPRQLALIKELVDLLGFTRLEVPGYEADDVLATLAKKAEKEGYEVRILTADRGLYQLVYDRVAVLHPEGHLIT

PEWLWEKYGLRPEQWVDFRALVGDPSDNLPGVKGIGEKTALKLLKEWGSLENLLKNLDRVKPENVREKIKAHLEDLRLSLE

LSRVRTDLPLEVDLAQGREPDREGLRAFLERLEFGSLLHEFGLLESPKALEEAPWPPPEGAFVGFVLSRKEPMWADLLALAAA

RGGRVHRAPEPYKALRDLKEARGLLAKDLSVLALREGLGLPPGDDPMLLAYLLDPSNTTPEGVARRYGGEWTEEAGERAAL

SERLFANLWGRLEGEERLLWLYREVERPLSAVLAHMEATGVRLDVAYLRALSLEVAEEIARLEAEVERLAGHPFNLNSRDQL

EMVLFDELRLPALGKTQKTGKRSTSAAVLEALREAHPIVEKILQYRELTKLKSTYIDPLSDLITIPRTGRLHTRFNQTATATGRL

SSSDPNLQNIPVRTPLGQRIRRAFIAEEGWLLVVLDYSQIELRVLAHLSGDENLIRVFQEGRDEFITETASWMFGVPREAVDPLM
```

-continued

RRAAKTINFGVLYGMSAHRLSQELAIPYEEAQAFIERYFQSFPKVRAWIEKTLEEGRRRGYVETLFGRRRYVPDLEARVKSVR

EAAERMAFNMPVQGTAADLMKLAMVKLEPRLEEMGARMLLQVHDELVLEAPKERAEAVARLAKEVMEGVYPLAVPLEVE

VGIGEDWLSAKE*

2G6:

(SEQ ID NO: 65)

ATGGCGATGCTTCCCTCTTTGAGCCCAAGGGCCGCGTCCTCCTGGTGGACGGCCACCACCTGGCCTACCGCACCTTCTT

CGCCCTGAAGGGCCCCACCACGAGCCGGGGCGAACCGGTGCAGGTGGTCTACGGCTTCGCCAAGAGCCTCCTCAAGGCC

CTGAAGGAGGACGGGTACAAGGCCGTCTTCGTGGTCTTTGACGCCAAGGCCCCTCATTCCGCCACAAGGCCTACGAGG

CCTACAGGGCGGGGAGGGCCCCGACCCCCGAGGACTTCCCCCGGCAGCTCGCCCTCATCAAGGAGCTGGTGGACCTCCT

GGGGTTTACCCGCCTCGAGGTCCCCGGCTACGAGGCGGACGACGTTCTCGCCACCTTCGCCAAGAAGGCGGAAAAGGAG

GGGTACGAGGTGCGCATCCTCACCGCCGACCGCGGCCTCTACCAACTCGTCTCTGACCGCGTCGCCGTCCTCCACCCCGA

GGGCCACCTCATCACCCCGGAGTGGCTTTGGGAGAAGTACGGCCTCAGGCCGGAGCAGTGGGTGGACTTCCGCGCCCTC

GTGGGGAACCCCTCCGACAACCTCCCCGGGGTCAAGGGCATCGGGGAGAAGACCGCCCTCAAGCTCCTCAAGGAGTGG

GGAAGCCTGGAAAACCTCCTCAAGAACCTGGACCGGGTAAAGCCAGAAACGTCCGGGAGAAGATCAAGGCCCACCTG

GAAGACCTCAGGCTCTCCTTGGAGCTCTCCCGGGTGCGCACCGACCTCCCCCTGGAGGTGGACCTCGCCCAGGGGCGGG

AGCCCGACCGGGAGGGGCTTAGGGCCTTTCTGGAGAGGCTTGAGTTTGGCAGCCTCCTCCACGAGTTCGGCCTTCTGGA

AAGCCCCAAGGCCCTGGAGGAGGCCCCCTGGCCCCCGCCGGAAGGGGCCTTCGTGGGCTTTGTGCTTTCCCGCAAGGAG

CCCATGTGGGCCGATCTTCTGGCCCTGGCCGCCGCCAGGGGTGGTCGAGTCCACCGGGCCCCGAGCCTTATAAAGCCC

TCAGGGACCTGAAGGAGGCGCGGGGGCTTCTCGCCAAAGACCTGAGCGTTCTGGCCCTAAGGGAAGGCCTTGGCCTCCC

GCCCGGCGACGACCCCATGCTCCTCGCCTACCTCCTGGACCCTTCCAACACCACCCCCGAGGGGTGGCCCGGCGCTAC

GGCGGGGAGTGGACGGAGGAGGCGGGGAGCGGGCCGCCCTTTCCGAGAGGCTCTTCGCCAACCTGTGGGGGAGGCTT

GAGGGGGAGGAGAGGCTCCTTTGGCTTTACCGGGAGGTGGAGAGGCCCCCTTTCCGCTGTCCTGGCCCACATGGAGGCCA

CGGGGGTGCGCCTGGACGTGGCCTATCTCAGGGCCTTGTCCCTGGAGGTGGCCGAGGAGATCGCCCGCCTCGAGGCCGA

GGTCTTCCGCCTGGCCGGCCACCCCCTTCAACCTCAACTCCCGGGACCAGCTGGAAAGGGTCCTCTTTGACGAGCTAGGGC

TTCCCGCCATCGGCAAGACGGAGAAGACCGGCAAGCGCTCCACCAGCGCCGCCGTCCTGGAGGCCCTCCGCGAGGCCC

ACCCCATCGTGGAGAAGATCCTGCAGTACCGGGAGCTCACCAAGCTGAAGAGCACCTACATTGACCCCTTGCCGGACCT

CATCCACCCCAGGACGGGCCGCCTCCACACCCGCTTCAACCAGACGGCCACGGCCACGGGCAGGCTAAGTAGCTCCGAT

CCCAACCTCCAGAACATCCCCGTCCGCACCCCGCTCGGGCAGAGGATCCGCCGGGCCTTCATCGCCGAGGAGGGTGGC

TATTGGTGGTCCTGGACTATAGCCAGATAGAGCTCAGGGTGCTGGCCCACCTCTCCGGCGACGAGAACCTGATCCGGGT

CTTCCAGGAGGGGCGGGACATCCACACGGAAACCGCCAGCTGGATGTTCGGCGTCCCCGGGAGGCCGTGGACCCCCTA

ATGCGCCGGGCGGCCAAGACCATCAACTTCGGGGTCCTCTACGGCATGTCGGCCCGCCGCCTCTCCCAGGAGCTAGCCA

TCCCTTACGAGGAGGCCCAGGCCTTCATTGAGCGCTACTTTCAGAGCTTCCCCAAGGTGCGGGCCTGGATTGAGAAGAC

CCTGGAGGAGGGCAGGAGGCGGGGGTACGTGGAGACCCTCTTCGGCCGCCGCCGCTACGTGCCAGACCTAGAGGCCCG

GGTGAAGAGCGTGCGGGAGGCGGCCGAGCGCATGGCCTTCAACATGCCCGTCCAGGGCACCGCCGCCGACCTCATGAA

GCTGGCTATGGTGAAGCTCTTCCCCAGGCTGGAGGAAATGGGGGCCAGGATGCTCCTTCAGGTCCACGACGAGCTGGTC

CTCGAGGCCCCAAAAGAGAGGGCGGAGGCCGTGGCCCGGCTGGCCAAGGAGGTCATGGAGGGGGTGTATCCCCTGGCC

GTGCCCCTGGAGGTGGAGGTGGGGATAGGGGAGGACTGGCTTTCCGCCAAGGGTTAG

Above: nucleic acid sequence of the clone (SEQ ID NO: 66)

MAMLPLFEPKGRVLLVDGHHLAYRTFFALKGPTTSRGEPVQVVYGFAKSLLKALKEDGYKAVFVVFDAKAPSFRHKAYEAY

RAGRAPTPEDFPRQLALIKELVDLLGFTRLEVPGYEADDVLATFAKKAEKEGYEVRILTADRGLYQLVSDRVAVLHPEGHLIT

PEWLWEKYGLRPEQWVDFRALVGNPSDNLPGVKGIGEKTALKLLKEWGSLENLLKNLDRVKPENVREKIAHLEDLRLSLE

LSRVRTDLPLEVDLAQGREPDREGLRAFLERLEFGSLLHEFGLLESPKALEEAPWPPPEGAFVGFVLSRKEPMWADLLALAAA

RGGRVHRAPEPYKALRDLKEARGLLAKDLSVLALREGLGLPPGDDPMLLAYLLDPSNTTPEGVARRYGGEWTEEAGERAAL

SERLFANLWGRLEGEERLLWLYREVERPLSAVLAHMEATGVRLDVAYLRALSLEVAEEIARLEAEVERLAGHPFNLNSRDQL

ERVLFDELGLPAIGKTEKTGKRSTSAAVLEALREAHPIVEKILQYRELTKLKSTYIDPLPDLIHPRTGRLHTRFNQTATATGRLS

SSDPNLQNIPVRTPLGQRIRRAFIAEEGWLLVVLDYSQIELRVLAHLSGDENLIRVFQEGRDIHTETASWMFGVPREAVDPLMR

RAAKTINFGVLYGMSARRLSQELAIPYEEAQAFIERYFQSFPKVRAWIEKTLEEGRRRGYVETLFGRRRYVPDLEARVKSVRE

AAERMAFNMPVQGTAADLMKLAMVKLEPRLEEMGARMLLQVHDELVLEAPKERAEAVARLAKEVMEGVYPLAVPLEVEV

GIGEDWLSAKG*

```
Above is the amino acid sequence of the clone
1A8:
                                                                    (SEQ ID NO: 67)
ATGGTGATGCTTCCCCTCTTTGAGCCCAAGGGCCGCGTCCTCCTGGTGGACGGCCACCACCTGGCCTACCGCACCTTCTT

CGCCCTGAAGGGCCTCACCACGAGCCGGGGCGAACCGGTGCAGGCGGTCTACGGCTTCGCCAAGAGCCTCCTCAAGGCC

CTGAAGGAGGACGGGTACAAGGCCGTCTTCGTGGTCTTTGACGCCAAGGCCTCCTCCTTCCGCCACGAGGCCTACGAGG

CCTACAAGGCGGGGAGGGCCCCGACCCCCGAGGACTTCCCCCGGCAGCTCGCCCTCATCAAGGAGCTGGTGGACCTCCT

GGGGTTTACCCGCCTCGAGGTCCCCGGCTACGAGGTGGACGACGTCCTGGCCAGCCTGGCCAAGAAGGTGGAAAAGGA

GGGGTACGAGGTGCGCATCCTCACCGCCGACCGCGACCTCTACCAACTCGTCTCCGACCGCGTCGCCGTCCTCCACCCCG

AGGGCCACCTCATCACCCCGGAGTGGCTTTGGGAGAAGTACGGCCTCAGGCCGGAGCAGTGGGTGGACTTCCGCGCCCT

CGTGGGGGACCCCTCCGACAACCTCCCCGGGGTCAAGGGCATCGGGGAGAAGACCGCCCTCAAGCTCCTCAAGGAGTG

GGGAGGCCTGGAAAACCTCCTCAAGAACCTGGACCGGGTAAAGCCAGAAAACGTCCGGGAGAAGATCAAGGCCCACCT

GGAAGACCTCAGGCTCTCCTTGGAGCTCTCCCGGGTGCGCACCGACCTCCCCCTGGAGGTGGACCTCGCCCAGGGGCGG

GAACCCGACCGGGAGAGGCTTAGGGCCTTTCTGGAGAGGCTTGAGTTTGGCAGCCTCCTCCACGAGTTCGGCCTTCTGG

AAAGCCCCAAGGCCCTGGAGGAGGCCCCCTGGCCCCCGCCGGAAGGGGCCTTCGTGGGCTTTGTGCTTTCCCGCAAGGA

GCCCATGTGGGCCGATCTTCTGGCCCTGGCCGCCGCCAGGGGTGGTCGGGTCCACCGGACCCCCGAGCCTTATAAAGCC

CTCAGGGACTTGAAGGAGGCGCGGGGGCTTCTCGCCAAAGACCTGAGCGTTCTGGCCCTAAGGGAAGGCCTTGGCCTCC

CGCCCGGCGACGACCCCATGCTCCTCGCCTACCTCCTGGACCCTTCCAACACCACCCCCGAGGGGGTGGCCCGGCGCTA

CGGCGGGAGTGGACGGAGGAGGCGGGGGAGCGGGCCGCCCTTTCCGAGAGGCTCTTCGCCAACCTGTGGGGGAGGCT

TGAGGGGGAGGAGAGGCTCCTTTGGCTTTACCGGGAGGTGGATAGGCCCCTTTCCGCTGTCCTGGCCCACATGGAGGCC

ACAGGGGTGCGCCTGGACGTGGCCTACCTCAGGGCCTTGTCCCTGGAGGTGGCCGAGGAGATCGCCCGCCTCGAGGCCG

AGGTCTTCCGCCTGGCCGGCCACCCCTTCAACCTCAACTCCCGGGACCAGCTGGAAAGGGTCCTCTTTGACGAGCTAGG

GCTTCCCGCCATCGGCAAGACGGAGAAGACCGGCAAGCGCTCCACCAGCGCCGCCGTCCTGGAGGCCCTCCGCGAGGC

CCACCCCATCGTGGAGAAGATCCTGCAGTACCGGGAGCTCACCAAGCTGAAGAGCACCTACATTGACCCCTTGCCGGAC

CTCATCCACCCCAGGACGGGCCGCCTCCACACCCGCTTCAACCAGACGGCCACGGCCACGGGCAGGCTAAGTAGCTCCG

ATCCCAACCTCCAGAACATCCCCGTCCGCACCCCGCTCGGGCAGAGGATCCGCCGGGCCTTCATCGCCGAGGAGGGGTG

GCTATTGGTGGTCCTGGACTATAGCCAGATAGAGCTCAGGGTGCTGGCCCACCTCTCCGGCGACGAGAACCTGATCCGG

GTCTTCCAGGAGGGGCGGGACATCCACACGGAAACCGCCAGCTGGATGTTCGGCGTCCCCCGGGAGGCCGTGGACCCCC

TAATGCGCCGGGCGGCCAAGACCATCAACTTCGGGGTTCTCTACGGCATGTCGGCCCACCGCCTCTCCCAGGAGCTAGC

CATCCCTTACGAGGAGGCCCAGGCCTTCATTGAGCGCTACTTTCAGAGCTTCCCCAAGGTGCGGGCCTGGATTGAGAAG

ACCCTGGAGGAGGGCAGGAGGCGGGGGTACGTGGAGACCCTCTTCGGCCGCCGTCGCTACGTGCCAGACCTAGAGGCC

CGGGTGAAGAGCGTGCGGGAGGCGGCCGAGCGCATGGCCTTCAACATGCCCGTCCAGGGCACCGCCGCCGACCTCATG

AAGCTGGCTATGGTGAAGCTCTTCCCCAGGCTGGAAGAAACGGGGGCCAGGATGCTCCTTCAGGTCCACGACGAGCTGG

TCCTCGAGGCCCCAAAAGAGAGGGCGGAGGCCGTGGCCCGGCTGGCCAAGGAGGCCATGGAGGGGGTGTATCCCCTGG

CCGTGCCCCTGGAGGTGGAGGTGGGGATAGGGGAGGACTGGCTCTCCGCCAAGGAGTGA
```

(SEQ ID NO: 68)
MVMLPLFEPKGRVLLVDGHHLAYRTFFALKGLTTSRGEPVQAVYGFAKSLLKALKEDGYKAVFVVFDAKASSFRHEAYEAY

KAGRAPTPEDFPRQLALIKELVDLLGFTRLEVPGYEVDDVLASLAKKVEKEGYEVRILTADRDLYQLVSDRVAVLHPEGHLIT

PEWLWEKYGLRPEQWVDFRALVGDPSDNLPGVKGIGEKTALKLLKEWGGLENLLKNLDRVKPENVREKIKAHLEDLRLSLE

LSRVRTDLPLEVDLAQGREPDRERLRAFLERLEFGSLLHEFGLLESPKALEEAPWPPPEGAFVGFVLSRKEPMWADLLALAAA

RGGRVHRTPEPYKALRDLKEARGLLAKDLSVLALREGLGLPPGDDPMLLAYLLDPSNTTPEGVARRYGGEWTEEAGERAAL

SERLFANLWGRLEGEERLLWLYREVDRPLSAVLAHMEATGVRLDVAYLRALSLEVAEEIARLEAEVERLAGHPFNLNSRDQL

ERVLFDELGLPAIGKTEKTGKRSTSAAVLEALREAHPIVEKILQYRELTKLKSTYIDPLPDLIHPRTGRLHTRFNQTATATGRLS

SSDPNLQNIPVRTPLGQRIRRAFIAEEGWLLVVLDYSQIELRVLAHLSGDENLIRVFQEGRDIHTETASWMFGVPREAVDPLMR

RAAKTINFGVLYGMSAHRLSQELAIPYEEAQAFIERYFQSFPKVRAWIEKTLEEGRRRGYVETLFGRRRYVPDLEARVKSVRE

AAERMAFNMPVQGTAADLMKLAMVKLEPRLEETGARMLLQVHDELVLEAPKERAEAVARLAKEAMEGVYPLAVPLEVEV

GIGEDWLSAKE*

2H1:
(SEQ ID NO: 69)
ATGGTGATGCTTCCCCTCTTTGAGCCCAAGGGCCGCGTCCTCCTGGTGGACGGCCACCACCTGGCCTACCGCACCTTCTT

CGCCCTGAAGGGCCTCACCACGAGCCGGGGCGAACCGGTGCAGGCGGTCTACGGCTTCGCCAAGAGCCTCCTCAAGGCC

CTGAAGGAGGACGGGTACAAGGCCGTCTTCGTGGTCTTTGACGCCAAGGCCTCCTCCTTCCGCCACGAGGCCTACGAGG

CCTACAAGGCGGGGAGGGCCCCGACCCCCGAGGACTTCCCCCGGCAGCTCGCCCTCATCAAGGAGCTGGTGGACCTCCT

GGGGTTTACCCGCCTCGAGGTCCCCGGCTACGAGGTGGACGACGTCCTGGCCAGCCTGGCCAAGAAGGTGGAAAAGGA

GGGGTACGAGGTGCGCATCCTCACCGCCGACCGCGGCCTCTACCAACTCGTCTCTGACCGCGTCGCCGTCCTCCACCCCG

AGGGCCACCTCATCACCCCGGAGTGGCTTTGGGAGAAGTACGGCCTCAGGCCGGAGCAGTGGGTGGACTTCCGCGCCCT

CGTGGGGGACCCCTCCGACAACCTCCCCGGGGTCAAGGGCATCGGGGAGAAGACCGCCCTCAAGCTCCTCAAGGAGTG

GGGAAGCCTGGAAAACCTCCTCAAGAACCTGGACCGGGTAAAGCCAGAAAACGTCCGGGAGAAGATCAAGGCCCACCT

GGAAGACCTCAGGCTCTCCTTGGAGCTCTCCCGGGTGCGCACCGACCTCCCCCTGGAGGTGGACCTCGCCCAGGGGCGG

GAGCCCGACCGGGAGAGGCTTAGGGCCTTTCTGGAGAGGCTTGAGTTTGGCAGCCTCCTCCACGAGTTCGGCCTTCTGG

AAAGCCCCAAGGCCCTGGAGGAGGCCCCCTGGCCCCCGCCGGAAGGGGCCTTCGTGGGCTTTGTGCTTTCCCGCAAGGA

GCCCATGTGGGCCGATCTTCTGGCCCTGGCCGCCGCCAGGGGTGGTCGGGTCCACCGGGCCCCCGAGCCTTATAAAGCC

CTCAGGGACTTGAAGGAGGCGCGGGGCTTCTCGCCAAAGACCTGAGCGTTCTGGCCCTAAGGGAAGGCCTTGGCCTCC

CGCCCGGCGACGACCCCATGCTCCTCGCCTACCTCCTGGACCCTTCCAACACCACCCCCGAGGGGGTGGCCCGGCGCTA

CGGCGGGGAGTGGACGGAGGAGGCGGGGGAGCGGGCCGCCCTTTCCGAGAGGCTCTTCGCCAACCTGTGGGGGAGGCT

TGAGGGGGAGGAGAGGCTCCTTTGGCTTTACCGGGAGGTGGATAGGCCCCTTTCCGCTGTCCTGGCCCACATGGAGGCC

ACAGGGGTGCGCCTGGACGTGGCCTATCTCAGGGCCTTGTCCCTGGAGGTGGCCGAGGAGATCGCCCGCCTCGAGGCCG

AGGTCTTCCGCCTGGCCGGCCACCCCTTCAACCTCAACTCCCGGGACCAGCTGGAAAGGGTCCTCTTTGACGAGCTAGG

GCTTCCCGCCATCGGCAAGACGGAGAAGACCGGCAAGCGCTCCACCAGCGCCGCCATCCTGGAGGCCCTCCGCGAGGC

CCACCCCATCGTGGAGAAGATCCTGCAGTACCGGGAGCTCACCAAGCTGAAGAGCACCTACATTGACCCCTTGCCGGAC

CTCATCCACCCCAGGACGGGCCGCCTCCACACCCGCTTCAACCAGACGGCCACGGCCACGGGCAGGCTAAGTAGCTCCG

ATCCCAACCTCCAGAACATCCCCGTCCGCACCCCGCTCGGGCAGAGGATCCGCCGGGCCTTCATCGCCGAGGAGGGGTG

GCTATTGGTGGTCCTGGACTATAGCCAGATAGAGCTCAGGGTGCTGGCCCACCTCTCCGGCGACGAGAACCTGACCCGG

GTCTTCCAGGAGGGGCGGGACATCCACACGGAAACCGCCAGCTGGATGTTCGGCGTCCCCGGGAGGCCGTGGACCCCC

TGATGCGCCGGGCGGCCAAGACCATCAACTTCGGGGTTCTCTACGGCATGTCGGCCCACCGCCTCTCCCAGGAGCTGGC

CATCCCTTACGAGGAGGCCCAGGCCTTCATAGAGCGCTACTTCCAAAGCTTCCCCAAGGTGCGGGCCTGGATAGAAAAG

ACCCTGGAGGAGGGGAGGAAGCGGGGCTACGTGGAAACCCTCTTCGGAAGAAGGCGCTACGTGCCCGACCTCAACGCC

```
CGGGTGAAGAGTGTCAGGGAGGCCGCGGAGCGCATGGCCTTCAACATGCCCGTCCAGGGCACCGCCGCCGACCTTATGA

AGCTCGCCATGGTGAAGCTCTTCCCCCGCCTCCGGGAGATGGGGGCCCGCATGCTCCTCCAGGTCCACGACGAGCTCCTC

CTGGAGGCCCCCCAAGCGCGGGCCGAGGAGGTGGCGGCTTTGGCCAAGGAGGCCATGGAGAAGGCCTATCCCCTCGCC

GTACCCCTGGAGGTGAAGGTGGGGATCGGGGAGGACTGGCTCTCCGCCCAAGGAGTGAGTCGACCTGCAGGCAGCGCT

TGGCGTCACCCGCAGTTCGGTGGTTAA
```

(SEQ ID NO: 70)
```
MVMLPLFEPKGRVLLVDGHHLAYRTFFALKGLTTSRGEPVQAVYGFAKSLLKALKEDGYKAVFVVFDAKASSFRHEAYEAY

KAGRAPTPEDFPRQLALIKELVDLLGFTRLEVPGYEVDDVLASLAKKVEKEGYEVRILTADRGLYQLVSDRVAVLHPEGHLIT

PEWLWEKYGLRPEQWVDFRALVGDPSDNLPGVKGIGEKTALKLLKEWGSLENLLKNLDRVKPENVREKIKAHLEDLRLSLE

LSRVRTDLPLEVDLAQGREPDRERLRAFLERLEFGSLLHEFGLLESPKALEEAPWPPPEGAFVGFVLSRKEPMWADLLALAAA

RGGRVHRAPEPYKALRDLKEARGLLAKDLSVLALREGLGLPPGDDPMLLAYLLDPSNTTPEGVARRYGGEWTEEAGERAAL

SERLFANLWGRLEGEERLLWLYREVDRPLSAVLAHMEATGVRLDVAYLRALSLEVAEEIARLEAEVFRLAGHPFNLNSRDQL

ERVLFDELGLPAIGKTEKTGKRSTSAAILEALREAHPIVEKILQYRELTKLKSTYIDPLPDLIHPRTGRLHTRFNQTATATGRLSS

SDPNLQNIPVRTPLGQRIRRAFIAEEGWLLVVLDYSQIELRVLAHLSGDENLTRVFQEGRDIHTETASWMFGVPREAVDPLMR

RAAKTINFGVLYGMSAHRLSQELAIPYEEAQAFIERYFQSFPKVRAWIEKTLEEGRKRGYVETLFGRRRYVPDLNARVKSVRE

AAERMAFNMPVQGTAADLMKLAMVKLFPRLREMGARMLLQVHDELLLEAPQARAEEVAALAKEAMEKAYPLAVPLEVKV

GIGEDWLSAQGVSRPAGSAWRHPQFGG*
```

2F11:

(SEQ ID NO: 71)
```
ATGCGTGGTATGCTTCCTCTTTTTGAGCCCAAGGGCCGCGTCCTCCTGGTGGACGGCCACCACCTGGCCTACCGCACCTT

CTTCGCCCTGAAGGGCCCCACCACGAGCCGGGGCGAACCGGTGCAGGCGGTCTACGGCTTCGCCAAGAGCCTCCTCAAG

GCCCTGAAGGAGGACGGGTACAAGGCCGCCTTCGTGGTCTTTGACGCCAAGGCCCCCTCCTTCCGCCACGAGGCCTACG

AGGCCTACAAGGCGGGGAGGGCCCCGACCCCCGAGGACTTCCCCCGGCAGCTCGCCCTCATCAAGGAGCTGGTGGACCT

CCTGGGGTTTACCCGCCTCGAGGTCCCTGGCTACGAGGCGGACGACGTCCTCGCCACCCTGGCCAAGAAGGCGGAAAAG

GAGGGGTACGAGGTGCGCATCCTCACCGCCGACCGCGACCTCTACCAACTCGTCTCCGACCGCGTCGCCGTCCTCCACC

CCGAGGGCCACCTCATCACCCCGGAGTGGCTTTGGGAGAAGTACGGCCTCAGGCCGGAGCAGTGGGTGGACTTCCGCGC

CCTCGTGGGGGACCCCTCCGACAACCTCCCCGGGGTCAAGGGCATCGGGGAGAAGACCGCCCTCAAGCTCCTCAAGGAG

TGGGGAAGCCTGGAAAACCTCCTCAAGAACCTGGACCGGGTAAAGCCAGAAAACGTCCGGGAGAAGATCAAGGCCCAC

DCTGGAAGACCTCAGGCTCTCCTTGGAGCTCTCCCGGGTGCGCACCGACCTCCCCCTGGAGGTGGACCTCGCCCAGGGGC

GGGAGCTCGACCGGGAGAGGCTTAGGGCCTTTCTGGAGAGGCTTGAGTTTGGCGGCCTCCTCCACGAGTTCGGCCTTCT

GGAAAGCCCCAAGGCCCTGGAGGAGGCCCCCTGGCCCCCGCCGGAAGGGGCCTTCGTGGGCTTTGTGCTTTCCCGCAAG

GAGCCCATGTGGGCCGATCTTCTGGCCCTGGCCGCCGCCAGGGGTGGTCGGGTCCACCGGGCCCCCGAGCCTTATAAAG

CCCTCAGGGACTTGAAGGAGGCGCGGGGGCTTCTCGCCAAAGACCTGAGCGTTCTGGCCCTAAGGGAAGGCCTTGGCCT

CCCGCCCGGCGACGACCCCATGCTCCTCGCCTACCTCCTGGACCCTTCCAACACCGCCCCCGAGGGGGTGGCCCGGCGC

TACGGCGGGGAGTGGACGGAGGAGGCGGGGGAGCGGGCCGCCCTTTCCGAGAGGCTCTTCGCCAACCTGTGGGGAGG

CTTGAGGGGAGGAGAGGCTCCTTTGGCTTTACCGGGAGGTGGATAGGCCCCTTTCCGCTGTCCTGGCCCACATGGAGG

CCACAGGGGTACGGCTGGACGTGGCCTGCCTGCAGGCCCTTTCCCTGGAGCTTGCGGAGGAGATCCGCCGCCTCGAGGA

GGAGGTCTTCCGCTTGGCGGGCCACCCCTTCAACCTCAACTCCCGGGACCAGCTGGAAAGGGTCCTCTTTGACGAGCTA

GGGCTTCCCGCCATCGGCAAGACGGAGAAGACCGGCAAGCGCTCCACCAGCGCCGCCATCCTGGAGGCCCTCCGCGAG

GCCCACCCCATCGTGGAGAAGATCCTGCAGTACCGGGAGCTCACCAAGCTGAAGAGCACCTACATTGACCCCTTGCCGG

ACCTCATCCACCCCAGGACGGGCCGCCTCCACACCCGCTTCAACCAGACGGCCACGGCCACGGGCAGGCTAAGTAGCTC

CGATCCCAACCTCCAGAACATCCCCGTCCGCACCCCGCTCGGGCAGAGGATCCGCCGGGCCTTCGTCGCCGAGGAGGGG
```

-continued

```
TGGCTATTGGTGGTCCTGGACTATAGCCAGATAGAGCTCAGGGTGCTGGCCCACCTCTCCGGCGACGAGAACCTGACCC

GGGTCTTCCTGGAGGGGCGGGACATCCACACGGAAACCGCCAGCTGGATGTTCGGCGTCCCCGGGAGGCCGTGGACCC

CCTGATGCGCCGGGCGGCCAAGACCATCAACTTCGGGGTTCTCTACGGCATGTCGGCCCACCGCCTCTCCCAGGAGCTG

GCCATCCCTTACGAGGAGGCCCAGGCCTTCATAGAGCGCTACTTCCAAAGCTTCCCCAAGGTGCGGGCCTGGATAGAA

AGACCCTGGAGGAGGGGAGGAAGCGGGGCTACGTGGAAACCCTCTTCGGAAGAAGGCGCTACGTGCCCGACCTCAACG

CCCGGGTGAAGAGTGTCAGGGAGGCCGCGGAGCGCATGGCCTTCAACATGCCCGTCCAGGGCACCGCCGCCGACCTTAT

GAAGCTCGCCATGGTGAAGCTCTTCCCCCGCCTCCGGGAGATGGGGGCCCGCATGCTCCTCCAGGTCCACGACGAGCTC

CTCCTGGAGGCCCCCAAGCGCGGGCCGAGGAGGTGGCGGCTTTGGCCAAGGAGGCCATGGAGAAGGCCTATCCCCTC

GCCGTACCCCTGGAGGTGAAGGTGGGGATCGGGGAGGACTGGCTCTCCGCCAAGGAGTGA
```

(SEQ ID NO: 72)
```
MRGMLPLFEPKGRVLLVDGHHLAYRTFFALKGPTTSRGEPVQAVYGFAKSLLKALKEDGYKAAFVVFDAKAPSFRHEAYEA

YKAGRAPTPEDFPRQLALIKELVDLLGFTRLEVPGYEADDVLATLAKKAEKEGYEVRILTADRDLYQLVSDRVAVLHPEGHLI

TPEWLWEKYGLRPEQWVDFRALVGDPSDNLPGVKGIGEKTALKLLKEWGSLENLLKNLDRVKPENVREKIKAHLEDLRLSL

ELSRVRTDLPLEVDLAQGRELDRERLRAFLERLEFGGLLHEFGLLESPKALEEAPWPPPEGAFVGFVLSRKEPMWADLLALAA

ARGGRVHRAPEPYKALRDLKEARGLLAKDLSVLALREGLGLPPGDDPMLLAYLLDPSNTAPEGVARRYGGEWTEEAGERAA

LSERLFANLWGRLEGEERLLWLYREVDRPLSAVLAHMEATGVRLDVACLQALSLELAEEIRRLEEEVFRLAGHPFNLNSRDQ

LERVLFDELGLPAIGKTEKTGKRSTSAAILEALREAHPIVEKILQYRELTKLKSTYIDPLPDLIHPRTGRLHTRFNQTATATGRLS

SSDPNLQNIPVRTPLGQRIRRAFVAEEGWLLVVLDYSQIELRVLAHLSGDENLTRVFLEGRDIHTETASWMFGVPREAVDPLM

RRAAKTINFGVLYGMSAHRLSQELAIPYEEAQAFIERYFQSFPKVRAWIEKTLEEGRKRGYVETLFGRRRYVPDLNARVKSVR

EAAERMAFNMPVQGTAADLMKLAMVKLFPRLREMGARMLLQVHDELLLEAPQARAEEVAALAKEAMEKAYPLAVPLEVK

VGIGEDWLSAKE*
```

2H4:

(SEQ ID NO: 73)
```
ATGGCGATGCTTCCCCTCTTTGAGCCCAAGGGCCGCGTCCTCCTGGTGGACGGCCACCACCTGGCCTACCGCACCTTCTT

CGCCCTGAAGGGCCCCACCACGAGCCGGGGCGAACCGGTGCAGGTGGTCTACGGCTTCGCCAAGAGCCTCCTCAAGGCC

CTGAAGGAGGACGGGTACAAGGCCGTCTTCGTGGTCTTTGACGCCAAGGCCCCCTCATTCCGCCACAAGGCCTACGAGG

CCTACAGGGCGGGGAGGGCCCCGACCCCCGAGGACTTCCCCCGGCAGCTCGCCCTCATCAAGGAGCTGGTGGACCTCCT

GGGGTTTACCCGCCTCGAGGTCCCCGGCTACGAGGCGGACGACGTTCTCGCCACCCTGGCCAAGAAGGCGGAAAAGGA

GGGGTACGAGGTGCGCATCCTCACCGCCGACCGCGGCCTCTACCAACTCGTCTCTGACCGCGTCGCCGTCCTCCACCCCG

AGGGCCACCTCATCACCCCGGAGTGGCTTTGGGAGAAGTACGGCCTCAGGCCGGAGCAGTGGGTGGACTTCCGCGCCCT

CGTGGGGACCCCTCCGACAACCTCCCCGGGGTCAAGGGCATCGGGGAGAAGACCGCCCTCAAGCTCCTCAAGGAGTG

GGGAAGCCTGGAAAACCTCCTCAAGAACCTGGACCGGGTAAAGCCAGAAAACGTCCGGGAGAAGATCAAGGCCCACCT

GGAAGACCTCAGGCTCTCCTTGGAGCTCTCCCGGGTGCGCACCGACCTCCCCCTGGAGGTGGACCTCGCCCAGGGGCGG

GAGCCCGACCGGGAGGGGCTTAGGGCCTTTCTGGAGAGGCTTGAGTTTGGCAGCCTCCTCCACGAGTTCGGCCTTCTGG

AAAGCCCCAAGGCCCTGGAGGAGGCCCCCTGGCCCCCGCCGGAAGGGGCCTTCGTGGGCTTTGTGCTTTCCCGCAAGGA

GCCCATGTGGGCCGATCTTCTGGCCCTGGCCGCCGCCAGGGGTGGTCGAGTCCACCGGGCCCCCGAGCCTTATAAAGCC

CTCAGGGACCTGAAGGAGGCGCGGGGGCTTCTCGCCAAAGACCTGAGCGTTCTGGCCCTAAGGGAAGGCCTTGGCCTCC

CGCCCGGCGACGACCCCATGCTCCTCGCCTACCTCCTGGACCCTTCCAACACCACCCCCGAGGGGGTGGCCCGGCGCTA

CGGCGGGAGTGGACGGAGGAGGCGGGGAGCGGGCCGCCCTTTCCGAGAGGCTCTTCGCCAACCTGTGGGGAGGCT

TGAGGGGGAGGAGAGGCTCCTTTGGCTTTACCGGGAGGTGGAGAGGCCCCTTTCCGCTGTCCTGGCCCACATGGAGGCC

ACGGGGGTGCGCCTGGACGTGGCCTATCTCAGGGCCTTGTCCCTGGAGGTGGCCGAGGAGATCGCCCGCCTCGAGGCG

AGGTCTTCCGCCTGGCCGGCCACCCCTTCAACCTCAACTCCCGGGACCAGCTGGAAATGGTGCTCTTTGACGAGCTTAGG
```

-continued

```
CTTCCCGCCTTGGGGAAGACGCAAAAGACGGGCAAGCGCTCCACCAGCGCCGCCGTCCTGGAGGCCCTCCGCGAGGCC
ACCCCATCGTGGAGAAGATCCTGCAGTACCGGGAGCTCACCAAGCTGAAGAGCACCTACATTGACCCCTTGTCGGACCT
CATCCACCCCAGGACGGGCCGCCTCCACACCCGCTTCAACCAGACGGCCACGGCCACGGGCAGGCTAAGTAGCTCCGAT
CCCAACCTCCAGAACATCCCCGTCCGCACCCCGCTTGGGCAGAGGATCCGCCGGGCCTTCATCGCCGAGGAGGGGTGGC
TACTGGTGGTCCTGGACTATAGCCAGATAGAGCTCAGGGTGCTGGCCCACCTCTCCGGCGACGAAAACCTGATCAGGGT
CTTCCAGGAGGGGCGGGACATCCACACGGAGACCGCCAGCTGGATGTTCGGCGTCCCCGGGAGGCCGTGGACCCCCTG
ATGCGCCGGGCGGCCAAGACCATCAACTTCGGGGTCCTCTACGGCATGTCGGCCCACCGCCTCTCCCAGGAGCTAGCCA
TCCCTTACGAGGAGGCCCAGGCCTTCATTGAGCGCTACTTTCAGAGCTTCCCCAAGGTGCGGGCCTGGATTGAGAAGAC
CCTGGAGGAGGGCAGGAGGCGGGGTACGTGGAGACCCTCTTCGGCCGCCGCCGCTACGTGCCAGACCTAGAGGCCCG
GGTGAAGAGCGTGCGGGAGGCGGCCGAGCGCATGGCCTTCAACATGCCCGTCCAGGGCACCGCCGCCGACCTCATGAA
GCTGGCTATGGTGAAGCTCTTCCCCAGGCTGGAGGAAACGGGGGCCAGGATGCTCCTTCAGGTCCACGACGAGCTGGTC
CTTGAGGCCCCAAAAGAGAGGGCGGAGGCCGTGGCCCGGCTGGCCAAGGAGGTCATGGAGGGGGTGTATCCCCTGGCC
GTGTCCCTGGAGGTGGAGGTGGGGATAGGGGAGGACTGGCTCTCCGCCAAGGAGTGA
```

(SEQ ID NO: 74)
MAMLPLFEPKGRVLLVDGHHLAYRTFFALKGPTTSRGEPVQVVYGFAKSLLKALKEDGYKAVFVVFDAKAPSFRHKAYEAY
RAGRAPTPEDFPRQLALIKELVDLLGFTRLEVPGYEADDVLATLAKKAEKEGYEVRILTADRGLYQLVSDRVAVLHPEGHLIT
PEWLWEKYGLRPEQWVDFRALVGDPSDNLPGVKGIGEKTALKLLKEWGSLENLLKNLDRVKPENVREKIKAHLEDLRLSLE
LSRVRTDLPLEVDLAQGREPDREGLRAFLERLEFGSLLHEFGLLESPKALEEAPWPPPEGAFVGFVLSRKEPMWADLLALAAA
RGGRVHRAPEPYKALRDLKEARGLLAKDLSVLALREGLGLPPGDDPMLLAYLLDPSNTTPEGVARRYGGEWTEEAGERAAL
SERLFANLWGRLEGEERLLWLYREVERPLSAVLAHMEATGVRLDVAYLRALSLEVAEEIARLEAEVFRLAGHPFNLNSRDQL
EMVLFDELRLPALGKTQKTGKRSTSAAVLEALREAHPIVEKILQYRELTKLKSTYIDPLSDLIHPRTGRLHTRFNQTATATGRL
SSSDPNLQNIPVRTPLGQRIRRAFIAEEGWLLVVLDYSQIELRVLAHLSGDENLIRVFQEGRDIHTETASWMFGVPREAVDPLM
RRAAKTINFGVLYGMSAHRLSQELAIPYEEAQAFIERYFQSFPKVRAWIEKTLEEGRRRGYVETLFGRRRYVPDLEARVKSVR
EAAERMAFNMPVQGTAADLMKLAMVKLFPRLEETGARMLLQVHDELVLEAPKERAEAVARLAKEVMEGVYPLAVSLEVE
VGIGEDWLSAKE*

2H9:

(SEQ ID NO: 75)
```
ATGGCGATGCTTCCCCTCTTTGAGCCCAAGGGCCGCGTCCTCCTGGTGGACGGCCACCACCTGGCCTACCGCACCTTCTT
CGCCCTGAAGGGCCCCACCGCGAGCCGGGGCGAACCGGTGCAGGTGGTCTACGGCTTCGCCAAGAGCCTCCTCAAGGCC
CTGAAGGAGGACGGGTACAAGGCCGTCTTCGTGGTCTTTGACGCCAAGGCCCCCTCATTCCGCCACAAGGCCTACGAGG
CCTACAGGGCGGGGAGGGCCCCGACCCCCGAGGACTTCCCCCGGCAGCTCGCCCTCATCAAGGAGCTGGTGGACCTCCT
GGGGTTTACCCGCCTCGAGGTCCCCGGCTACGAGGCGGACGACGTTCTCGCCCCCCTGGCCAAGAAGGCGGAAAAGGA
GGGGTTCGAGGTGCGCATCCTCCCCGCCGTCCGCGGCCTCTGCCCTCTCGTCTCTGACCGCGTCGCCGTCCTCCTCCCCG
AGGGCCACCTCATCACCCCGGAGTGGCTTTGGGAGAAGTACGGCCTCAGGCCGGAGCAGTGGGTGGACTTCCGCGCCCT
CGTGGGGGACCCCTCCGACAACCTCCCCGGGGTCAAGGGCATCGGGAAGAAGACCGCCCTCAAGCTCCTCAAGGAGTG
GGGAAGCCTGGAAAACCTCCTCAAGAACCTGGACCGGGTAAAGCCAGAAAACGTCCGGGAGAAGATCAAGGCCCACCT
GGAAGACCTCAGGCTCTCCTTGGAGCTCTCCCGGGTGCGCACCGACCTCCCCCTGGAGGTGGACCTCGCCCAGGGGCGG
GAGCCCGACCGGGAGGGGCTTAGGGCCTTTCTGGAGAGGCTTGAGTTTGGCAGCCTCCTCCACGAGTTCGGCCTTCTGG
AAAGCCCCAAGGCCCTGGAGGAGGCCCCTGGCCCCCGCCGGAAGGGGCCTTCGTGGGCTTTGTGCTTTCCCGCAAGGA
GCCCATGTGGGCCGATCTTCTGGCCCTGGCCGCCGCCAGGGGTGGTCGGGTCCACCGGGCCCCCGAGCCTTATAAAGCC
CTCAGGGACTTGAAGGAGGCGCGGGGGCTTCTCGCCAAAGACCTGAGCGTTCTGGCCCTAAGGGAAGGCCTTGGCCTCC
CGCCCGGCGACGACCCCATGCTCCTCGCCTACCTCCTGGACCCTTCCAACACCACCCCCGAGGGGGTGGCCCGGCGCTA
```

```
CGGCGGGGAGTGGACGGAGGAGGCGGGGGAGCGGGCCGCCCTTTCCGAGAGGCTCTTCGCCAACCTGTGGGGAGGCT

TGAGGGGAGGAGAGGCTCCTGTGGCTTTACCGGGAGGTGGATAGGCCCCTTTCCGCTGTCCTGGCCCACATGGAGGCC

ACAGGGGTACGGCTGGACGTGGCCTGCCTGCAGGCCCTTTCCCTGGAGCTTGCGGAGGAGATCCGCCGCCTCGAGGAG

AGGTCTTCCGCTTGGCGGGCCACCCCTTCAACCTCAACTCCCGGGACCAGCTGGAAAGGGTCCTCTTTGACGAGCTAGG

GCTTCCCGCCATCGGCAAGACGGAGAAGACCGGCAAGCGCTCCACCAGCGCCGCCATCCTGGAGGCCCTCCGCGAGGC

CCACCCCATCGTGGAGAAGATCCTGCAGTACCGGGAGCTCACCAAGCTGAAGAGCACCTACATTGACCCCTTGCCGGAC

CTCATCCACCCCAGGACGGGCCGCCTCCACACCCGCTTCAACCAGACGGCCACGGCCACGGGCAGGCTAAGTAGCTCCG

ATCCCAACCTCCAGAACATCCCCGTCCGCACCCCGCTCGGGCAGAGGATCCGCCGGGCCTTCATCGCCGAGGAGGGGTG

GCTATTGGTGGTCCTGGACTATAGCCAGATAGAGCTCAGGGTGCTGGCCCACCTCTCCGGCGACGAGAACCTGACCCGG

GTCTTCCAGGAGGGGCGGGACATCCACACGGAAACCGCCAGCTGGATGTTCGGCGTCCCCGGGAGGCCGTGGACCCCC

TGATGCGCCGGGCGGCCAAGACCATCAACTTCGGGGTTCTCTACGGCATGTCGGCCCACCGCCTCTCCCAGGAGCTGGC

CATCCCTTACGAGGAGGCCCAGGCCTTCATAGAGCGCTACTTCCAAAGCTTCCCCAAGGTGCGGGCCTGGATAGAAAAG

ACCCTGGAGGAGGGGAGGAAGCGGGGCTACGTGGAAACCCTCTTCGGAAGAAGGCGCTACGTGCCCGACCTCAACGCC

CGGGTGAAGAGTGTCAGGGAGGCCGCGGAGCGCATGGCCTTCAACATGCCCGTCCAGGGCACCGCCGCCGACCTTATGA

AGCTCGCCATGGTGAAGCTCTTCCCCCGCCTCCGGGAGATGGGGGCCCGCATGCTCCTCCAGGTCCACGACGAGCTCCTC

CTGGAGGCCCCCCAAGCGCGGGCCGAGGAGGTGGCGGCTTTGGCCAAGGAGGCCATGGAGAAGGCCTATCCCCTCGCC

GTACCCCTGGAGGTGAAGGTGGGGATCGGGGAGGACTGGCTCTCCGCCAAGGAGTGA
```

(SEQ ID NO: 76)
```
MAMLPLFEPKGRVLLVDGHHLAYRTFFALKGPTASRGEPVQVVYGFAKSLLKALKEDGYKAVFVVFDAKAPSFRHKAYEAY

RAGRAPTPEDFPRQLALIKELVDLLGFTRLEVPGYEADDVLAPLAKKAEKEGFEVRILPAVRGLCPLVSDRVAVLLPEGHLITP

EWLWEKYGLRPEQWVDFRALVGDPSDNLPGVKGIGKKTALKLLKEWGSLENLLKNLDRVKPENVREKIKAHLEDLRLSLEL

SRVRTDLPLEVDLAQGREPDREGLRAFLERLEFGSLLHEFGLLESPKALEEAPWPPPEGAFVGFVLSRKEPMWADLLALAAAR

GGRVHRAPEPYKALRDLKEARGLLAKDLSVLALREGLGLPPGDDPMLLAYLLDPSNTTPEGVARRYGGEWTEEAGERAALS

ERLFANLWGRLEGEERLLWLYREVDRPLSAVLAHMEATGVRLDVACLQALSLELAEEIRRLEEEVFRLAGHPFNLNSRDQLE

RVLFDELGLPAIGKTEKTGKRSTSAAILEALREAHPIVEKILQYRELTKLKSTYIDPLPDLIHPRTGRLHTRFNQTATATGRLSSS

DPNLQNIPVRTPLGQRIRRAFIAEEGWLLVVLDYSQIELRVLAHLSGDENLTRVFQEGRDIHTETASWMFGVPREAVDPLMRR

AAKTINFGVLYGMSAHRLSQELAIPYEEAQAFIERYFQSFPKVRAWIEKTLEEGRKRGYVETLFGRRRYVPDLNARVKSVREA

AERMAFNMPVQGTAADLMKLAMVKLFPRLREMGARMLLQVHDELLLEAPQARAEEVAALAKEAMEKAYPLAVPLEVKVG

IGEDWLSAKE*
```

1B12:

(SEQ ID NO: 77)
```
ATGGCGATGCTTCCCCTCTTTGAGCCCAAAGGCCGGGTCCTCCTGGTGGACGGCCACCACCTGGCCTACCGCACCTTCTT

CGCCCTGAAGGGCCTCATCACGAGCCGGGGCGAACCGGTGCAGGCGGTCTACGGTTTCGCCAAGAGCCTCCTCAAGGCC

CTGAAGGAGGACGGGTACAAGGCCGTCTTCGTGGTCTTTGACGCCAAGGCCCCCTCCTTCCGCCACGAGGCCTACGAGG

CCTACAAGGCGGGGAGGGCCCCGACCCCCGAGGACTTCCCCCGGCAGCTCGCCCTCATCAAGGAGCTGGTGGACCTCCT

GGGGTTTACCCGCCTCGAGGTCCAAGGCTACGAGGCGGACGACGTCCTCGCCACCCTGGCCAAGAAGGCGGAAAAAGA

AGGGTACGAGGTGCGCATCCTCACCGCCGACCGGGACCTCTACCAGCTCGTCTCCGACCGCGTCGCCGTCCTCCACCCC

GAGGGCCACCTCATCACCCCGGAGTGGCTTTGGGAGAAGTACGGCCTCAGGCCGGAGCAGTGGGTGGACTTCCGCGCCC

TCGTGGGGACCCCTCCGACAACCTCCCCGGGGTCAAGGGCATCGGGGAGAAGACCGCCCTCAAGCTCCTCAAGGAGTG

GGGAAGCCTGGAAAATCTCCTCAAGAACCTGGATCGGGTAAAGCCGGAAAACGTCCGGGAGAAGATCAAGGCCCACCT

GGAAGACCTCAGGCTCTCCTTGGAGCTCTCCCGGGTGCGTACCGACCTCCCCCTGGAGGTGGACCTCGCCCAGGGGCGG

GAGCCCGACCGGGAAGGGCTTAGGGCCTTCCTGGAGAGGCTGGAGTTCGGCAGCCTCCTCCATGAGTTCGGCCTTCTGG
```

-continued

```
AAAGCCCCAAGGCCCTGGAGGAGGCCCCCTGGCCCCCGCCGGAAGGGGCCTTCGTGGGCTTTGTGCTTTCCCGCAAGGA
GCCCATGTGGGCCGATCTTCTGGCCCTGGCCGCCGCCAGGGGTGGTCGGGTCCACCGGGCCCCCGAGCCTTATAAAGCC
CTCAGGGACTTGAAGGAGGCGCGGGGCTTCTCGCCAAAGACCTGAGCGTTCTGGCCCTAAGGGAAGGCCTTGGCCTCC
CGCCCGGCGACGACCCCATGCTCCTCGCCTACCTCCTGGACCCTTCCAACACCACCCCCGAGGGGGTGGCCCGGCGCTA
CGGCGGGGAGTGGACGGAGGAGGCGGGGGAGCGGGCCGCCCTTTCCGAGAGGCTCTTCGCCAACCTGTGGGGGAGGCT
TGAGGGGAGGAGAGGCTCCTTTGGCTTTACCGGGAGGTGGATAGGCCCCTTTCCGCTGTCCTGGCCCACATGGAGGCC
ACAGGGGTGCGCCTGGACGTGGCCTATCTCAGGGCCTTGTCCCTGGAGGTGGCCGAGGAGATCGCCCGCCTCGAGGCCG
AGGTCTTCCGCCTGGCCGGCCACCCCTTCAACCTCAACTCCCGGGACCAGCTGGAAAGGGTCCTCTTTGACGAGTTAGGG
CTTCCCGCCATCGGCAAGACGGAGAGGACCGGCAAGCGCTCCACCAGCGCCGCCGTCCTGGAGGCCCTCCGCGAGGCCC
ACCCCATCGTGGAGAAGATCCTGCAGTACCGGGAGCTCACCAAGCTGAAGAGCACCTACATTGACCCCTTGCCGGACCT
CATCCACCCCAGGACGGGCCGCCTCCACACCCGCTTCAACCAGACGGCCACGGCCACGGGCAGGCTAAGTAGCTCCGAT
CCCAACCTCCAGAACATCCCCGTCCGCACCCCGCTTGGGCAGAGGATCCGCCGGGCCTTCATCGCCGAGGAGGGGTGGC
TATTGGTGGCCCTGGACTATAGCCAGATAGAGCTCAGGGTGCTGGCCCACCTCTCCGGCGACGAGAACCTGATCCGGGT
CTTCCAGGAGGGGCGGGACATCCACACGGAGACCGCCAGCTGGATGTTCGGTGTCCCCCCGGAGGCCGTGGACCCCCTG
ATGCGCCGGGCGGCCAAGACGGTGAACTTCGGCGTCCTCTACGGCATGTCCGCCCATAGGCTCTCCCAGGAGCTTTCCAT
CCCCTACGAGGAGGCGGTGGCCTTTATAGAGCGCTACTTCCAAAGCTTCCCCAAGGTGCGGGCCTGGATAGAAAAGACC
CTGGAGGAGGGGAGGAAGCGGGGCTACGTGGAAACCCTCTTCGGAAGAAGGCGCTACGTGCCCGACCTCAACGCCCGG
GTGAAGAGCGTCAGGGAGGCCGCGGAGCGCATGGCCTTCAACATGCCCGTCCAGGGCACCGCCGCCGACCTCATGAAG
CTCGCCATGGTGAAGCTCTTCCCCCGCCTCCGGGAGATGGGGGCCCGCATGCTCCTCCAGGTCCACGACGAGCTCCTCCT
GGAGGCCCCCCAAGCGCGGGCCGAGGAGGTGGCGGCTTTGGCCAAGGAGGCCATGGAGAAGGCCTATCCCCTCGCCGT
ACCCCTGGAGGTGGAGGTGGGGATCGGGGAGGACTGGCTCTCCGCCAAGGAGTGA
```

(SEQ ID NO: 78)
MAMLPLFEPKGRVLLVDGHHLAYRTFFALKGLITSRGEPVQAVYGFAKSLLKALKEDGYKAVFVVFDAKAPSFRHEAYEAY
KAGRAPTPEDFPRQLALIKELVDLLGFTRLEVQGYEADDVLATLAKKAEKEGYEVRILTADRDLYQLVSDRVAVLHPEGHLIT
PEWLWEKYGLRPEQWVDFRALVGDPSDNLPGVKGIGEKTALKLLKEWGSLENLLKNLDRVKPENVREKIKAHLEDLRLSLE
LSRVRTDLPLEVDLAQGREPDREGLRAFLERLEFGSLLHEFGLLESPKALEEAPWPPPEGAFVGFVLSRKEPMWADLLALAAA
RGGRVHRAPEPYKALRDLKEARGLLAKDLSVLALREGLGLPPGDDPMLLAYLLDPSNTTPEGVARRYGGEWTEEAGERAAL
SERLFANLWGRLEGEERLLWLYREVDRPLSAVLAHMEATGVRLDVAYLRALSLEVAEEIARLEAEVFRLAGHPFNLNSRDQL
ERVLFDELGLPAIGKTERTGKRSTSAAVLEALREAHPIVEKILQYRELTKLKSTYIDPLPDLIHPRTGRLHTRFNQTATATGRLSS
SDPNLQNIPVRTPLGQRIRRAFIAEEGWLLVALDYSQIELRVAHLSGDENLIRVFQEGRDIHTETASWMFGVPPEAVDPLMRR
AAKTVNFGVLYGMSAHRLSQELSIPYEEAVAFIERYFQSFPKVRAWIEKTLEEGRKRGYVETLFGRRRYVPDLNARVKSVREA
AERMAFNMPVQGTAADLMKLAMVKLFPRLREMGARMLLQVHDELLLEAPQARAEEVAALAKEAMEKAYPLAVPLEVEVG
IGEDWLSAKE*

2H2:

(SEQ ID NO: 79)
```
ATGGCGATGCTTCCCCTCTTTGAGCCCAAGGGCCGCGTCCTCCTGGTGGACGGCCACCACCTGGCCTACCGCACCTTCTT
CGCCCTGAAGGGCCCCACCACGAGCCGGGGCGAACCGGTGCAGGTGGTCTACGGCTTCGCCAAGAGCCTCCTCAAGGCC
CTGAAGGAGGACGGGTACAAGGCCGTCTTCGTGGTCTTTGACGCCAAGGCCCCCTCATTCCGCCACAAGGCCTACGAGG
CCTACAGGGCGGGGAGGGCCCCGACCCCCGAGGACTTCCCCCGGCAGCTCGCCCTCATCAAGGAGCTGGTGGACCTCCT
GGGGTTTACCCGCCTCGAGGTCCCCGGCTACGAGGCGGACGACGTTCTCGCCACCCTGGCCAAGAAGGCGGAAAAGGA
GGGGTACGAGGTGCGCATCCTCACCGCCGACCGCGGCCTCTACCAACTCGTCTCTGACCGCGTCGCCGTCCTCCACCCCG
AGGGCCACCTCATCACCCCGGAGTGGCTTTGGGAGAAGTACGGCCTCAGGCCGGAGCAGTGGGTGGACTTCCGCGCCCT
```

```
CGTGGGGGACCCCTCCGACAACCTCCCCGGGGTCAAGGGCATCGGGGAGAAGACCGCCCTCAAGCTCCTCAAGGAGTG

GGGAAGCCTGGAAAACCTCCTCAAGAACCTGGACCGGGTAAAGCCAGAAAACGTCCGGGAGAAGATCAAGGCCCACCT

GGAAGACCTCAGGCTCTCCTTGGAGCTCTCCCGGGTGCGCACCGACCTCCCCCTGGAGGTGGACCTCGCCCAGGGGCGG

GAGCCCGACCGGGAGAGGCTTAGGGCCTTTCTGGAGAGGCTTGAGTTTGGCGGCCTCCTCCACGAGTTCGGCCTTCTGG

AAAGCCCCAAGGCCCTGGAGGAGGCCCCCTGGCCCCGCCGGAAGGGGCCTTCGTGGGCTTTGTGCTTTCCCGCAAGGA

GCCCATGTGGGCCGATCTTCTGGCCCTGGCCGCCGCCAGGGGTGGTCGGGTCCACCGGGCCCCGAGCCTTATAAAGCC

CTCAGGGACTTGAAGGAGGCGCGGGGCTTCTCGCCAAAGACCTGAGCGTTCTGGCCCTGAGGGAAGGCCTTGGCCTCC

CGCCCGGCGACGACCCCATGCTCCTCGCCTACCTCCTGGACCCTTCCAACACCACCCCCGAGGGGGTGGCCCGGCGCTA

CGGCGGGGAGTGGACGGAGGAGGCGGGGGAGCGGGCCGCCCTTTCCGAGAGGCTCTTCGCCAACCTGTGGGGAGGCT

TGAGGGGGAGGAGAGGCTCCTTTGGCTTTACCGGGAGGTGGAGAGGCCCCTTTCCGTTGTCCTGGCCCACATGGAGGCC

ACAGGGGTGCGCCTGGACGTGGCCTATCTCAGGGCCTTGTCCCTGGAGGTGGCCGAGGAGATCGCCCGCCTCGAGGCCG

AGGTCTTCCGCCTGGCCGGCCACCCCTTCAACCTCAACTCCCGGGACCAGCTGGAAAGGGTCCTCTTTGACGAGCTAGG

GCTTCCCGCCATCGGCAAGACGGAGAAGACCGGCAAGCGCTCCACCGGCGCCGCCGTCCTGGAGGCCCTCCGCGAGGC

CCACCCCACCGTGGAGAAGATCCTGCAGTACCGGGAGCTCACCAAGCTGAAGAGCACCTACATTGACCCCTTGCCGGAC

CTCATCCACCCCAGGACGGGCCGCCTCCACACCCGCTTCAACCAGACGGCCACGGCCACGGGCAGGCTAAGTAGCTCCG

ACCCCAACCTCCAGAACATCCCCGTCCGCACCCCGCTCGGGCAGAGGATCCGCCGGGCCTTCATCGCCGAGGAGGGGTG

GCTATTGGTGGTCCTGGACTATAGCCAGATAGAGCTCAGGGTGCTGGCCCACCTCTCCGGCGACGAGAACCTGATCCGG

GTCTTCCAGGAGGGGCGGGACATCCACACGGAAACCGCCAGCTGGATGTTCGGCGTCCCCGGGAGGCCGTGGACCCCC

TAATGCGCCGGGCGGCCAAGACCATCAACTTCGGGGTTCTCTACGGCATGTCGGCCCACCGCCTCTCCCAGGAGCTAGC

CATCCCTTACGAGGAGGCCCAGGCCTTCATTGAGCGCTACATTCAGAGCTTCCCCAAGGTGCGGGCCTGGATTGAGAAG

ACCCTGGAGGAGGGCAGGAGGCGGGGGTACGTGGAGACCCTCTTCGGCCGCCGTCGCTACGTGCCAGACCTAGAGGCC

CGGGTGAAGAGCGTGCGGGAGGCGGCCGAGCGCATGGCCTTCAACATGCCCGTCCAGGGCACCGCCGCCGACCTCATG

AAGCTGGCTATGGTGAAGCTCTTCCCCAGGCTGGAAGAAACGGGGGCCAGGATGCTCCTTCAGGTCCACGACGAGCTGG

TCCTCGAGGCCCCAAAAGAGAGGGCGGAGGCCGTGGCCCGGCTGGCCAAGGAGGCCATGGAGGGGGTGTATCCCCTGG

CCGTGCCCCTGGAGGTGGAGGTGGGGATAGGGGAGGACTGGCTCTCCGCCAAGGAGTGA
```

(SEQ ID NO: 80)
MAMLPLFEPKGRVLLVDGHHLAYRTFFALKGPTTSRGEPVQVVYGFAKSLLKALKEDGYKAVFVVFDAKAPSFRHKAYEAY

RAGRAPTPEDFPRQLALIKELVDLLGFTRLEVPGYEADDVLATLAKKAEKEGYEVRILTADRGLYQLVSDRVAVLHPEGHLIT

PEWLWEKYGLRPEQWVDFRALVGDPSDNLPGVKGIGEKTALKLLKEWGSLENLLKNLDRVKPENVREKIKAHLEDLRLSLE

LSRVRTDLPLEVDLAQGREPDRERLRAFLERLEFGGLLHEFGLLESPKALEEAPWPPPEGAFVGFVLSRKEPMWADLLALAAA

RGGRVHRAPEPYKALRDLKEARGLLAKDLSVLALREGLGLPPGDDPMLLAYLLDPSNTTPEGVARRYGGEWTEEAGERAAL

SERLFANLWGRLEGEERLLWLYREVDRPLSVVLAHMEATGVRLDVAYLRALSLEVAEEIARLEAEVFRLAGHPFNLNSRDQL

ERVLFDELGLPAIGKTEKTGKRSTGAAVLEALREAHPTVEKILQYRELTKLKSTYIDPLPDLIHPRTGRLHTRFNQTATATGRLS

SSDPNLQNIPVRTPLGQRIRRAFIAEEGWLLVVLDYSQIELRVLAHLSGDENLIRVFQEGRDIHTETASWMFGVPREAVDPLMR

RAAKTINFGVLYGMSAHRLSQELAIPYEEAQAFIERYIQSFPKVRAWIEKTLEEGRRRGYVETLFGRRRYVPDLEARVKSVRE

AAERMAFNMPVQGTAADLMKLAMVKLFPRLEETGARMLLQVHDELVLEAPKERAEAVARLAKEAMEGVYPLAVPLEVEV

GIGEDWLSAKE*

1C8:

(SEQ ID NO: 81)
ATGCGTGGTATGCTTCCTCTTTTTGAGCCCAAGGGCCGCGTCCTCCTGGTGGACGGCCACCACCTGGCCTACCGCACCTT

CTTCGCCCTGAAGGGCCCCACCACGAGCCGGGGCGAACCGGTGCAGGCGGTCTACGGCTTCGCCAAGAGCCTCCTCAAG

GCCCTGAAGGAGGACGGGTACAAGGCCGCCTTCGTGGTCTTTGACGCCAAGGCCCCCTCCTTCCGCCACGAGGCCTACG

-continued

```
AGGCCTACAAGGCGGGGAGGGCCCCGACCCCCGAGGACTTCCCCCGGCAGCTCGCCCTCATCAAGGAGCTGGTGGACCT
CCTGGGGTTTACCCGCCTCGAGGTCCCTGGCTACGAGGCGGACGACGTCCTCGCCACCCTGGCCAAGAAGGCGGAAAAG
GAGGGGTACGAGGTGCGCATCCTCACCGCCGACCGCGACCTCTACCAACTCGTCTCCGACCGCGTCGCCGTCCTCCACC
CCGAGGGCCACCTCATCACCCCGGAGTGGCTTTGGGAGAAGTACGGCCTCAGGCCGGAGCAGTGGGTGGACTTCCGCGC
CCTCGTGGGGACCCCTCCGACAACCTCCCCGGGGTCAAGGGCATCGGGGAGAAGACCGCCCTCAAGCTCCTCAAGGAG
TGGGGAAGCCTGGAAAACCTCCTCAAGAACCTGGACCGGGTAAAGCCAGAAAACGTCCGGGAGAAGATCAAGGCCCAC
CTGGAAGACCTCAGGCTCTCCTTGGAGCTCTCCCGGGTGCGCACCGACCTCCCCCTGGAGGTGGACCTCGCCCAGGGGC
GGGAGCCCGACCGGGAGAGGCTTAGGGCCTTTCTGGAGAGGCTTGAGTTTGGCGGCCTCCTCCACGAGTTCGGCCTTCT
GGAAAGCCCCAAGGCCCTGGAGGAGGCCCCCTGGCCCCCGCCGGAAGGGGCCTTCGTGGGCTTTGTGCTTTCCCGCAAG
GAGCCCATGTGGGCCGATCTTCTGGCCCTGGCCGCCGCCAGGGGTGGTCGGGTCCACCGGGCCCCCGAGCCTTATAAAG
CCCTCAGGGACTTGAAGGAGGCGCGGGGGCTTCTCGCCAAAGACCTGAGCGTTCTGGCCCTAAGGGAAGGCCTTGGCCT
CCCGCCCGGCGACGACCCCATGCTCCTCGCCTACCTCCTGGACCCTTCCAACACCACCCCCGAGGGGGTGGCCCGGCGC
TACGGCGGGGAGTGGACGGAGGAGGCGGGGAGCGGGCCGCCCTTTCCGAGAGGCTCTTCGCCAACCTGTGGGGGAGG
CTTGAGGGGGAGGAGAGGCTCCTTTGGCTTTACCGGGAGGTGGATAGGCCCCTTCCCGCTGTCCTGGCCCACATGGAGG
CCACAGGGGTACGGCTGGACGTGGCCTGCCTGCAGGCCCTTTCCCTGGAGCTTGCGGAGGAGATCCGCCGCCTCGAGGA
GGAGGTCTTCCGCTTGGCGGGCCACCCCTTCAACCTCAACTCCCGGGACCAGCTGGAAAGGGTCCTCTTTGACGAGCTA
GGGCTTCCCGCCATCGGCAAGACGGAGAAGACCGGCAAGCGCTCCACCAGCGCCGCCATCCTGGAGGCCCTCCGCGAG
GCCCACCCCATCGTGGAGAAGATCCTGCAGTACCGGGAGCTCACCAAGCTGAAGAGCACCTACATTGACCCCTTGCCGG
ACCTCATCCACCCCAGGACGGGCCGCCTCCACACCCGCTTCAACCAGACGGCCACGGCCACGGGCAGGCTAAGTAGCTC
CGATCCCAACCTCCAGAACATCCCCGTCCGCACCCCGCTCGGGCAGAGGATCCGCCGGGCCTTCATCGCCGAGGAGGGG
TGGCTATTGGTGGTCCTGGACTATAGCCAGATAGAGCTCAGGGTGCTGGCCCACCTCTCCGGCGACGAGAACCTGACCC
GGGTCTTCCAGGAGGGGCGGGACATCCACACGGAAACCGCCAGCTGGATGTTCGGCGTCCCCGGGAGGCCGTGGACC
CCCTGATGCGCCGGGCGGCCAAGACCATCAACTTCGGGGTTCTCTACGGCATGTCGGCCCACCGCCTCTCCCAGGAGCT
GGCCATCCCTTACGAGGAGGCCCAGGCCTTCATAGAGCGCTACTTCCAAAGCTTCCCCAAGGTGCGGGCCTGGATAGAA
AAGACCCTGGAGGAGGGGAGGAAGCGGGGCTACGTGGAAACCCTCTTCGGAAGAAGGCGCTACGTGCCCGACCTCAAC
GCCCGGGTGAAGAGTGTCAGGGAGGCCGCGGAGCGCATGGCCTTCAACATGCCCGTCCAGGGCACCGCCGCCGACCTTA
TGAAGCTCGCCATGGTGAAGCTCTTCCCCCGCCTCCGGGAGATGGGGGCCCGCATGCTCCTCCAGGTCCACGACGAGCT
CCTCCTGGAGGCCCCCAAGCGCGGGCCGAGGAGGTGGCGGCTTTGGCCAAGGAGGCCATGGAGAAGGCCTATCCCCTC
GCCGTACCCCTGGAGGTGAAGGTGGGGATCGGGGAGGACTGGCTCTCCGCCAAGGAGTGA
```

(SEQ ID NO: 82)
MRGMLPLFEPKGRVLLVDGHHLAYRTFFALKGPTTSRGEPVQAVYGFAKSLLKALKEDGYKAAFVVFDAKAPSFRHEAYEA
YKAGRAPTPEDFPRQLALIKELVDLLGFTRLEVPGYEADDVLATLAKKAEKEGYEVRILTADRDLYQLVSDRVAVLHPEGHLI
TPEWLWEKYGLRPEQWVDFRALVGDPSDNLPGVKGIGEKTALKLLKEWGSLENLLKNLDRVKPENVREKIKAHLEDLRLSL
ELSRVRTDLPLEVDLAQGREPDRERLRAFLERLEFGGLLHEFGLLESPKALEEAPWPPPEGAFVGFVLSRKEPMWADLLALAA
ARGGRVHRAPEPYKALRDLKEARGLLAKDLSVLAREGLGLPPGDDPMLLAYLLDPSNTTPEGVARRYGGEWTEEAGERAA
LSERLFANLWGRLEGEERLLWLYREVDRPLSAVLAHMEATGVRLDVACLQALSLELAEEIRRLEEEVFRLAGHPFNLNSRDQ
LERVLFDELGLPAIGKTEKTGKRSTSAAILEALREAHPIVEKILQYRELTKLKSTYIDPLPDLIHPRTGRLHTRFNQTATATGRLS
SSDPNLQNIPVRTPLGQRIRRAFIAEEGWLLVVLDYSQIELRVLAHLSGDENLTRVFQEGRDIHTETASWMFGVPREAVDPLM
RRAAKTINFGVLYGMSAHRLSQELAIPYEEAQAFIERYFQSFPKVRAWIEKTLEEGRKRGYVETLFGRRRYVPDLNARVKSVR
EAAERMAFNMPVQGTAADLMKLAMVKLFPRLREMGARMLLQVHDELLLEAPQARAEEVAALAKEAMEKAYPLAVPLEVK
VGIGEDWLSAKE*

2H10X:

(SEQ ID NO: 83)

ATGGCGATGCTTCCCCTCTTTGAGCCCAAGGGCCGTGTCCTCCTGGTGGACGGCCACCACCTGGCCTACCGCACCTTCTT

CGCCCTGAAGGGCCCCACCACGAGCCGGGGCGAACCGGTGCAGGTGGTCTACGGCTTCGCCAAGAGCCTCCTCAAGGCC

CTGAAGGAGGACGGGTACAAGGCCGTCTTCGTGGTCTTTGACGCCAAGGCCCCCCCATTCCGCCACAAGGCCTACGAGG

CCTACAGGGCGGGGAGGGCCCCGACCCCCGAGGACTTCCCCCGGCAGCTCGCCCTCATCAAGGAGCTGGTGGACCTCCT

GGGGTTTACCCGCCTCGAGGTCCCCGGCTACGAGGCGGACGACGTTCTCGCCACCCTGGCCAAGAAGGCGGAAAAGGA

GGGGTACGAGGTGCGCATCCTCACCGCCGACCGCGGCCTCTACCAACTCGTCTCTGACCGCGTCGCCGTCCTCCACCCCG

AGGGCCACCTCATCACCCCGGAGTGGCTTTGGGAGAAGTACGGCCTCAGGCCGGAGCAGTGGGTGGACTTCCGCGCCCT

CGTGGGGGACCCCTCCGACAACCTCCCCGGGGTCAAGGGCATCGGGGAGAAGACCGCCCTCAAGCTCCTCAAGGAGTG

GGGAAGCCTGGAAAACCTCCTCAAGAACCTGGACCGGGTAAAGCCAGAAAACGTCCGGGAGAAGATCAAGGCCCACCT

GGAAGATCTCAGGCTCTCCTTGGAGCTCTCCCGGGTGCGCACCGACCTCCCCCTGGAGGTGGACCTCGCCCAGGGGCGG

GAGCCCGACCGGGAGGGGCTTAGGGCCTTTCTGGAGAGGCTTGAGTTTGGCAGCCTCCTCCACGAGTTCGGCCTTCTGG

AAAGCCCCAAGGCCCTGGAGGAGGCCCCCTGGCCCCGCCGGAAGGGGCCTTCGTGGGCTTTGTGCTTTCCCGCAAGGA

GCCCATGTGGGCCGATCTTCTGGCCCTGGCCGCCGCCAGGGGTGGTCGAGTCCACCGGGCCCCCGAGCCTTATAAAGCC

CTCAGGGACCTGAAGGAGGCGCGGGGGCTTCTCGCCAAAGACCTGAGCGTTCTGGCCCTAAGGGAAGGCCTTGGCCTCC

CGCCCGGCGACGACCCCATGCTCCTCGCCTACCTCCTGGACCCTTCCAACACCACCCCCGAGGGGGTGGCCCGGCGCTA

CGGCGGGGAGTGGACGGAGGAGGCGGGGGAGCGGGCCGCCCTTTCCGAGAGGCTCTTCGCCAACCTGTGGGGGAGGCT

TGAGGGGGAGGAGAGGCTCCTTTGGCTTTACCGGGAGGTGGAGAGGCCCCTTTCCGCTGTCCTGGCCCACATGGAGGCC

ACGGGGGTGCGCCTGGACGTGGCCTATCTCAGGGCCTTGTCCCTGGAGGTGGCCGAGGAGATCGCCCGCCTCGAGGCCG

AGGTCTTCCGCCTGGCCGGCCACCCCTTCAACCTCAACTCCCGGGACCAGCTGGAAATGGTGCTCTTTGACGAGCTTAGG

CTTCCCGCCTTGGGGAAGACGCAAAAGACGGGCAAGCGCTCCACCAGCGCCGCCGTCCTGGAGGCCCTCCGCGAGGCCC

ACCCCATCGTGGAGAAGATCCTGCAGTACCGGGAGCTCACCAAGCTGAAGAGCACCTACATTGACCCCTTGTCGGACCT

CATCCACCCCAGGACGGGCCGCCTCCACACCCGCTTCAACCAGACGGCCACGGCCACGGGCAGGCTAAGTAGCTCCGAT

CCCAACCTCCAGAACATCCCCGTCCGCACCCCGCTTGGGCAGAGGATCCGCCGGGCCTTCATCGCCGAGGAGGGGTGGC

TACTGGTGGTCCTGGACTATAGCCAGATAGAGCTCAGGGTGCTGGCCCACCTCTCCGGCGACGAAAACCTGATCAGGGT

CTTCCAGGAGGGGCGGGACATCCACACGGAGACCGCCAGCTGGATGTTCGGCGTCCCCCGGGAGGCCGTGGACCCCCTG

ATGCGCCGGGCGGCCAAGACCATCAACTTCGGGGTCCTCTACGGCATGTCGGCCCACCGCCTCTCCCAGGAGCTAGCCA

TCCCTTACGAGGAGGCCCAGGCCTTCATTGAGCGCTACTTTCAGAGCTTCCCCAAGGTGCGGGCCTGGATTGAGAAGAC

CCTGGAGGAGGGCAGGAGGCGGGGGTACGTGGAGACCCTCTTCGGCCGCCGCCGCTACGTGCCAGACCTAGAGGCCCG

GGTGAAGAGCGTGCGGGAGGCGGCCGAGCGCATGGCCTTCAACATGCCCGTCCAGGGCACCGCCGCCGACCTCATGAA

GCTGGCTATGGTGAAGCTCTTCCCCAGGCTGGAGGAAATGGGGGCCAGGATGCTCCTTCAGGTCCACGACGAGCTGGTC

CTCGAGGCCCCAAAAGAGAGGGCGGAGGCCGTGGCCCGGCTGGCCAAGGAGGTCATGGAGGGGGTGTATCCCCTGGCC

GTGCCCCTGGAGGTGGAGGTGGGGATAGGGGAGGACTGGCTCTCCGCCAAGGAGTGA (SEQ ID NO: 84)

MAMLPLFEPKGRVLLVDGHHLAYRTFFALKGPTTSRGEPVQVVYGFAKSLLKALKEDGYKAVFVVFDAKAPPFRHKAYEAY

RAGRAPTPEDEPRQLALIKELVDLLGETRLEVPGYEADDVLATLAKKAEKEGYEVRILTADRGLYQLVSDRVAVLHPEGHLIT

PEWLWEKYGLRPEQWVDFRALVGDPSDNLPGVKGIGEKTALKLLKEWGSLENLLKNLDRVKPENVREKIKAHLEDLRLSLE

LSRVRTDLPLEVDLAQGREPDREGLRAFLERLEFGSLLHEFGLLESPKALEEAPWPPPEGAFVGFVLSRKEPMWADLLALAAA

RGGRVHRAPEPYKALRDLKEARGLLAKDLSVLALREGLGLPPGDDPMLLAYLLDPSNTTPEGVARRYGGEWTEEAGERAAL

SERLFANLWGRLEGEERLLWLYREVERPLSAVLAHMEATGVRLDVAYLRALSLEVAEEIARLEAEVFRLAGHPFNLNSRDQL

EMVLFDELRLPALGKTQKTGKRSTSAAVLEALREAHPIVEKILQYRELTKLKSTYIDPLSDLIHPRTGRLHTRFNQTATATGRL

SSSDPNLQNIPVRTPLGQRIRRAFIAEEGWLLVVLDYSQIELRVLAHLSGDENLIRVFQEGRDIHTETASWMFGVPREAVDPLM

RRAAKTINFGVLYGMSAHRLSQELAIPYEEAQAFIERYFQSFPKVRAWIEKTLEEGRRRGYVETLFGRRRYVPDLEARVKSVR

EAAERMAFNMPVQGTAADLMKLAMVKLFPRLEEMGARMLLQVHDELVLEAPKERAEAVARLAKEVMEGVYPLAVPLEVE

VGIGEDWLSAKE*

3A10

(SEQ ID NO: 85)

ATGGCGATGCTTCCCCTCTTTGAGCCCAAAGGCCGGGTCCTCCTGGTGGACGGCCACCACCTGGCCTACCGCACCTTCTT

CGCCCTGAAGGGCCTCACCACGAGCCGGGGCGAACCGGTGCAGGTGGTCTACGGCTTCGCCAAGAGCCTCCTCAAGGCC

CTGAAGGAGGACGGGTACAAGGCCGTCTTCGTGGTCTTTGACGCCAAGGCCCCCTCATTCCGCCACAAGGCCTACGAGG

CCTACAGGGCGGGGAGGGCCCCGACCCCCCAGGACTTCCCCCGGCAGCTCGCCCTCATCAAGGAGCTGGTGGACCTCCT

GGGGTTTACCCGCCTCGAGGTCCCCGGCTACGAGGCGGACGACGTTCTCGCCACCCTGGCCAAGAAGGCGGAAAAGGA

GGGGTACGAGGTGCGCATCCTCACCGCCGACCGCGGCCTCTACCAACTCGTCTCCGACCGCGTCGCCGTCCTCCACCCCG

AGGGCCACCTCATCACCCCGGAGTGGCTTTGGGAGAAGTACGGCCTCAGGCCGGAGCAGTGGGTGGACTTCCGCGCCCT

CGTGGGGGACCCCTCCGACAACCTCCCCGGGGTCAAGGGCATCGGGGAGAAGACCGCCCTCAAGCTCCTCAAGGAGTG

GGGAAGCCTGGAAAACCTCCTCAAGAACCTGGACCGGGTAAAGCCAGAAAACGTCCGGGAGAAGATCAAGGCCCACCT

GGAAGACCTCAGGCTCTCCTTGGAGCTCTCCCGGGTGCGCACCGACCTCCCCCTGGAGGTGGACCTCGCCCAGGGGCGG

GAGCCCGACCGGGAGGGGCTTAGGGCCTTTCTGGAGAGGCTTGAGTTTGGCAGCCTCCTCCACGAGTTCGGCCTTCTGG

AAAGCCCCAAGGCCCTGGAGGAGGCCCCCTGGCCCCGCCGGAAGGGGCCTTCGTGGGCTTTGTGCTTTCCCGCAAGGA

GCCCATGTGGGCCGATCTTCTGGCCCTGGCCGCCGCCAGGGGTGGTCGAGTCCACCAGGCCCCCGAGCCTTATAAAGCC

CTCAGGGACCTGAAGGAGGCGCGGGGGCTTCTCGCCAAAGACCTGAGCGTTCTGGCCCTAAGGGAAGGCCTTGGCCTCC

CGCCCGGCGACGACCCCATGCTCCTCGCCTACCTCCTGGACCCTTCCAACACCACCCCCGAGGGGGTGGCCCGGCGCTA

CGGCGGGGAGTGGACGAGGAGGCGGGGGAGCGGGCCGCCCTTTCCGAGAGGCTCTTCGCCAACCTGTGGGGAGGCT

TGAGGGGGAGGAGAGGCTCCTTTGGCTTTACCGGGAGGTGGAGAGGCCCCTTTCCGCTGTCCTGGCCCACATGGAGACC

ACGGGGGTGCGCCTGGACGTGGCCTATCTCAGGGCCTTGTCCCTGGAGGTGGCCGAGGAGATCGCCCGCCTCGAGGCCG

AGGTCTTCCGCCTGGCCGGCCGCCCCCTTCAACCTCAACTCCCGAGACCAGCTGGAAAGGGTCCTCTTTGACGAGCTAGG

GCTTCCCGCCATCGGCAAGACGGAGAAGACCGGCAAGCGCTCCACCAGCGCCGCCGTCCTGGAGGCCCTCCGCGAGGC

CCACCCCATCGTGGAGAAGATCCTGCAGTACCGGGAGCTCACCAAGCTGAAGAGCACCTACATTGACCCCTTGCCGGAC

CTCATCCACCCCAGGACGGGCCGCCTCCACACCCGCTTCAACCAGACGGCCACGGCCACGGGCAGGCTAAGTAGCTCCG

ATCCCAACCTCCAGAACATCCCCGTCCGCACCCCGCTTGGGCAGAGGATCCGCCGGGCCTTCATCGCCGAGGAGGGGTG

GCTATTGGTGGTCCTGGACTATAGCCAGATGGAGCTCAGGGTGCTGGCCCACCTCTCCGGCGACGAGAACCTGATCAGG

GTCTTCCAGGAGGGGAAGGACATCCACACCCAGACCGCAAGCTGGATGTTCGGTGTCCCCCCGGAGGCCGTGGACCCCC

TGATGCGCCGGGCGGCCAAGACGGTGAACTTCGGCGTCCTCTACGGCATGTCCGCCCATAGGCTCTCCCAGGAGCTTTCC

ATCCCCTACGAGGAGGCGGTGGCCTTCATAGAGCGCTACTTCCAAAGCTTCCCCAAGGTGCGGGCCTGGATTGAGAAGA

CCCTGGAGGAGGGCAGGAGGCGGGGGTACGTGGAGACCCTCTTCGGCCGCCGCCGCTACGTGCCCGACCTCAACGCCCG

GATGAAGAGCGTCAGGGGGGCCGCGGAGCGCATGGCCTTCAACATGCCCGTCCAGGGCACCGCCGCCGACCTCATGAA

GCTCGCCATGGTGAAGCTCTTCCCCCGCCTCCGGGAGATGGGGGCCCGCATGCTCCTCCAGGTCCACGACGAGCTCCTCC

TGGAGGCCCCCAAGCGCGGGCCGAGGAGGTGGCGGCTTTGGCCAAGGAGGCCATGGAGAAGGCCTATCCCCTCGCCG

TACCCCTGGAGGTGGAGGTGGGGATCGGGGAGGACTGGCTCTCCGCCAAGGAGTGA (SEQ ID NO: 86)

MAMLPLFEPKGRVLLVDGHHLAYRTFFALKGLTTSRGEPVQVVYGFAKSLLKALKEDGYKAVFVVFDAKAPSFRHKAYEAY

RAGRAPTPQDFPRQLALIKELVDLLGFTRLEVPGYEADDVLATLAKKAEKEGYEVRILTADRGLYQLVSDRVAVLHPEGHLIT

PEWLWEKYGLRPEQWVDFRALVGDPSDNLPGVKGIGEKTALKLLKEWGSLENLLKNLDRVKPENVREKIKAHLEDLRLSLE

LSRVRTDLPLEVDLAQGREPDREGLRAFLERLEFGSLLHEFGLLESPKALEEEAPWPPPEGAFVGFVLSRKEPMWADLLALAAA
RGGRVHQAPEPYKALRDLKEARGLLAKDLSVLALREGLGLPPGDDPMLLAYLLDPSNTTPEGVARRYGGEWTEEAGERAAL
SERLFANLWGRLEGEERLLWLYREVERPLSAVLAHMETTGVRLDVAYLRALSLEVAEEIARLEAEVFRLAGRPFNLNSRDQL
ERVLFDELGLPAIGKTEKTGKRSTSAAVLEALREAHPIVEKILQYRELTKLKSTYIDPLPDLIHPRTGRLHTRFNQTATATGRLS
SSDPNLQNIPVRTPLGQRIRRAFIAEEGWLLVVLDYSQMELRVLAHLSGDENLIRVFQEGKDIHTQTASWMFGVPPEAVDPLM
RRAAKTVNFGVLYGMSAHRLSQELSIPYEEAVAFIERYFQSFPKVRAWIEKTLEEGRRRGYVETLFGRRRYVPDLNARMKSV
RGAAERMAFNMPVQGTAADLMKLAMVKLFPRLREMGARMLLQVHDELLLEAPQARAEEVAALAKEAMEKAYPLAVPLEV
EVGIGEDWLSAKE*

3B5
(SEQ ID NO: 87)
ATGGCGATGCTTCCCCTCTTTGAGCCCAAGGGCCGTGTCCTCCTGGTGGACGGCCACCACCTGGCCTACCGCACCTCCTTCG
CCCTGAAGGGCCCCACCACGAGCCGGGGCGAACCGGTGCAGGTGGTCTACGGCTTCGCCAAGAGCCTCCTCAAGGCCCTGA
AGGAGGACGGGTACAAGGCCGTCTTCGTGGTCTTTGACGCCAAGGCCCCCCCATTCCGCCACAAGGCCTACGAGGCCTACA
GGGCGGGGAGGGCCCCGACCCCCGAGGACTTCCCCCGGCAGCTCGCCCTCGTCAAGGAGCTGGTGGACCTCCTGGGGTTTA
CCCGCCTCGAGGTCCCCGGCTACGAGGCGGACGACGTTCTCGCCACCCTGGCCAAGAAGGCGGAAAAGGAGGGGTACGAG
GTGCGCATCCTCACCGCCGACCGCGGCCTCTACCAACTCGTCTCTGACCGCGTCGCCGTCCTCCACCCCGAGGGCCACCTCA
TCACCCCGGAGTGGCTTTGGGAGAAGTACGGCCTCAGGCCGGAGCAGTGGGTGGACTTCCGCGCCCTCGTGGGGGACCCCT
CCGACAACCTCCCCGGGGTCAAGGGCATCGGGGAGAAGACCGCCCTCAAGCTCCTCAAGGAGTGGGGAAGCCTGGAAAAC
CTCCTCAAGAACCTGGACCGGGTAAAGCCAGAAAACGTCCGGGAGAAGATCAAGGCCCACCTGGAAGACCTCAGGCTCTCC
TTGGAGCTCTCCCGGGTGCGCACCGACCTCCCCCTGGAGGTGGACCTCGCCCAGGGGCGGGAGCCCGACCGGGAAAGGCTT
AGGGCCTTTCTGGAGAGGCTTGAGTTTGGCAGCCTCCTCCATGAGTTCGGCCTTCTGGAAAGCCCCAAGGCCCTGGAGGAGG
CCCCCTGGCCCCCGCCGGAAGGGGCCTTCGTGGGCTTTGTGCTTTCCCGCAAGGCGCCCATGTGGGCCGATCTTCTGGCCCT
GGCCGCCGCCAGGGGTGGTCGGGTCTACCGGGCCCCCGAGCCTTATAAAGCCCTCAGGGACTTGAAGGAGGCGCGGGGCT
TCTCGCCAAAGACCTGAGCGTTCTGGCCCTAAGGGAAGGCCTTGGCCTCCCGCCCGGCGACGACCCCATGCTCCTCGCCTAC
CTCCTGGACCCTTCCAACACCACCCCCGAGGGGGTGGCCCGGCGCTACGGCGGGGAGTGGACGGAGGAGGCGGGGGAGCG
GGCCGCCCTTTCCGAGAGGCTCTTCGCCAACCTGTGGGGGAGGCTTGAGGGGAGGAGAGGCTCCTTTGGCTTTACCGGGA
GGTGGATAGGCCCCTTTCCGCTGTCCTGGCCCACATGGAGGCCACAGGGGTACGGCTGGACGTGGCCTGCCTGCAGGCCCTT
TCCCTGGAGCTTGCGGAGGAGATCCGCCGCCTCGAGGAGGAGGTCTTCCGCTTGGCGGGCCACACCTTCAACCTCAACTCCC
GGGACCAGCTGGAAAGGGTCCTCTTTGACGAGCTAGGGCTTCCCGCCATCGGCAAGACGGAGAAGACCGGCAAGCGCTCCA
CCAGCGCCGCCATCCTGGAGGCCCTCCGCGAGGCCCACCCCATCGTGGAGAAGATCCTGCAGTACCGGGAGCTCACCAAGC
TGAAGAGCACCTACATTGACCCCTTGCCGGACCTCATCCACCCCAGGACGGGCCGCCTCCACACCCGCTTCAACCAGACGGC
CACGGCCACGGGCAGGCTAAGTAGCTCCGATCCCAACCTCCAGAACATCCCCGTCCGCACCCCGCTTGGGCAGAGGATCCG
CCGGGCCTTCATCGCCGAGGAGGGTGGCTACTGGTGGTCCTGGACTATAGCCAGATAGAGCTCAGGGTGCTGGCTCACCT
CTCCGGCGACGAAAACCTGATCAGGGTCTTCCAGGAGGGGCGGGACATCCACACGGAGACCGCCAGCTGGATGTTCGGCGT
CCCCCGGGAGGCCGTGGACCCCCTGATGCGCCGGGCGGCCAAGACCATCAACTTCGGGGTCCTCTACGGCATGTCGGCCCA
CCGCCTCTCCCAGGAGCTAGCCATCCCTTACGAGGAGGCCCAGGCCTTCATTGAGCGCTACTTTCAGAGCTTCCCCAAGGTG
CGGGCCTGGATTGAGAAGGCCCTGGAGGAGGGCAGGAGGCGGGGTACGTGGAGACCCTCTTCGGAAGAAGGCGCTACGT
GCCCGACCTCAACGCCCGGGTGAAGAGTGTCAGGGAGGCCGCGGAGCGCATGGCCTTCAACATGCCCGTCCAGGGCACCGC
CGCCGACCTTATGAAGCTCGCCATGGTGAAGCTCTTCCCCCGCCTCCGGGAGATGGGGGCCCGCATGCTCCTCCAGGTCCAC
GACGAGCTCCTCCTGGAGGCCCCCCAAGCGCGGGCCGAGGAGGTGGCGGCTTTGGCCAAGGAGGCCATGGAGAAGGCCTA
TCCCCTCGCCGTACCCCTGGAGGTGAAGGTGGGGATCGGGGAGGACTGGCTCTCCGCCAAGGAGTGA

-continued (SEQ ID NO: 88)
MAMLPLFEPKGRVLLVDGHHLAYRTSFALKGPTTSRGEPVQVVYGFAKSLLKALKEDGYKAVFVVFDAKAPPFRHKAYEAYRA
GRAPTPEDFPRQLALVKELVDLLGFTRLEVPGYEADDVLATLAKKAEKEGYEVRILTADRGLYQLVSDRVAVLHPEGHLITPEWL
WEKYGLRPEQWVDFRALVGDPSDNLPGVKGIGEKTALKLLKEWGSLENLLKNLDRVKPENVREKIKAHLEDLRLSLELSRVRTD
LPLEVDLAQGREPDRERLRAFLERLEFGSLLHEFGLLESPKALEEAPWPPPEGAFVGFVLSRKAPMWADLLALAAARGGRVYRAP
EPYKALRDLKEARGLLAKDLSVLALREGLGLPPGDDPMLLAYLLDPSNTTPEGVARRYGGEWTEEAGERAALSERLFANLWGRL
EGEERLLWLYREVDRPLSAVLAHMEATGVRLDVACLQALSLELAEEIRRLEEEVFRLAGHTFNLNSRDQLERVLFDELGLPAIGK
TEKTGKRSTSAAILEALREAHPIVEKILQYRELTKLKSTYIDPLPDLIHPRTGRLHTRFNQTATATGRLSSSDPNLQNIPVRTPLGQRI
RRAFIAEEGWLLVVLDYSQIELRVLAHLSGDENLIRVFQEGRDIHTETASWMFGVPREAVDPLMRRAAKTINFGVLYGMSAHRLS
QELAIPYEEAQAFIERYFQSFPKVRAWIEKALEEGRRRGYVETLFGRRRYVPDLNARVKSVREAAERMAFNMPVQGTAADLMKL
AMVKLFPRLREMGARMLLQVHDELLLEAPQARAEEVAALAKEAMEKAYPLAVPLEVKVGIGEDWLSAKE*

3B6

(SEQ ID NO: 89)
ATGGCGATGCTTCCCCTCTTTGAGCCCAAGGGCCGCGTCCTCCTGGTGGACGGCCACCACCTGGCCTACCGCGCCTTCTTCG
CCCTGAAGGGCCTCACCACGAGCCGGGGCGAACCGGTGCAGGCGGTCTACGGCTTCGCCAAGAGCCTCCTCAAGGCCCTGA
AGGAGGACGGGTACAAGGCCGTCTTCGTGGTCTTTGACGCCAAGGCCCCCTCCTTCCGCCACGAGGCCTACGAGGCCTACA
AGGCGGGGAGGGCCCCGACCCCCGAGGACTTCCCCCGGCAGCTCGCCCTCATCAAGGAGCTGGTGGACCTCCTGGGGTTTA
CCCGCCTCGAGGTCCAAGGCTACGAGGCGGACGACGTCCTCGCCACCCTGGCCAAGAAGGCGGAAAAAGAAGGGTACGAG
GTGCGCATCCTCACCGCCGACCGGGACCTCTACCAGCTCGTCTCCGACCGCGTCGCCGTCCTCCACCCCGAGGGCCACCTCA
TCACCCCGGAGTGGCTTTGGGAGAAGTACGGCCTCAGGCCGGAGCAGTGGGTGGACTTCCGCGCCCTCGTGGGGGACCCCT
CCAACAACCTCCCCGGGGTCAAGGGCATCGGGGAGAAGACCGCCCTCAAGCTCCTCAAGGAGTGGGGAAGCCTGGAAAAC
CTCCTCAAGAACCTGGACCGGGTAAAGCCAGAAAACGTCCGGGAGAAGATCAAGGCCCACCTGGAAGACCTCAGGCTCTCC
TTGGAGCTCTCCCGGGTGCGCACCGACCTCCCCCTGGAGGTGGACCTCGCCCAGGGGCGGGAGCTCGACCGGGAGAGGCTT
AGGGCCTTTCTGGAGAGGCTTGAGTTTGGCGCCTCCTCCACGAGTTCGGCCTTCTGGAAAGCCCCAAGGCCCTGGAGGAG
GCCCCCTGGCCCCCGCCGGAAGGGGCCTTCGTGGGCTTTGTGCTTTCCCGCAAGGAGCCCATGTGGGCCGATCTTCTGGCCC
TGGCCGCCGCCAGGGGTGGTCGGGTCCACCGGGCCCCCGAGCCTTATAAAGCCCTCAGGGACTTGAAGGAGGCGCGGGGGC
TTCTCGCCAAAGACCTGAGCGTTCTGGCCCTAAGGGAAGGCCTTGGCCTCCCGCCCGGCGACGACCCCATGCTCCTCGCCTA
CCTCCTGGACCCTTCCAACACCGCCCCCGAGGGGGTGGCCCGGCGCTACGGCGGGGAGTGGACGGAGGAGGCGGGGGAGC
GGGCCGCCCTTTCCGAGAGGCTCTTCGCCAACCTGTGGGGGAGGCTTGAGGGGGAGGAGAGGCTCCTTTGGCTTTACCGGG
AGGTGGATAGGCCCCTTTCCGCTGTCCTGGCCCACATGGAGGCCACAGGGGTACGGCTGGACGTGGCCTATCTCAGGGCCTT
GTCCCTGGAGGTGGCCGAGGAGATCGCGCGCCTCGAGGCCGAGGTCTTCCGCCTGGCCGGCCACCCCTTCAACCTCAACTCC
CGAGACCAGCTGGAAAGGGTCCTCTTTGACGAGCTAGGGCTTCCCGCCATCGGCAAGACGGAGAAGACCGGCAAGCGCTCC
ACCAGCGCCGCCGTCCTGGAGGCCCTCCGCGAGGCCCACCCCATCGTGGAGAAGATCCTGCAGTACCGGGAGCTCACCAAG
CTGAAGAGCACCTACATTGACCCCTTGCCGAACCTCATCCATCCCAGGACGGGCCGCCTCCACACCCGCTTCAACCAGACGG
CCACGGCCACGGGCAGGCTAAGTAGCTCCGATCCCAACCTCCAGAACATCCCCGTCCGCACCCCGCTCGGGCAGAGGATCC
GCCGGGCCTTCATCGCCGAGGAGGGGTGGCTATTGGTGGTCCTGGACTATAGCCAGATAGAGCTCAGGGTGCTGGCCCACC
TCTCCGGCGACGAGAACCTGATCCGGGTCTTCCAGGAGGGGCGGGACATCCACACGGAAACCGCCAGCTGGATGTTCGGCG
TCCCCCGGGAGGCCGTGGACCCCCTGATGCGCCGGGCGGCCAAGACCATCAACTTCGGGGTTCTCTACGGCATGTCGGCCC
ACCGCCTCTCCCAGGAGCTAGCCATCCCTTACGAGGAGGCCCAGGCCTTCATTGAGCGCTACTTTCAGAGCTTCCCCAAGGT
GCGGGCCTGGATAGAAAAGACCCTGGAGGAGGGGAGGAAGCGGGGCTACGTGGAAACCCTCTTCGGAAGAAGGCGCTACG
TGCCCGACCTCAACGCCCGGGTGAAGGGCGTCAGGGAGGCCGCGGAGCGCATGGCCTTCAACATGCCCGTCCAGGGCACCG
CCGCCGACCTCATGAAGCTCGCCATGGTGAAGCTCTTCCCCCGCCTCCGGGAGATGGGGGCCCGCATGCTCCTCCAGGTCCA

-continued

CGACGAGCTCCTCCTGGAGGCCCCCCAAGCGCGGGCCGGGGAGGTGGCGGCTTTGGCCAAGGAGGCCATGGAGAAGGCCT
ATCCCCTCGCCGTACCCCTGGAGGTGAAGGTGGGGATCGGGGAGGACTGGCTCTCCGCCAAGGAGTGA (SEQ ID NO: 90)
MAMLPLFEPKGRVLLVDGHHLAYRAFFALKGLTTSRGEPVQAVYGFAKSLLKALKEDGYKAVFVVFDAKAPSFRHEAYEAYKA
GRAPTPEDFPRQLALIKELVDLLGFTRLEVQGYEADDVLATLAKKAEKEGYEVRILTADRDLYQLVSDRVAVLHPEGHLITPEWL
WEKYGLRPEQWVDFRALVGDPSNNLPGVKGIGEKTALKLLKEWGSLENLLKNLDRVKPENVREKIKAHLEDLRLSLELSRVRTD
LPLEVDLAQGRELDRERLRAFLERLEFGGLLHEFGLLESPKALEEAPWPPPEGAFVGFVLSRKEPMWADLLALAAARGGRVHRAP
EPYKALRDLKEARGLLAKDLSVLALREGLGLPPGDDPMLLAYLLDPSNTAPEGVARRYGGEWTEEAGERAALSERLFANLWGR
LEGEERLLWLYREVDRPLSAVLAHMEATGVRLDVAYLRALSLEVAEEIARLEAEVFRLAGHPFNLNSRDQLERVLFDELGLPAIG
KTEKTGKRSTSAAVLEALREAHPIVEKILQYRELTKLKSTYIDPLPNLIHPRTGRLHTRFNQTATATGRLSSSDPNLQNIPVRTPLGQ
RIRRAFIAEEGWLLVVLDYSQIELRVLAHLSGDENLIRVFQEGRDIHTETASWMFGVPREAVDPLMRRAAKTINFGVLYGMSAHR
LSQELAIPYEEAQAFIERYFQSFPKVRAWIEKTLEEGRKRGYVETLFGRRRYVPDLNARVKGVREAAERMAFNMPVQGTAADLM
KLAMVKLFPRLREMGARMLLQVHDELLLEAPQARAGEVAALAKEAMEKAYPLAVPLEVKVGIGEDWLSAKE*

3B8

(SEQ ID NO: 91)
ATGGCGATGCTTCCCCTCTTTGAGCCCAAAGGCCGGGTCCTCCTGGTGGACGGCCACCACCTGGCCTACCGCACCTTCTTCG
CCCTGAAGGGCCTCACCACGAGCCGGGGCGAACCGGTGCAGGTGGTCTACGGCTTCGCCAAGAGCCTCCTCAAGGCCCTGA
AGGAGGACGGGTACAAGGCCGTCTTCGTGGTCTTTGACGCCAAGGCCCCCTCCCTCCGCCACGAGGCCTACGAGGCCTACA
AGGCGGGAGGGCCCCGACCCCCGAGGACTTCCTCCGGCAGCTCGCCCTCATCAAGGAGCTGGTGGACCTCCTGGGGTTTA
CCCGCCTCGAGGTCCAAGGCTACGAGGCGGACGACGTCCTCGCCACCCTGGCCAAGAAGGCGGAAAAAGAAGGGTACGAG
GTGCGCATCCTCACCGCCGACCGGGACCTCTACCAGCTCGTCTCCGACCGCGTCGCCGTCCTCCACCCCGAGGGCCACCTCA
TCACCCCGGAGTGGCTTTGGGAGAAGTACGGCCTCAGGCCGGAGCAGTGGGTGGACTTCCGCGCCCTCGTGGGGGACCCCT
CCGACAACCTCCCCGGGGTCAAGGGCATCGGGGAGAAGACCGCCCTCAAGCTCCTCAAGGAGTGGGGAAGCCTGGAAAAC
CTCCTCAAGAACCTGGACCGGCTGAAGCCCGCCATCCGGGAGAAGATCCTGGCCCACATGGACGATCTGAAGCTCTCCTGG
GACCTGGCCAAGGTGCGCACCGACCTGCCCCTAGAGGTGGACTTCGCCAAAAGGCGGGAGCCCGACCGGGAGAGGCTTAG
GGCCTTTCTGGAGAGGCTTGAGCTTGGCAGCCTCCTCCACGAGTTCGGCCTTCTGGAAAGCCCCAAGACCCTGGAGGAGGCC
TCCTGGCCCCCGCCGGAAGGGGCCTTCGTGGGCTTTGTGCTTTCCCGCAAGGAGCCCATGTGGGCCGATCTTCTGGCCCTGG
CCGCCGCCAGGGGGGGCCGGGTCCACCGGGCCCCCGAGCCTTATAAAGCCCTCAGGGACCTGAAGGAGGCGCGGGGCTTC
TCGCCAAAGACCTGAGCGTTCTGGCCCTAAGGGAAGGCCTTGGCCTCCCGCCCGGCGACGACCCCATGCTCCTCGCCTACCT
CCTGGACCCTTCCAACACCACCCCCGAGGGGTGGCCCGGCGCTACGGCGGGAGTGGACGAAGGAGGCGGGGAGCGGG
CCGCCCTTTCCGAGAGGCTCTTCGCCAACCTGTGGGGAGGCTTGAGGGGAGGAGAGGCTCCTTTGGCTTTACCGGGAGG
TGGATAGGCCCCTTTCCGCTGTCCTGGCCCACATGGAGGCCACAGGGGTGCGCTTGGACGTGGCCTATCTCAGGGCCTTGTC
CCTGGAGGTGGCCGAGGAGATCGCCCGCCTCGAGGCCGAGGTCTTCCGCCTGGCCGGCCATCCCTTCAACCTCAACTCCCGG
GACCAGCTGGAAAGGGTCCTCTTTGACGAGCTAGGGCTTCCCGCCATCGGCAAGACGGAGAAGACCGGCAAGCGCTCCACC
AGCGCCGCCGTCCTGGAGGCCCTCCGCGAGGCCCACCCCATCGTGGAGAAGATCCTGCAGTACCGGGAGCTCACCAAGCTG
AAGAGCACCTACATTGACCCCTTGCCGGACCTCATCCACCCCAGGACGGGCCGCCTCCACACCCGCTTCAACCAGACGGCC
ACGGCCACGGGCAGGCTAAGTAGCTCCGATCCCAACCTCCAGAACATCCCCGTCCGCACCCCGCTCGGGCAGAGGATCCGC
CGGGCCTTCGTCGCCGAGGAGGGTGGCTATTGGTGGTCCTGGACTATAGCCAGATAGAGCTCAGGGTGCTGGCCCACCTCT
CCGGCGACGAGAACCTGACCCGGGTCTTCCTGGAGGGGCGGGACATCCACACGGAAACCGCCAGCTGGATGTTCGGCGTCC
CCCGGGAGGCCGTGGACCCCCTGATGCGCCGGGCGGCCAAGACCATCAACTTCGGGGTTCTCTACGGCATGTCGGCCCACC
GCCTCTCCCAGGAGCTGGCCATCCCTTACGAGGAGGCCCAGGCCTTCATAGAGCGCTACTTCCAAAGCTTCCCCAAGGTGCG
GGCCTGGATAGAAAAGACCCTGGAGGAGGGGAGGAAGCGGGGCTACGTGGAAACCCTCTTCGGAAGAAGGCGCTACGTGC

```
CCGACCTCAACGCCCGGGTGAAGAGTGTCAGGGAGGCCGCGGAGCGCATGGCCTTCAACATGCCCGTCCAGGGCACCGCCG

CCGACCTTATGAAGCTCGCCATGGTGAAGCTCTTCCCCCGCCTCCGGGAGATGGGGGCCCGCATGCTCCTCCAGGTCCACGA

CGAGCTCCTCCTGGAGGCCCCCCAAGCGCGGGCCGAGGAGGTGGCGGCTTTGGCCAAGGAGGCCATGGAGAAGGCCTATCC

CCTCGCCGTACCCCTGGAGGTGAAGGAGGGGATCGGGGAGGACTGGCTCTCCGCCAAGGAGTGA
```

(SEQ ID NO: 92)
```
MAMLPLFEPKGRVLLVDGHHLAYRTFFALKGLTTSRGEPVQVVYGFAKSLLKALKEDGYKAVFVVFDAKAPSLRHEAYEAYKA

GRAPTPEDFLRQLALIKELVDLLGFTRLEVQGYEADDVLATLAKKAEKEGYEVRILTADRDLYQLVSDRVAVLHPEGHLITPEWL

WEKYGLRPEQWVDFRALVGDPSDNLPGVKGIGEKTALKLLKEWGSLENLLKNLDRLKPAIREKILAHMDDLKLSWDLAKVRTD

LPLEVDFAKRREPDRERLRAFLERLELGSLLHEFGLLESPKTLEEASWPPPEGAFVGFVLSRKEPMWADLLALAAARGGRVHRAP

EPYKALRDLKEARGLLAKDLSVLALREGLGLPPGDDPMLLAYLLDPSNTTPEGVARRYGGEWTKEAGERAALSERLFANLWGR

LEGEERLLWLYREVDRPLSAVLAHMEATGVRLDVAYLRALSLEVAEEIARLEAEVFRLAGHPFNLNSRDQLERVLFDELGLPAIG

KTEKTGKRSTSAAVLEALREAHPIVEKILQYRELTKLKSTYIDPLPDLIHPRTGRLHTRFNQTATATGRLSSSDPNLQNIPVRTPLGQ

RIRRAFVAEEGWLLVVLDYSQIELRVAHLSGDENLTRVFLEGRDIHTETASWMFGVPREAVDPLMRRAAKTINFGVLYGMSAH

RLSQELAIPYEEAQAFIERYFQSFPKVRAWIEKTLEEGRKRGYVETLFGRRRYVPDLNARVKSVREAAERMAFNMPVQGTAADL

MKLAMVKLFPRLREMGARMLLQVHDELLLEAPQARAEEVAALAKEAMEKAYPLAVPLEVKEGIGEDWLSAKE*
```

3B10

(SEQ ID NO: 93)
```
ATGGCGATGCTTCCCCTCTTTGAGCCCAAGGGCCGCGTCCTCCTGGTGGACGGCCACCACCTGGCCTACCGCACCTTCTTCG

CCCTGAAGGGCCCCACCACGAGCCGGGGCGAACCGGTGCAGGTGGTCTACGGCTTCGCCAAGAGCCTCCTCAAGGCCCTGA

AAGAGGACGGGTACAAGGCCGTCTTCGTGGTCTTTGACGCCAAGGCCCCCTCATTCGCCACAAGGCCTACGAGGCCTACA

GGGCGGGGAGGGCCCCGACCCCCGAGGACTTCCCCCGGCAGCTCGCCCTCATCAAGGAGCTGGTGGACCTCCTGGGGTTTA

CCCGCCTCGAGGTCCCCGGCTACGAGGCGGACGACGTTCTCGCCACCCTGGCCAAGAAGGCGGAAAAGGAGGGGTACGAG

GTGCGCATCCTCACCGCCGACCGCGGCCTCTACCAACTCGTCTCTGACCGCGTCGCCGTCCTCCACCCCGAGGGCCACCTCA

TCACCCCGGAGTGGCTTTGGGAGAAGTACGGCCTCAGGCCGGAGCAGTGGGTGGACTTCCGCGCCCTCGTGGGGGACCCCT

CCGACAACCTCCCCGGGGTCAAGGGCATCGGGGAGAAGACCGCCCTCAAGCTCCTCAAGGAGTGGGGAAGCCTGGAAAAC

CTCCTCAAGAACCTGGACCGGGTAAAGCCAGAAAACGTCCGGGAGAAGATCAAGGCCCACCTGGAAGACCTCAGGCTCTCC

TTGGAGCTCTCCCGGGTGCGCACCGACCTCCCCCTGGAGGTGGACCTCGCCCAGGGGCGGGAGCCCGACCGGGAGAGGCTT

AGGGCCTTTCTGGAGAGGCTTGAGTTTGGCGGCCTCCTCCACGAGTTCGGCCTTCTGGAAAGCCCCAAGGCCCTGGAGGAG

GCCCCCTGGCCCCCGCCGGAAGGGCCTTCGTGGGCTTTGTGCTTTCCCGCAAGGAGCCCATGTGGGCCGATCTTCTGGCCC

TGGCCGCCGCCAGGGGTGGTCGGGTCCACCGGGCCCCTGAGCCTTATAAAGCCCTCAGGGACTTGAAGGAGGCGCGGGGGC

TTCTCGCCAAAGACCTGAGCGTTCTGGCCCTGAGGGAAGGCCTTGGCCTCCCGCCCGGCGACGACCCCATGCTCCTCGCCTA

CCTCCTGGACCCTTCCAACACCACCCCCGAGGGGGTGGCCCGGCGCTACGGCGGGGAGTGGACGGAGGAGGCGGGGAGC

GGGCCGCCCTTTCCGAGAGGCTCTTCGCCAACCTGTGGGGAGGCTTGAGGGGGAGGAGAGGCTCCTTTGGCTTTACCGGG

AGGTGGAGAGACCCCTTTCCGCTGTCCTGGCCCACATGGAGGCCACGGGGTGCGCCTGGACGTGGCCTATCTCAGGGCCTT

GTCCCTGGAGGTGGCCGAGGAGATCGCCCGCCTCGAGGCCGAGGTCTTCCGCCTGGCCGGCCACCCCTTCAACCTCAACTCC

CGAGACCAGCTGGAAAGGGTCCTCTTTGACGAGCTAGGGCTTCCCGCCATCGGCAAGACGGAGAAGACCGGCAAGCGCTCC

ACCAGCGCCGCCGTCCTGGAGGCCCTCCGCGAGGCCCACCCCATCGTGGAGAAGATCCTGCAGTACCGGGAGCTCACCAAG

CTGAAGAGCACCTACATTGACCCCTTGCCGGACCACATCCACCCCAGGACGGGCCGCCTCCACACCCGCTTCAACCAGACG

GCCACGGCCACGGGCAGGCTAAGTAGCTCCGATCCCAACCTCCAGAACATCCCCGTCCGCACCCCGCTCGGGCAGAGGATC

CGCCGGGCCTTCATCGCCGAGGAGGGGTGGCTATTGGTGGTCCTGGACTATAGCCAGATAGAGCTCAGGGTGCTGGCCCAC

CTCTCCGGCGACGAGAACCTGACCCGGGTCTTCCAGGAGGGGCGGGACATCCACACGGAAACCGCCAGCTGGATGTTCGGC

GTCCCCCGGGAGGCCGTGGACCCCCTGATGCGCCGGGCGGCCAAGACCATCAACTTCGGGGTTCTCTACGGCATGTCGGCC
```

-continued

CACCGCCTCTCCCAGGAGCTGGCCATCCCTTACGAGGAGGCCCAGGCCTTCATAGAGCGCTACTTCCAAAGCTTCCCCAAGG

TGCGGGCCTGGATAGAAAAGACCCTGGAGGAGGGGAGGAAGCGGGGCTACGTGGAAACCCTCTTCGGAAGAAGGCGCTAC

GTGCCCGACCTCAACGCCCGGGTGAAGAGTGTCAGGGAGGCCGCGGAGCGCATGGCCTTCAACATGCCCGTCCAGGGCACC

GCCGCCGACCTTATGAAGCTCGCCATGGTGAAGCTCTACCCCCGCCTCCGGGAGATGGGGGCCCGCATGCTCCTCCAGGTCC

ACGACGAGCTCCTCCTGGAGGCCCCCAAGCGCGGGCCGAGGAGGTGGCGGCTTTGGCCAAGGAGGCCATGGAGAAGGCC

TATCCCCTCGCCGTACCCCTGGAGGTGAAGGTGGGGATCGGGGAGGACTGGCTCTCCGCCCAAGGAGTGAGTCGACCTGCA

GGCAGCGCTTGGCGTCACCCGCAGTTCGGTGGTTAA (SEQ ID NO: 94)
MAMLPLFEPKGRVLLVDGHHLAYRTFFALKGPTTSRGEPVQVVYGFAKSLLKALKEDGYKAVFVVFDAKAPSFRHKAYEAYRA

GRAPTPEDFPRQLALIKELVDLLGFTRLEVPGYEADDVLATLAKKAEKEGYEVRILTADRGLYQLVSDRVAVLHPEGHLITPEWL

WEKYGLRPEQWVDFRALVGDPSDNLPGVKGIGEKTALKLLKEWGSLENLLKNLDRVKPENVREKIKAHLEDLRLSLELSRVRTD

LPLEVDLAQGREPDRERLRAFLERLEFGGLLHEFGLLESPKALEEAPWPPPEGAFVGFVLSRKEPMWADLLALAAARGGRVHRAP

EPYKALRDLKEARGLLAKDLSVLALREGLGLPPGDDPMLLAYLLDPSNTTPEGVARRYGGEWTEEAGERAALSERLFANLWGRL

EGEERLLWLYREVERPLSAVLAHMEATGVRLDVAYLRALSLEVAEEIARLEAEVFRLAGHPFNLNSRDQLERVLFDELGLPAIGK

TEKTGKRSTSAAVLEALREAHPIVEKILQYRELTKLKSTYIDPLPDHIHPRTGRLHTRFNQTATATGRLSSSDPNLQNIPVRTPLGQR

IRRAFIAEEGWLLVVLDYSQIELRVLAHLSGDENLTRVFQEGRDIHTETASWMFGVPREAVDPLMRRAAKTINFGVLYGMSAHRL

SQELAIPYEEAQAFIERYFQSFPKVRAWIEKTLEEGRKRGYVETLFGRRRYVPDLNARVKSVREAAERMAFNMPVQGTAADLMK

LAMVKLYPRLREMGARMLLQVHDELLLEAPQARAEEVAALAKEAMEKAYPLAVPLEVKVGIGEDWLSAQGVSRPAGSAWRHP

QFGG*

3C12

(SEQ ID NO: 95)
ATGGCGATGCTTCCCCTCTTTGAGCCCAAGGGCCGCGTCCTCCTGGTGGACGGCCACCACCTGGCCTACCGCACCTTCTTCG

CCCTGAAGGGCCCCACCACGAGCCGGGGCGAACCGGTGCAGGTGGTCTACGGCTTCGCCAAGAGCCTCCTCAAGGCCCTGA

AGGAGGACGGGTACAAGGCCGTCTTCGTGGTCTTTGACGCCAAGGCCCCCTCATTCCGCCACAAGGCCTACGAGGCCTACA

GGGCGGGGAGGGCCCCGACCCCCGAGGACTTCCCCCGGCAGCTCGCCCTCATCAAGGAGCTGGTGGACCTCCTGGGGTTTA

CCCGCCTCGAGGTCCCCGGCTACGAGGCGGACGACGTTCTCGCCACCCTGGCCAAGAAGGCGGAAAAGGAGGGGTACGAG

GTGCGCATCCTCACCGCCGACCGCGGCCTCTACCAACTCGTCTCTGACCGCGTCGCCGTCCTCCACCCCGAGGGCCACCTCA

TCACCCCGGAGTGGCTTTGGGAGAAGTACGGCCTCAGGCCGGAGCAGTGGGTAGACTTCCGCGCCCTCGTGGGGGACCCCT

CCGACAACCTCCCCGGGGTCAAGGGCATCGGGGAGAAGACCGCCCTCAAGCTCCTCAAGGAGTGGGGAAGCCTGGAAAAC

CTCCTCAAGAACCTGGACCGGGTAAAGCCAGAAAACGTCCGGGAGAAGATCAAGGCCCACCTGGAAGACCTCAGGCTCTCC

TTGGAGCTCTCCCGGGTGCGCACCGACCTCCCCCTGGAGGTGGACCTCGCCCAGGGGCGGGAGCCCGACCGGGAGGGGCTT

AGGGCCTTTCTGGAGAGGCTTGAGTTTGGCAGCCTCCTCCACGAGTTCGGCCTTCTGGAAAGCCCCAAGGCCCTGGAGGAG

GCCCCCTGGCCCCGCCGGAAGGGCCTTCGTGGGCTTTGTGCTTTCACGCAAGGAGCCCATGTGGGCCGATCTTCTGGCCC

TGGCCGCCGCCAGGGGTGGTCGGGTCCACCGGGCCCCGAGCCTTATAAAGCCCTCAGGGACTTGAAGGAGGCGCGGGGC

TTCTCGCCAAAGACCTGAGCGTTCTGGCCCTAAGGGAAGGCCTTGGCCTCCCGCCCGGCGACGACCCCATGCTCCTCGCCTA

CCTCCTGGACCCTTCCAACACCGCCCCCGAGGGGGTGGCCCGGCGCTACGGCGGGGAGTGGACGGAGGAGGCGGGGAGC

GGGCCGCCCTTTCCGAGAGGCTCTTCGCCAACCTGTGGGGGAGGCTTGAGGGGGAGGAGAGGCTCCTTTGGCTTTACCGGG

AGGTGGATAGGCCCCTTTCCGCTGTCCTGGCCCACATGGAGGCCACAGGGGTACGGCTGGACGTGGCCTGCCTGCAGGCCC

TTTCCCTGGAGCTTGCGGAGGAGATCCGCCGCCTCGAGGAGGAGGTCTTCCGCTTGGCGGGCCACCCCTTCAACCTCAACTC

-continued

```
CCGGGACCAGCTGGAAAGGGTCCTCTTTGACGAGCTAGGGCTTCCCGCCATCGGCAAGACGGAGAAGACCGGCAAGCGCTC
CACCAGCGCCGCCATCCTGGAGGCCCTCCGCGAGGCCCACCCCATCGTGGAGAAGATCCTGCAGTACCGGGAGCTCACCAA
GCTGAAGAGCACCTACATTGACCCCTTGCCGGACCTCATCCACCCCAGGACGGGCCGCCTCCACACCCGCTTCAACCAGACG
GCCACGGCCACGGGCAGGCTAAGTAGCTCCGTCCCAACCTCCAGAACATCCCCGTCCGCACCCCGCTCGGGCAGAGGATC
CGCCGGGCCTTCGTCGCCGAGGAGGGGTGGCTATTGGTGGTCCTGGACTATAGCCAGATAGAGCTCAGGGTGCTGGCCCAC
CTCTCCGGCGACGAGAACCTGACCCGGGTCTTCCTGGAGGGGCGGGACATCCACACGGAAACCGCCAGCTGGATGTTCGGC
GTCCCCCGGGAGGCCGTGGACCCCCTGATGCGCCGGGCGGCCAAGACCATCAACTTCGGGGTTCTCTACGGCATGTCGGCC
CACCGCCTCTCCCAGGAGCTGGCCATCCCTTACGAGGAGGCCCAGGCCTTCATAGAGCGCTACTTCCAAAGCTTCCCCAAGG
TGCGGGCCTGGATAGAAAAGACCCTGGAGGAGGGGAGGAAGCGGGGCTACGTGGAAACCCTCTTCGGAAGAAGGCGCTAC
GTGCCCGACCTCAACGCCCGGGTGAAGAGTGTCAGGGAGGCCGCGGAGCGCATGGCCTTCAACATGCCCGTCCAGGGCACC
GCCGCCGACCTTATGAAGCTCGCCATGGTGAAGCTCTTCCCCCGCCTCCGGGAGATGGGGGCCCGCATGCTCCTCCAGGTCC
ACGACGAGCTCCTCCTGGAGGCCCCCCAAGCGCGGGCCGAGGAAGTGGCGGCTTTGGCCAAGGAGGCCATGGAGAAGGCC
TATCCCCTCGCCGTACCCCTGGAGGTGAAGGTGGGGATCGGGGAGGACTGGCTCTCCGCCAAGGAGTGA
```

(SEQ ID NO: 96)
```
MAMLPLFEPKGRVLLVDGHHLAYRTFFALKGPTTSRGEPVQVVYGFAKSLLKALKEDGYKAVFVVFDAKAPSFRHKAYEAYRA
GRAPTPEDFPRQLALIKELVDLLGFTRLEVPGYEADDVLATLAKKAEKEGYEVRILTADRGLYQLVSDRVAVLHPEGHLITPEWL
WEKYGLRPEQWVDFRALVGDPSDNLPGVKGIGEKTALKLLKEWGSLENLLKNLDRVKPENVREKIKAHLEDLRLSLELSRVRTD
LPLEVDLAQGREPDREGLRAFLERLEFGSLLHEFGLLESPKALEEAPWPPPEGAFVGFVLSRKEPMWADLLALAAARGGRVHRAP
EPYKALRDLKEARGLLAKDLSVLALREGLGLPPGDDPMLLAYLLDPSNTAPEGVARRYGGEWTEEAGERAALSERLFANLWGR
LEGEERLLWLYREVDRPLSAVLAHMEATGVRLDVACLQALSLELAEEIRRLEEEVFRLAGHPFNLNSRDQLERVLFDELGLPAIG
KTEKTGKRSTSAAILEALREAHPIVEKILQYRELTKLKSTYIDPLPDLIHPRTGRLHTRFNQTATATGRLSSSGPNLQNIPVRTPLGQ
RIRRRAFVAEEGWLLVVLDYSQIELRVAHLSGDENLTRVFLEGRDIHTETASWMFGVPREAVDPLMRRAAKTINFGVLYGMSAH
RLSQELAIPYEEAQAFIERYFQSFPKVRAWIEKTLEEGRKRGYVETLFGRRRYVPDLNARVKSVREAAERMAFNMPVQGTAADL
MKLAMVKLFPRLREMGARMLLQVHDELLLEAPQARAEEVAALAKEAMEKAYPLAVPLEVKVGIGEDWLSAKE*
```
3D1

(SEQ ID NO: 97)
```
ATGGCGATGCTTCCCCTCTTTGAGCCCAAGGGCCGCGTCCTCCTGGTGGACGGCCACCACCTGGCCTACCGCACCTTCTTCG
CCCTGAAGGGCCCCACCACGAGCCGGGGCGAACCGGTGCAGGTGGTCTACGGCTTCGCCAAGAGCCTCCTCAAGGCCCTGA
AGGAGGACGGGTACAAGGCCGTCTTCGTGGTCTTTGACGCCAAGGCCCCCTCATTCCGCCACAAGGCCTACGAGGCCTACA
GGGCGGGGAGGCCCCGACCCCCGAGGACTTCCCCCGGCAGCTCGCCCTCATCAAGGAGCTGGTGGACCTCCTGGGGTTTA
CCCGCCTCGAGGTCCCCGGCTACGAGGCGGACGACGTTCTCGCCACCCTGGCCAAGAAGGCGGAAAAGGAGGGGTACGAG
GTGCGCATCCTCACCGCCGACCGCGGCCTCTACCAACTCGTCTCTGACCGCGTCGCCGTCCTCCACCCCGAGGGCCACCTCA
TCACCCCGGAGTGGCTTTGGGAGAAGTACGGCCTCAGGCCGGAGCAGTGGGTGGACTTCCGCGCCCTCGTGGGGACCCCT
CCGACAACCTCCCCGGGGTCAAGGGCATCGGGGAGAAGACCGCCCTCAAGCTCCTCAAGGAGTGGGGAAGCCTGGAAAAC
CTCCTCAAGAACCTGGACCGGGTAAAGCCAGAAAACGTCCGGGAGAAGATCAAGGCCCACCTGGAAGACCTCAGGCTCTCC
TTGGAGCTCTCCCGGGTGCGCACCGACCTCCCCCTGGAGGTGGACCTCGCCCAGAGGCGGGAGCCCGACCGGGAGGGGCTT
AGGGCCTTTCTGGAGAGGCTTGAGTTTGGCAGCCTCTTCCACGAGTTCGGCCTTCTGGAAAGCCCCAAGGCCCTGGAGGAGG
CCCCCTGGCCCCCGCCGGAAGGGGCCTTCGTGGGCTTTGTGCTTTCCCGCAAGGAGCCCATGTGGGCCGATCTTCTGGCCCT
GGCCGCCGCCAGGGGTGGTCGAGTCCACCGGGCCCCCGAGCCTTATAAAGCCCTCAGGGACCTGAAGGAGGCGCGGGGCT
TCTCGCCAAAGACCTGAGCGTTCTGGCCCTAAGGGAAGGCCTTGGCCTCCCGCCCGGCGACGACCCCATGCTCCTCGCCTAC
CTCCTGGACCCTTCCAACACCACCCCCGAGGGGTGGCCCGGCGCTACGGCGGGAGTGGACGGAGGAGGCGGGGAGCG
GGCCGCCCTTTCCGAGAGGCTCTTCGCCAACCTGTGGGGGAGGCTTGAGGGGGAGGAGAGGCTCCTTTGGCTTTACCGGGA
```

```
GGTGGAGAGGCCCCTTTCCGCTGTCCTGGCCCACATGGAGGCCACGGGGTGCGCCTGGACGTGGCCTATCTCAGGGCCTTG

TCCCTGGAGGTGGCCGAGGAGATCGCCCGCCTCGAGGCCGAGGTCTTCCGCCTGGCCGGCCACCCCTTCAACCTCAACTCCC

GGGACCAGCTGGAAATGGTGCTCTTTGACGAGCTTAGGCTTCCCGCCTTGGGGAAGACGCAAAAGACGGGCAAGCGCTCCA

CCAGCGCCGCCGTCCTGGAGGCCCTCCGCGAGGCCCACCCCATCGTGGAGAAGATCCTGCAGTACCGGGAGCTCACCAAGC

TGAAGAGCACCTACATTGACCCCTTGTCGGACCTCATCCACCCCAGGACGGGCCGCCTCCACACCCGCTTCAACCAGACGGC

CACGGCCACGGGCAGGCTAAGTAGCTCCGATCCCAACCTCCAGAACATCCCCGTCCGCACCCCGCTTGGGCAGAGGATCCG

CCGGGCCTTCATCGCCGAGGAGGGGTGGCTACTGGTGGTCCTGGACTATAGCCAGATAGAGCTCAGGGTGCTGGCCCACCT

CTCCGGCGACGAAAACCTGATCAGGGTCTTCCAGGAGGGGCGGGACATCCACACGGAGACCGCCAGCTGGATGTTCGGCGT

CCCCCGGGAGGCCGTGGACCCCCTGATGCGCCGGGCGGCCAAGACCATCAACTTCGGGGTCCTCTACGGCATGTCGGCCCA

CCGCCTCTCCCAGGAGCTAGCCATCCCTTACGAGGAGGCCCAGGCCTTCATTGAGCGCTACTTTCAGAGCTTCCCCAAGGTG

CGGGCCTGGATTGAGAAGACCCTGGAGGAGGGCAGGAGGCGGGGGTACGTGGAGACCCTCTTCGGCCGCCGCCGCTACGT

GCCAGACCTAGAGGCCCGGGTGAAGAGCGTGCGGGAGGCGGCCGAGCGCATGGCCTTCAACATGCCCGTCCAGGGCACCG

CCGCCGACCTCATGAAGCTGGCTATGGTGAAGCTCTTCCCCAGGCTGGGAGAAACGGGGCCAGGATGCTCCTTCAGGTCC

ACGACGAGCTGGTCCTCGAGGCCCCAAAAGAGAGGGCGGAGGCCGTGGCCCGGCTGGCCAAGGAGGCCATGGAGGGGGTG

TATCCCCTGGCCGTGCCCCTGGAGGTGGAGGTGGGGATAGGGGAGGACTGGCTCTCCGCCAAGGGTTAG
```

(SEQ ID NO: 98)

```
MAMLPLFEPKGRVLLVDGHHLAYRTFFALKGPTTSRGEPVQVVYGFAKSLLKALKEDGYKAVFVVFDAKAPSFRHKAYEAYRA

GRAPTPEDFPRQLALIKELVDLLGETRLEVPGYEADDVLATLAKKAEKEGYEVRILTADRGLYQLVSDRVAVLHPEGHLITPEWL

WEKYGLRPEQWVDFRALVGDPSDNLPGVKGIGEKTALKLLKEWGSLENLLKNLDRVKPENVREKIKAHLEDLRLSLELSRVRTD

LPLEVDLAQRREPDREGLRAFLERLEFGSLFHEFGLLESPKALEEAPWPPPEGAFVGFVLSRKEPMWADLLALAAARGGRVHRAP

EPYKALRDLKEARGLLAKDLSVLALREGLGLPPGDDPMLLAYLLDPSNTTPEGVARRYGGEWTEEAGERAALSERLFANLWGRL

EGEERLLWLYREVERPLSAVLAHMEATGVRLDVAYLRALSLEVAEEIARLEAEVFRLAGHPFNLNSRDQLEMVLFDELRLPALG

KTQKTGKRSTSAAVLEALREAHPIVEKILQYRELTKLKSTYIDPLSDLIHPRTGRLHTRFNQTATATGRLSSSDPNLQNIPVRTPLGQ

RIRRAFIALEGWLLVVLDYSQIELRVLAHLSGDENLIRVFQEGRDIHTETASWMFGVPREAVDPLMRRAAKTINFGVLYGMSAHR

LSQELAIPYEEAQAFIERYFQSFPKVRAWIEKTLEEGRRRGYVETLFGRRRYVPDLEARVKSVREAAERMAFNMPVQGTAADLM

KLAMVKLEPRLGETGARMLLQVHDELVLEAPKERAEAVARLAKEAMEGVYPLAVPLEVEVGIGEDWLSAKG*
```

Example 11

Abasic Site Bypass by Mismatch Extension Clone in PCR

Figure 10:
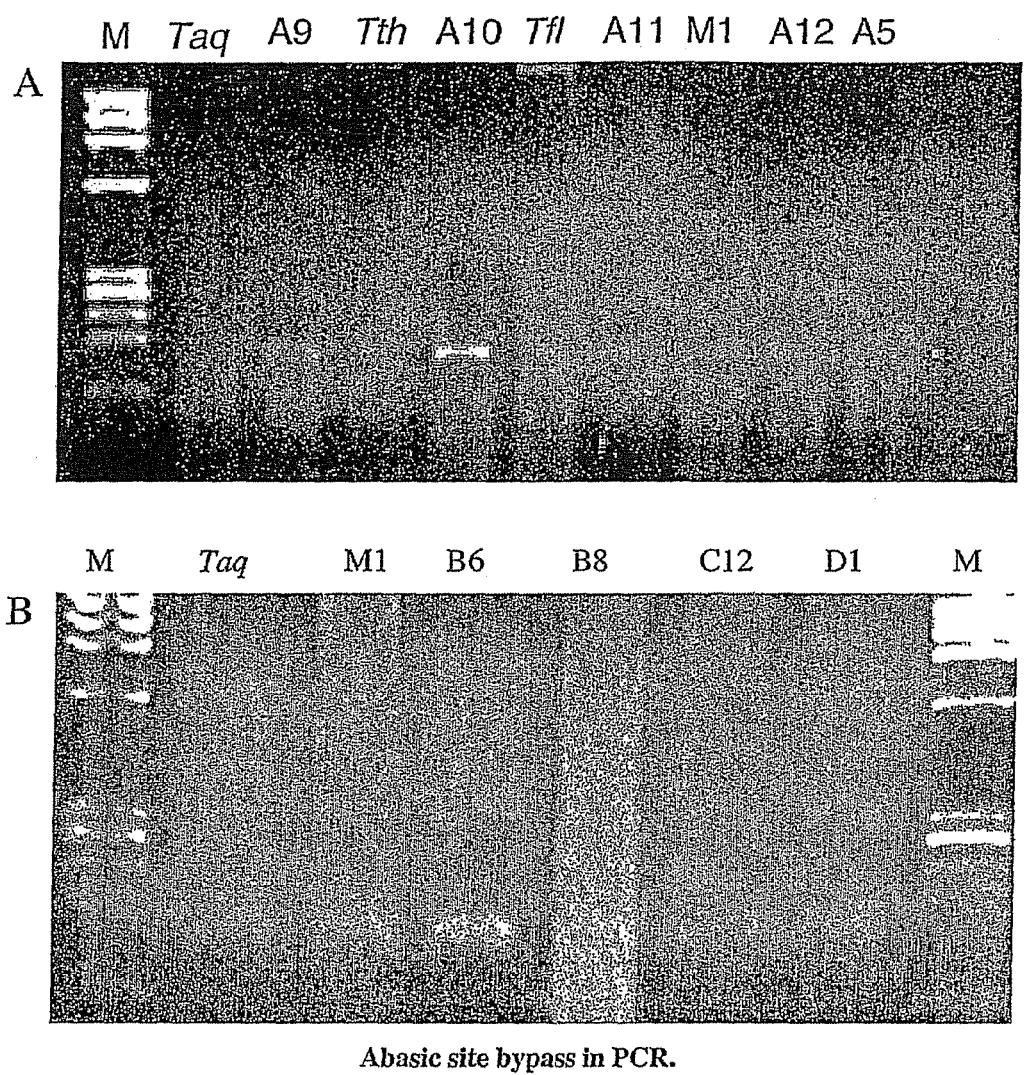
FIG. 10. A list of polymerases selected to extend four mismatches were assayed for their ability to extend abasic sites in PCR. Primers with an abasic site seven bases from their 3' end were designed. Such primers will prevent exponential amplification of the target sequence, restricting it to geometric amplification, unless the abasic site is bypassed. 20 cycles of PCR were sufficient to produce the 176 bp product with the selected polymerases but not with the wild type. (A) Screen which identified clone A10. (B) A further 4 polymerases that display good abasic site bypass. Lane M: markers, Hae III digest of Φ X174.

A list of polymerases selected to extend four mismatches were assayed for their ability to extend abasic sites in PCR (FIG. 10). C12 and D1, which can also extend four mismatched primers in PCR, as well as A10, B6 and B8, which cannot, all produced an amplification product.

Example 12

Abasic Site Bypass by Mismatch Extension Clone in PCR

A list of polymerases selected to extend four mismatches were assayed for their ability to extend abasic sites in PCR (FIG. 10). C12 and D1, which can also extend four mismatched primers in PCR, as well as A10, B6 and B8, which cannot, all produced an amplification product.

Example 13

Figure 11A:
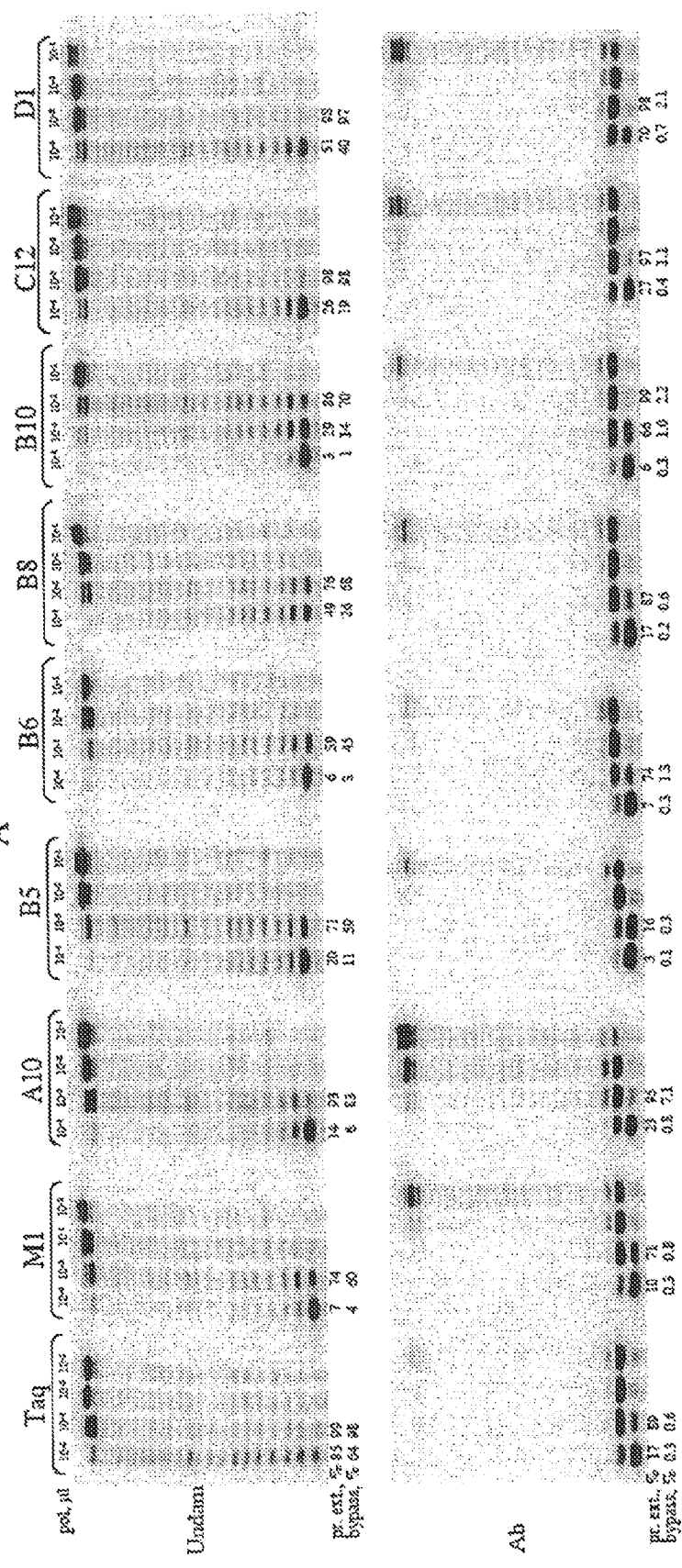
FIG. 11. Seven polymerases were assayed for their ability to bypass abasic sites in a primer extension assay. Translesion synthesis activity on an undamaged template, on a template containing an abasic site or a cis-syn cyclobutane thymine-thymine dimer (CPD) tend a radiolabelled primer (pr) annealed to template. The c site or a CPD located immediately downstream of the primer.
(A) On the template containing an abasic site, wtTaq efficiently inserted a base opposite the lesion, but further extension was negligible. In contrast, M1 is capable of both insertion opposite the abasic site and lesion bypass. Of the four mismatch extension polymerases, polymerases A10 and D1 clearly display better abasic site bypass than either wtTaq or M1, with a number of other polymerases displaying improved abasic site activity (notably C12).
(B) The Polymerase A10 was chosen for further investigation and displays superior elongation and bypass when compared to wild type for both the abasic site and the CPD.
Figure 11:
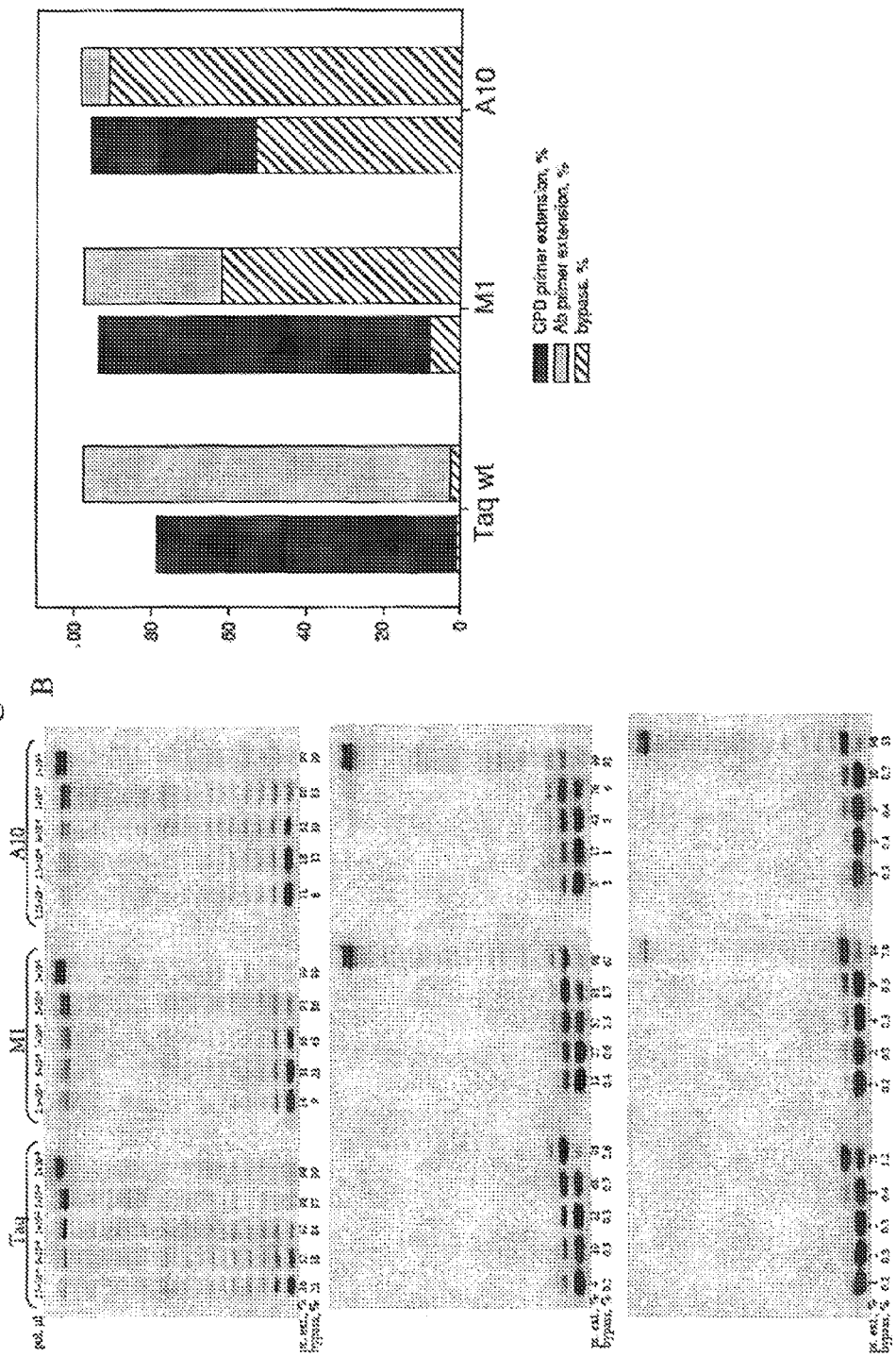

Translesion Synthesis Activity by Mismatch Extension Clone as Determined by Primer Extension Assays Seven polymerases were assayed for their ability to bypass abasic sites in a primer extension assay (FIG. 11).

Primer extension assays were essentially as described in (Ghadessy et al., 2004). Briefly, undamaged oligonucleotides and a 51mer containing a synthetic abasic site were synthesized by Lofstrand Laboratories (Gaithersburg, Md.) using standard techniques and were gel purified prior to use. A 20mer primer (LES_20 P) with the sequence 5'-CGTG-GTCGCGACGGATGCCG-3' (SEQ ID NO: 99) was 5'-labeled with [$^{32}$P]ATP (5000 Ci/mmole; 1 Ci=37 GBq) (Pharmacia) using T4 polynucleotide kinase (Invitrogen, Carlsbad Calif.). Radiolabeled primer-template DNAs were prepared by annealing the 5'[$^{32}$P] labeled 20mer primer to one of the two following 51mer templates (at a primer template ratio of molar 1:1.5). 1) undamaged DNA (UNDT51T); 5'-AGC TAC CAT GCC TGC ACG AAT TCG GCA TCC GTC GCG ACC ACG GTC GCA GCG-3' (SEQ ID NO: 100); 2) an oligo (LABA51T) containing a synthetic abasic site (indicated as an X in bold font); 5'-AGC TAC CAT GCC TGC ACG ACA XCG GCA TCC GTC GCG ACC ACG GTC GCA GCG-3' (SEQ ID NO: 101). Standard replication reactions of 10 contained 40 mM Tris.HCl at pH 8.0, 5 mM $MgCl_2$, 100 µM of each ultrapure dNTP (Amersham Pharmacia Biotech, NJ), 10 mM DTT, 250 µg/ml BSA, 2.5% glycerol, 10 nM 5'[32P] primer-template DNA and 0.1 Unit of polymerase. After incubation at 60° C. for various times reactions were terminated by the addition of 10 µl of 95% formamide/10 mM EDTA and the samples heated to 100° C. for 5 min. Reaction mixtures (5 µl) were subjected to 20% polyacrylamide/7 M Urea gel electrophoresis and replication products visualized by PhosphorImager analysis.

Polymerases A10 was the most active and was chosen for further analysis (FIG. 26JRF nomenclature) on abasic sites and cyclobutane thymine-thymine dimers (CPD). A10 was clearly better at both abasic site and CPD extension and bypass than both wild type and M1.

Example 14

Error Rate Investigation of Mismatch Extension Clones as Determined by MutS ELISA Relaxed specificity might be expected to be achieved at the cost of lower fidelity. We used a MutS ELISa to investigate this possibility.

MutS is an *E. coli* derived mismatch binding protein that binds single base pair mismatches or small (1-4 base) additions or deletions. It can be used to monitor PCR fidelity in an ELISA based assay (Debbie et al., 1997).

Immobilised Mismatch Binding protein plates (Genecheck, Ft Collins, USA) were used for fidelity measurements as per manufacturer's instructions, essentially as described in (Debbie et al., 1997).

The mutation rate of D1 was compared that of wtTaq and M1 M1 was already known to have a modestly increased mutation rate (approximately 2 fold) (Ghadessy et al., 2004). The data presented here suggests that D1 has a 2 fold increased error rate compared to M1 and a four fold increased error rate compared to wtTaq. This corresponds approximately to a 1 in 2500 error ratio and is sufficiently low to not be problematic for many applications.

Example 15

Investigation of Mismatch Extension Clones for the Amplification of Damaged DNA Such as is Found in Ancient Samples DNA recovered from ancient samples is invariably damaged, limiting the information it can yield. Polymerases that can bypass damage (such as abasic site or hydantoins) might therefore be useful in increasing the information that can be recovered from ancient samples of DNA.

Experiment 1

Figure 12:
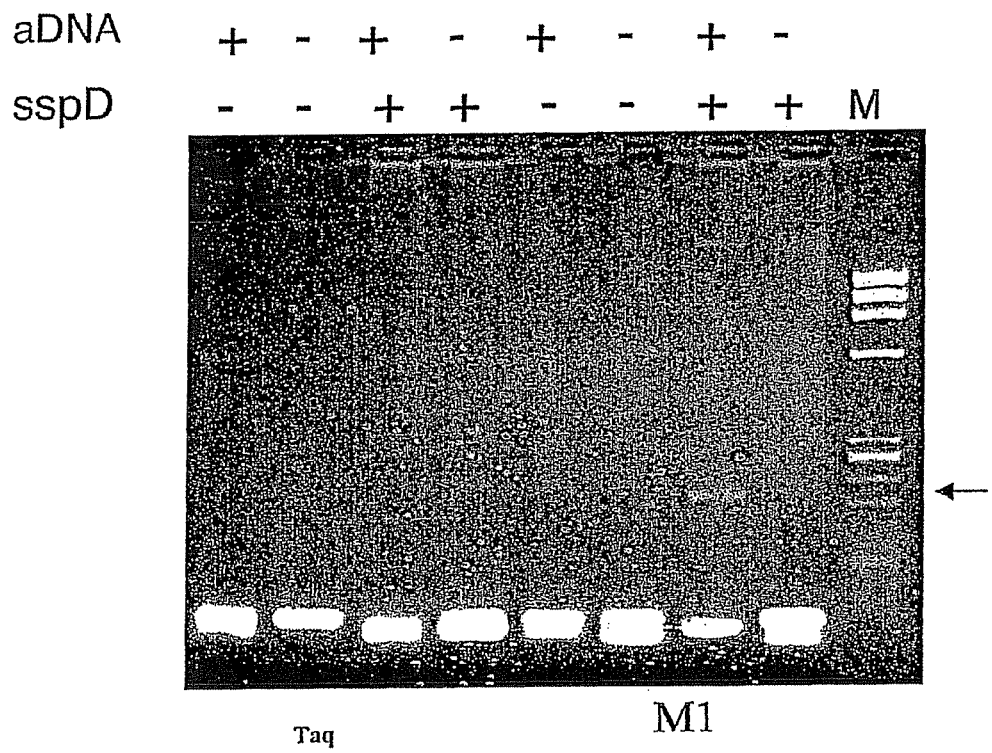
FIG. 12. Several samples of cave hyena (*Crocuta spelaea*) were extracted and analysed. The seven samples were from Teufelslucke cave (Austria, 40 000 years old), Aufhausener Höhle (Germany, no date determined (2 samples)); Irpfelhöhle (Germany, no date determined); Kiskevelyi (Romania 48 500 years old); Miskolc III (Hungary, 44 000 years old); Mala ladnica (Slovakia, no date determined). The target was a 215 bp fragment from the cytochrome B gene in the mitochondrial genome. The amplification was only successful in the presence of sspDNA.

A Mismatch Extending Polymerase can Amplify Previously Un-Amplifiable Cave Hyena DNA Several samples of cave hyena (*Crocuta spelaea*) were extracted and analysed. Of those, seven samples (see FIG. 12 for the list) failed to ever produce an amplification product. These samples were chosen to test the efficacy of the expanded substrate spectrum polymerases.

M1 has a slightly reduced kcat/Km, 14% of Taq wild type, and is hence slightly less efficient in PCR. Therefore, M1 was blended with a commercial preparation of Taq (SuperTaq (HT biotechnology Ltd)) in a ratio of 1 unit to 10 and compared to Taq in the absence of M1. It was hoped that if M1 could bypass the blocking lesions, then the wild type Taq would amplify the resulting translesion synthesis product. On two separate occasions, the M1/SuperTaq mix was able to produce an amplification product whereas SuperTaq alone did not (see FIG. 12 for one example)

The DNA was cloned and sequence and found to differ in two positions (A71→G, 77A→G) from the expected sequence. This could either be a miscoding lesion resulting from a deamination of C or a population variant sequence not seen previously in aDNA. Indeed, both mutations exist in modern spotted hyena (*Crocuta crocuta*), arguing for the second interpretation. Of the 10 sequences obtained from the same successful PCR, two each had a further unique single mutation, an A to G in different places. These are most likely errors incurred during amplification. Such errors are frequently seen in aDNA PCR and are one reason why multiple sequences need to be obtained from the same PCR product.

Contamination problems prevented an exhaustive analysis of the benefits of M1 polymerase. However, this result strongly suggested that a suitable altered polymerase could be usefully applied to aDNA.

Experiment 2

A Blend of Mismatch Extending Polymerase Needs Less Ancient DNA for a Successful PCR Polymerases that displayed interesting properties: B5, B8, C12 and D1, which can extend mismatches as well as A10, B6 and B10 which are proficient at abasic site bypass were purified. In order to keep the number of experiments manageable, they were blended in equal volumes with M1, SuperTaq and heparin purified wild-type Taq. This mix of polymerases was used in almost all subsequent experiments and is referred to as the blend.

To ensure that no polymerase would negatively affect the PCR through its mutant activity, each one was individually blended with SuperTaq and used to perform an aDNA PCR with an ancient sample known to contain amplifiable DNA. All PCRs were successful (data not shown), indicating that it was unlikely that any of the mutant enzymes would be a liability in the blend.

The activity of the blend was checked against the activity of SuperTaq by a PCR activity dilution series. By this measure, the blend was less active than SuperTaq, by a factor of two.

Figure 13:
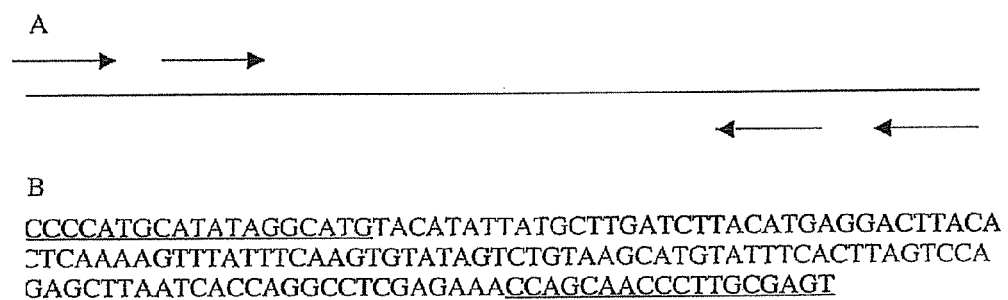
FIG. 13. Appropriate primers for use in the method of the invention. See example 15 for details.
(A) Schematic representation of two step nested PCR. In the first round a pair of outer primers (represented in green) are used; in the second step a pair of nested inner primers (red) are used.
(B) Target sequences in the cave bear mitochondrial D loop (SEQ ID NO: 12). Outer primer sequences are underlined, Inner primer sequences are in red.

The conditions that are usually used in aDNA PCR did not transfer readily to the blend or to SuperTaq as they had been optimised for AmpliTaqGold (Applied Biosystems), a chemically modified version of Taq that allows a hot start and slow enzyme release through heat activation. Manual hot starts are not advisable in aDNA analysis because opening the PCR tube outside the clean room prior to thermocycling carries a high risk of contamination. Furthermore, alternative hot start techniques could not be utilised either: antibodies used to inactivate wtTaq at low temperatures might not bind to the chimerical proteins selected from the Molecular Breeding library and hot start buffers proved ineffective (data not shown). A new two step nested PCR strategy was used. In the first step, the aDNA is amplified over 28 cycles with either SuperTaq or the blend. In the second step, the first PCR is diluted 20 fold in a secondary clean room and amplified with SuperTaq using in-nested primers. This is the approach subsequently used to compare SuperTaq and the blend Briefly, 2 µl of ancient sample were added to a 20 µl PCR in SuperTaq buffer (HT Biotech) with 1 µM of the appropriate primers (see FIG. 13), 2 µM of each deoxyribonucleoside triphosphate (dNTP) as well as 0.1 µl of SuperTaq or an equal volume of mutant polymerases and amplified for 28 cycles. This PCR was set up in a clean room following precautions appropriate for aDNA. The first step PCR was then diluted 1 in 20 in a secondary clean room and thermocycled for a further 32 cycles with the same buffer and dNTPs conditions, using in-nested primers and SuperTaq. No template controls were used to test for contamination.

A two fold dilution series of aDNA with equal volumes of SuperTaq and the blend (and therefore approximately equal activities, with the blend slightly less active) was performed and repeated this four times This experiment showed that the blend was more likely to produce a band at a lower concentration of aDNA than SuperTaq. This therefore represented the second experiment that indicated that the mismatch extension polymerases were more proficient at amplifying aDNA than wild-type Taq.

Experiment 3

The Mismatch Extension Polymerases Perform Consistently Better in Ancient DNA PCR Sample heterogeneity and the inherent stochasticity of aDNA analysis make the interpretation of a single positive or negative PCR problematic. To address this, multiple PCRs of a same sample and count the number of successful PCR amplifications at a limiting sample dilution were performed. Comparison of SuperTaq with the blend would allowed a statistical analysis. As the amount of aDNA required for this type of approach is large, samples previously shown to be of high quality were chosen and tested at limiting dilutions to increase the amount of material available for analysis. A short target sequence was chosen to allow maximal dilutions.

This has the additional advantage that at a sufficiently high dilution, the undamaged DNA will have been diluted out, leaving only damaged template. In such conditions, the difference between a polymerase that can bypass blocking lesions and one that cannot should become clearly apparent.

A total of nine experiments at limiting amounts of aDNA, where the PCR would only be stochastically successful (FIGS. 14 and 15) were performed. In eight out of nine experiments, the blend resulted in more successful PCRs than SuperTaq. The probability of this occurring by chance is 1.76%, as determined by binomial distribution analysis. It is commonly accepted that chance can be dismissed as an explanation when an event is expected to occur at 5% probability or less.

We can therefore state that this effect is not due to chance and that the blend is repeatedly performing better than SuperTaq in the conditions of the experiment. This proves beyond reasonable doubt that the mismatch extension polymerases are a more sensitive tool for the recovery of ancient DNA sequences.

Example 16

Selection of a Polymerases Capable of Replicating the Unnatural Base Analogue 5-Nitroindol (5NI)

We selected for extension and bypass of 5NI directly from the polymerase chimera library described in example 8 using an analogous strategy to the mismatch selection using flanking primers (5'-CAG GAA ACA GCT ATG ACA AAA ATC TAG ATA ACG AGG GCA 5NI-3' (SEQ ID NO: 102), 5'-GTA AAA CGA CGG CCA GTA CCA CCG AAC TGC GGG TGA CGC CAA GC5NI-3' (SEQ ID NO: 103)) comprising 5NI (or a derivative) at their 3' ends. After round 3, we used flanking primers (5'-CAG GAA ACA GCT ATG ACA AAA ATC TAG ATA 5NICG AGG GCA 5NI-3' (SEQ ID NO: 104), 5'-GTA AAA CGA CGG CCA GTA CCA C5NIG AAC TGC GGG TGA CGC CAA GC5NI-3' (SEQ ID NO: 105)) comprising internal 5NI (or a derivative) as well as 3' terminal 5NI (or a derivative) to increase selection pressure for 5NI replication.

Five rounds of selection yielded a number of clones with greatly increased ability to replicate 5NI. Among the best clones were round 4 clone 4D11 and round 5 clone 5D4:

```
4D11:
                                                             (SEQ ID NO: 106)
5'-
ATGGCGATGCTTCCCCTCTTTGAGCCCAAAGGCCGGGTCCTCCTGGTGGACGGCCACCACCTGGCCTACCGC

ACCTTCTTCGCCCTGAAGGGCCTCACCACGAGCCGGGGCGAACCGGTGCAGGCGGTTTACGGCTTCGCCAAG

AGCCTCCTCAAGGCCCTGAAGGAGGACGGGTACAAGGCCGTCTTCGTGGTCTTTGACGCCAAGGCCCCCTCC

TTCCGCCACGAGGCCTACGAGGCCTACAAGGCGGGGAGGGCCCCGACCCCCGAGGACTTCCCCCGGCAGCTC

GCCCTCATCAAGGAGCTGGTGGACCTCCTGGGGTTTACCCGCCTCGAGGTCCAAGGCTACGAGGCGGACGAC

GTCCTCGCCACCCTGGCCAAGAAGGCGGAAAAAGAAGGGTACGAGGTGCGCATCCTCACCGCCGACCGGGAC

CTCTACCAGCTCGTCTCCGACCGCGTCGCCGTCCTCCACCCCGAGGGCCACCTCATCACCCCGGAGTGGCTT

TGGGAGAAGTACGGCCTCAGGCCGGAGCAGTGGGTGGACTTCCGCGCCCTCGTGGGGGACCCCTCCGACAAC

CTCCCCGGGATCAAGGGCATCGGGGAGAAGACCGCCCTCAAGCTCCTCAAGGAGTGGGGAAGCCTGGAAAAC

CTCCTCAAGAACCTGGACCGGGTAAAGCCAGAAAATGTCCGGGAGAAGATCAAGGCCCACCTGGAAGACCTC

AGGCTCTCCTTGGAGCTCTCCCGGGTGCGCACCGACCTCCCCCTGGAGGTGGACTTCGCCAAAAGGCGGGAG

CCCGACCGGGAGAGGCTTAGGGCCTTTCTGGAGAGGCTTGAGTTTGGCAGCCTCCTCCACGAGTTCGGCCTT
```

-continued

```
CTGGAAAGCCCCAAGGCCCTGGAGGAGGCCCCCTGGCCCCCGCCGGAAGGGGCCTTCGTGGGCTTTGTGCTT
TCCCGCAAGGAGCCCATGTGGGCCGATCTTCTGGCCCTGGCCGCCGCCAAGGGTGGCCGGGTCCACCGGGCC
CCCGAGCCTTATAAAGCCCTCAGGGACTTGAAGGAGGCGCGGGGCTTCTCGCCAAAGACCTGAGCGTTCTG
GCCCTAAGGGAAGGCCTTGGCCTCCCGCCCGGCGACGACCCCATGCTCCTCGCCTACCTCCTGGACCCTTCC
AACACCACCCCCGAGGGGGTGGCCCGGCGCTACGGCGGGGAGTGGACGGAGGAGGCGGGGGAGCGGGCCGCC
CTTTCCGAGAGGCTCTTCGCCAACCTGTGGGGGAGGCTTGAGGGGGAGGAGAGGCTCCTTTGGCTTTACCGG
GAGGTGGAGAGGCCCCTTTCCGCTGTCCTGGCCCACATGGAGGCCACGGGGGTGCGCCTGGACGTGGCCTAT
CTCAGGGCCTTGTCCCTGGAGGTGGCCGAGGAGATCGCCCGCCTCGAGGCCGAGGTCTTCCGCCTGGCCGGC
CACCCCTTCAACCTCAACTCCCGAGACCAGCTGGAAAGGGTCCTCTTTGACGAGCTAGGGCTTCCCGCCATC
GGCAAGACGGAGAAGACCGGCAAGCGCTCCACCAGCGCCGCCGTCCTGGAGGCCCTCCGCGAGGCCCACCCC
ATCGTGGAGAAGATCCTGCAGTACCGGGAGCTCACCAAGCTGAAGAGCACCTACATTGACCCCTTGCCGGAC
CTCATCCACCCCAGGACGGGCCGCCTCCACACCCGCTTCAACCAGACGGCCACGGCCACGGGCAGGCTAAGT
AGCTCCGATCCCAACCTCCAGAACATCCCCGTCCGCACCCCGCTCGGGCAGAGGATCCGCCGGGCCTTCATC
GCCGAGGGGGGTGGCTATTGGTGGTCCTGGACTATAGCCAGATGGAGCTCAGGGTGCTGGCCCACCTCTCC
GGCGACGAGAACCTGATCCGGGTCTTCCAGGAGGGGCGGGACATCCACACGGAAACCGCCAGCTGGATGTTC
GGCGTCCCCCGGGAGGCCGTGGACCCCCTGATGCGCCGGGCGGCCAAGACCATCAACTTCGGGGTTCTCTAC
GGCATGTCGGCCCACCGCCTCTCCCAGGAGCTAGCCATCCCTTACGAGGAGGCCCAGGCCTTCATTGAGCGC
TACTTTCAGAGCTTCCCCAAGGTGCGGGCCTGGATTGAGAAGACCCTGGAGGAGGGCAGGAGGCGGGGGTAC
GTGGAGACCCTCTTCGGCCGCCGCCGCTACGTGCCAGACCTAGAGGCCCGGGTGAAGAGCGTGCGGGAGGCG
GCCGAGCGCATGGCCTTCAACATGCCCGTCCAGGGCACCGCCGCCGACCTCATGAAGCTGGCTATGGTGAAG
CTCTTCCCCAGGCTGGAGGAAACGGGGGCCAGGATGCTCCTTCAGGTCCACGACGAGCTGGTCCTCGAGGCC
CCAAAAGAGAGGGCGGAGGCCGTGGCCCGGCTGGCCAAGGAGGTCATGGAGGGGGTGTATCCCCTGGCCGTG
CCCCTGGAGGTGGAGGTGGGGATAGGGGAGGACTGGCTCTCCGCCAAGGAGTGA-3'
```

4D11 amino acid sequence:

(SEQ ID NO: 107)

```
MAMLPLFEPKGRVLLVDGHHLAYRTFFALKGLTTSRGEPVQAVYGFAKSLLKALKEDGYKAVFVVFDAKAPS
FRHEAYEAYKAGRAPTPEDFPRQLALIKELVDLLGFTRLEVQGYEADDVLATLAKKAEKEGYEVRILTADRD
LYQLVSDRVAVLHPEGHLITPEWLWEKYGLRPEQWVDFRALVGDPSDNLPGIKGIGEKTALKLLKEWGSLEN
LLKNLDRVKPENVREKIKAHLEDLRLSLELSRVRTDLPLEVDFAKRREPDRERLRAFLERLEFGSLLHEFGL
LESPKALEEAPWPPPEGAFVGFVLSRKEPMWADLLALAAAKGGRVHRAPEPYKALRDLKEARGLLAKDLSVL
ALREGLGLPPGDDPMLLAYLLDPSNTTPEGVARRYGGEWTEEAGERAALSERLFANLWGRLEGEERLLWLYR
EVERPLSAVLAHMEATGVRLDVAYLRALSLEVAEEIARLEAEVFRLAGHPFNLNSRDQLERVLFDELGLPAI
GKTEKTGKRSTSAAVLEALREAHPIVEKILQYRELTKLKSTYIDPLPDLIHPRTGRLHTRFNQTATATGRLS
SSDPNLQNIPVRTPLGQRIRRAFIAEGGWLLVVLDYSQMELRVLAHLSGDENLIRVFQEGRDIHTETASWMF
GVPREAVDPLMRRAAKTINFGVLYGMSAHRLSQELAIPYEEAQAFIERYFQSFPKVRAWIEKTLEEGRRRGY
VETLFGRRRYVPDLEARVKSVREAAERMAFNMPVQGTAADLMKLAMVKLFPRLEETGARMLLQVHDELVLEA
PKERAEAVARLAKEVMEGVYPLAVPLEVEVGIGEDWLSAKE*
```

5D4:

(SEQ ID NO: 108)

```
5'-
ATGGCGATGCTTCCCCTCTTTGAGCCCAAAGGCCGGGTCCTCCTGGTGGACGGCCACCACCTGGCCTACCGC
ACCTTCTTCGCCCTGAAGGGCCTCACCACGAGTCGGGGCGAACCGGTGCAGGCGGTCTACGGCTTCGCCAAG
AGCCTCCTCAAGGCCCTGAAGGAGGACGGGTACAAGGCCATCTTCGTGGTCTTTGACGCCAAGGCCCCCTCC
```

-continued

```
TTCCGCCACGAGGCCCACGAGGCCTACAAGGCGGGGAGGGCCCCGAGCCCCGAGGACTTCCCCCGGCAGCTC
GCCCTCATCAAGGAGCTGGTGGACCTCCTGGGGTTTACCCGCCTCGAGGTCCAAGGCTACGAGGCGGACGAC
GTCCTCGCCACCCTGGCCAAGAAGGCGGAAAAGAAGGGTACGAGGTGCGCATCCTCACCGCCGACCGGGAC
CTCTACCAGCTCGTCTCCGACCGCGTCGCCGTCCTCCACCCCGAGGGCCACCTCATCACCCCGGAGTGGCTT
TGGGAGAAGTACGGCCTCAGGCCGGAGCAGTGGGTGGACTTCCGCGCCCTCGTGGGGGACCCCTCCGACAAC
CTCCCCGGGGTCAAGGGCATCGGGGAGAAGACCGCCCTCAAGCTCCTCAAGGAGTGGGGAAGCCTGGAAAAC
CTCCTCAAGAACCTGGACCGGCTGAAGCCCGCCATCCGGGAGAAGATCCTGGCCCACATGGACGATCTGAAG
CTCTCCTGGGACCTGGCCAAGGTGCGCACCGACCTGCCCCTGGAGGTGGACTTCGCCAAAAGGCGGGAGTCC
GATCGGGAGAGGCTTAGGGCCTTTCTGGAGAGGCTTGAGTTTGGCAGCCTCCTCCACGAGTTCGGCCTTCTG
GAAAGCCCCAAGGCCCTGGAGGAGGCCCCCTGGCCCCCGCCGGTAGGGGCCTTCGTGGGCTTTGTGCTTTCC
CGCAAGGAGCCCATGTGGGCCGATCTTCTGGCCCTGGCCGCCGCCAGGGGTGGTCGGGTCCACCGGGCCCCC
GAGCCTTATAAAGCCCTCAGAGACCTGAAGGAGGCGCGGGGCTTCTCGCCAAAGACCTGAGCGTTCTGGCC
CTGAGGGAAGGCCTTGGCCTCCCGCCCGGCGACGACCCCATGCTCCTCGCCTACCTCCTGGACCCTTCCAAC
ACCACCCCCGAGGTGGTGGCCCGGCGCTACGGCGGGGAGTGGACGGAGGAGGCGGGGGAGCGGGCCGCCCTT
TCCGAGAGGCTCTTCGCCAACCTGTGGGGGAGGCTTGAGGGGGAGGGGAGGCTCCTTTGGCTTTACCGGGGG
GTGGAGAGGCCCCTTTCCGCTGTCCTGGCCCACATGGAGGCCACAGGGGTGCGCCTGGACGTGGCCTATCTC
AGGGCCTTGTCCCTGGAGGTGGCCGAGGAGATCGCCCGCCTCGAGGCCGAGGTCTTCCGCCTGGCCGGCCAC
CCCTTCAACCTCAACTCCCGGGACCAGCTGGAAAGGGTCCTCTTTGACGAGCTAGGGCTTCCCGCCATCGGC
AAGACGGAGAAGACCGGCAAGCGCTCCACCAGCGCCGCCGTCCTGGAGGCCCTCCGCGAGGCCCACCCCATC
GTGGAGAAGATCCTGCAGTACCGGGAGCTCACCAAGCTGAAGAGCACTTACATTGACCCCTTGCCGGACCTC
ATCCACCCCAGGACGGGCCGCCTCCACACCCGCTTCAACCAGACGGCCACGGCCACGGGCAGGCTAAGTAGC
TCCGATCCCAACCTCCAGAACATCCCCGTCCGCACCCCGCTCGGGCAGAGGATCCGCCGGGCCTTCATCGCC
GAGGGGGGTGGCTATTGGTGGTCCTGGACTATAGCCAGATGGAGCTCAGGGTGCTGGCCCACCTCTCCGGC
GACGAGAACCTGATCCGGGTCTTCCAGGAGGGGCGGGACATCCACACGGAAACCGCCAGCTGGATGTTCGGC
GTCCCCCGGGAGGCCGTGGACCCCCTGATGCGCCGGGCGGCCAAGACCATCAACTTCGGGGTTCTCTACGGC
ATGTCGGCCCACCGCCTCTCCCAGGAGCTAGCCATCCCTTACGAGGAGGCCCAGGCCTTCATTGAGCGCTAC
TTCCAAAGCTTCCCCAAGGTGCGGGCCTGGATAGAAAAGACCCTGGAGGAGGGGAGGAAGCGGGGCTACGTG
GAAACCCTCTTCGGAAGAAGGCGCTACGTGCCCGACCTCAACGCCCGGGTGAAGAGCGTCAGGGAGGCCGCG
GAGCGCATGGCCTTCAACATGCCCGTCCAGGGCACCGCCGCCGACCTCACGAAGCTGGCTATGGTGAAGCTC
TTCCCCAGGCTGGAGGAAACGGGGGCCAGGATGCTCCTTCAGGTCCACGACGAGCTGGTCCTCGAGGCCCCA
AAAGAGAGGGCGGAGGCCGTGGCCCGGCTGGCCAAGGAGGTCATGGAGGGGGTGTATCCCCTGGCCGTGCCC
CTGGAGGTGGAGGTGGGGATAGGGGAGGACTGGCTTTCCGCCAAGGGTTAG-3'
```

5D4 amino acid sequence:
(SEQ ID NO: 109)

```
MAMLPLFEPKGRVLLVDGHHLAYRTFFALKGLTTSRGEPVQAVYGFAKSLLKALKEDGYK
AIFVVFDAKAPSFRHEAHEAYKAGRAPSPEDFPRQLALIKELVDLLGFTRLEVQGYEADD
VLATLAKKAEKEGYEVRILTADRDLYQLVSDRVAVLHPEGHLITPEWLWEKYGLRPEQWV
DFRALVGDPSDNLPGVKGIGEKTALKLLKEWGSLENLLKNLDRLKPAIREKILAHMDDLK
LSWDLAKVRTDLPLEVDFAKRRESDRERLRAFLERLEFGSLLHEFGLLESPKALEEAPWP
PPVGAFVGFVLSRKEPMWADLLALAAARGGRVHRAPEPYKALRDLKEARGLLAKDLSVLA
LREGLGLPPGDDPMLLAYLLDPSNTTPEVVARRYGGEWTEEAGERAALSERLFANLWGRL
```

```
-continued
EGEGRLLWLYRGVERPLSAVLAHMEATGVRLDVAYLRALSLEVAEEIARLEAEVFRLAGH

PFNLNSRDQLERVLFDELGLPAIGKTEKTGKRSTSAAVLEALREAHPIVEKILQYRELTK

LKSTYIDPLPDLIHPRTGRLHTRFNQTATATGRLSSSDPNLQNIPVRTPLGQRIRRAFIA

EGGWLLVVLDYSQMELRVLAHLSGDENLIRVFQEGRDIHTETASWMFGVPREAVDPLMRR

AAKTINFGVLYGMSAHRLSQELAIPYEEAQAFIERYFQSFPKVRAWIEKTLEEGRKRGYV

ETLFGRRRYVPDLNARVKSVREAAERMAFNMPVQGTAADLTKLAMVKLFPRLEETGARML

LQVHDELVLEAPKERAEAVARLAKEVMEGVYPLAVPLEVEVGIGEDWLSAKG*
```

Example 17

Expanded Spectrum of Polymerases Selected for Replication of 5NI

Round 5 polymerases selected for replication of 5NI were tested for activity with a range of substrates using the hairpin ELISA assay described in example 8. tUTP and ceATP were kind gifts from the laboratory of P. Herdewijin, Rega Institute, Katholieke Universiteit Leuven, Belgium. Results are shown in FIG. 14

1. ELISA with tUTP:

The ability of round 5 clones selected for 5NI replication extension to sequentially incorporate 2 or 3 of the TNA UTP derivative (3', 2')-beta-L-threonyl-UTP was assayed using the hairpin primers (ELISAT2p: 5'-TAG CTC GGT AA CGC CGG CTT CCG TCG CGA CCA CGT TX TTC GTG GTC GCG ACG GAA GCC G-3' (SEQ ID NO: 110), ELISAT3p: 5'-TAG CTC GGT AAA CGC CGG CTT CCG TCG CGA CCA CGT TX TTC GTG GTC GCG ACG GAA GCC G-3' (SEQ ID NO: 10) (X=dU-biotin (Glen research)). The lysates used were concentrated 4-fold. ELISA protocol was a described except that The DIG labelled dUTP in the extension reaction was replaced with Fluorescein 12-dATP (Perkin-Elmer) (at 3% of dATP) and the incorporation of Fluorescein 12-dATP was detected by anti-Fluorescein-POD Fab fragments (Roche).

2. ELISA with ceATP:

The ability of round 5 clones selected for 5NI replication extension to sequentially incorporate the cyclohexenyl ATP derivative ceATP was assayed using the hairpin primers (ELISA2p: 5'-TAG CTC GGA TTTT CGC CGG CTT CCG TCG CGA CCA CGT TX TTC GTG GTC GCG ACG GAA GCC G-3' (SEQ ID NO: 111), (X=dU-biotin (Glen research)). The lysates used were concentrated 4-fold.

3. ELISA with CyDye 5-dCTP and CyDye 3-dCTP:

The ability of round 5 clones selected for 5NI replication extension to sequentially incorporate the fluorescent dye-labelled nucleotides Cy5-dCTP and Cy3-dCTP (Amersham Biosciences) was assayed using the hairpin primers (ELISA2p: 5'-TAG CTA CCA GGG CTC CGG CTT CCG TCG CGA CCA CGT TXT TCG TGG TCG CGA CGG AAG CCG-3' (SEQ ID NO: 112), (X=dU-biotin (Glen research)). The lysates used were concentrated 4-fold.

4. Basic Site Bypass ELISA

The ability of round 5 clones selected for 5NI replication extension to bypass an abasic site was assayed using the hairpin primer (PScreenlabas: 5'-AGC TAC CAT GCT GCC TGC ACG CAG YCG GCA TCC GTC GCG ACC ACG TTX TTC GTG GTC GCG ACG GAT GCC G-3' (SEQ ID NO: 113), (X=dU-biotin, Y=abasic site (Glen research)). The lysates used were concentrated 4-fold.

Example 18

Primer Extension Reaction with Polymerases 4D11 and 5D4

1: Extension Opposite 5-Nitroindole.

```
Primer
                                          (SEQ ID NO: 114)
5'-TAATACGACTCACTATAGGGAGA Template
                                          (SEQ ID NO: 115)
3'-ATTATGCTGAGTGATATCCCTCT5ATCGAT
```

5=5-Nitroindole

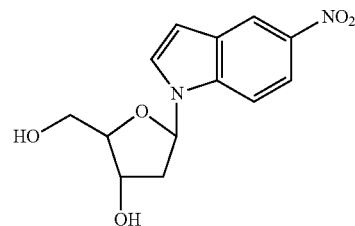 [SMILES: O=[N+]([O-])c1ccc2c(ccn2C2CC(O)C(CO)O2)c1]

Primer extension reactions were carried out as follows:

50 pmol of $^{32}$P-labelled primer and 100 pmol of template in a volume of 44 µl were annealed in 1× Taq buffer. 4D11 or 5D4 polymerase as cell lysate (6 µl) was added and reactions were incubated at 50° C. for 15 minutes followed by addition of one dNTP (1 µl in total volume of 50 µl, final dNTP concentration 40 µM). 8 µl samples were taken at various time points and added to 8 µl stop solution (7M urea, 100 mM EDTA containing xylene cyanol F). At the end of the time course the remaining 3 dNTPs were added (final concentration each dNTP 40 µM) and reactions incubated at 50° C. for a further 30 minutes. Reaction samples were electrophoretically separated using 20% polyacrylamide gels at 25 W for 4 hours. The resultant gels were dried and scanned using a phosphorimager (Molecular Dynamics). Data was processed using the program ImageQuant (Molecular Dynamics). Results are shown in FIGS. 35, 36:

Similar reactions using Taq, Tth and Tfl wild-type polymerases under identical conditions leads to almost undetectable extension reactions (data not shown).

2. Incorporation and Extension of 5-nitroindole-5'-triphosphate (5NITP).

Primer extension reactions were carried out as follows:

50 pmol of $^{32}$P-labelled primer and 100 pmol of template in a volume of 44 μl were annealed in 1× Taq buffer. 4D11 or 5D4 polymerase as cell lysate (6 μl) was added and reactions were incubated at 50° C. for 15 minutes followed by addition of d5NITP (1 μl in total volume of 504 final dNTP concentration 40 μM). 8 μl samples were taken at various time points and added to 8 μl stop solution (7M urea, 100 mM EDTA containing xylene cyanol F). At the end of the time course the 4 native dNTPs were added (final concentration each dNTP 40 μM) and reactions incubated at 50° C. for a further 30 minutes.

Reaction samples were electrophoretically separated using 20% polyacrylamide gels at 25 W for 4 hours. The resultant gels were dried and scanned using a phosphorimager (Molecular Dynamics). Data was processed using the program ImageQuant (Molecular Dynamics). Results are shown in FIGS. 17, 18):

The NI-NI self-pair is also formed exceptionally well, though further extension is reduced (data not shown). Similar reactions using Taq, Tth and Tfl wild-type polymerases under identical conditions leads to almost undetectable extension reactions (data not shown).

Example 19

Array Manufacture and Hybridization Using M1

Targets were prepared by PCR amplification of 2.5 kb Taq gene using primers 29, 28 or 2 kb of the HIV pol gene using primers 30, 31. Salmon sperm DNA (Invitrogen) was prepared at 100 ng/μl in 50% DMSO. FITC and Cy5 probes were prepared by PCR amplification of 0.4 kb fragment of Taq using primers 8, 28 with either 100% (FITC100$_{M1}$) or 10% of dATP (FITC10$_{M1}$, FITC10$_{Taq}$) replaced by FITC-12-dATP or 10% of dCTP replaced by Cy5-dCTP (Cy5$_{Taq}$). Cy5 and Cy3 random 20mers (MWG) were used at 250 nM. Targets were purified using PCR purification kit (Qiagen) and prepared in 50% DMSO and spotted onto GAPSII aminosilane-coated glass slides (Corning) using a MicroGrid (BioRobotics). Array hybridizations were performed according to standard protocols:

Printed slides were baked for 2 hr at 80° C., incubated with agitation for 30 min at 42° C. in 5×SSC/0.1% BSA Fraction V (Roche)/0.1% SDS, boiled for 2 min in ultrapure water, washed 20× in ultrapure water at room temperature (RT), rinsed in propan-2-ol and dried in a clean airstream. 50 ng of FITC- and Cy5-labelled probes were prepared in 20 μl of hybridization buffer (1 mM Tris-HCl pH7.4, 50 mM tetrasodium pyrophosphate, lx Denhardts solution, 40% deionised formamide, 0.1% SDS, 100 μg/ml sheared salmon sperm DNA). Each sample was heated to 95° C. for 5 min, centrifuged for 2 min, applied to the surface of an array and covered with a 22×22 mm HybriSlip (Sigma). Hybridizations were performed at 48° C. for 16 hr in a hybridization chamber (Corning). Arrays were washed once with 2×SSC/0.1% SDS at 65° C. for 5 min once with 0.2×SSC at RT for 5 min and twice with 0.05×SSC at RT for 5 min. Slides were dried in a clean airstream, scanned with an ArrayWoRx autoloader (Applied Precision Instruments) and the array images analysed using SoftWoRx tracker (Molecularware).

Complete substitution of natural nucleotides with their unnatural counterparts altered the properties of the resulting amplification products. For example, fully alphaS substituted DNA was completely resistant to nuclease digestion (not shown).

The 0.4 kb fragment, in which all adenines (dA) on both strands had been replaced with FITC-12-dAMP (FITC100$_{M1}$), displayed extremely bright fluorescence. The frequency of fluorophore incorporation per 1000 nucleotides (FOI) is commonly used to specify the fluorescence intensity of a probe. FOIs of microarray probes commonly range from 10-50, while FITC100$_{M1}$ has an FOI of 295. To investigate if such a high level of fluorophore substitution would affect hybridisation characteristics we performed a series of microarray experiments. We compared the fluorescent signal generated by FITC100$_{M1}$ with equivalent probes generated using either wtTaq or M1 and replacing only 10% of dAMP with FITC-12-dAMP (FITC10$_{Taq}$, FITC10$_{M1}$ (FOI=30)). In competitive co-hybridisation with a standard Cy5-labelled probe (Cy5$_{Taq}$), FITC100$_{M1}$ hybridised specifically only with its cognate Taq polymerase target sequence and not with any non-cognate control DNA. Hybridisation of FITC100$_{M1}$ generated an up to 20-fold higher specific signal than equimolar amounts of the FITC10 probes (FIG. 20) without showing increased background binding (FIGS. 19, 21).

Example 20

Mutation Rates & Spectra of Selected Polymerases M1 and M4

Mutation rates were determined using the mutS ELISA assay[26] (Genecheck, Ft. Collins, Colo.) according to manufacturers instructions. Alternatively, amplification products derived from 2×50 cycles of PCR of 2 targets with different GC content (HIV pol (38% GC), Taq (68% GC)) were cloned, 40 clones (800 bp each) were sequenced and mutations (wt-Taq (51), M1 (75)) analyzed.

Promiscuous mismatch extension might be expected to come at the price of reduced fidelity, as misincorporation no longer leads to termination. Measurement of the overall mutation rate using both the MutS assay (FIG. 22A) and direct sequencing of amplification products, however, indicated an only modestly (1.6 fold) increased mutation rate in M1 (or M4). However, M1 displays a significantly altered mutation spectrum compared to wtTaq, with a clearly increased propensity for transversions, in particular G/C→C/G transversions (FIG. 22B).

Example 21

Processivity

Naturally occurring translesion polymerases are mostly poorly processive. We therefore investigated, if processivity of M1 and M4 was similarly reduced but found that, even at the lowest enzyme concentrations, primer extension and termination probabilities by M1 and M4 closely matched those of wtTaq (FIG. 23), indicating that both M1 and M4 exhibit processivity equal (or higher) than wtTaq. This is also reflected in the striking proficiency of M1 in long-range PCR (see example 6).

Processivity was measured using a primer extension assay the presence and absence of trap DNA. Termination probabilities were calculated according to the method of Kokoska et al.

Oligonucleotide primer 32 (5'-GCG GTG TAG AGA CGA GTG CGG AG-3') (SEQ ID NO: 117) was $^{32}$P-labelled and annealed to the template 33 (5'-CTC TCA CAA GCA GCC AGG CAA GCT CCG CAC TCG TCT CTA CAC CGC TCC GC-3' (SEQ ID NO: 118)) (at a primer/template ratio of molar 1/1.5). wtTaq (0.0025 nM; 0.025 nM; 0.25 nM), M1 (0.05 nM; 0.5 nM; 5 nM), and M4 (0.05 nM; 0.5 nM; 5 nM) were preincubated with the primer-template DNA substrates (10 nM) in 10 mM Tris-HCl at pH 9.0, 5 mM $MgCl_2$, 50 mM KCl, 0.1% Triton X 100 at 25° C. for 15 min. Reactions were initiated by addition of 100 µM dNTPs with or without trap DNA (1000-fold excess of unlabeled primer-templates). Reactions were performed at 60° C. for 2 min. Preincubation of polymerases with the trap DNA substrate and labelled primer-template before the addition of dNTPs completely abolished primer extension (not shown) demonstrating trap effectiveness. Thus, in the presence of trap DNA, all DNA synthesis resulted from a single DNA binding event. Gel band intensities were calculated using a Phosphoimager and ImageQuant (both Molecular Dynamics) software. Percentage of polymerase molecules, which extended primers to the end of the template was calculated using the formula: In×100%/(I1+I2+ . . . +In), where In is the intensity of the band at position 22 or 23; I1, I2 . . . is the intensity of the band at position 1, 2 . . . . Termination probabilities (τ) were calculated according to the method of Kokoska et al[1], whereby t at a particular template position was calculated as the intensity of the band at this position divided by the sum of the intensity of this band and the band intensities of all longer products.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry, molecular biology and biotechnology or related fields are intended to be within the scope of the following claims.

REFERENCES

1. Schaaper, R. M. (1993) *J. Biol. Chem.* 268, 23762-23765.
2. Li, Y., Korolev, S. & Waksman, G. (1998) *Embo J.* 17, 7514-7525.
3. Doublié, S., Tabor, S., Long, A. M., Richardson, C. C. & Ellenberger, T. (1998) *Nature* 391, 251-258.
4. Johnson, S. J., Taylor, J. S. & Beese, L. S. (2003) *Proc. Natl. Acad. Sci. USA* 100, 38895-38900.
5. Li, Y., Mitaxov, V. & Waksman, G. (1999) *Proc. Natl. Acad. Sci. USA* 96, 9491-9496.
6. Astatke, M., Ng, K., Grindley, N. D. & Joyce, C. M. (1998) *Proc. Natl. Acad. Sci. USA* 95, 3402-3407.
7. Patel, P. H. & Loeb, L. A. (2000) *J. Biol. Chem.* 275, 40266-40272.
8. Jestin, J. L., Kristensen, P. & Winter, G. (1999) *Angew. Chem. Int. Ed.* 38, 1124-1127.
9. Xia, G., Chen, L., Sera, T., Fa, M., Schultz, P. G. & Romesberg, F. E. (2002) *Proc. Natl. Acad. Sci. USA* 99, 6597-6602.
10. Ghadessy, F. J., Ong, J. L. & Holliger, P. (2001) *Proc. Natl. Acad. Sci. USA* 98, 4552-4557.
11. Tawfik, D. S. & Griffiths, A. D. (1998) *Nature Biotechnol* 16, 652-656.
12. Huang, M.-M., Arnheim, N. & Goodman, M. F. (1992) *Nucleic Acids Res.* 20, 4567-4573.
13. Kool, E. T. (2000) *Curr. Op. Chem. Biol.* 4, 602-608.
14. Kwok, S., Kellogg, D. E., McKinney, N., Spasic, D., Goda, L., Levenson, C. & Sninsky, J. J. (1990) *Nucleic Acids Res* 18, 999-1005.
15. Eom, S. H., Wang, J. & Steitz, T. A. (1996) *Nature* 382, 278-281.
16. Creighton, S., Bloom, L. B. & Goodman, M. F. (1995) *Meth. Enzymol.* 262, 232-56.
17. Mendelman, L. V., Petruska, J. & Goodman, M. F. (1990) *J. Biol. Chem.* 265, 2338-2346.
18. Boudsocq, F., Iwai, S., Hanaoka, F. & Woodgate, R. (2001) *Nucleic Acids Res* 29, 4607-4616.
19. Verma, S. & Eckstein, F. (1998) *Annu. Rev. Biochem.* 67, 99-134.
20. Loakes, D. (2001) *Nucleic Acids Res* 29, 2437-2447.
21. Berger, M., Wu, Y., Ogawa, A. K., McMinn, D. L., Schultz, P. G. & Romesberg, F. E. (2000) *Nucleic Acids Res,* 2911-2914.
22. Barnes, W. M. (1994) *Proc. Natl. Acad. Sci. USA* 91, 2216-2220.
23. Goodman, M. F. (2002) *Annu. Rev. Biochem.* 71, 17-50.
24. Kunkel, T. A. & Bebenek, K. (2000) *Annu. Rev. Biochem.* 69, 497-529.
25. Patel, P. H., Suzuki, M., Adman, E., Shinkai, A. & Loeb, L. A. (2001) *J. Mol. Biol.* 18, 823-837.
26. Lawyer, F. C., Stoffel, S., Saiki, R. K., Chang, S. Y., Landre, P. A., Abramson, R. D. & Gelfand, D. H. (1993) *PCR Meth. Appl.* 2, 275-87.
27. Tada, M., Omata, M., Kawai, S., Saisho, H., Ohto, M., Saiki, R. K. & Sninsky, J. J. (1993) *Cancer Res* 53, 2472-2474.
28. Ling, H., Boudsocq, F., Woodgate, R. & Yang, W. (2001) *Cell* 107, 91-102.
29. Trincao, J., Johnson, R. E., Escalante, C. R., Prakash, S., Prakash, L. & Aggarwal, A. K. (2001) *Mol. Cell* 8, 417-426.
30. Cho, Y. S., Zhu, F. C., Luxon, B. A. & Gorenstein, D. G. *J Biomol Struct Dyn* 11, 685-702.
31. Eigen, M. (1971) *Naturwissenschaften* 58, 465-523.
32. Engelke, D. R., Krikos, A., Bruck, M. E. & Ginsburg, D. (1990) *Anal. Biochem.* 191, 396-400.
33. Zhao, H., Giver, L., Shao, Z., Affholter, J. A. & Arnold, F. H. (1998) *Nature Biotechnol.* 16, 258-61.
34. Murata, T., Iwai, S. & Ohtsuka, E. (1990) *Nucleic Acids Res* 18, 7279-7286.

The invention claimed is:

1. An isolated pol A DNA polymerase having at least 95% identity to the amino acid sequence of SEQ ID NO:86, wherein said pol A DNA polymerase is capable of abasic site bypass and has an expanded substrate range relative to a wild type polA DNA polymerase selected from the group consisting of Taq, Tth and Tfl, and wherein said pol A DNA polymerase comprises the following amino acids at the following positions: K at position 76, Q at position 90, G at position 144, Q at position 335, T at position 447, M at position 615, M at position 738 and G at position 743 with reference to the amino acid positions of SEQ ID NO:86.

2. The isolated pol A DNA polymerase of claim 1, wherein said pol A DNA polymerase comprises the amino acid sequence of SEQ ID NO:86.

3. The isolated pol A DNA polymerase of claim 2, wherein said DNA polymerase consists of the amino acid sequence of SEQ ID NO:86.

4. The isolated pol A DNA polymerase of claim 1, wherein said pol A DNA polymerase comprises a 5'-3' exonuclease domain which is derived from Tth.

5. An isolated pol A DNA polymerase having at least 95% identity to the amino acid sequence of SEQ ID NO:86, wherein said pol A DNA polymerase is capable of abasic site bypass, and has an expanded substrate range relative to a polymerase consisting of the amino acid sequence of SEQ ID NO: 1, and wherein said pol A DNA polymerase comprises the following amino acids at the following positions: K at position 76, Q at position 90, G at position 144, Q at position 335, T at position 447, M at position 615, M at position 738 and G at position 743 with reference to the amino acid positions of SEQ ID NO: 86.

* * * * *